United States Patent
Li et al.

(10) Patent No.: US 11,312,724 B2
(45) Date of Patent: Apr. 26, 2022

(54) SPIROCYCLIC TETRAHYDROQUINAZOLINES

(71) Applicants: ASCENTAGE PHARMA (SUZHOU) CO., LTD., Jiangsu (CN); ASCENTAGE PHARMA GROUP CORP LIMITED, Hong Kong (CN)

(72) Inventors: Chao Li, Jiangsu (CN); Guozhi Tang, Jiangsu (CN); Jianyong Chen, Jiangsu (CN); Lingling Jiao, Jiangsu (CN); Liugen Li, Jiangsu (CN)

(73) Assignees: ASCENTAGE PHARMA (SUZHOU) CO., LTD.; ASCENTAGE PHARMA GROUP CORP LIMITED

( * ) Notice: Subject to any disclaimer, the term of this patent is extended or adjusted under 35 U.S.C. 154(b) by 0 days.

(21) Appl. No.: 17/200,342

(22) Filed: Mar. 12, 2021

(65) Prior Publication Data

US 2021/0230174 A1    Jul. 29, 2021

Related U.S. Application Data

(63) Continuation of application No. PCT/CN2021/070795, filed on Jan. 8, 2021.

(51) Int. Cl.
| | | |
|---|---|---|
| C07D 491/107 | (2006.01) | |
| C07D 487/04 | (2006.01) | |
| C07D 403/14 | (2006.01) | |
| A61P 35/00 | (2006.01) | |
| C07D 471/10 | (2006.01) | |
| C07D 495/10 | (2006.01) | |
| C07D 519/00 | (2006.01) | |

(52) U.S. Cl.
CPC .......... *C07D 491/107* (2013.01); *A61P 35/00* (2018.01); *C07D 403/14* (2013.01); *C07D 471/10* (2013.01); *C07D 487/04* (2013.01); *C07D 495/10* (2013.01); *C07D 519/00* (2013.01)

(58) Field of Classification Search
CPC ................................................ C07D 491/107
See application file for complete search history.

(56) References Cited

U.S. PATENT DOCUMENTS

2019/0144444 A1    5/2019   Blake et al.

FOREIGN PATENT DOCUMENTS

| WO | WO 96/11934 A1 | 4/1996 |
| WO | WO 2018/217651 A1 | 11/2018 |
| WO | WO 2019/051291 A1 | 3/2019 |
| WO | WO-2019099524 A1 | 5/2019 |
| WO | WO 2019/155399 A1 | 8/2019 |
| WO | WO2021/093758 | * 5/2021 |

OTHER PUBLICATIONS

Written Opinion of the International Search Authority for International Appl. No. PCT/CN2021/070795, dated Apr. 9, 2021, National Intellectual Property Administration, PRC, Beijing, China.
CAS:1340521-98-3, STN-Registry, Nov. 3, 2011.
Seiser, T. et al., "Rhodium(I)-catalyzed enantioselective activation of cyclobutanols: formation of cyclohexane derivatives with quaternary stereogenic centers.", Chem. Eur. J. 16(11): 3383-3391, Wiley-VCH Verlag GmbH & Co, Germany (2010).
Canon, J., et al., "The clinical KRAS(G12C) inhibitor AMG 510 drives anti-tumour immunity," *Nature* 575(7781):217-223, Nature Publishing Group, United Kingdom (published online Oct. 2019, published in print Nov. 2019).
Fell, J. B., et al., "Discovery of Tetrahydropyridopyrimidines as Irreversible Covalent Inhibitors of KRAS-G12C with In Vivo Activity," *ACS Medicinal Chemistry Letters* 9(12):1230-1234, American Chemical Society, United States (Nov. 2018).
Hallin, J., et al., "The KRAS$^{G12C}$ Inhibitor MRTX849 Provides Insight toward Therapeutic Susceptibility of KRAS-Mutant Cancers in Mouse Models and Patients," *Cancer Discovery* 10(1):54-71, American Association for Cancer Research, United States (published online Oct. 2019, published in print Jan. 2020).
Liu, P., et al., "Targeting the untargetable KRAS in cancer therapy," *Acta Pharmaceutica Sinica B* 9(5):871-879, Elsevier, Netherlands (published online Mar. 2019, published in print Sep. 2019).

(Continued)

*Primary Examiner* — Brian E McDowell
(74) *Attorney, Agent, or Firm* — Sterne, Kessler, Goldstein & Fox P.L.L.C.

(57) ABSTRACT

The present disclosure provides compounds represented by Formula I:

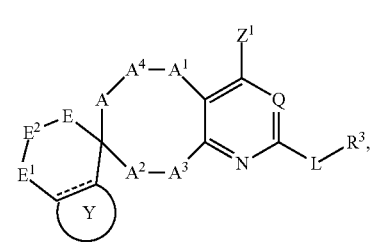

wherein $R^3$, A, $A^1$, $A^2$, $A^3$, E, $E^1$, $E^2$, L, Q, Z, and

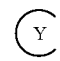

are as defined in the specification, and the pharmaceutically acceptable salts and solvates thereof. Compounds of Formula I are KRAS inhibitors and are thus useful to treat cancer and other diseases.

14 Claims, No Drawings

(56) References Cited

OTHER PUBLICATIONS

Shin, Y., et al., "Discovery of N-(1-Acryloylazetidin-3-yl)-2-(1H-indol-1-yl)acetamides as Covalent Inhibitors of KRAS$^{G12C}$," *ACS Medicinal Chemistry Letters* 10(9):1302-1308, American Chemical Society, United States (Aug. 2019).

* cited by examiner

SPIROCYCLIC TETRAHYDROQUINAZOLINES

BACKGROUND OF THE INVENTION

Field of the Invention

The present disclosure provides KRAS inhibitors, synthetic intermediates used to prepare KRAS inhibitors, and therapeutic methods of treating conditions and diseases, e.g., cancer, wherein the inhibition of KRAS provides a benefit.

Background

RAS represents a group of monomeric globular proteins of 189 amino acids (21 kDa molecular mass) that are associated with the plasma membrane and that bind either GDP or GTP. RAS acts as a molecular switch. When RAS contains bound GDP, it is in the resting or off position and is "inactive". In response to exposure of the cell to certain growth promoting stimuli, RAS is induced to exchange its bound GDP for a GTP. With GTP bound, RAS is "switched on" and is able to interact with and activate other proteins (its "downstream targets"). The RAS protein itself has a very low intrinsic ability to hydrolyze GTP back to GDP, thus turning itself into the off state. Switching RAS off requires extrinsic proteins termed GTPase-activating proteins (GAPs) that interact with RAS and greatly accelerate the conversion of GTP to GDP. Any mutation in RAS that affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. The most notable members of the RAS are HRAS, KRAS, and NRAS.

Structurally, RAS proteins contain a G domain that is responsible for the enzymatic activity of RAS, i.e., the guanine nucleotide binding and the hydrolysis (GTPase reaction). It also contains a C-terminal extension, known as the CAAX box, which may be post-translationally modified, and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues that are essential for nucleotide binding and hydrolysis (Glycine 12, Threonine 26 and Lysine 16). The G domain also contains the Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the gamma-phosphate of GTP that maintain the Switch 1 and Switch 2 regions, respectively, in their active conformation. After hydrolysis of GTP and release of phosphate, these two relax into the inactive GDP conformation.

Mutations in the KRAS gene are common events in human tumorigenesis. Indeed, mutations in KRAS are prevalent in the some of the most deadly cancer types: pancreatic (95%), colorectal (45%), and lung (35%). The most common KRAS mutations are found at residue G12 and G13 in the P-loop and at residue Q61.

The glycine-12 to cysteine (G12C) mutation is a frequent mutation of the KRAS gene. This mutation has a causal role in 14% of lung adenocarcinomas and 5% of colorectal adenocarcinomas. Collectively, KRAS-G12C mutations comprise a patient population with a worldwide annual incidence of >100,000 individuals. See, e.g., Fell et al., *ASC Med. Chem. Lett.* 9:1230-1234 (2018); Shin et al., *ACS Med. Chem. Lett.* 10:1302-1308 (2019); Canon et al., *Nature* 575:217-223 (2019). There exists a need in the art for KRAS inhibitors for the treatment of cancer and other diseases.

BRIEF SUMMARY OF THE INVENTION

In one aspect, the present disclosure provides compounds represented by any one of Formulae I-XV, below, and the pharmaceutically acceptable salts and solvates, e.g., hydrates, thereof, collectively referred to as "Compounds of the Disclosure." Compounds of the Disclosure are KRAS inhibitors and are thus useful in treating or preventing diseases or conditions such as cancer wherein the inhibition of KRAS provides a benefit.

In another aspect, the present disclosure provides compounds represented by any one of Formulae XVI-LXI, below, and the pharmaceutically acceptable salts and solvates, e.g., hydrates, thereof, collectively referred to as "Intermediates of the Disclosure." Intermediates of the Disclosure are synthetic intermediates that can be used to prepare Compounds of the Disclosure.

In another aspect, the present disclosure provides methods of treating or preventing a condition or disease by administering a therapeutically effective amount of a Compound of the Disclosure to a subject, e.g., a human patient, in need thereof. The disease or condition of interest that is treatable or preventable by inhibition or of KRAS is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, Compounds of the Disclosure may reduce the proliferation of unwanted cells by inducing apoptosis in those cells. In some embodiments, Compounds of the Disclosure are administered in combination with an optional therapeutic agent.

In another aspect, the present disclosure provides a method of inhibiting KRAS in a subject, comprising administering to the subject a therapeutically effective amount of a Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of KRAS provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising an optional therapeutic agent useful in the treatment of a disease or condition of interest, and a package insert containing directions for use in the treatment of a disease or condition, e.g., cancer.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

In one embodiment, Compounds of the Disclosure are compounds of Formula I:

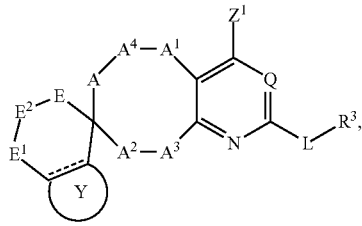

I wherein:
Z is

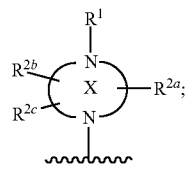

X represents a 6- to 12-membered monocyclic or bicyclic heterocyclo;

$R^1$ is selected from the group consisting of —C(=O)$R^{1a}$, —C(=O)—C$R^{4a}$=C$R^{4b}R^{4c}$, —C(=O)—C≡C$R^{5a}$, —S(=O)$_2$C$R^{4e}$=C$R^{4f}R^{4g}$, and —S(=O)$_2$—C≡C$R^{5b}$;

$R^{1a}$ is selected from the group consisting of $C_1$-$C_4$ alkyl, $C_1$-$C_4$ haloalkyl, and $C_3$-$C_6$ cycloalkyl;

$R^{4a}$, $R^{4b}$, and $R^{4c}$ are independently selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (heterocyclo)$C_1$-$C_4$ alkyl;

$R^{5a}$ is selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (heterocyclo)$C_1$-$C_4$ alkyl;

$R^{4e}$, $R^{4f}$, and $R^{4g}$ are independently selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (heterocyclo)$C_1$-$C_4$ alkyl;

$R^{5b}$ is selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (heterocyclo)$C_1$-$C_4$ alkyl;

$R^{2a}$ is selected from the group consisting of hydrogen, $C_1$-$C_4$ alkyl, $C_1$-$C_4$ haloalkyl, (cyano)$C_1$-$C_4$ alkyl, (hydroxy)$C_1$-$C_4$ alkyl, (alkoxy)$C_1$-$C_4$ alkyl, (amino)$C_1$-$C_4$ alkyl, (heterocyclo)$C_1$-$C_4$ alkyl, (aryl)$C_1$-$C_4$ alkyl, (hetereoaryl)$C_1$-$C_4$ alkyl, $C_2$-$C_4$ alkynyl, heteroalkyl, cyano, —C(=O)$OR^{5c}$, —C(=O)$NR^{5d}R^{5e}$, and —$NR^{5f}R^{5g}$;

$R^{2b}$ and $R^{2c}$ are independently selected from the group consisting of hydrogen and $C_1$-$C_4$ alkyl; or $R^{2b}$ and $R^{2c}$ are attached to the same carbon atom and are taken together to form a —C(=O)— group;

$R^{5c}$ is selected from the group consisting hydrogen and $C_1$-$C_4$ alkyl;

$R^{5d}$ and $R^{5e}$ are independently selected from the group consisting hydrogen and $C_1$-$C_4$ alkyl; or $R^{5d}$ and $R^{5e}$ taken together with the nitrogen atom to which they are attached form an optionally substituted 4- to 8-membered heterocyclo;

$R^{5f}$ and $R^{5g}$ are independently selected from the group consisting hydrogen and $C_1$-$C_4$ alkyl; or $R^{5f}$ and $R^{5g}$ taken together with the nitrogen atom to which they are attached form an optionally substituted 4- to 8-membered heterocyclo;

L is selected from the group consisting of —O—, —S—, and —N($R^7$)—; or L is a bond;

$R^7$ is selected from the group consisting of hydrogen and $C_1$-$C_4$ alkyl;

$R^3$ is selected from the group consisting of hydrogen, $C_1$-$C_4$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, (carboxamido)$C_1$-$C_4$ alkyl, (heterocyclo)$C_1$-$C_4$ alkyl, (aryl)$C_1$-$C_4$ alkyl, and (hetereoaryl)$C_1$-$C_4$ alkyl;

A is selected from the group consisting of —(C$R^{6a}R^{6b})_m$—, —O—, —S—, and —N($R^{7a}$)—;

$A^1$ is selected from the group consisting of —(C$R^{6c}R^{6d})_n$—, —O—, —S—, and —N($R^{7b}$)—;

$A^2$ is selected from the group consisting of —(C$R^{6e}R^{6f})_o$—, —O—, —S—, and —N($R^{7c}$)—;

$A^3$ is selected from the group consisting of —(C$R^{6g}R^{6h})_p$—, —O—, —S—, and —N($R^{7d}$)—;

$A^4$ is selected from the group consisting of —O—, —S—, and —N($R^{7e}$)—; or $A^4$ is a bond, with the provisos that:

(1) when A is —O—, —S—, or —N($R^{7a}$)—, then $A^4$ is a bond, $A^1$ is —(C$R^{6c}R^{6d})_n$—, n is 1 or 2, and E is —(C$R^{8a}R^{8b})_q$;

(2) when $A^1$ is —O—, —S—, or —N($R^{7b}$)—, then $A^4$ is a bond, A is —(C$R^{6a}R^{6b})_m$—, and m is 1 or 2;

(3) when $A^2$ is —O—, —S—, or —N($R^{7c}$)—, then $A^3$ is —(C$R^{6g}R^{6h})_p$— p is 1 or 2, and E is —(C$R^{8a}R^{8b})_q$; and (4) when $A^3$ is —O—, —S—, or —N($R^{7d}$)—, then $A^2$ is —(C$R^{6e}R^{6f})_o$— and o is 1 or 2, $R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and $C_1$-$C_4$ alkyl;

m is 0, 1, or 2;
n is 0, 1, or 2;
o is 0, 1, or 2;
p is 0, 1, or 2;
with the proviso that the sum of m, n, o, and p is 2, 3, 4, or 5;

$R^{7a}$, $R^{7b}$, $R^{7c}$, $R^{7d}$, and $R^{7e}$ are independently selected from the group consisting of hydrogen and $C_1$-$C_4$ alkyl;

E is selected from the group consisting of —$(CR^{8a}R^{8b})_q$—, —O—, —S—, and —$N(R^{9a})$—;

$E^1$ is selected from the group consisting of —$(CR^{8c}R^{8d})_r$—, —O—, —S—, —$N(R^{9b})$—, and —C(=O)—;

$E^2$ is selected from the group consisting of —O—, —S—, and —$N(R^{9c})$—, or $E^2$ is a bond with the provisos that:
(1) when E is —O—, —S—, or —$N(R^{9a})$—, then $E^2$ is a bond, $E^1$ is —$(CR^{8c}R^{8d})_q$—, A is —$(CR^{6a}R^{6b})_m$—, m is 1 or 2, $A^2$ is —$(CR^{6e}R^{6f})_o$—, and o is 1 or 2; and
(2) when $E^1$ is —O—, —S—, or —$N(R^{9b})$—, then $E^2$ is a bond, E is —$(CR^{8a}R^{8b})_r$—, and r is 1 or 2, q is 1, 2, or 3;
r is 0, 1, or 2;
with the proviso that the sum of q and r is 2, 3, 4, or 5;

$R^{8a}$ and $R^{8b}$ are each independently selected from the group consisting of hydrogen and $C_1$-$C_4$ alkyl; or $R^{8a}$ and $R^{8b}$ taken together with the carbon atom to which they are attached form a $C_3$-$C_6$ cycloalkyl;

$R^{8c}$ and $R^{8d}$ are each independently selected from the group consisting of hydrogen and $C_1$-$C_4$ alkyl; or $R^{8c}$ and $R^{8d}$ taken together with the carbon atom to which they are attached form a $C_3$-$C_6$ cycloalkyl;

$R^{9a}$, $R^{9b}$, and $R^{9c}$ are independently selected from the group consisting of hydrogen and $C_1$-$C_4$ alkyl;

Q is selected from the group consisting of =C($R^{10}$)— and =N—;

$R^{10}$ is selected from the group consisting of hydrogen, $C_1$-$C_4$ alkyl and $C_3$-$C_6$ cycloalkyl;

represents a fused optionally substituted $C_3$-$C_8$ cycloalkyl, a fused optionally substituted heterocylo, a fused optionally substituted $C_6$-$C_{10}$ aryl, or a fused optionally substituted 5- to 10-membered heteroaryl; and ═══ represents a single or double bond, or a pharmaceutically acceptable salt or solvate thereof.

In another embodiment, Compounds of the Disclosure are compounds of Formula II:

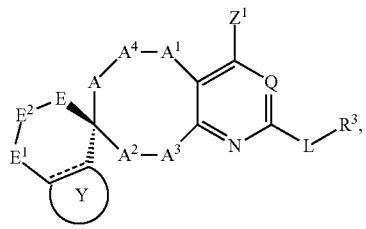

II wherein $R^3$, A, $A^1$, $A^2$, $A^3$, $A^4$, E, $E^1$, $E^2$, L, Q, Z,

and ═══ are as defined in connection with Formula I, or a pharmaceutically acceptable salt or solvate thereof.

In another embodiment, Compounds of the Disclosure are compounds of Formula III:

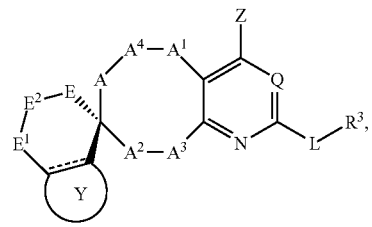

III wherein $R^3$, A, $A^1$, $A^2$, $A^3$, $A^4$, E, $E^1$, $E^2$, L, Q, Z,

and ═══ are as defined in connection with Formula I, or a pharmaceutically acceptable salt or solvate thereof.

In another embodiment, Compounds of the Disclosure are compounds of Formula IV:

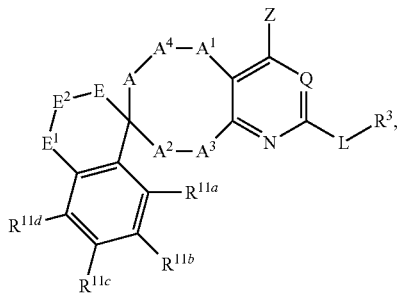

IV wherein $R^{11a}$, $R^{11b}$, $R^{11c}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^3$, A, $A^1$, $A^2$, $A^3$, $A^4$, E, $E^1$, $E^2$, L, Q, and Z are as defined in connection with Formula I, or a pharmaceutically acceptable salt or solvate thereof.

In another embodiment, Compounds of the Disclosure are compounds of Formula V:

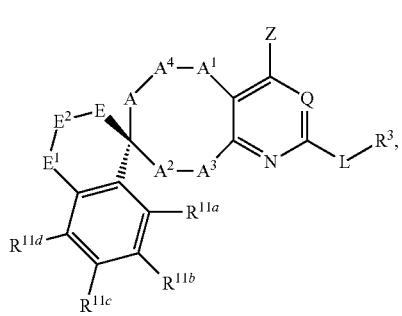

V wherein $R^{11a}$, $R^{11b}$, $R^{11c}$, $R^{11d}$, $R^3$, A, $A^1$, $A^2$, $A^3$, $A^4$, E, $E^1$, $E^2$, L, Q, and Z are as defined in connection with Formula IV, or a pharmaceutically acceptable salt or solvate thereof.

In another embodiment, Compounds of the Disclosure are compounds of Formula VI:

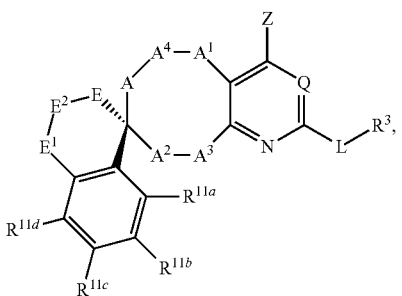

VI wherein $R^{11a}$, $R^{11b}$, $R^{11c}$, $R^{11d}$, $R^3$, A, $A^1$, $A^2$, $A^3$, $A^4$, E, $E^1$, $E^2$, L, Q, and Z are as defined in connection with Formula IV, or a pharmaceutically acceptable salt or solvate thereof.

In another embodiment, Compounds of the Disclosure are compounds of Formula VII:

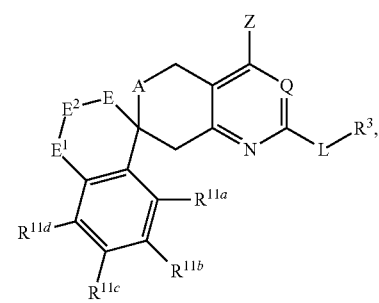

VII wherein $R^{11a}$, $R^{11b}$, $R^{11c}$, $R^{11d}$, $R^3$, A, E, $E^1$, $E^2$, L, Q, and Z are as defined in connection with Formula IV, or a pharmaceutically acceptable salt or solvate thereof.

In another embodiment, Compounds of the Disclosure are compounds of Formula VIII:

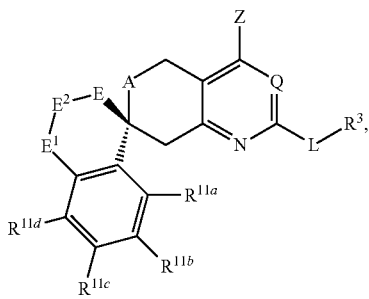

VIII wherein $R^{11a}$, $R^{11b}$, $R^{11c}$, $R^{11d}$, $R^3$, A, E, $E^1$, $E^2$, L, Q, and Z are as defined in connection with Formula IV, or a pharmaceutically acceptable salt or solvate thereof.

In another embodiment, Compounds of the Disclosure are compounds of Formula IX:

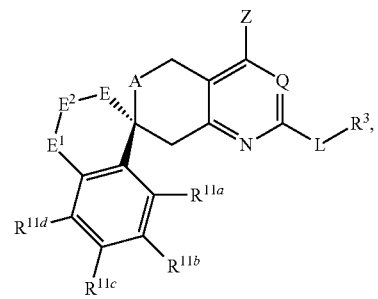

IX wherein $R^{11a}$, $R^{11b}$, $R^{11c}$, $R^{11d}$, $R^3$, A, E, $E^1$, $E^2$, L, Q, and Z are as defined in connection with Formula IV, or a pharmaceutically acceptable salt or solvate thereof.

In another embodiment, Compounds of the Disclosure are compounds of any one of Formulae I-IX, wherein A is —(CH$_2$)$_m$— and m is 0 or 1, or a pharmaceutically acceptable salt or solvate thereof. In another embodiment, m is 1.

In another embodiment, Compounds of the Disclosure are compounds of Formula X:

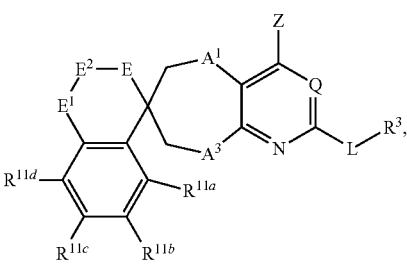

X wherein $R^{11a}$, $R^{11b}$, $R^{11c}$, $R^{11d}$, $R^3$, $A^1$, $A^3$, E, $E^1$, $E^2$, L, Q, and Z are as defined in connection with Formula IV, or a pharmaceutically acceptable salt or solvate thereof.

In another embodiment, Compounds of the Disclosure are compounds of Formula XI:

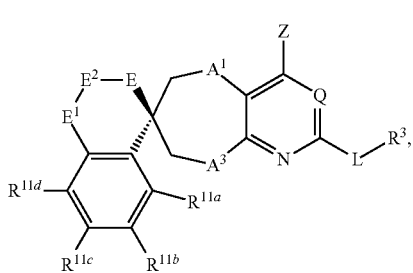

XI wherein $R^{11a}$, $R^{11b}$, $R^{11c}$, $R^{11d}$, $R^3$, $A^1$, $A^3$, E, $E^1$, $E^2$, L, Q, and Z are as defined in connection with Formula IV, or a pharmaceutically acceptable salt or solvate thereof.

In another embodiment, Compounds of the Disclosure are compounds of Formula XII:

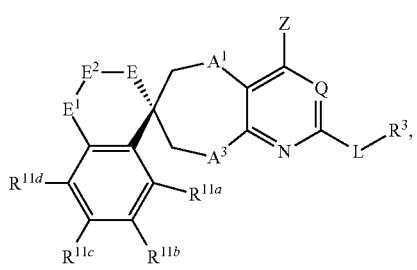

XII wherein $R^{11a}$, $R^{11b}$, $R^{11c}$, $R^{11d}$, $R^3$, $A^1$, $A^3$, E, $E^1$, $E^2$, L, Q, and Z are as defined in connection with Formula IV, or a pharmaceutically acceptable salt or solvate thereof.

In another embodiment, Compounds of the Disclosure are compounds of Formula XIII:

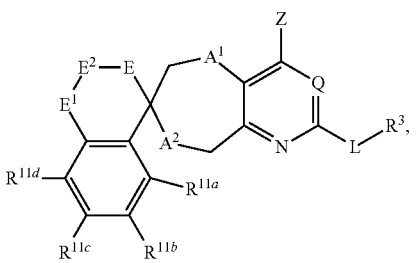

XIII wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q $R^3$, $A^1$, $E^1$, $E^2$, L, Q, and Z are as defined in connection with Formula I, and $R^{11a}$, $R^{11b}$, $R^{11c}$, and $R^{11d}$ are defined in connection with Formula IV, or a pharmaceutically acceptable salt or solvate thereof.

In another embodiment, Compounds of the Disclosure are compounds of Formula XIV:

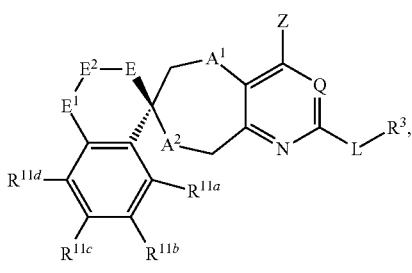

XIV wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q $R^3$, $A^1$, $E^1$, $E^2$, L, Q, and Z are as defined in connection with Formula I, and $R^{11a}$, $R^{11b}$, $R^{11c}$, and $R^{11d}$ are defined in connection with Formula IV, or a pharmaceutically acceptable salt or solvate thereof.

In another embodiment, Compounds of the Disclosure are compounds of Formula XV:

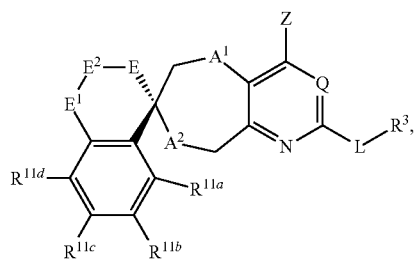

XV wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q $R^3$, $A^1$, $E^1$, $E^2$, L, Q, and Z are as defined in connection with Formula I, and $R^{11a}$, $R^{11b}$, $R^{11c}$, and $R^{11d}$ are as defined in connection with Formula IV, or a pharmaceutically acceptable salt or solvate thereof.

In another embodiment, Compounds of the Disclosure are compounds of any one of Formulae I-XV, wherein E is —($CH_2$)$_q$—; $E^1$ is selected from the group consisting of —$CH_2$—, —O—, and —N($R^{9b}$)—; and $E^2$ is a bond, or a pharmaceutically acceptable salt or solvate thereof.

In another embodiment, Compounds of the Disclosure are compounds of any one of Formulae I-XV, wherein E is —($CH_2$)$_2$—, or a pharmaceutically acceptable salt or solvate thereof.

In another embodiment, Compounds of the Disclosure are compounds of any one of Formulae I-XV, $E^1$ is —($CH_2$)—, or a pharmaceutically acceptable salt or solvate thereof.

In another embodiment, Compounds of the Disclosure are compounds of any one of Formulae I-XV, $E^2$ is a bond, or a pharmaceutically acceptable salt or solvate thereof.

In another embodiment, Compounds of the Disclosure are compounds of any one of Formulae I-XV, wherein E is selected from the group consisting of —O— and —N($R^{9a}$)—; $E^1$ is —($CH_2$)$_r$—; $E^2$ is a bond; and r is 1 or 2, or a pharmaceutically acceptable salt or solvate thereof.

In another embodiment, Compounds of the Disclosure are compounds of any one of Formulae I-XV, wherein E is —($CH_2$)—; $E^1$ is —($CH_2$)—; and $E^2$ is selected from the group consisting of —O— and —N($R^{9c}$)—, or a pharmaceutically acceptable salt or solvate thereof.

In another embodiment, Compounds of the Disclosure are compounds of any one of Formulae I-XV, wherein E is —(CH$_2$)$_q$—; $E^1$ is —C(=O)—; and $E^2$ is selected from the group consisting of —O— and —N($R^{9c}$)—, or $E^2$ is a bond, or a pharmaceutically acceptable salt or solvate thereof.

In another embodiment, Compounds of the Disclosure are compounds of any one of Formulae I-XV, wherein E is —(CH$_2$)$_2$—; $E^1$ is —CH$_2$—; and $E^2$ is a bond, or a pharmaceutically acceptable salt or solvate thereof.

In another embodiment, Compounds of the Disclosure are compounds of any one of Formulae I-XV, wherein E is —(CH$_2$)—; $E^1$ is —CH$_2$—; and $E^2$ is a bond, or a pharmaceutically acceptable salt or solvate thereof.

In another embodiment, Compounds of the Disclosure are compounds of any one of Formulae I-IX, wherein E is —(CH$_2$)$_2$—; $E^1$ is —CH$_2$—; $E^2$ is a bond; and A is —CH$_2$—, or a pharmaceutically acceptable salt or solvate thereof.

In another embodiment, Compounds of the Disclosure are compounds of any one of Formulae I-IX, wherein E is —(CH$_2$)—; $E^1$ is —CH$_2$—; $E^2$ is a bond; and A is —CH$_2$—, or a pharmaceutically acceptable salt or solvate thereof.

In another embodiment, Compounds of the Disclosure are compounds of any one of Formulae I-XV, wherein Q is =N—, or a pharmaceutically acceptable salt or solvate thereof.

In another embodiment, Compounds of the Disclosure are compounds of any one of Formulae I-XV, wherein L is —O—, or a pharmaceutically acceptable salt or solvate thereof.

In another embodiment, Compounds of the Disclosure are compounds of any one of Formulae I-XV, wherein $R^3$ is selected from the group consisting of (amino)C$_1$-C$_4$ alkyl, (carboxamido)C$_1$-C$_4$ alkyl, and (heterocyclo)C$_1$-C$_4$ alkyl, or a pharmaceutically acceptable salt or solvate thereof.

In another embodiment, Compounds of the Disclosure are compounds of any one of Formulae I-XV, wherein $R^3$ is selected from the group consisting of:

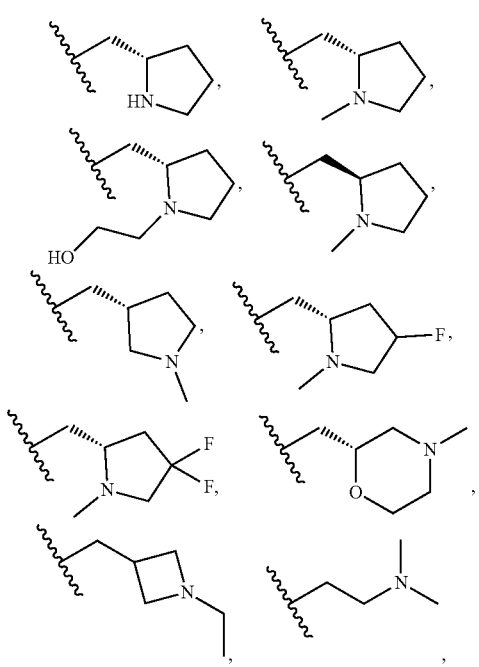

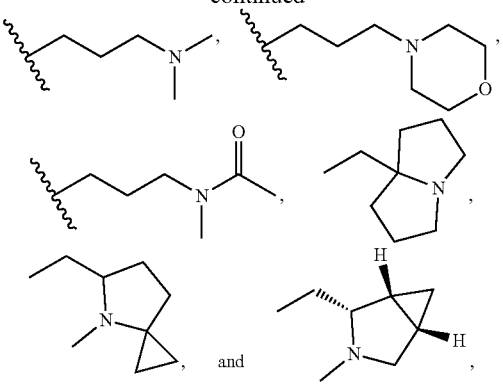

-continued or a pharmaceutically acceptable salt or solvate thereof.

In another embodiment, Compounds of the Disclosure are compounds of any one of Formulae I-XV, wherein $R^3$ is:

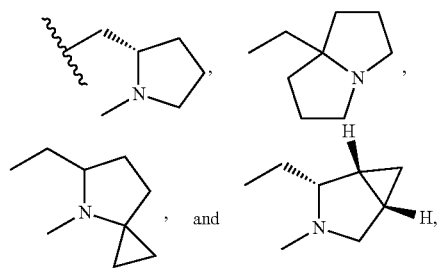

or a pharmaceutically acceptable salt or solvate thereof.

In another embodiment, Compounds of the Disclosure are compounds of any one of Formulae I-XV, wherein Z is selected from the group consisting of:

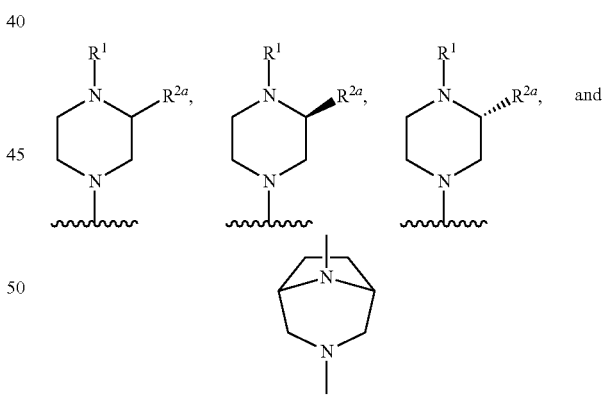

or a pharmaceutically acceptable salt or solvate thereof.

In another embodiment, Compounds of the Disclosure are compounds of any one of Formulae I-XV, wherein $R^{2a}$ is —CH$_2$CN, or a pharmaceutically acceptable salt or solvate thereof.

In another embodiment, Compounds of the Disclosure are compounds of any one of Formulae I-XV, wherein $R^1$ is selected from the group consisting of —C(=O)—CR$^{4a}$=CHR$^{4b}$, —C(=O)—C≡CR$^{5a}$, and —S(=O)$_2$CH=CHR$^{4f}$, or a pharmaceutically acceptable salt or solvate thereof.

In another embodiment, Compounds of the Disclosure are compounds of any one of Formulae I-XV, wherein R¹ is selected from the group consisting of:

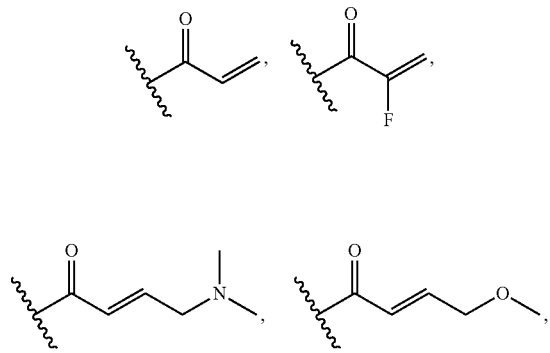

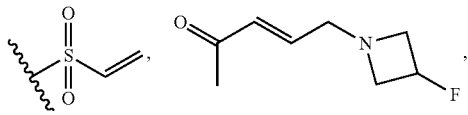

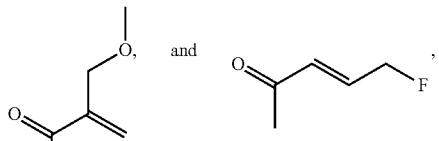

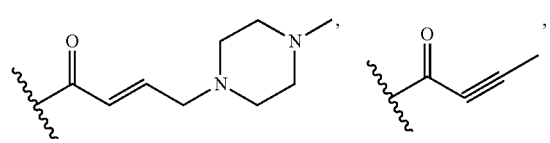

or a pharmaceutically acceptable salt or solvate thereof.

In another embodiment, Compounds of the Disclosure are compounds of any one of Formulae I-XV, wherein R¹ is:

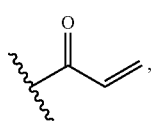 [SMILES: *C(=O)C=C]

or a pharmaceutically acceptable salt or solvate thereof.

In another embodiment, Compounds of the Disclosure are any one or more of the compounds listed in Table 1, or a pharmaceutically acceptable salt or solvate thereof.

TABLE 1

| Cpd. No. | Structure | MIA PaCa-2 IC$_{50}$ (μM) | H358 IC$_{50}$ (μM) |
|---|---|---|---|
| 1 | 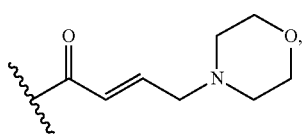 | 0.0036 | 0.016 |

TABLE 1-continued

| Cpd. No. | Structure | MIA PaCa-2 IC$_{50}$ (μM) | H358 IC$_{50}$ (μM) |
|---|---|---|---|
| 2 | 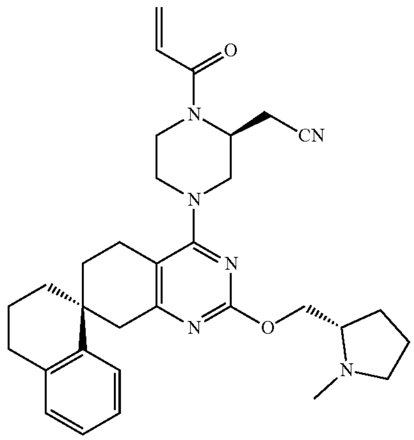 [SMILES: C=CC(=O)N1CCN(c2nc(OC[C@@H]3CCCN3C)nc3c2CC[C@@]2(CCCc4ccccc42)C3)C[C@@H]1CC#N] | 0.076 | 0.44 |
| 3 | 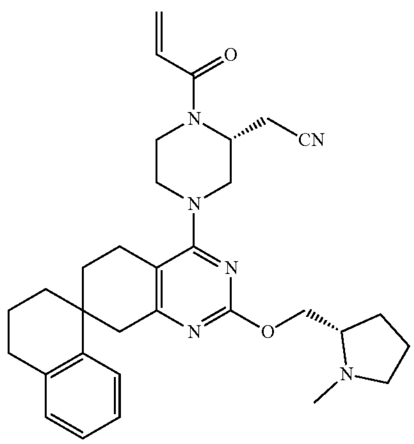 [SMILES: C=CC(=O)N1CCN(c2nc(OC[C@@H]3CCCN3C)nc3c2CCC2(CCCc4ccccc42)C3)C[C@H]1CC#N] | 0.14 | 0.29 |
| 4 | 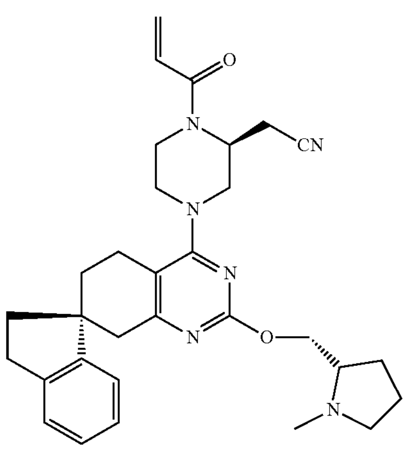 | 0.005 | 0.013 |

TABLE 1-continued
| Cpd. No. | Structure | MIA PaCa-2 IC$_{50}$ (μM) | H358 IC$_{50}$ (μM) |
|---|---|---|---|
| 5 | 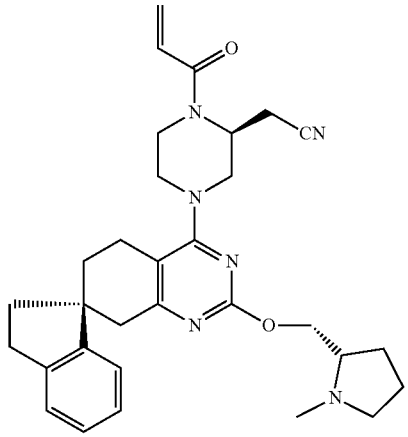 | 0.4 | 0.52 |
| 6 | 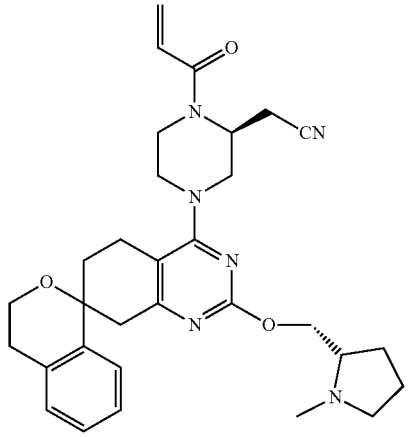 | 0.17 | 0.21 |
| 7 | 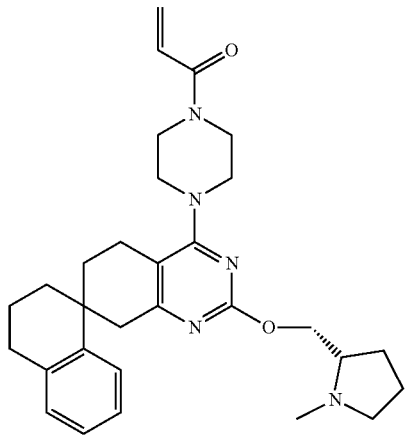 | 0.85 | 1.39 |

TABLE 1-continued

| Cpd. No. | Structure | MIA PaCa-2 IC$_{50}$ (μM) | H358 IC$_{50}$ (μM) |
|---|---|---|---|
| 8 | 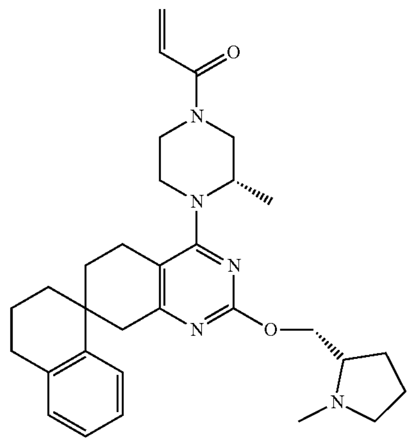 | 0.5 | 0.94 |
| 9 | 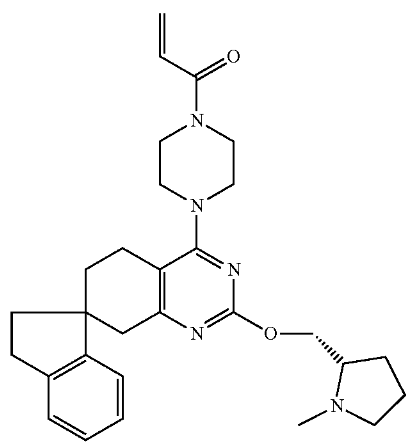 | 1.73 | 3.27 |
| 10 | 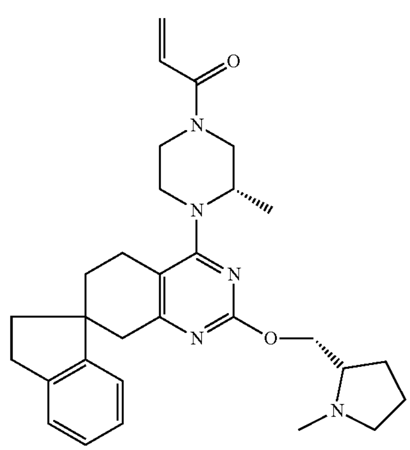 | 1.18 | 2.23 |

TABLE 1-continued
| Cpd. No. | Structure | MIA PaCa-2 IC$_{50}$ (μM) | H358 IC$_{50}$ (μM) |
|---|---|---|---|
| 11 | 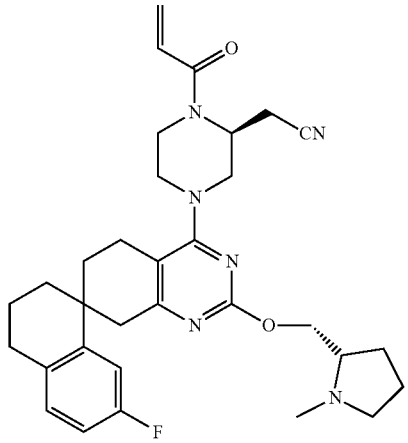 | 0.11 | 0.2 |
| 12 | 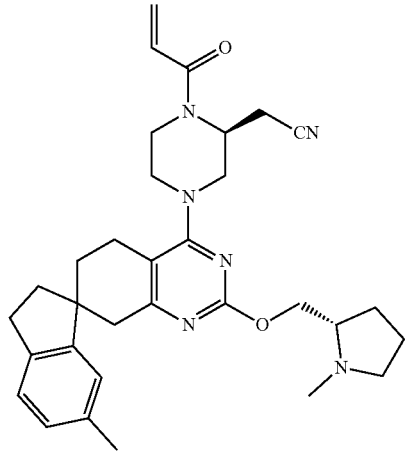 [SMILES: C=CC(=O)N1CCN(c2nc(OC[C@@H]3CCCN3C)nc3c2CCC2(CCc4ccc(C)cc42)C3)C[C@@H]1CC#N] | 0.055 | 0.065 |
| 13 | 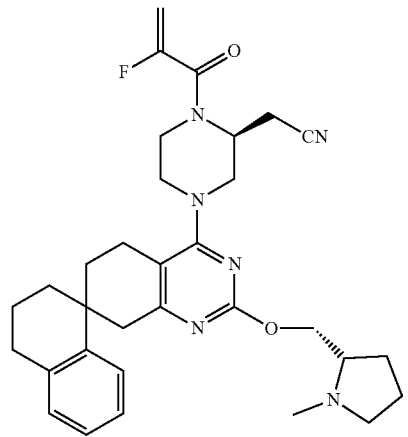 | 0.22 | 0.29 |

TABLE 1-continued

| Cpd. No. | Structure | MIA PaCa-2 IC$_{50}$ (μM) | H358 IC$_{50}$ (μM) |
|---|---|---|---|
| 14 | 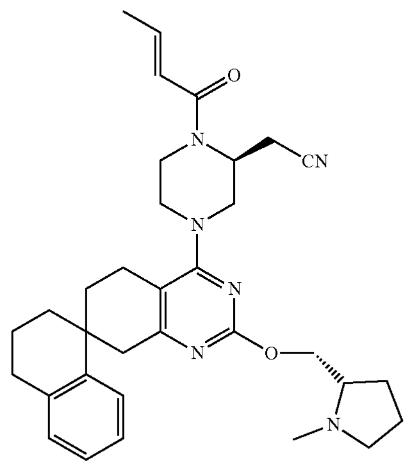 | 1.67 | 1.67 |
| 15 | 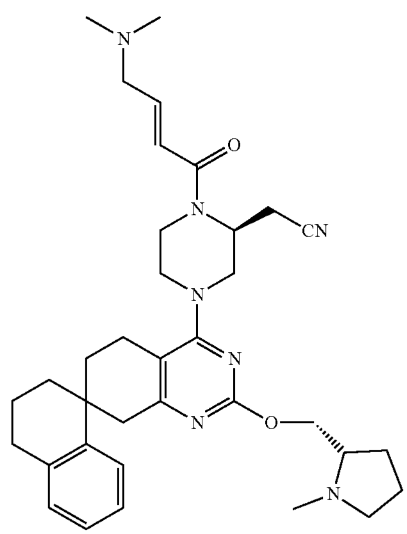 | 0.29 | 0.51 |
| 16 | 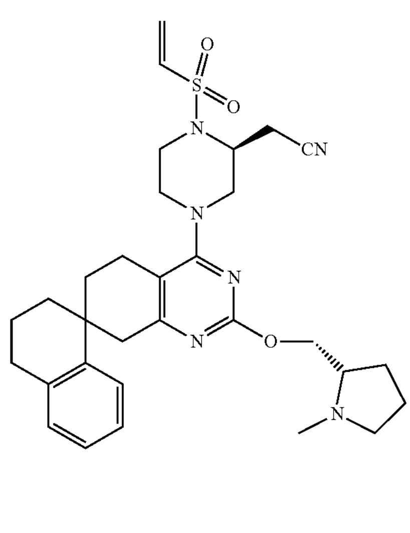 | 2.96 | 1.9 |

TABLE 1-continued
| Cpd. No. | Structure | MIA PaCa-2 IC$_{50}$ (μM) | H358 IC$_{50}$ (μM) |
|---|---|---|---|
| 17 | 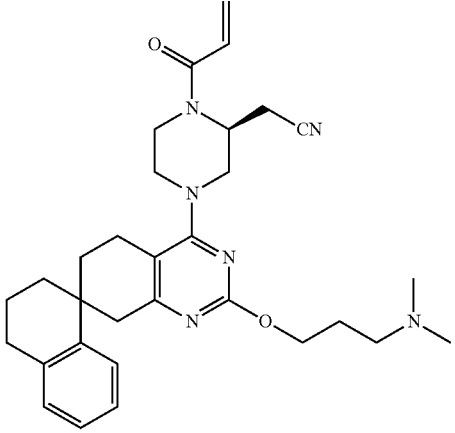 [SMILES: C=CC(=O)N1CCN(c2nc(OCCCN(C)C)nc3c2CCC2(CCCc4ccccc42)C3)C[C@@H]1CC#N] | 0.054 | 0.1 |
| 18 | 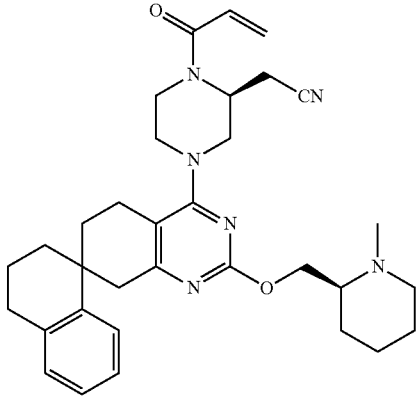 [SMILES: C=CC(=O)N1CCN(c2nc(OC[C@@H]3CCCCN3C)nc3c2CCC2(CCCc4ccccc42)C3)C[C@@H]1CC#N] | 0.11 | 0.16 |
| 19 | 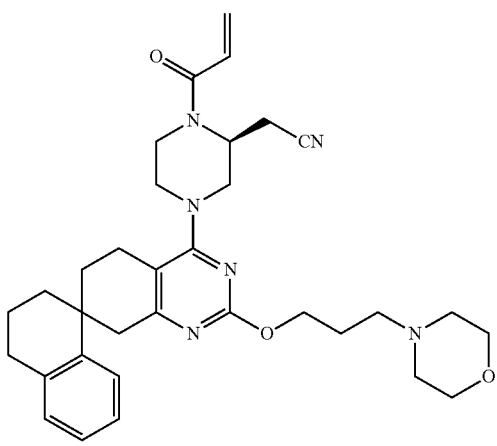 [SMILES: C=CC(=O)N1CCN(c2nc(OCCCN3CCOCC3)nc3c2CCC2(CCCc4ccccc42)C3)C[C@@H]1CC#N] | 0.11 | 0.13 |

TABLE 1-continued
| Cpd. No. | Structure | MIA PaCa-2 IC$_{50}$ (µM) | H358 IC$_{50}$ (µM) |
|---|---|---|---|
| 20 | 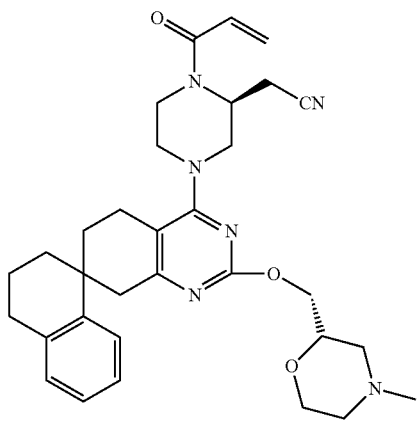 | 0.046 | 0.072 |
| 21 | 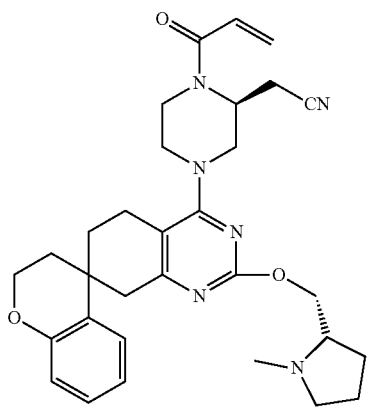 | 0.44 | 0.47 |
| 22 | 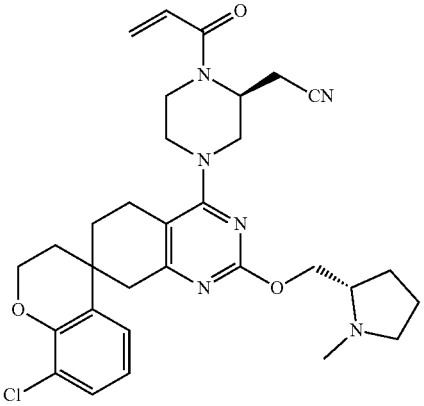 [SMILES: C=CC(=O)N1CCN(c2nc(OC[C@@H]3CCCN3C)nc3c2CCC2(CCOc4c(Cl)cccc42)C3)C[C@@H]1CC#N] | 0.49 | 0.94 |

TABLE 1-continued

| Cpd. No. | Structure | MIA PaCa-2 IC$_{50}$ (μM) | H358 IC$_{50}$ (μM) |
|---|---|---|---|
| 23 | 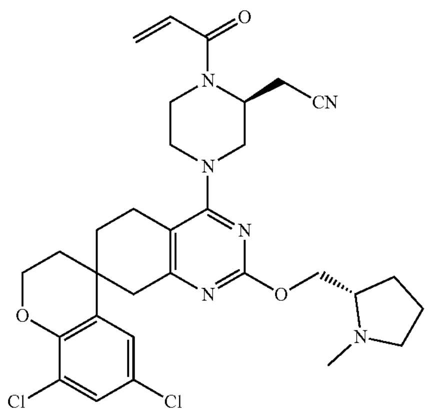 [SMILES: C=CC(=O)N1CCN(c2nc(OC[C@@H]3CCCN3C)nc3c2CCC2(CCOc4c(Cl)cc(Cl)cc42)C3)C[C@@H]1CC#N] | 0.74 | 1.24 |
| 24 | 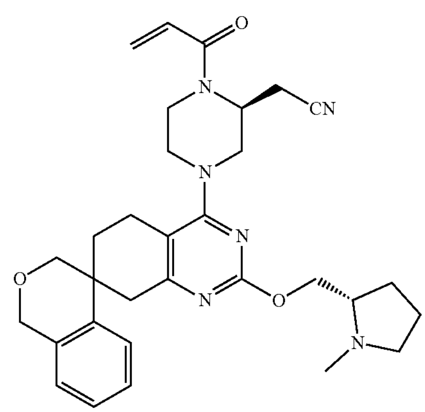 | 0.006 | 0.011 |
| 25 | 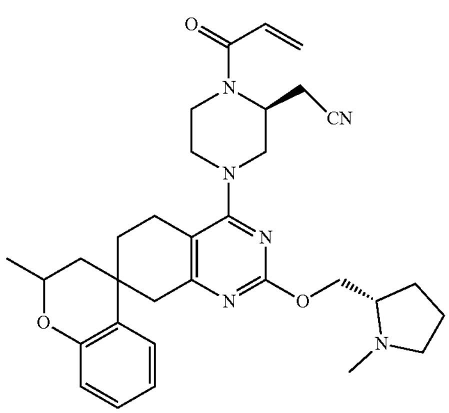 [SMILES: C=CC(=O)N1CCN(c2nc(OC[C@@H]3CCCN3C)nc3c2CCC2(C3)CC(C)Oc3ccccc32)C[C@@H]1CC#N] | 1.28 | 1.84 |

TABLE 1-continued
| Cpd. No. | Structure | MIA PaCa-2 IC$_{50}$ (μM) | H358 IC$_{50}$ (μM) |
|---|---|---|---|
| 26 | 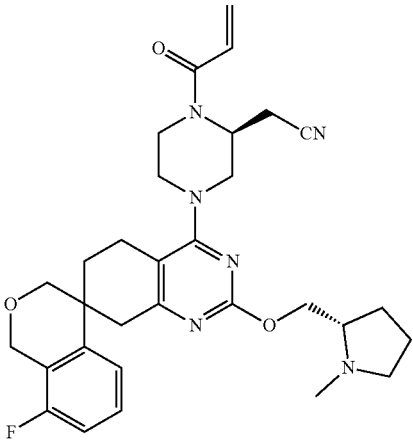 | 0.0018 | 0.0022 |
| 27 | 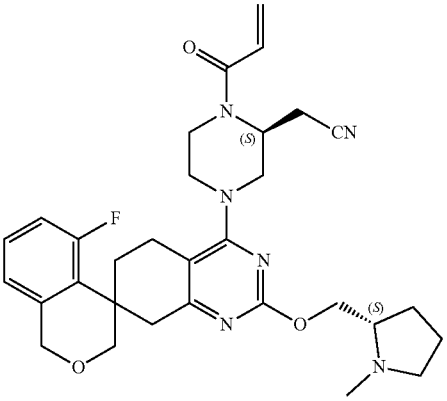 | 0.019 | 0.055 |
| 28 | 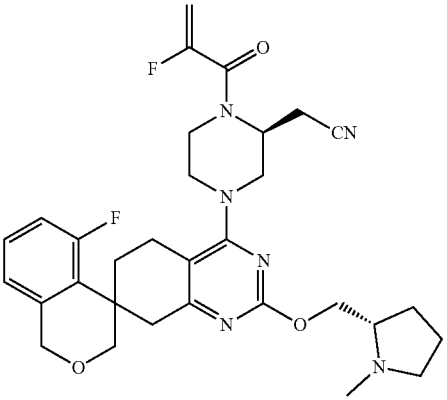 [SMILES: C=C(F)C(=O)N1CCN(c2nc(OC[C@@H]3CCCN3C)nc3c2CCC2(COCc4cccc(F)c42)C3)C[C@@H]1CC#N] | 0.81 | 0.66 |

TABLE 1-continued

| Cpd. No. | Structure | MIA PaCa-2 IC$_{50}$ (μM) | H358 IC$_{50}$ (μM) |
|---|---|---|---|
| 29 | 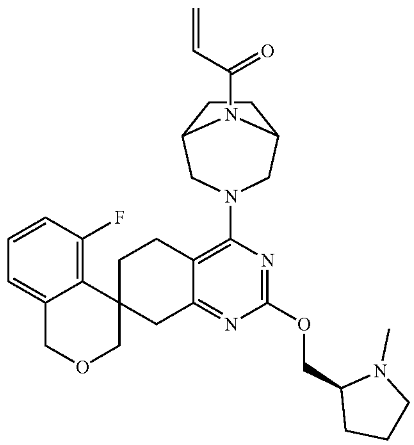 [SMILES: C=CC(=O)N1C2CCC1CN(c1nc(OC[C@@H]3CCCN3C)nc3c1CCC1(COCc4cccc(F)c41)C3)C2] | >10 | 8.1 |
| 30 | 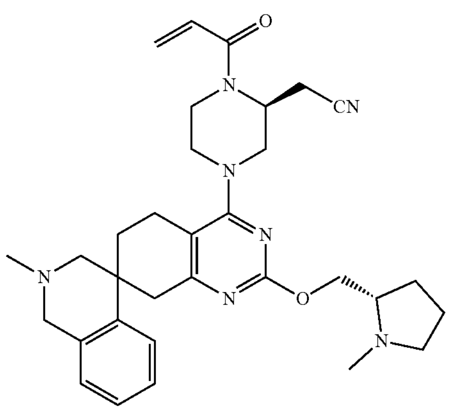 [SMILES: C=CC(=O)N1CCN(c2nc(OC[C@@H]3CCCN3C)nc3c2CCC2(C3)CN(C)Cc3ccccc32)C[C@@H]1CC#N] | 4.78 | 2.06 |
| 31 | 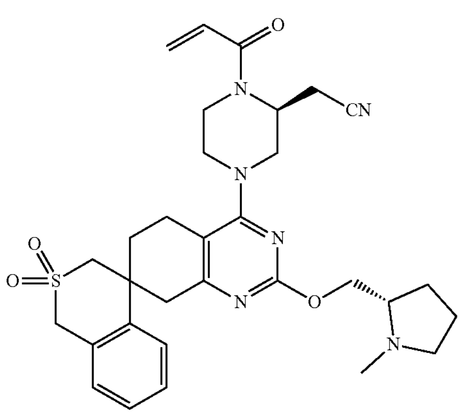 [SMILES: C=CC(=O)N1CCN(c2nc(OC[C@@H]3CCCN3C)nc3c2CCC2(C3)CS(=O)(=O)Cc3ccccc32)C[C@@H]1CC#N] | >10 | >10 |

TABLE 1-continued

| Cpd. No. | Structure | MIA PaCa-2 IC$_{50}$ (μM) | H358 IC$_{50}$ (μM) |
|---|---|---|---|
| 32 | 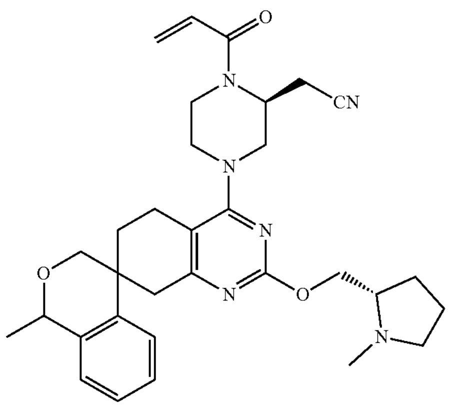 [SMILES: C=CC(=O)N1CCN(c2nc(OC[C@@H]3CCCN3C)nc3c2CCC2(COC(C)c4ccccc42)C3)C[C@@H]1CC#N] | 0.022 | 0.083 |
| 33 | 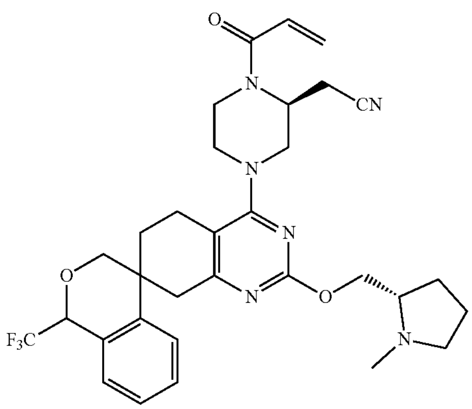 [SMILES: C=CC(=O)N1CCN(c2nc(OC[C@@H]3CCCN3C)nc3c2CCC2(COC(C(F)(F)F)c4ccccc42)C3)C[C@@H]1CC#N] | 0.03 | 0.045 |
| 34 | 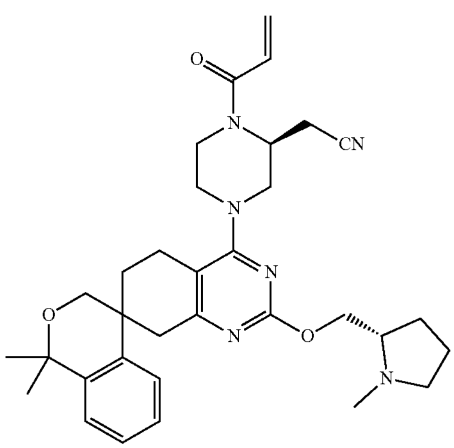 [SMILES: C=CC(=O)N1CCN(c2nc(OC[C@@H]3CCCN3C)nc3c2CCC2(COC(C)(C)c4ccccc42)C3)C[C@@H]1CC#N] | 0.75 | 1.35 |

TABLE 1-continued
| Cpd. No. | Structure | MIA PaCa-2 IC$_{50}$ (μM) | H358 IC$_{50}$ (μM) |
|---|---|---|---|
| 35 | 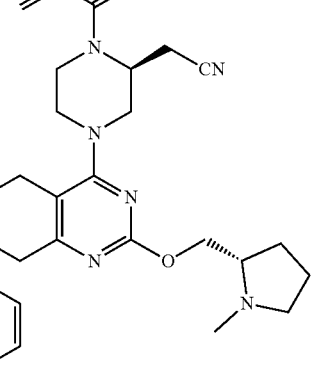 | 0.02 | 0.043 |
| 36 | 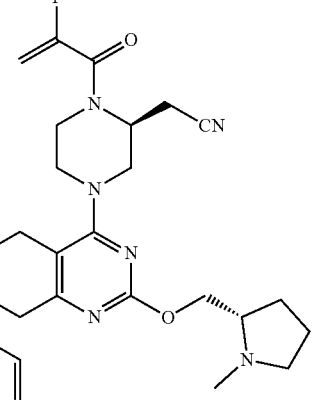 | 0.16 | 0.26 |
| 37 | 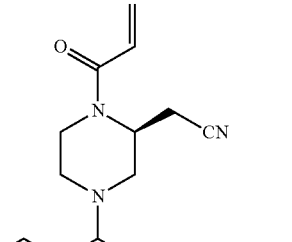 | >10 | >10 |

TABLE 1-continued
| Cpd. No. | Structure | MIA PaCa-2 IC$_{50}$ (µM) | H358 IC$_{50}$ (µM) |
| --- | --- | --- | --- |
| 38 | 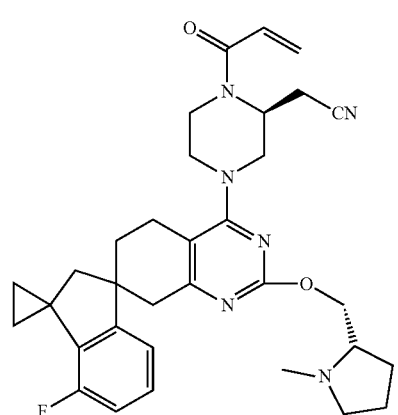 | 0.093 | 0.29 |
| 39 | 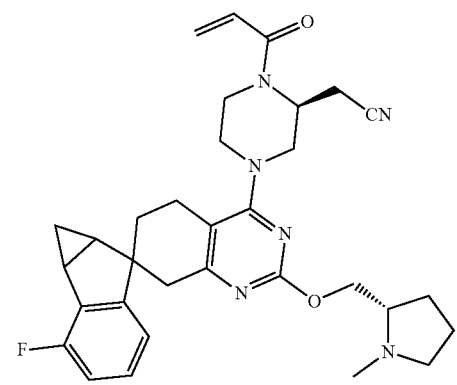 [SMILES: C=CC(=O)N1CCN(c2nc(OC[C@@H]3CCCN3C)nc3c2CCC2(C3)c3cccc(F)c3C3CC32)C[C@@H]1CC#N] | 0.37 | 0.67 |
| 40 | 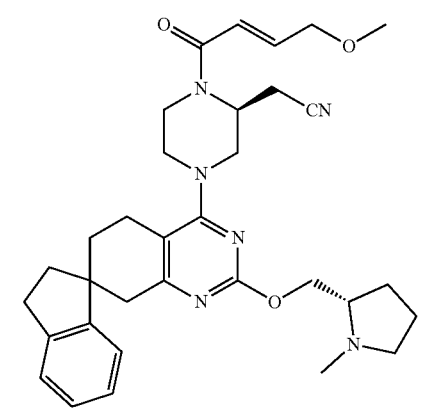 [SMILES: COC/C=C/C(=O)N1CCN(c2nc(OC[C@@H]3CCCN3C)nc3c2CCC2(CCc4ccccc42)C3)C[C@@H]1CC#N] | 0.44 | 0.56 |

TABLE 1-continued

| Cpd. No. | Structure | MIA PaCa-2 IC$_{50}$ (μM) | H358 IC$_{50}$ (μM) |
|---|---|---|---|
| 41 | 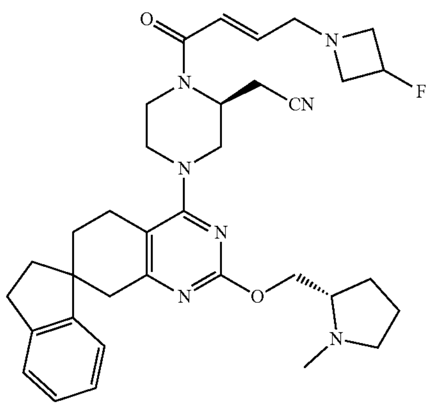 [SMILES: CN1CCC[C@H]1COc1nc2c(c(N3CCN(C(=O)/C=C/CN4CC(F)C4)[C@@H](CC#N)C3)n1)CCC1(CCc3ccccc31)C2] | 0.091 | 0.32 |
| 42 | 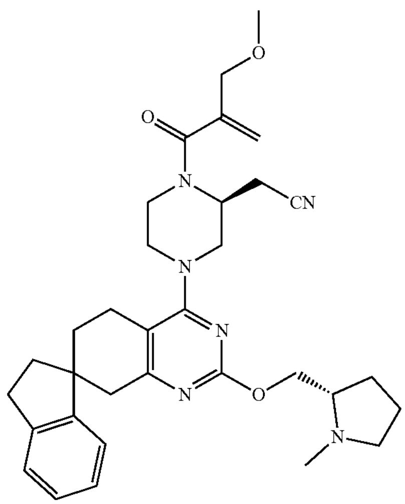 [SMILES: C=C(COC)C(=O)N1CCN(c2nc(OC[C@@H]3CCCN3C)nc3c2CCC2(CCc4ccccc42)C3)C[C@@H]1CC#N] | 5.8 | 10.4 |
| 43 | 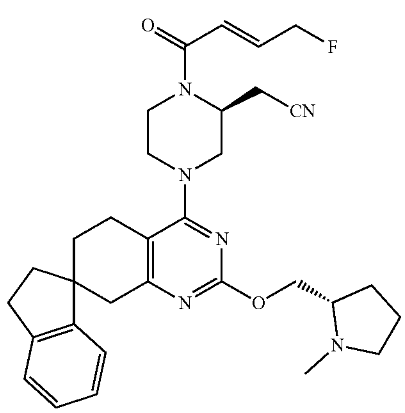 [SMILES: CN1CCC[C@H]1COc1nc2c(c(N3CCN(C(=O)/C=C/CF)[C@@H](CC#N)C3)n1)CCC1(CCc3ccccc31)C2] | 0.13 | 0.12 |

TABLE 1-continued
| Cpd. No. | Structure | MIA PaCa-2 IC$_{50}$ (μM) | H358 IC$_{50}$ (μM) |
| --- | --- | --- | --- |
| 44 | 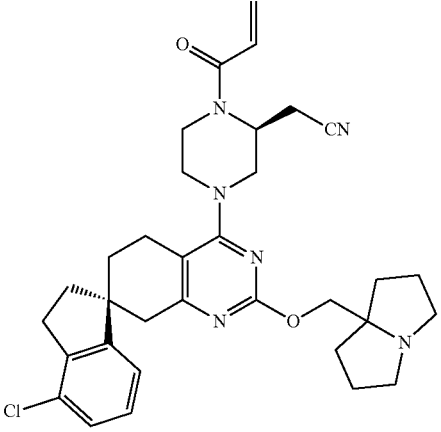 [SMILES: C=CC(=O)N1CCN(c2nc(OCC34CCCN3CCC4)nc3c2CC[C@@]2(CCc4c(Cl)cccc42)C3)C[C@@H]1CC#N] | 0.0015 | 0.0046 |
| 45 | 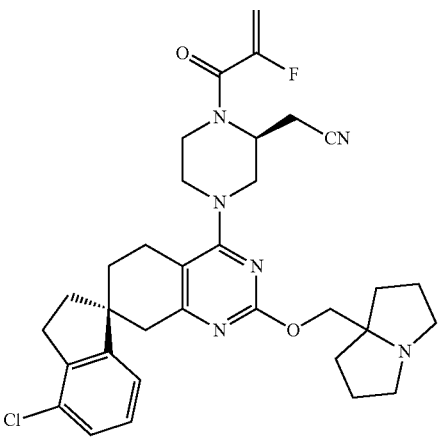 [SMILES: C=C(F)C(=O)N1CCN(c2nc(OCC34CCCN3CCC4)nc3c2CC[C@@]2(CCc4c(Cl)cccc42)C3)C[C@@H]1CC#N] | 0.0028 | 0.0076 |
| 46 | 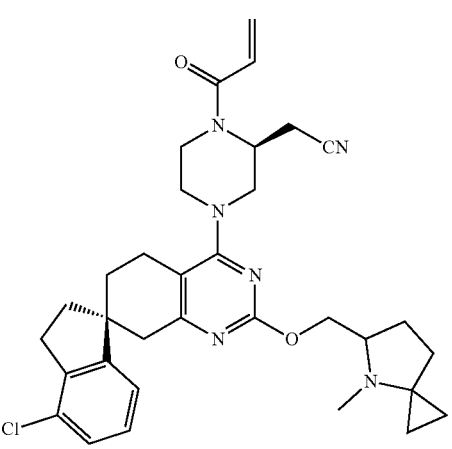 [SMILES: C=CC(=O)N1CCN(c2nc(OCC3CCC4(CC4)N3C)nc3c2CC[C@@]2(CCc4c(Cl)cccc42)C3)C[C@@H]1CC#N] | 0.015 | 0.025 |

TABLE 1-continued

| Cpd. No. | Structure | MIA PaCa-2 IC$_{50}$ (μM) | H358 IC$_{50}$ (μM) |
|---|---|---|---|
| 47 | 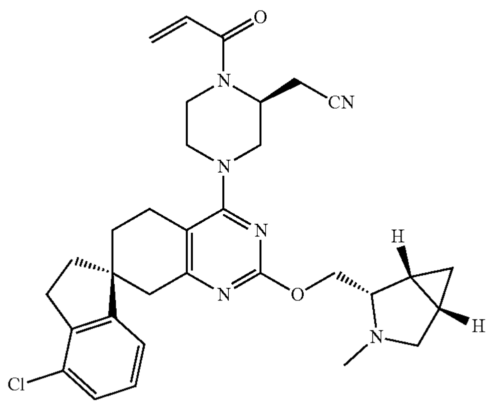 [SMILES: C=CC(=O)N1CCN(c2nc(OC[C@@H]3[C@@H]4C[C@@H]4CN3C)nc3c2CC[C@@]2(CCc4c(Cl)cccc42)C3)C[C@@H]1CC#N] | 0.0049 | 0.015 |
| 48 | 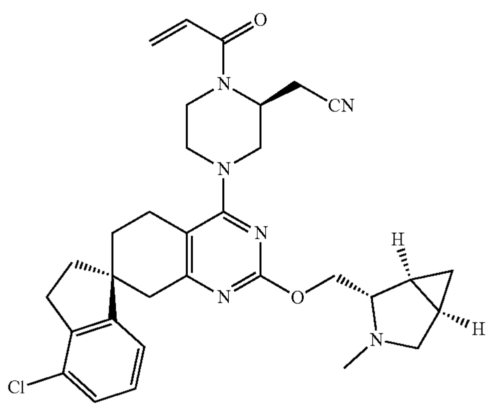 [SMILES: C=CC(=O)N1CCN(c2nc(OC[C@@H]3[C@H]4C[C@H]4CN3C)nc3c2CC[C@@]2(CCc4c(Cl)cccc42)C3)C[C@@H]1CC#N] | 0.0043 | 0.006 |
| 49 | 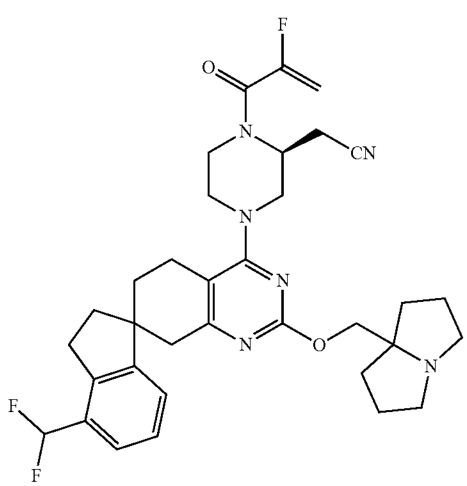 [SMILES: C=C(F)C(=O)N1CCN(c2nc(OCC34CCCN3CCC4)nc3c2CCC2(CCc4c(C(F)F)cccc42)C3)C[C@@H]1CC#N] | 0.06 | 0.061 |

TABLE 1-continued

| Cpd. No. | Structure | MIA PaCa-2 IC$_{50}$ (μM) | H358 IC$_{50}$ (μM) |
|---|---|---|---|
| 50 | 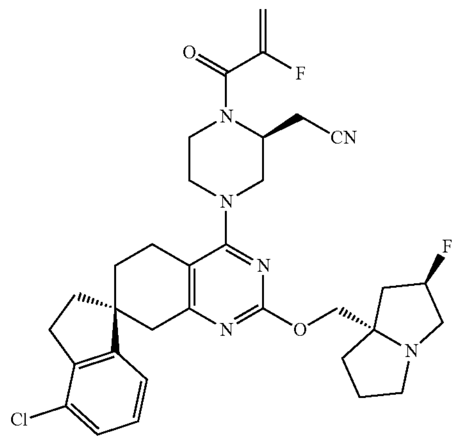 [SMILES: C=C(F)C(=O)N1CCN(c2nc(OC[C@@]34CCCN3C[C@H](F)C4)nc3c2CC[C@@]2(CCc4c(Cl)cccc42)C3)C[C@@H]1CC#N] | 0.0029 | 0.0012 |
| 51 | 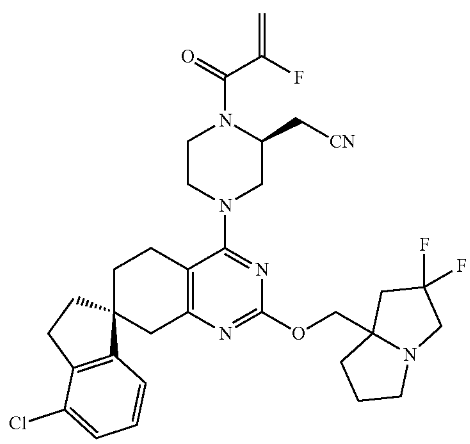 [SMILES: C=C(F)C(=O)N1CCN(c2nc(OCC34CCCN3CC(F)(F)C4)nc3c2CC[C@@]2(CCc4c(Cl)cccc42)C3)C[C@@H]1CC#N] | 0.11 | 0.052 |
| 52 | 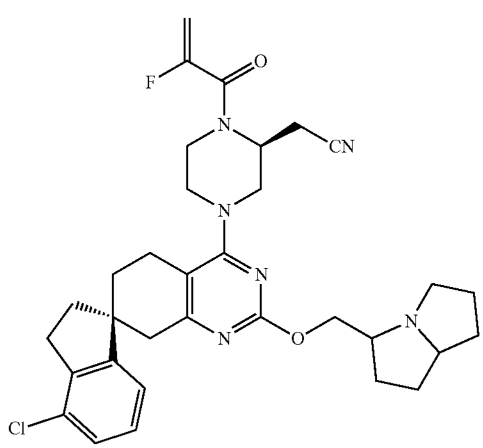 [SMILES: C=C(F)C(=O)N1CCN(c2nc(OCC3CCC4CCCN43)nc3c2CC[C@@]2(CCc4c(Cl)cccc42)C3)C[C@@H]1CC#N] | 0.34 | 0.26 |

TABLE 1-continued

| Cpd. No. | Structure | MIA PaCa-2 IC$_{50}$ (μM) | H358 IC$_{50}$ (μM) |
|---|---|---|---|
| 53 | 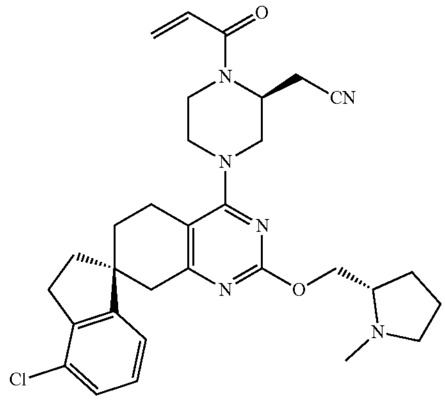 [SMILES: C=CC(=O)N1CCN(c2nc(OC[C@@H]3CCCN3C)nc3c2CC[C@@]2(CCc4c(Cl)cccc42)C3)C[C@@H]1CC#N] | 0.0011 | 0.0025 |
| 54 | 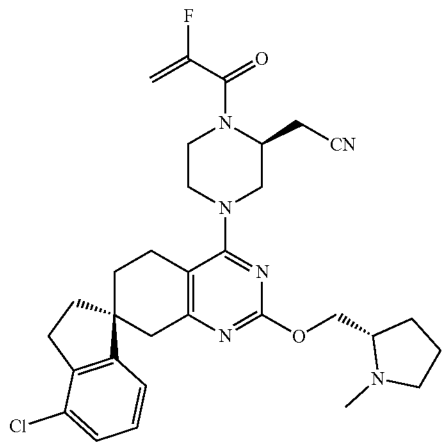 [SMILES: C=C(F)C(=O)N1CCN(c2nc(OC[C@@H]3CCCN3C)nc3c2CC[C@@]2(CCc4c(Cl)cccc42)C3)C[C@@H]1CC#N] | 0.016 | 0.028 |

The present disclosure encompasses the preparation and use of salts of Compounds of the Disclosure. As used herein, the term "pharmaceutically acceptable salt" refers to salts or zwitterionic forms of Compounds of the Disclosure that are suitable for administration to a subject, e.g., a human. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of Compounds of the Disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

II. Intermediates of the Disclosure

The disclosure also provides synthetic intermediates, collectively referred to as "Intermediates of the Disclosure," that can be used to prepare Compounds of the Disclosure.

In one embodiment, Intermediates of the Disclosure are compounds of Formula XVI:

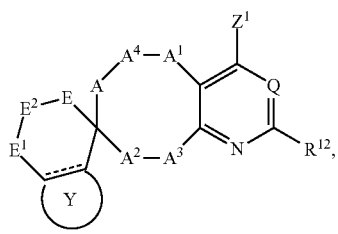

XVI wherein:

$Z^1$ is selected from the group consisting of halo and

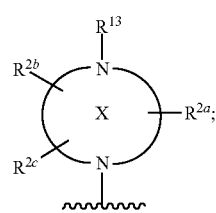

X represents a 6- to 12-membered monocyclic or bicyclic heterocyclo;

$R^{13}$ is selected from the group consisting of hydrogen, —C(=O)$R^{14a}$, and —C(=O)O$R^{14b}$;

$R^{14a}$ is $C_1$-$C_6$ alkyl;

$R^{14b}$ is selected from the group consisting of $C_1$-$C_6$ alkyl, $C_2$-$C_6$ alkenyl, and aralkyl;

$R^{12}$ is selected from the group consisting of halo and -L$R^3$;

L is selected from the group consisting of —O—, —S—, and —N($R^7$)—; or L is a bond;

$R^7$ is selected from the group consisting of hydrogen and $C_1$-$C_4$ alkyl;

$R^3$ is selected from the group consisting of hydrogen, $C_1$-$C_4$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, (carboxamido)$C_1$-$C_4$ alkyl, (heterocyclo)$C_1$-$C_4$ alkyl, (aryl)$C_1$-$C_4$ alkyl, and (hetereoaryl)$C_1$-$C_4$ alkyl;

$R^{2a}$ is selected from the group consisting of hydrogen, $C_1$-$C_4$ alkyl, $C_1$-$C_4$ haloalkyl, (cyano)$C_1$-$C_4$ alkyl, (hydroxy)$C_1$-$C_4$ alkyl, (alkoxy)$C_1$-$C_4$ alkyl, (amino)$C_1$-$C_4$ alkyl, (heterocyclo)$C_1$-$C_4$ alkyl, (aryl)$C_1$-$C_4$ alkyl, (hetereoaryl)$C_1$-$C_4$ alkyl, $C_2$-$C_4$ alkynyl, heteroalkyl, cyano, —C(=O)O$R^{5c}$, —C(=O)N$R^{5d}R^{5e}$, and —N$R^{5f}R^{5g}$;

$R^{2b}$ and $R^{2c}$ are independently selected from the group consisting of hydrogen and $C_1$-$C_4$ alkyl; or $R^{2b}$ and $R^{2c}$ are attached to the same carbon atom and are taken together to form a —C(=O)— group;

$R^{5c}$ is selected from the group consisting hydrogen and $C_1$-$C_4$ alkyl;

$R^{5d}$ and $R^{5e}$ are independently selected from the group consisting hydrogen and $C_1$-$C_4$ alkyl; or $R^{5d}$ and $R^{5e}$ taken together with the nitrogen atom to which they are attached form an optionally substituted 4- to 8-membered heterocyclo;

$R^{5f}$ and $R^{5g}$ are independently selected from the group consisting hydrogen and $C_1$-$C_4$ alkyl; or $R^{5f}$ and $R^{5g}$ taken together with the nitrogen atom to which they are attached form an optionally substituted 4- to 8-membered heterocyclo;

A is selected from the group consisting of —(C$R^{6a}R^{6b}$)$_m$—, —O—, —S—, and —N($R^{7a}$)—;

$A^1$ is selected from the group consisting of —(C$R^{6c}R^{6d}$)$_n$—, —O—, —S—, and —N($R^{7b}$)—;

$A^2$ is selected from the group consisting of —(C$R^{6e}R^{6f}$)$_o$—, —O—, —S—, and —N($R^{7c}$)—;

$A^3$ is selected from the group consisting of —(C$R^{6g}R^{6h}$)$_p$—, —O—, —S—, and —N($R^{7d}$)—;

$A^4$ is selected from the group consisting of —O—, —S—, and —N($R^{7e}$)—; or $A^4$ is a bond, with the provisos that:

(1) when A is —O—, —S—, or —N($R^{7a}$)—, then $A^4$ is a bond, $A^1$ is —(C$R^{6c}R^{6d}$)$_n$—, n is 1 or 2, and E is —(C$R^{8a}R^{8b}$)$_q$;

(2) when $A^1$ is —O—, —S—, or —N($R^{7b}$)—, then $A^4$ is a bond, A is —(C$R^{6a}R^{6b}$)$_m$—, and m is 1 or 2;

(3) when $A^2$ is —O—, —S—, or —N($R^{7c}$)—, then $A^3$ is —(C$R^{6g}R^{6h}$)$_p$— p is 1 or 2, and E is —(C$R^{8a}R^{8b}$)$_q$; and (4) when $A^3$ is —O—, —S—, or —N($R^{7d}$)—, then $A^2$ is —(C$R^{6e}R^{6f}$)$_o$— and o is 1 or 2, $R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and $C_1$-$C_4$ alkyl;

m is 0, 1, or 2;

n is 0, 1, or 2;

o is 0, 1, or 2;

p is 0, 1, or 2;

with the proviso that the sum of m, n, o, and p is 2, 3, 4, or 5;

$R^{7a}$, $R^{7b}$, $R^{7c}$, $R^{7d}$, and $R^{7e}$ are independently selected from the group consisting of hydrogen and $C_1$-$C_4$ alkyl;

E is selected from the group consisting of —(C$R^{8a}R^{8b}$)$_q$—, —O—, —S—, and —N($R^{9a}$)—;

E¹ is selected from the group consisting of —(CR^{8c}R^{8d})_r—, —O—, —S—, —N(R^{9b})—, and —C(=O)—;

E² is selected from the group consisting of —O—, —S—, and —N(R^{9c})—, or E² is a bond with the provisos that:

(1) when E is —O—, —S—, or —N(R^{9a})—, then E² is a bond, E¹ is —(CR^{8c}R^{8d})_q—, A is —(CR^{6a}R^{6b})_m—, m is 1 or 2, A² is —(CR^{6e}R^{6f})_o—, and o is 1 or 2; and (2) when E¹ is —O—, —S—, or —N(R^{9b})—, then E² is a bond, E is —(CR^{8a}R^{8b})_r—, and r is 1 or 2, q is 1, 2, or 3;

r is 0, 1, or 2;

with the proviso that the sum of q and r is 2, 3, 4, or 5;

R^{8a} and R^{8b} are each independently selected from the group consisting of hydrogen and C₁-C₄ alkyl; or R^{8a} and R^{8b} taken together with the carbon atom to which they are attached form a C₃-C₆ cycloalkyl;

R^{8c} and R^{8d} are each independently selected from the group consisting of hydrogen and C₁-C₄ alkyl; or R^{8c} and R^{8d} taken together with the carbon atom to which they are attached form a C₃-C₆ cycloalkyl;

R^{9a}, R^{9b}, and R^{9c} are independently selected from the group consisting of hydrogen and C₁-C₄ alkyl;

Q is selected from the group consisting of =C(R^{10})— and =N—;

R^{10} is selected from the group consisting of hydrogen, C₁-C₄ alkyl and C₃-C₆ cycloalkyl;

represents a fused optionally substituted C₃-C₈ cycloalkyl, a fused optionally substituted heterocylo, a fused optionally substituted C₆-C₁₀ aryl, or a fused optionally substituted 5- to 10-membered heteroaryl; and --- represents a single or double bond, or a salt or solvate thereof.

In another embodiment, Intermediates of the Disclosure are compounds of Formula XVII:

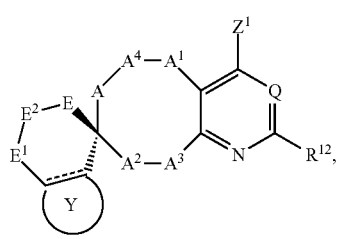

XVII wherein R¹², A, A¹, A², A³, A⁴, E, E¹, E², Q, Z¹,

and --- are as defined in connection with Formula XVI, or a salt or solvate thereof.

In another embodiment, Intermediates of the Disclosure are compounds of Formula XVIII:

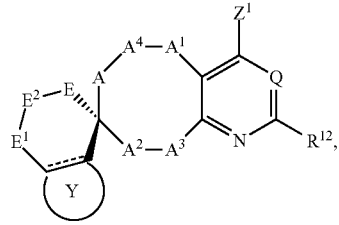

XVIII wherein R¹², A, A¹, A², A³, A⁴, E, E¹, E², Q, Z¹,

and --- are as defined in connection with Formula XVI, or a salt or solvate thereof.

In another embodiment, Intermediates of the Disclosure are compounds of Formula XIX:

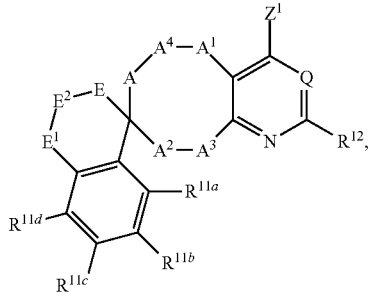

XIX wherein R^{11a}, R^{11b}, R^{11c}, and R^{11d} are independently selected from the group consisting of hydrogen, halo, cyano, hydroxy, C₁-C₄ alkyl, C₁-C₄ haloalkyl, C₃-C₆ cycloalkyl, C₁-C₄ alkoxy, C₁-C₄ haloalkoxy, and (hydroxy)C₁-C₄ alkyl; and R¹², A, A¹, A², A³, A⁴, E, E¹, E², Q, and Z¹ are as defined in connection with Formula XVI, or a salt or solvate thereof.

In another embodiment, Intermediates of the Disclosure are compounds of Formula XX:

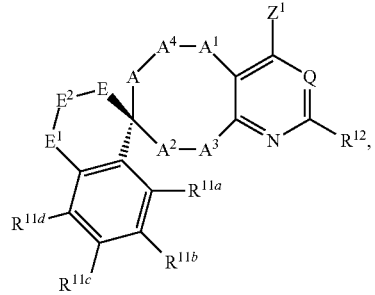

XX wherein R^{11a}, R^{11b}, R^{11c}, R^{11d}, R¹², A, A¹, A², A³, A⁴, E, E¹, E², Q, and Z¹ are as defined in connection with Formula XIX, or a salt or solvate thereof.

In another embodiment, Intermediates of the Disclosure are compounds of Formula XXI:

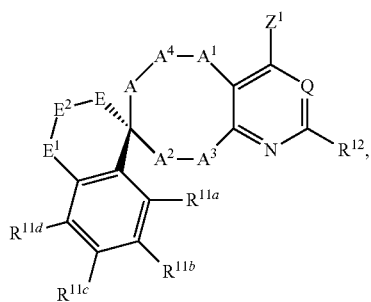

XXI wherein $R^{11a}$, $R^{11b}$, $R^{11c}$, $R^{11d}$, $R^{12}$, A, $A^1$, $A^2$, $A^3$, $A^4$, E, $E^1$, $E^2$, Q, and $Z^1$ are as defined in connection with Formula XIX, or a salt or solvate thereof.

In another embodiment, Intermediates of the Disclosure are compounds of Formula XXII:

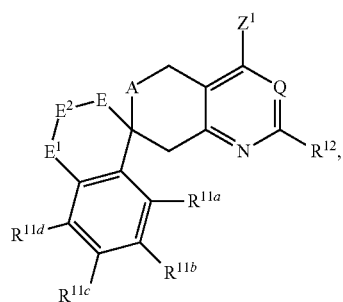

XXII wherein $R^{11a}$, $R^{11b}$, $R^{11c}$, $R^{11d}$, $R^{12}$, A, E, $E^1$, $E^2$, Q, and $Z^1$ are as defined in connection with Formula XIX, or a salt or solvate thereof.

In another embodiment, Intermediates of the Disclosure are compounds of Formula XXIII:

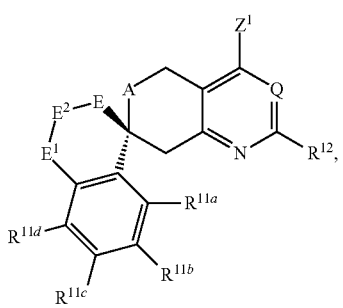

XXIII wherein $R^{11a}$, $R^{11b}$, $R^{11c}$, $R^{11d}$, $R^{12}$, A, E, $E^1$, $E^2$, Q, and $Z^1$ are as defined in connection with Formula XIX, or a salt or solvate thereof.

In another embodiment, Intermediates of the Disclosure are compounds of Formula XXIV:

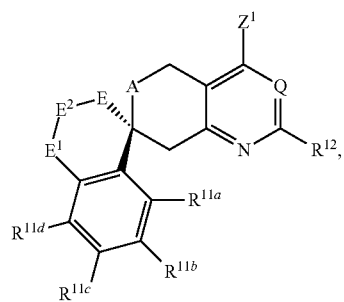

XXIV wherein $R^{11a}$, $R^{11b}$, $R^{11c}$, $R^{11d}$, $R^{12}$, A, E, $E^1$, $E^2$, Q, and $Z^1$ are as defined in connection with Formula XIX, or a salt or solvate thereof.

In another embodiment, Intermediates of the Disclosure are compounds of any one of Formulae XVI-XIX, wherein A is —$(CH_2)_m$— and m is 0 or 1, or a salt or solvate thereof. In another embodiment, m is 1, or a salt or solvate thereof.

In another embodiment, Intermediates of the Disclosure are compounds of Formula XXV:

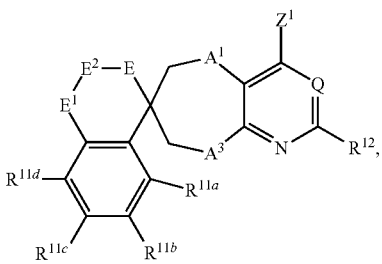

XXV wherein $R^{11a}$, $R^{11b}$, $R^{11c}$, $R^{11d}$, $R^{12}$, $A^1$, $A^3$, E, $E^1$, $E^2$, Q, and $Z^1$ are as defined in connection with Formula XIX, or a salt or solvate thereof.

In another embodiment, Intermediates of the Disclosure are compounds of Formula XXVI:

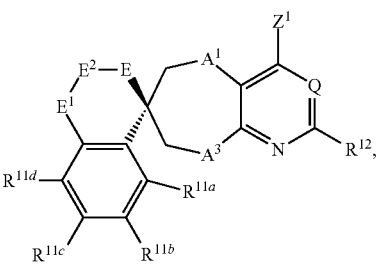

XXVI wherein $R^{11a}$, $R^{11b}$, $R^{11c}$, $R^{11d}$, $R^{12}$, $A^1$, $A^3$, E, $E^1$, $E^2$, Q, and $Z^1$ are as defined in connection with Formula XIX, or a salt or solvate thereof.

In another embodiment, Intermediates of the Disclosure are compounds of Formula XXVII:

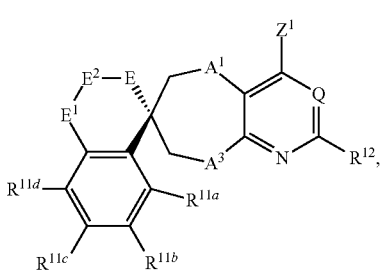

XXVII wherein $R^{11a}$, $R^{11b}$, $R^{11c}$, $R^{11d}$, $R^{12}$, $A^1$, $A^3$, E, $E^1$, $E^2$, Q, and $Z^1$ are as defined in connection with Formula XIX, or a salt or solvate thereof.

In another embodiment, Intermediates of the Disclosure are compounds of Formula XXVIII:

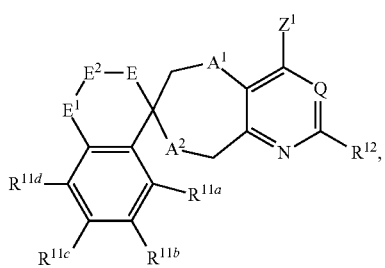

XXVIII wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q, $R^{12}$, $A^1$, $E^1$, $E^2$, Q, and $Z^1$ are as defined in connection with Formula XVI, and $R^{11a}$, $R^{11b}$, $R^{11c}$, and $R^{11d}$ are as defined in connection with Formula XIX, or a salt or solvate thereof.

In another embodiment, Intermediates of the Disclosure are compounds of Formula XXIX:

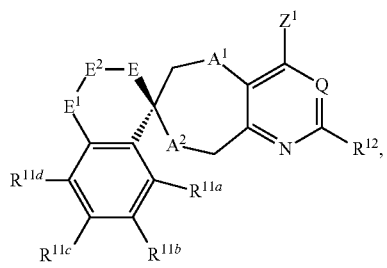

XXIX wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q, $R^{12}$, $A^1$, $E^1$, $E^2$, Q, and $Z^1$ are as defined in connection with Formula XVI, and $R^{11a}$, $R^{11b}$, $R^{11c}$, and $R^{11d}$ are as defined in connection with Formula XIX, or a salt or solvate thereof.

In another embodiment, Intermediates of the Disclosure are compounds of Formula XXX:

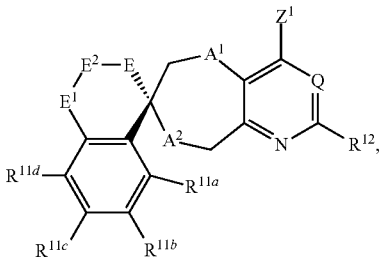

XXX wherein $A^2$ is selected from the group consisting of —O—, —S—, and —N($R^{7c}$)—; E is —($CR^{8a}R^{8b}$)$_q$—; $R^{7c}$, $R^{8a}$, $R^{8b}$, q, $R^{12}$, $A^1$, $E^1$, $E^2$, Q, and $Z^1$ are as defined in connection with Formula XVI, and $R^{11a}$, $R^{11b}$, $R^{11c}$, and $R^{11d}$ are as defined in connection with Formula XIX, or a salt or solvate thereof.

In another embodiment, Intermediates of the Disclosure are compounds of any one of Formula XVI-XXX, wherein E is —($CH_2$)$_q$—; $E^1$ is selected from the group consisting of —$CH_2$—, —O—, and —N($R^{9b}$)—; and $E^2$ is a bond, or a salt or solvate thereof.

In another embodiment, Intermediates of the Disclosure are compounds of any one of Formula XVI-XXX, wherein E is —($CH_2$)$_2$—, or a salt or solvate thereof.

In another embodiment, Intermediates of the Disclosure are compounds of any one of Formula XVI-XXX, wherein $E^1$ is —($CH_2$)—, or a salt or solvate thereof.

In another embodiment, Intermediates of the Disclosure are compounds of any one of Formula XVI-XXX, wherein E is selected from the group consisting of —O— and —N($R^{9a}$)—; $E^1$ is —($CH_2$)$_r$—; $E^2$ is a bond; and r is 1 or 2, or a salt or solvate thereof.

In another embodiment, Intermediates of the Disclosure are compounds of any one of Formula XVI-XXX, wherein E is —($CH_2$)—; $E^1$ is —($CH_2$)—; and $E^2$ is selected from the group consisting of —O— and —N($R^{9c}$)—, or a salt or solvate thereof.

In another embodiment, Intermediates of the Disclosure are compounds of any one of Formula XVI-XXX, wherein E is —($CH_2$)$_q$—; $E^1$ is —C(=O)—; and $E^2$ is selected from the group consisting of —O— and —N($R^{9c}$)—, or $E^2$ is a bond, or a salt or solvate thereof.

In another embodiment, Intermediates of the Disclosure are compounds of any one of Formula XVI-XXX, wherein Q is =N—, or a salt or solvate thereof.

In another embodiment, Intermediates of the Disclosure are compounds of any one of Formula XVI-XXX, wherein $Z^1$ halo, or a salt or solvate thereof.

In another embodiment, Intermediates of the Disclosure are compounds of any one of Formula XVI-XXX, wherein $Z^1$ is selected from the group consisting of:

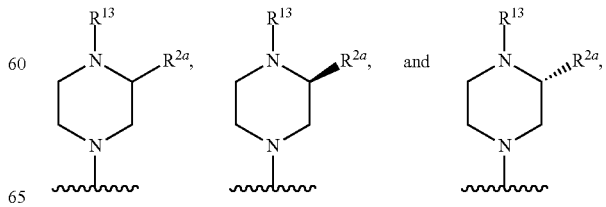

or a salt or solvate thereof.

In another embodiment, Intermediates of the Disclosure are compounds of any one of Formula XVI-XXX, wherein $R^{13}$ is hydrogen, or a salt or solvate thereof.

In another embodiment, Intermediates of the Disclosure are compounds of any one of Formula XVI-XXX, wherein $R^{13}$ is —C(=O)OR$^{14b}$, or a salt or solvate thereof. In another embodiment, $R^{14b}$ is —C(CH$_3$)$_3$.

In another embodiment, Intermediates of the Disclosure are compounds of any one of Formula XVI-XXX, wherein $R^{2a}$ is —CH$_2$CN, or a salt or solvate thereof.

In another embodiment, Intermediates of the Disclosure are compounds of any one of Formula XVI-XXX, wherein $R^{12}$ is chloro, or a salt or solvate thereof.

In another embodiment, Intermediates of the Disclosure are compounds of any one of Formula XVI-XXX, wherein $R^{12}$ is -LR$^3$, or a salt or solvate thereof. In another embodiment, L is —O—. In another embodiment, R$^3$ is selected from the group consisting of (amino)C$_1$-C$_4$ alkyl, (carboxamido)C$_1$-C$_4$ alkyl, and (heterocyclo)C$_1$-C$_4$ alkyl.

In another embodiment, Intermediates of the Disclosure are any one or more of the compounds listed in Table 2, or a salt or solvate thereof.

TABLE 2

| Intermediate No. | Structure |
|---|---|
| 1 | 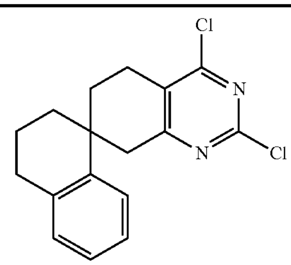 |
| 2 | 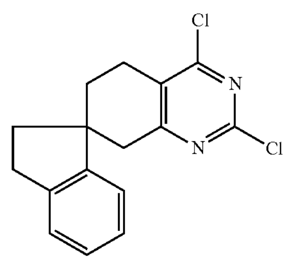 [SMILES: Clc1nc(Cl)c2c(n1)CC1(CCc3ccccc31)CC2] |
| 3 | 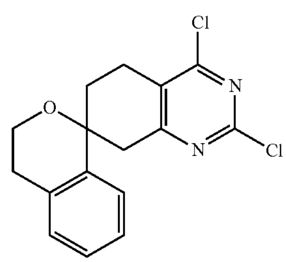 [SMILES: Clc1nc(Cl)c2c(n1)CC1(CC2)OCCc2ccccc21] |
| 4 | 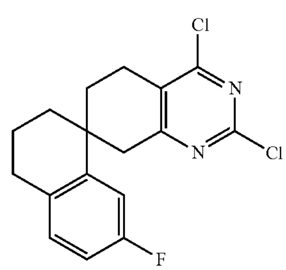 [SMILES: Fc1ccc2c(c1)C1(CCC2)CCc2c(Cl)nc(Cl)nc2C1] |
| 5 | |
| 6 | |
| 7 | |
| 8 | |

TABLE 2-continued
| Intermediate No. | Structure |
|---|---|
| 9 | 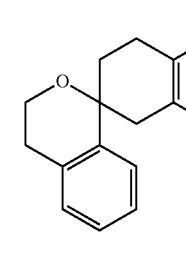 |
| 10 | |
| 11 | |
| 12 | |
| Intermediate No. | Structure |
|---|---|
| 13 | 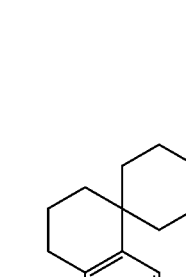 |
| 14 | |
| 15 | |
| 29 | |

TABLE 2-continued

| Intermediate No. | Structure |
|---|---|
| 30 | 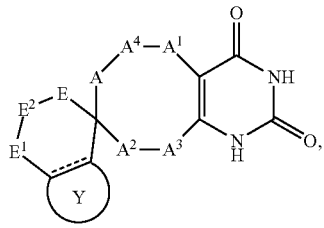 |
| 31 | 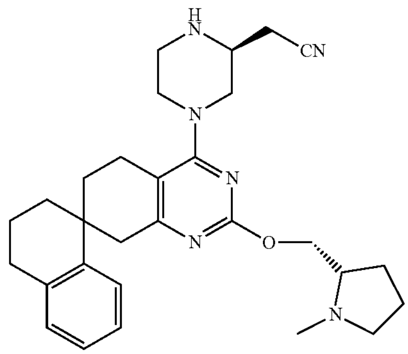 |

In another embodiment, Intermediates of the Disclosure are compounds of Formula XXXI:

XXXI wherein:

A is selected from the group consisting of $-(CR^{6a}R^{6b})_m-$, $-O-$, $-S-$, and $-N(R^{7a})-$;

$A^1$ is selected from the group consisting of $-(CR^{6c}R^{6d})_n-$, $-O-$, $-S-$, and $-N(R^{7b})-$;

$A^2$ is selected from the group consisting of $-(CR^{6e}R^{6f})_o-$, $-O-$, $-S-$, and $-N(R^{7c})-$;

$A^3$ is selected from the group consisting of $-(CR^{6g}R^{6h})_p-$, $-O-$, $-S-$, and $-N(R^{7d})-$;

$A^4$ is selected from the group consisting of $-O-$, $-S-$, and $-N(R^{7e})-$; or $A^4$ is a bond, with the provisos that:

(1) when A is $-O-$, $-S-$, or $-N(R^{7a})-$, then $A^4$ is a bond, $A^1$ is $-(CR^{6c}R^{6d})_n-$, n is 1 or 2, and E is $-(CR^{8a}R^{8b})_q-$;

(2) when $A^1$ is $-O-$, $-S-$, or $-N(R^{7b})-$, then $A^4$ is a bond, A is $-(CR^{6a}R^{6b})_m-$, and m is 1 or 2;

(3) when $A^2$ is $-O-$, $-S-$, or $-N(R^{7c})-$, then $A^3$ is $-(CR^{6g}R^{6h})_p-$ p is 1 or 2, and E is $-(CR^{8a}R^{8b})_q-$; and (4) when $A^3$ is $-O-$, $-S-$, or $-N(R^{7d})-$, then $A^2$ is $-(CR^{6e}R^{6f})_o-$ and o is 1 or 2, $R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and $C_1$-$C_4$ alkyl;

m is 0, 1, or 2;
n is 0, 1, or 2;
o is 0, 1, or 2;
p is 0, 1, or 2;
with the proviso that the sum of m, n, o, and p is 2, 3, 4, or 5;

$R^{7a}$, $R^{7b}$, $R^{7c}$, $R^{7d}$, and $R^{7e}$ are independently selected from the group consisting of hydrogen and $C_1$-$C_4$ alkyl;

E is selected from the group consisting of $-(CR^{8a}R^{8b})_q-$, $-O-$, $-S-$, and $-N(R^{9a})-$;

$E^1$ is selected from the group consisting of $-(CR^{8c}R^{8d})_r-$, $-O-$, $-S-$, $-N(R^{9b})-$, and $-C(=O)-$;

$E^2$ is selected from the group consisting of $-O-$, $-S-$, and $-N(R^{9c})-$, or $E^2$ is a bond with the provisos that:

(1) when E is $-O-$, $-S-$, or $-N(R^{9a})-$, then $E^2$ is a bond, $E^1$ is $-(CR^{8c}R^{8d})_q-$, A is $-(CR^{6a}R^{6b})_m-$, m is 1 or 2, $A^2$ is $-(CR^{6e}R^{6f})_o-$, and o is 1 or 2; and (2) when $E^1$ is $-O-$, $-S-$, or $-N(R^{9b})-$, then $E^2$ is a bond, E is $-(CR^{8a}R^{8b})_r-$, and r is 1 or 2, q is 1, 2, or 3;
r is 0, 1, or 2;

with the proviso that the sum of q and r is 2, 3, 4, or 5;

$R^{8a}$ and $R^{8b}$ are each independently selected from the group consisting of hydrogen and $C_1$-$C_4$ alkyl; or $R^{8a}$ and $R^{8b}$ taken together with the carbon atom to which they are attached form a $C_3$-$C_6$ cycloalkyl;

$R^{8c}$ and $R^{8d}$ are each independently selected from the group consisting of hydrogen and $C_1$-$C_4$ alkyl; or $R^{8c}$ and $R^{8d}$ taken together with the carbon atom to which they are attached form a $C_3$-$C_6$ cycloalkyl;

$R^{9a}$, $R^{9b}$, and $R^{9c}$ are independently selected from the group consisting of hydrogen and $C_1$-$C_4$ alkyl;

represents a fused optionally substituted $C_3$-$C_8$ cycloalkyl, a fused optionally substituted heterocylo, a fused optionally substituted $C_6$-$C_{10}$ aryl, or a fused optionally substituted 5- to 10-membered heteroaryl; and --- represents a single or double bond, or a salt or solvate thereof.

In another embodiment, Intermediates of the Disclosure are compounds of Formula XXXII:

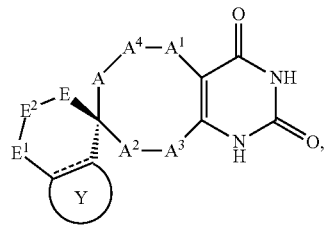

XXXII wherein A, A$^1$, A$^2$, A$^3$, A$^4$, E, E$^1$, E$^2$,

and $==$ are as defined in connection with Formula XXXI, or a salt or solvate thereof.

In another embodiment, Intermediates of the Disclosure are compounds of Formula XXXIII:

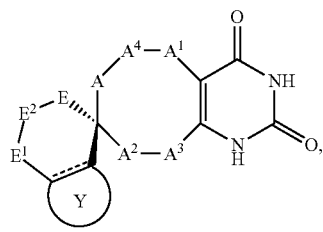

XXXIII wherein A, A$^1$, A$^2$, A$^3$, A$^4$, E, E$^1$, E$^2$,

and $==$ are as defined in connection with Formula XXXI, or a salt or solvate thereof.

In another embodiment, Intermediates of the Disclosure are compounds of Formula XXXIV:

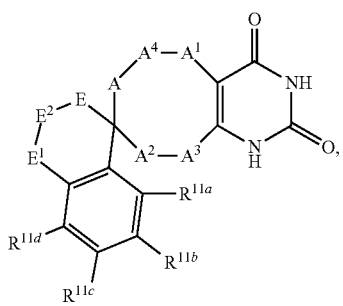

XXXIV wherein R$^{11a}$, R$^{11b}$, R$^{11c}$, and R$^{11d}$ are independently selected from the group consisting of hydrogen, halo, cyano, hydroxy, C$_1$-C$_4$ alkyl, C$_1$-C$_4$ haloalkyl, C$_3$-C$_6$ cycloalkyl, C$_1$-C$_4$ alkoxy, C$_1$-C$_4$ haloalkoxy, and (hydroxy)C$_1$-C$_4$ alkyl; and A, A$^1$, A$^2$, A$^3$, A$^4$, E, E$^1$, and E$^2$, are as defined in connection with Formula XXXI, or a salt or solvate thereof.

In another embodiment, Intermediates of the Disclosure are compounds of Formula XXXV:

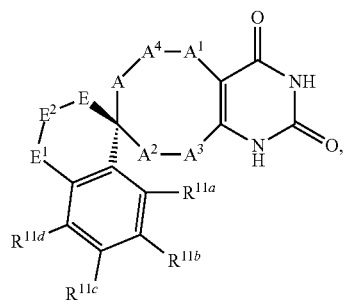

XXXV wherein R$^{11a}$, R$^{11b}$, R$^{11c}$, R$^{11d}$, A, A$^1$, A$^2$, A$^3$, A$^4$, E, E$^1$, and E$^2$ are as defined in connection with Formula XXXIV, or a salt or solvate thereof.

In another embodiment, Intermediates of the Disclosure are compounds of Formula XXXVI:

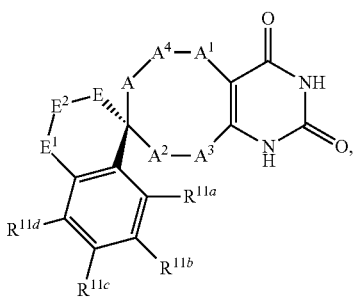

XXXVI wherein R$^{11a}$, R$^{11b}$, R$^{11c}$, R$^{11d}$, A, A$^1$, A$^2$, A$^3$, A$^4$, E, E$^1$, and E$^2$ are as defined in connection with Formula XXXIV, or a salt or solvate thereof.

In another embodiment, Intermediates of the Disclosure are compounds of Formula XXXVII:

XXXVII wherein R$^{11a}$, R$^{11b}$, R$^{11c}$, R$^{11d}$, A, E, E$^1$, and E$^2$ are as defined in connection with Formula XXXIV, or a salt or solvate thereof.

In another embodiment, Intermediates of the Disclosure are compounds of Formula XXXVIII:

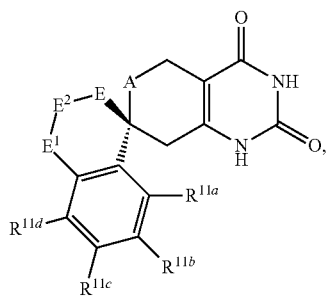

XXXVIII wherein $R^{11a}$, $R^{11b}$, $R^{11c}$, $R^{11d}$, A, E, $E^1$, and $E^2$ are as defined in connection with Formula XXXIV, or a salt or solvate thereof.

In another embodiment, Intermediates of the Disclosure are compounds of Formula XXXIX:

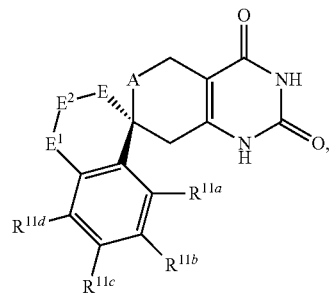

XXXIX wherein $R^{11a}$, $R^{11b}$, $R^{11c}$, $R^{11d}$, A, E, $E^1$, and $E^2$ are as defined in connection with Formula XXXIV, or a salt or solvate thereof.

In another embodiment, Intermediates of the Disclosure are compounds of any one of Formulae XXXI-XXXIX, wherein A is —(CH$_2$)$_m$— and m is 0 or 1, or a salt or solvate thereof. In another embodiment, m is 1.

In another embodiment, Intermediates of the Disclosure are compounds of Formula XL:

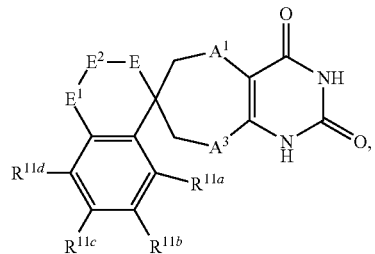

XL wherein $R^{11a}$, $R^{11b}$, $R^{11c}$, $R^{11d}$, $A^1$, $A^3$, E, $E^1$, and $E^2$ are as defined in connection with Formula XXXIV, or a salt or solvate thereof.

In another embodiment, Intermediates of the Disclosure are compounds of Formula XLI:

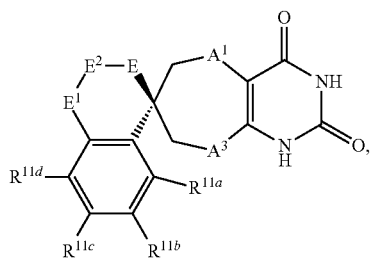

XLI wherein $R^{11a}$, $R^{11b}$, $R^{11c}$, $R^{11d}$, $A^1$, $A^3$, E, $E^1$, and $E^2$ are as defined in connection with Formula XXXIV, or a salt or solvate thereof.

In another embodiment, Intermediates of the Disclosure are compounds of Formula XLII:

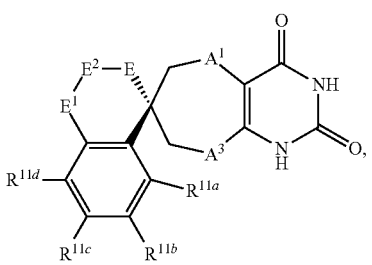

XLII wherein $R^{11a}$, $R^{11b}$, $R^{11c}$, $R^{11d}$, $A^1$, $A^3$, E, $E^1$, and $E^2$ are as defined in connection with Formula XXXIV, or a salt or solvate thereof.

In another embodiment, Intermediates of the Disclosure are compounds of Formula XLIII:

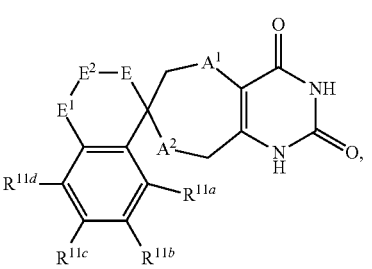

XLIII wherein $A^2$ is selected from the group consisting of —O—, —S—, and —N($R^{7c}$)—; E is —(CR$^{8a}$R$^{8b}$)$_q$—; $R^{11a}$, $R^{11b}$, $R^{11c}$, $R^{11d}$, $A^1$, $E^1$, and $E^2$ are as defined in connection with Formula XXXIV; and $R^{7c}$, $R^{8a}$, $R^{8b}$, and q are as defined in connection with Formula XXXI, or a salt or solvate thereof.

In another embodiment, Intermediates of the Disclosure are compounds of Formula XLIV:

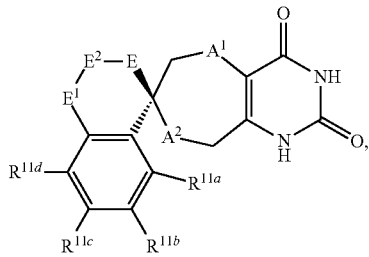

XLIV wherein $A^2$, E, $R^{11a}$, $R^{11b}$, $R^{11c}$, $R^{11d}$, $A^1$, $E^1$, $E^2$ are as defined in connection with Formula XLIII, or a salt or solvate thereof.

In another embodiment, Intermediates of the Disclosure are compounds of Formula XLV:

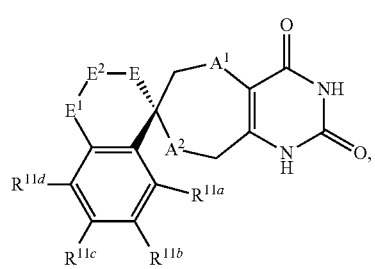

XLV wherein $A^2$, E, $R^{11a}$, $R^{11b}$, $R^{11c}$, $R^{11d}$, $A^1$, $E^1$, $E^2$ are as defined in connection with Formula XLIII, or a salt or solvate thereof.

In another embodiment, Intermediates of the Disclosure are compounds of any one of Formulae XXXI-XLV, wherein E is —(CH$_2$)$_q$—; $E^1$ is selected from the group consisting of —CH$_2$—, —O—, and —N(R$^{9b}$)—; and $E^2$ is a bond, or a salt or solvate thereof.

In another embodiment, Intermediates of the Disclosure are compounds of any one of Formulae XXXI-XLV, wherein E is —(CH$_2$)$_2$—, or a salt or solvate thereof.

In another embodiment, Intermediates of the Disclosure are compounds of any one of Formulae XXXI-XLV, wherein $E^1$ is —(CH$_2$)—, or a salt or solvate thereof.

In another embodiment, Intermediates of the Disclosure are compounds of any one of Formulae XXXI-XLV, wherein E is selected from the group consisting of —O— and —N(R$^{9a}$)—; $E^1$ is —(CH$_2$)$_r$—; $E^2$ is a bond; and r is 1 or 2, or a salt or solvate thereof.

In another embodiment, Intermediates of the Disclosure are compounds of any one of Formulae XXXI-XLV, wherein E is —(CH$_2$)—; $E^1$ is —(CH$_2$)—; and $E^2$ is selected from the group consisting of —O— and —N(R$^{9c}$)—, or a salt or solvate thereof.

In another embodiment, Intermediates of the Disclosure are compounds of any one of Formulae XXXI-XLV, wherein E is —(CH$_2$)$_q$—; $E^1$ is —C(=O)—; and $E^2$ is selected from the group consisting of —O— and —N(R$^{9c}$)—, or $E^2$ is a bond, or a salt or solvate thereof.

In another embodiment, Intermediates of the Disclosure are any one or more of the compounds of Table 3, or a salt or solvate thereof.

TABLE 3

| Intermediate No. | Structure |
|---|---|
| 16 | ![structure] |
| 17 | ![structure] |
| 18 | ![structure] |
| 19 | ![structure] |
| 20 | ![structure] |

In another embodiment, Intermediates of the Disclosure are compounds of Formula XLVI

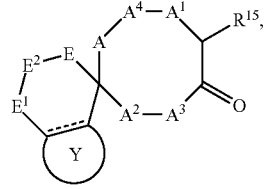

XLVI wherein:
$R^{15}$ is selected from the group consisting of hydrogen and —C(=O)OR$^{16}$;
$R^{16}$ is $C_1$-$C_6$ alkyl;
A is selected from the group consisting of —(CR$^{6a}$R$^{6b}$)$_m$—, —O—, —S—, and —N(R$^{7a}$)—;
$A^1$ is selected from the group consisting of —(CR$^{6c}$R$^{6d}$)$_n$—, —O—, —S—, and —N(R$^{7b}$)—;
$A^2$ is selected from the group consisting of —(CR$^{6e}$R$^{6f}$)$_o$—, —O—, —S—, and —N(R$^{7c}$)—;
$A^3$ is selected from the group consisting of —(CR$^{6g}$R$^{6h}$)$_p$—, —O—, —S—, and —N(R$^{7d}$)—;
$A^4$ is selected from the group consisting of —O—, —S—, and —N(R$^{7e}$)—; or $A^4$ is a bond,
with the provisos that:
(1) when A is —O—, —S—, or —N(R$^{7a}$)—, then $A^4$ is a bond, $A^1$ is —(CR$^{6c}$R$^{6d}$)$_n$—, n is 1 or 2, and E is —(CR$^{8a}$R$^{8b}$)$_q$;
(2) when $A^1$ is —O—, —S—, or —N(R$^{7b}$)—, then $A^4$ is a bond, A is —(CR$^{6a}$R$^{6b}$)$_m$—, and m is 1 or 2;
(3) when $A^2$ is —O—, —S—, or —N(R$^{7c}$)—, then $A^3$ is —(CR$^{6g}$R$^{6h}$)$_p$— p is 1 or 2, and E is —(CR$^{8a}$R$^{8b}$)$_q$; and
(4) when $A^3$ is —O—, —S—, or —N(R$^{7d}$)—, then $A^2$ is —(CR$^{6e}$R$^{6f}$)$_o$— and o is 1 or 2,
$R^{6a}$, $R^{6b}$, $R^{6c}$, $R^{6d}$, $R^{6e}$, $R^{6f}$, $R^{6g}$, and $R^{6h}$ are each independently selected from the group consisting of hydrogen and $C_1$-$C_4$ alkyl;
m is 0, 1, or 2;
n is 0, 1, or 2;
o is 0, 1, or 2;
p is 0, 1, or 2;
with the proviso that the sum of m, n, o, and p is 2, 3, 4, or 5;
$R^{7a}$, $R^{7b}$, $R^{7c}$, $R^{7d}$, and $R^{7e}$ are independently selected from the group consisting of hydrogen and $C_1$-$C_4$ alkyl;
E is selected from the group consisting of —(CR$^{8a}$R$^{8b}$)$_q$—, —O—, —S—, and —N(R$^{9a}$)—;
$E^1$ is selected from the group consisting of —(CR$^{8c}$R$^{8d}$)$_r$—, —O—, —S—, —N(R$^{9b}$)—, and —C(=O)—;
$E^2$ is selected from the group consisting of —O—, —S—, and —N(R$^{9c}$)—, or $E^2$ is a bond
with the provisos that:
(1) when E is —O—, —S—, or —N(R$^{9a}$)—, then $E^2$ is a bond, $E^1$ is —(CR$^{8c}$R$^{8d}$)$_q$—, A is —(CR$^{6a}$R$^{6b}$)$_m$—, m is 1 or 2, $A^2$ is —(CR$^{6e}$R$^{6f}$)$_o$—, and o is 1 or 2; and
(2) when $E^1$ is —O—, —S—, or —N(R$^{9b}$)—, then $E^2$ is a bond, E is —(CR$^{8a}$R$^{8b}$)$_r$—, and r is 1 or 2,
q is 1, 2, or 3;
r is 0, 1, or 2;
with the proviso that the sum of q and r is 2, 3, 4, or 5;
$R^{8a}$ and $R^{8b}$ are each independently selected from the group consisting of hydrogen and $C_1$-$C_4$ alkyl; or $R^{8a}$ and $R^{8b}$ taken together with the carbon atom to which they are attached form a $C_3$-$C_6$ cycloalkyl;
$R^{8c}$ and $R^{8d}$ are each independently selected from the group consisting of hydrogen and $C_1$-$C_4$ alkyl; or
$R^{8c}$ and $R^{8d}$ taken together with the carbon atom to which they are attached form a $C_3$-$C_6$ cycloalkyl;
$R^{9a}$, $R^{9b}$, and $R^{9c}$ are independently selected from the group consisting of hydrogen and $C_1$-$C_4$ alkyl;
Q is =N—;

represents a fused optionally substituted $C_3$-$C_8$ cycloalkyl, a fused optionally substituted heterocylo, a fused optionally substituted $C_6$-$C_{10}$ aryl, or a fused optionally substituted 5- to 10-membered heteroaryl; and ═══ represents a single or double bond, or a salt or solvate thereof,
with the proviso that the compound is not:

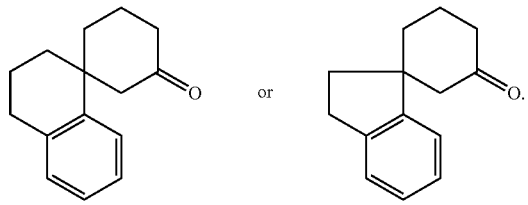 [SMILES: O=C1CCCC2(CCCc3ccccc32)C1 ; "or" ; O=C1CCCC2(CCc3ccccc32)C1]

In another embodiment, Intermediates of the Disclosure are compounds of Formula XLVII:

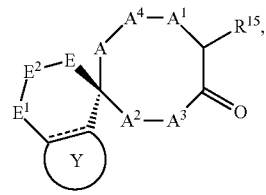

XLVII wherein $R^{15}$, A, $A^1$, $A^2$, $A^3$, $A^4$, E, $E^1$, $E^2$,

and ═══ are as defined in connection with Formula XLVI, or a salt or solvate thereof.

In another embodiment, Intermediates of the Disclosure are compounds of Formula XLVIII:

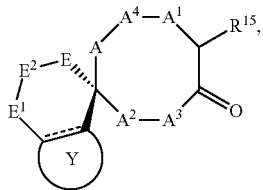

XLVIII wherein $R^{15}$, A, $A^1$, $A^2$, $A^3$, $A^4$, E, $E^1$, $E^2$,

and $\text{---}$ are as defined in connection with Formula XLVI, or a salt or solvate thereof, In another embodiment, Intermediates of the Disclosure are compounds of Formula XLIX:

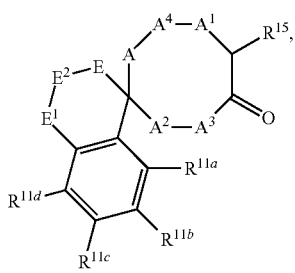

XLIX wherein $R^{11a}$, $R^{11b}$, $R^{11c}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^{15}$, A, $A^1$, $A^2$, $A^3$, $A^4$, E, $E^1$, and $E^2$ are as defined in connection with Formula XLVI, or a salt or solvate thereof.

In another embodiment, Intermediates of the Disclosure are compounds of Formula L:

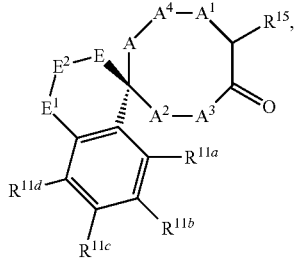

L wherein $R^{11a}$, $R^{11b}$, $R^{11c}$, $R^{11d}$, $R^{15}$, A, $A^1$, $A^2$, $A^3$, $A^4$, E, $E^1$, and $E^2$ are as defined in connection with Formula XLIX, or a salt or solvate thereof.

In another embodiment, Intermediates of the Disclosure are compounds of Formula LI:

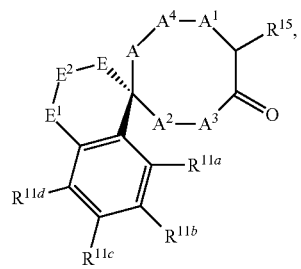

LI wherein $R^{11a}$, $R^{11b}$, $R^{11c}$, $R^{11d}$, $R^{15}$, A, $A^1$, $A^2$, $A^3$, $A^4$, E, $E^1$, and $E^2$ are as defined in connection with Formula XLIX, or a salt or solvate thereof.

In another embodiment, Intermediates of the Disclosure are compounds of Formula LII:

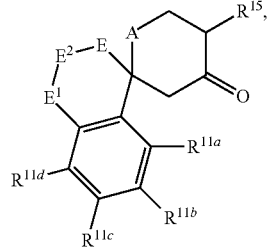

LII wherein $R^{11a}$, $R^{11b}$, $R^{11c}$, $R^{11d}$, $R^{15}$, A, E, $E^1$, and $E^2$ are as defined in connection with Formula XLIX, or a salt or solvate thereof.

In another embodiment, Intermediates of the Disclosure are compounds of Formula LIII:

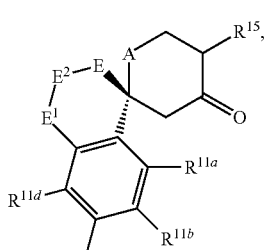

LIII wherein $R^{11a}$, $R^{11b}$, $R^{11c}$, $R^{11d}$, $R^{15}$, A, E, $E^1$, and $E^2$ are as defined in connection with Formula XLIX, or a salt or solvate thereof.

In another embodiment, Intermediates of the Disclosure are compounds of Formula LIV:

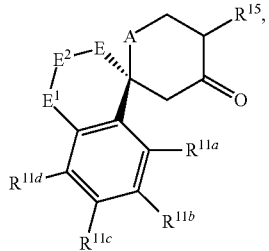

LIV wherein $R^{11a}$, $R^{11b}$, $R^{11c}$, $R^{11d}$, $R^{15}$, A, E, $E^1$, and $E^2$ are as defined in connection with Formula XLIX, or a salt or solvate thereof.

In another embodiment, Intermediates of the Disclosure are compounds of any one of Formulae XLVI-LIV, wherein A is —(CH$_2$)$_m$— and m is 0 or 1, or a salt or solvate thereof. In another embodiment, m is 1.

In another embodiment, Intermediates of the Disclosure are compounds of Formula LV:

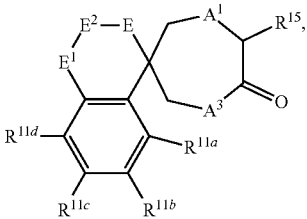

LV wherein $R^{11a}$, $R^{11b}$, $R^{11c}$, $R^{11d}$, $R^{15}$, $A^1$, $A^3$, E, $E^1$, and $E^2$ are as defined in connection with Formula XLIX, or a salt or solvate thereof.

In another embodiment, Intermediates of the Disclosure are compounds of Formula LVI:

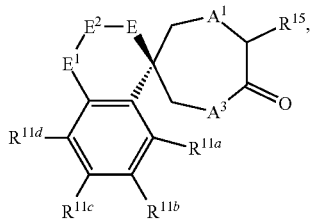

LVI wherein $R^{11a}$, $R^{11b}$, $R^{11c}$, $R^{11d}$, $R^{15}$, $A^1$, $A^3$, E, $E^1$, and $E^2$ are as defined in connection with Formula XLIX, or a salt or solvate thereof.

In another embodiment, Intermediates of the Disclosure are compounds of Formula LVII:

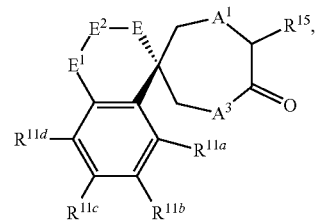

LVIII wherein $R^{11a}$, $R^{11b}$, $R^{11c}$, $R^{11d}$, $R^{15}$, $A^1$, $A^3$, E, $E^1$, and $E^2$ are as defined in connection with Formula XLIX, or a salt or solvate thereof.

In another embodiment, Intermediates of the Disclosure are compounds of Formula LIX:

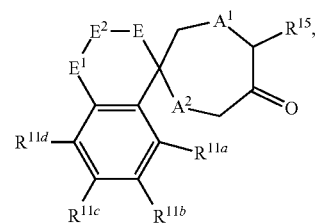

LIX wherein $A^2$ is selected from the group consisting of —O—, —S—, and —N($R^{7c}$)—; E is —(CR$^{8a}$R$^{8b}$)$_q$—; $R^{11a}$, $R^{11b}$, $R^{11c}$, $R^{11d}$, $R^{15}$, $A^1$, $E^1$, and $E^2$ are as defined in connection with Formula XLIX; and $R^{7c}$, $R^{8a}$, $R^{8b}$, and q are as defined in connection with Formula XLVI, or a salt or solvate thereof.

In another embodiment, Intermediates of the Disclosure are compounds of Formula LX:

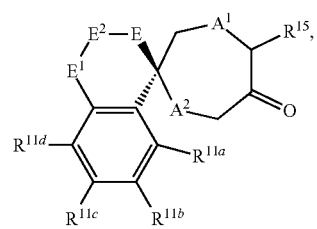

LX wherein $A^2$, E, $R^{11a}$, $R^{11b}$, $R^{11c}$, $R^{11d}$, $R^{15}$, $A^1$, $E^1$, and $E^2$ are as defined in connection with Formula LIX, or a salt or solvate thereof.

In another embodiment, Intermediates of the Disclosure are compounds of Formula LXI:

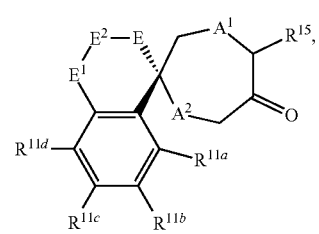

LXI wherein $A^2$, E, $R^{11a}$, $R^{11b}$, $R^{11c}$, $R^{11d}$, $R^{15}$, $A^1$, $E^1$, and $E^2$ are as defined in connection with Formula LIX, or a salt or solvate thereof.

In another embodiment, Intermediates of the Disclosure are compounds of any one of Formulae XLIX-LXI, wherein $R^{11a}$ is selected from the group consisting of halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^{11b}$, $R^{11c}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl, or a salt or solvate thereof.

In another embodiment, Intermediates of the Disclosure are compounds of any one of Formulae XLIX-LXI, wherein $R^{11b}$ is selected from the group consisting of halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^{11a}$, $R^{11c}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl, or a salt or solvate thereof.

In another embodiment, Intermediates of the Disclosure are compounds of any one of Formulae XLIX-LXI, wherein $R^{11c}$ is selected from the group consisting of halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^{11a}$, $R^{11b}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl, or a salt or solvate thereof.

In another embodiment, Intermediates of the Disclosure are compounds of any one of Formulae XLIX-LXI, wherein $R^{11d}$ is selected from the group consisting of halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl; and $R^{11a}$, $R^{11b}$, and $R^{11c}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl, or a salt or solvate thereof.

In another embodiment, Intermediates of the Disclosure are compounds of any one of Formulae XLVI-LXI, wherein E is —($CH_2$)$_q$—; $E^1$ is selected from the group consisting of —$CH_2$—, —O—, and —N($R^{9b}$)—; and $E^2$ is a bond, or a salt or solvate thereof.

In another embodiment, Intermediates of the Disclosure are compounds of any one of Formulae XLVI-LXI, wherein E is —($CH_2$)$_2$—, or a salt or solvate thereof.

In another embodiment, Intermediates of the Disclosure are compounds of any one of Formulae XLVI-LXI, wherein $E^1$ is —($CH_2$)—, or a salt or solvate thereof.

In another embodiment, Intermediates of the Disclosure are compounds of any one of Formulae XLVI-LXI, wherein E is selected from the group consisting of —O— and —N($R^{9a}$)—; $E^1$ is —($CH_2$)$_r$—; $E^2$ is a bond; and r is 1 or 2, or a salt or solvate thereof.

In another embodiment, Intermediates of the Disclosure are compounds of any one of Formulae XLVI-LXI, wherein E is —($CH_2$)—; $E^1$ is —($CH_2$)—; and $E^2$ is selected from the group consisting of —O— and —N($R^{9c}$)—, or a salt or solvate thereof.

In another embodiment, Intermediates of the Disclosure are compounds of any one of Formulae XLVI-LXI, wherein E is —($CH_2$)$_q$—; $E^1$ is —C(=O)—; and $E^2$ is selected from the group consisting of —O— and —N($R^{9c}$)—, or $E^2$ is a bond, or a salt or solvate thereof.

In another embodiment, Intermediates of the Disclosure are compounds of any one of Formulae XLVI-LXI, wherein $R^{15}$ is hydrogen, or a salt or solvate thereof.

In another embodiment, Intermediates of the Disclosure are compounds of any one of Formulae XLVI-LXI, wherein $R^{15}$ is —C(=O)$OR^{16}$, or a salt or solvate thereof.

In another embodiment, Intermediates of the Disclosure are compounds of any one of Formulae XLVI-LXI, wherein $R^{15}$ is —C(=O)$OR^{16}$ and $R^{16}$ is selected from the group consisting of methyl and ethyl, or a salt or solvate thereof.

In another embodiment, Intermediates of the Disclosure are compounds selected from any one or more of the compounds of Table 4, or a salt or solvate thereof.

TABLE 4

| Intermediate No. | Structure |
| --- | --- |
| 21 | 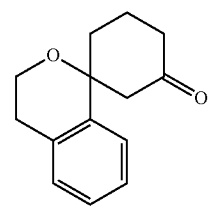 |
| 22 | 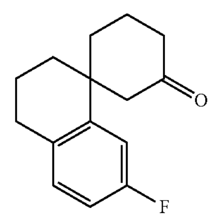 [SMILES: O=C1CCCC2(CCCc3ccc(F)cc32)C1] |
| 23 | 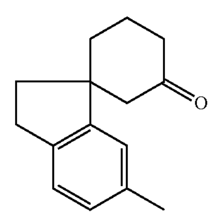 [SMILES: Cc1ccc2c(c1)C1(CCCC(=O)C1)CC2] |
| 24 | 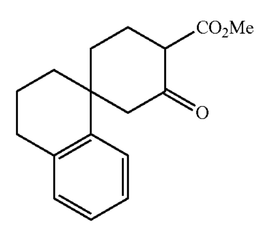 [SMILES: COC(=O)C1CCC2(CCCc3ccccc32)CC1=O] |
| 25 | 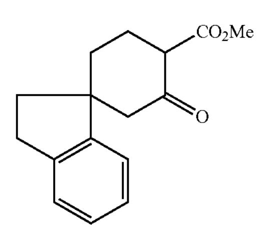 [SMILES: COC(=O)C1CCC2(CCc3ccccc32)CC1=O] |

TABLE 4-continued

| Intermediate No. | Structure |
|---|---|
| 26 | (chroman-spiro-cyclohexanone with CO₂Et substituent) |
| 27 | (fluoro-tetrahydronaphthalene-spiro-cyclohexanone with CO₂Me substituent) |
| 28 | (methyl-indane-spiro-cyclohexanone with CO₂Me substituent) |

III. Methods of Preparing Compounds and Intermediates of the Disclosure

The disclosure also provides methods of preparing Compounds of the Disclosure and/or Intermediates of the Disclosure.

Exemplary methods of preparing Compounds of the Disclosure and/or Intermediates of the Disclosure are provided in General Scheme 1 and the EXAMPLES.

IV. Methods of Treating Disease with Compounds of the Disclosure

Compounds of the Disclosure inhibit KRAS, e.g., KRAS-G12C, and are thus useful in the treatment or prevention of a variety of diseases and conditions. In particular, Compounds of the Disclosure are useful in methods of treating or preventing a disease or condition wherein inhibition of KRAS provides a benefit. Foremost among these diseases and conditions are cancers and proliferative diseases. In one embodiment, such a cancer is referred to as a "KRAS-mediated cancer." KRAS-mediated cancers are known in the art. The therapeutic methods of this disclosure comprise administering a therapeutically effective amount of a Compound of the Disclosure to a subject, e.g., human, in need thereof. The present methods also encompass optionally administering an optional therapeutic agent to the subject in addition to the Compound of the Disclosure. The optional therapeutic agent is selected from drugs known as useful in treating the disease or condition afflicting the subject in need thereof, e.g., a chemotherapeutic agent and/or radiation known as useful in treating a particular cancer.

In another embodiment, the present disclosure relates to a method of treating an individual suffering from a disease or condition wherein inhibition of KRAS provides a benefit, the method comprising administering a therapeutically effective amount of a Compound of the Disclosure.

Since Compounds of the Disclosure are inhibitors of KRAS, a number of diseases and conditions mediated by KRAS can be treated by employing these compounds. The present disclosure is thus directed generally to a method for treating a condition or disorder responsive to KRAS inhibition in a subject, e.g., a human subject, suffering from, or at risk of suffering from, the condition or disorder, the method comprising administering to the subject an effective amount of one or more Compounds of the Disclosure.

In another embodiment, the present disclosure is directed to a method of inhibiting KRAS, e.g., KRAS-G12C, in a subject in need thereof, said method comprising administering to the subject an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, an optional therapeutic agent, packaged separately or together, and an insert having instructions for using these active agents.

In one embodiment, a Compound of the Disclosure is administered in conjunction with an optional therapeutic agent useful in the treatment of a disease or condition wherein inhibition of KRAS provides a benefit. The optional therapeutic agent is different from the Compound of the Disclosure. A Compound of the Disclosure and the optional therapeutic agent can be administered simultaneously or sequentially to achieve the desired effect. In addition, the Compound of the Disclosure and optional therapeutic agent can be administered from a single composition or two separate compositions.

The optional therapeutic agent is administered in an amount to provide its desired therapeutic effect. The effective dosage range for each optional therapeutic agent is known in the art, and the optional therapeutic agent is administered to an individual in need thereof within such established ranges.

A Compound of the Disclosure and the optional therapeutic agent can be administered together as a single-unit dose or separately as multi-unit doses, wherein the Compound of the Disclosure is administered before the optional therapeutic agent or vice versa. One or more doses of the Compound of the Disclosure and/or one or more dose of the optional therapeutic agent can be administered. The Compound of the Disclosure therefore can be used in conjunction with one or more optional therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human subject is treated with a Compound of the Disclosure, or a pharmaceutical composition comprising a Compound of the Disclosure, wherein the compound is administered in an amount sufficient to inhibit KRAS protein in the subject.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting KRAS. In another embodiment, the cancer is a KRAS-mutant cancer. In another embodiment, the cancer is a KRAS-G12C-mutant cancer.

In another embodiment, the KRAS-mutant cancer is lung cancer, pancreatic cancer, or colorectal cancer.

In another embodiment, the KRAS-mutant cancer is lung cancer.

In another embodiment, the KRAS-mutant cancer is non-small cell lung cancer.

In another embodiment, the KRAS-mutant cancer is pancreatic cancer.

In another embodiment, the KRAS-mutant cancer is colorectal cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the subject, and ultimately is determined by the attendant physician. Dosage amounts and intervals can be adjusted individually to provide plasma levels of the Compound of the Disclosure that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

Compounds of the Disclosure typically are administered in admixture with a pharmaceutical carrier to give a pharmaceutical composition selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in *Remington's Pharmaceutical Sciences*, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a subject to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

V. Optional Therapeutic Agents

In some therapeutic methods and uses of the disclosure, a Compound of the Disclosure is administered to a subject having a disease, disorder, or condition, e.g., cancer, as a single agent. In other therapeutic methods and uses of the disclosure, a Compound of the Disclosure is administered to a subject having a disease, disorder, or condition, e.g., cancer, in combination with one or more optional therapeutic agents. In one embodiment, a Compound of the Disclosure is administered in combination with one optional therapeutic agent. In another embodiment, a Compound of the Disclosure is administered in combination with two optional therapeutic agents. In another embodiment, a Compound of the Disclosure is administered in combination with three optional therapeutic agents. Optional therapeutic agents useful in treating cancer patients include those known in the art as well as those developed in the future.

Optional therapeutic agents are administered in an amount to provide their desired therapeutic effect. The effective dosage range for each optional therapeutic agent is known in the art, and the optional therapeutic agent is administered to an individual in need thereof within such established ranges.

A Compound of the Disclosure and the optional therapeutic agent(s) can be administered together as a single-unit dose or separately as multi-unit doses, and in any order, e.g., wherein a Compound of the Disclosure is administered before the optional therapeutic agent(s), or vice versa. One or more doses of a Compound of the Disclosure and the optional therapeutic agent(s) can be administered to the subject.

The disclosure provides the following particular embodiments in connection with treating a disease in a subject.

Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is a KRAS-mutant cancer.

Embodiment IV. The method of Embodiments II or III, wherein the cancer is lung cancer, pancreatic cancer, or colorectal cancer.

Embodiment V. The method of Embodiment IV, wherein the cancer is non-small cell lung cancer.

Embodiment VI. The method of any one of Embodiments I-V further comprising administering a therapeutically effective amount of an optional therapeutic agent useful in the treatment of the disease or condition, e.g., an immune checkpoint inhibitor or other anticancer agent.

Embodiment VII. The method of any one of Embodiments I-VI, wherein the Compound of the Disclosure is a compound of any one of Formulae IV-XV, or a pharmaceutically acceptable salt or solvate thereof.

Embodiment VIII. The method of any one of Embodiments I-VI, wherein the Compound of the Disclosure is a compound of Table 1, or a pharmaceutically acceptable salt or solvate thereof.

Embodiment IX. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment X. The pharmaceutical composition of Embodiment IX for use in treating cancer.

Embodiment XI. The pharmaceutical composition of Embodiment X, wherein the cancer is a KRAS-mutant cancer.

Embodiment XII. The pharmaceutical composition of Embodiment X or XI, wherein the cancer is lung cancer, pancreatic cancer, or colorectal cancer.

Embodiment XIII. The pharmaceutical composition of Embodiment XII, wherein the cancer is non-small cell lung cancer.

Embodiment XIV. The pharmaceutical composition of any one of Embodiments IX-XIII, wherein the Compound of the Disclosure is a compound of any one of Formulae IV-XV, or a pharmaceutically acceptable salt or solvate thereof.

Embodiment XV. The pharmaceutical composition of any one of Embodiments IX-XIII, wherein the Compound of the Disclosure is a compound of Table 1, or a pharmaceutically acceptable salt or solvate thereof.

Embodiment XVI. A Compound of the Disclosure for use in treatment of cancer, a chronic autoimmune disorder, an inflammatory condition, a proliferative disorder, sepsis, or a viral infection.

Embodiment XVII. The compound of Embodiment XVI for use in treating cancer.

Embodiment XVIII. The compound of Embodiment XVII, wherein the cancer is a KRAS-mutant cancer.

Embodiment XIX. The compound of Embodiment XVII or XVIII, wherein the cancer is lung cancer, pancreatic cancer, or colorectal cancer.

Embodiment XX. The compound of Embodiment XIX, wherein the cancer is non-small cell lung cancer.

Embodiment XXI. The compound of any one of Embodiments XVI-XX, wherein the Compound of the Disclosure is a compound of any one of Formulae IV-XV, or a pharmaceutically acceptable salt or solvate thereof.

Embodiment XXII. The compound of any one of Embodiments XVI-XX, wherein the Compound of the Disclosure is a compound of Table 1, or a pharmaceutically acceptable salt or solvate thereof.

Embodiment XXIII. Use of a Compound of the Disclosure for the manufacture of a medicament for treatment of cancer, a chronic autoimmune disorder, an inflammatory condition, a proliferative disorder, sepsis, or a viral infection.

Embodiment XXIV. The use of Embodiment XXIII for the treatment of cancer.

Embodiment XXV. The use of Embodiment XXIV, wherein the cancer is a KRAS-mutant cancer.

Embodiment XXVI. The use of Embodiments XXIV or XXV, wherein the cancer is lung cancer, pancreatic cancer, or colorectal cancer.

Embodiment XXVII. The use of Embodiment XXVI, wherein the cancer is non-small cell lung cancer.

Embodiment XXVIII. The use of any one of Embodiments XXIII-XXVII, wherein the Compound of the Disclosure is a compound of any one of Formulae IV-XV, or a pharmaceutically acceptable salt or solvate thereof.

Embodiment XXIX. The use of any one of Embodiments XXIII-XXVII, wherein the Compound of the Disclosure is a compound of Table 1, or a pharmaceutically acceptable salt or solvate thereof.

Embodiment XXX. A method of inhibiting KRAS within a cell of a subject in need thereof, the method comprising administering to the subject a Compound of the Disclosure, or a pharmaceutically acceptable salt or solvate thereof.

Embodiment XXXI. The method of Embodiment XXX, wherein the Compound of the Disclosure is a compound of Table 1, or a pharmaceutically acceptable salt or solvate thereof.

V. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition of KRAS provides a benefit" and the like pertains to a disease or condition in which KRAS is important or necessary, e.g., for the onset, progress, expression of that disease or condition, or a disease or a condition which is known to be treated by an KRAS inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a KRAS inhibitor for any particular cell type, for example, by assays which conveniently can be used to assess the activity of particular compounds. See, e.g., Yue and Turkson, *Expert Opinion Invest Drugs* 18:45-56 (2009).

The term "KRAS" as used herein refers collectively to the wild-type KRAS gene and protein, and mutant forms thereof. The mutations found most frequently in the KRAS gene are primarily at codons 12, 13, or 61. KRAS mutations also occur in codons 63, 117, 119, and 146. Liu et al., *Acta Pharmaceutica Sinica* B 9:871-879 (2019).

The term "KRAS inhibitor" as used herein refers a compound that inhibits wild-type KRAS and/or mutant KRAS, and includes electrophilic compounds that form irreversible covalent bonds with the KRAS protein. Without wishing to be bound by any particular theory, Compounds of the Disclosure are KRAS inhibitors that form irreversible covalent bonds with the nucleophilic sulfur atom of Cys-12 and thus target the KRAS-G12C mutation and leave wild-type KRAS untouched.

The term "KRAS-mutant cancer" as used herein refers to a cancer that contains a KRAS mutatation. KRAS-mutant cancers include, but are not limited to, KRAS-mutant lung cancer, KRAS-mutant pancreatic cancer, or KRAS-mutant colorectal cancer. In some embodiments, the KRAS-mutant cancer has a KRAS-G12C mutation.

The term "optional therapeutic agent" refers to a therapeutic agent different from a Compound of the Disclosure and that is known to treat the disease or condition of interest. For example, when a cancer is the disease or condition of interest, the optional therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. Compounds of the Disclosure are inhibitors of KRAS and can be used in treating or preventing diseases and conditions wherein inhibition of KRAS provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and subject to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as an optional therapeutic agent. A Compound of the Disclosure and the optional therapeutic agent can be administered separately, in any appropriate form and by any suitable route. When a Compound of the Disclosure and the optional therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an optional therapeutic agent treatment modality (e.g., radiotherapy), to a subject in need thereof. In various embodiments, a Compound of the Disclosure and the optional therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "halo" as used herein by itself or as part of another group refers to —Cl, —F, —Br, or —I.

The term "nitro" as used herein by itself or as part of another group refers to —$NO_2$.

The term "cyano" as used herein by itself or as part of another group refers to —CN.

The term "hydroxy" as herein used by itself or as part of another group refers to —OH.

The term "alkyl" as used herein by itself or as part of another group refers to a straight- or branched-chain aliphatic hydrocarbon containing one to twelve carbon atoms, i.e., a $C_1$-$C_{12}$ alkyl, or the number of carbon atoms designated, e.g., a $C_1$ alkyl such as methyl, a $C_2$ alkyl such as ethyl, etc. In one embodiment, the alkyl is a $C_1$-$C_{10}$ alkyl. In another embodiment, the alkyl is a $C_1$-$C_6$ alkyl. In another embodiment, the alkyl is a $C_1$-$C_4$ alkyl. In another embodiment, the alkyl is a $C_1$-$C_3$ alkyl, i.e., methyl, ethyl, propyl, or isopropyl. Non-limiting exemplary $C_1$-$C_{12}$ alkyl groups include methyl, ethyl, propyl, isopropyl, butyl, sec-butyl, tert-butyl, No-butyl, 3-pentyl, hexyl, heptyl, octyl, nonyl, and decyl. In another embodiment, one or more of the hydrogen atoms of the alkyl group are replaced by deuterium atoms, i.e., the alkyl group is isotopically-labeled with deuterium. A non-limiting exemplary deuterated alkyl group is —$CD_3$. In another embodiment, none of the hydrogen atoms of the alkyl group are replaced by deuterium atoms, i.e., the alkyl group is isotopically-labeled with deuterium The term "optionally substituted alkyl" as used herein by itself or as part of another group refers to an alkyl group that is either unsubstituted or substituted with one, two, or three substituents, wherein each substituent is independently nitro, haloalkoxy, aryloxy, aralkyloxy, alkylthio, sulfonamido, alkylcarbonyl, arylcarbonyl, alkylsulfonyl, arylsulfonyl, ureido, guanidino, carbamate, carboxy, alkoxycarbonyl, carboxyalkyl, —N($R^{56a}$)C(=O)$R^{56b}$, —N($R^{56c}$)S(=O)$_2R^{56d}$, —C(=O)$R^{57}$, —S(=O)$R^{56e}$, or —S(=O)$_2R^{58}$; wherein:

$R^{56a}$ is hydrogen or alkyl;

$R^{56b}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56C}$ is hydrogen or alkyl;

$R^{56d}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{56e}$ is alkyl, haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, optionally substituted $C_6$-$C_{10}$ aryl, or optionally substituted heteroaryl;

$R^{57}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl; and $R^{58}$ is haloalkyl, optionally substituted cycloalkyl, alkoxy, (alkoxy)alkyl, (aryl)alkyl, (heteroaryl)alkyl, (amino)alkyl, (hydroxy)alkyl, (cyano)alkyl, optionally substituted alkenyl, optionally substituted alkynyl, optionally substituted cycloalkyl, optionally substituted heterocycle, or optionally substituted heteroaryl. Non-limiting exemplary optionally substituted alkyl groups include —CH(CO$_2$Me)CH$_2$CO$_2$Me and —CH(CH$_3$)CH$_2$N(H)C(=O)O(CH$_3$)$_3$.

The term "alkenyl" as used herein by itself or as part of another group refers to an alkyl group containing one, two, or three carbon-to-carbon double bonds. In one embodiment, the alkenyl group is a $C_2$-$C_6$ alkenyl group. In another embodiment, the alkenyl group is a $C_2$-$C_4$ alkenyl group. In another embodiment, the alkenyl group has one carbon-to-carbon double bond. Non-limiting exemplary alkenyl groups include ethenyl, propenyl, isopropenyl, butenyl, sec-butenyl, pentenyl, and hexenyl.

The term "optionally substituted alkenyl" as used herein by itself or as part of another refers to an alkenyl group that is either unsubstituted or substituted with one, two or three substituents, wherein each substituent is independently halo, nitro, cyano, hydroxy, amino (e.g., alkylamino, dialkylamino), haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkenyl groups include —CH=CHPh.

The term "alkynyl" as used herein by itself or as part of another group refers to an alkyl group containing one, two, or three carbon-to-carbon triple bonds. In one embodiment, the alkynyl is a $C_2$-$C_6$ alkynyl. In another embodiment, the alkynyl is a $C_2$-$C_4$ alkynyl. In another embodiment, the alkynyl has one carbon-to-carbon triple bond. Non-limiting exemplary alkynyl groups include ethynyl, propynyl, butynyl, 2-butynyl, pentynyl, and hexynyl groups.

The term "optionally substituted alkynyl" as used herein by itself or as part of another group refers to an alkynyl group that is either unsubstituted or substituted with one, two or three substituents, wherein each substituent is independently halo, nitro, cyano, hydroxy, amino, e.g., alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted cycloalkyl, alkenyl, alkynyl, optionally substituted aryl, optionally substituted heteroaryl, or optionally substituted heterocyclo. Non-limiting exemplary optionally substituted alkynyl groups include —C≡CPh and —CH(Ph)C≡CH.

The term "haloalkyl" as used herein by itself or as part of another group refers to an alkyl group substituted by one or more fluorine, chlorine, bromine, and/or iodine atoms. In one embodiment, the alkyl is substituted by one, two, or three fluorine and/or chlorine atoms. In another embodiment, the alkyl is substituted by one, two, or three fluorine atoms. In another embodiment, the alkyl is a $C_1$-$C_6$ alkyl. In another embodiment, the alkyl is a $C_1$-$C_4$ alkyl. In another embodiment, the alkyl group is a $C_1$ or $C_2$ alkyl. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

The terms "hydroxyalkyl" or "(hydroxy)alkyl" as used herein by themselves or as part of another group refer to an alkyl group substituted with one, two, or three hydroxy groups. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. In another embodiment, the hydroxyalkyl is a monohydroxyalkyl group, i.e., substituted with one hydroxy group. In another embodiment, the hydroxyalkyl group is a dihydroxyalkyl group, i.e., substituted with two hydroxy groups. Non-limiting exemplary (hydroxy)alkyl groups include hydroxymethyl, hydroxyethyl, hydroxypropyl and hydroxybutyl groups, such as 1-hydroxy ethyl, 2-hydroxy ethyl, 1,2-dihydroxy ethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

The term "alkoxy" as used herein by itself or as part of another group refers to an alkyl group attached to a terminal oxygen atom. In one embodiment, the alkyl is a $C_1$-$C_6$ alkyl and resulting alkoxy is thus referred to as a "$C_1$-$C_6$ alkoxy." In another embodiment, the alkyl is a $C_1$-$C_4$ alkyl group and resulting alkoxy is thus referred to as a $C_1$-$C_4$ alkoxy. Non-limiting exemplary alkoxy groups include methoxy, ethoxy, and/e/V-butoxy.

The term "haloalkoxy" as used herein by itself or as part of another group refers to a haloalkyl group attached to a terminal oxygen atom. In one embodiment, the haloalkyl group is a $C_1$-$C_6$ haloalkyl. In another embodiment, the haloalkyl group is a $C_1$-$C_4$ haloalkyl group. Non-limiting exemplary haloalkoxy groups include fluoromethoxy, difluoromethoxy, trifluoromethoxy, and 2,2,2-trifluoroethoxy.

The term "alkylthio" as used herein by itself or as part of another group refers to an alkyl group attached to a terminal sulfur atom. In one embodiment, the alkyl group is a $C_1$-$C_4$ alkyl group. Non-limiting exemplary alkylthio groups include —SCH$_3$, and —SCH$_2$CH$_3$.

The terms "alkoxyalkyl" or "(alkoxy)alkyl" as used herein by themselves or as part of another group refers to an alkyl group substituted with one alkoxy group. In one embodiment, the alkoxy is a $C_1$-$C_6$ alkoxy. In another embodiment, the alkoxy is a $C_1$-$C_4$ alkoxy. In another embodiment, the alkyl is a $C_1$-$C_6$ alkyl. In another embodiment, the alkyl is a $C_1$-$C_4$ alkyl. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

The term "heteroalkyl" as used by itself or part of another group refers to unsubstituted straight- or branched-chain aliphatic hydrocarbons containing from three to twenty chain atoms, i.e., 3- to 20-membered heteroalkyl, or the number of chain atoms designated, wherein at least one —CH$_2$— is replaced with at least one of —O—, —N(H)—, —N($C_1$-$C_4$ alkyl)-, or —S—. The —O—, —N(H)—, —N($C_1$-$C_4$ alkyl)-, or —S— can independently be placed at any interior position of the aliphatic hydrocarbon chain so long as each —O—, —N(H)—, —N($C_1$-$C_4$ alkyl)-, and —S— group is separated by at least two —CH$_2$— groups. In one embodiment, one —CH$_2$— group is replaced with one —O— group. In another embodiment, two —CH$_2$— groups are replaced with two —O— groups. In another embodiment, three —CH$_2$— groups are replaced with three —O— groups. In another embodiment, four —CH$_2$— groups are replaced with four —O— groups. Non-limiting exemplary heteroalkyl groups include —CH$_2$OCH$_3$, —CH$_2$OCH$_2$CH$_3$, —CH$_2$CH$_2$CH$_2$OCH$_3$, —CH$_2$CH$_2$OCH$_2$CH$_2$OCH$_2$CH$_3$, —CH$_2$CH$_2$OCH$_2$CH$_2$OCH—$_2$CH$_2$OCH$_2$CH$_3$.

The term "cycloalkyl" as used herein by itself or as part of another group refers to saturated and partially unsaturated, e.g., containing one or two double bonds, monocyclic, bicyclic, or tricyclic aliphatic hydrocarbons containing three to twelve carbon atoms, i.e., a C$_{3-12}$ cycloalkyl, or the number of carbons designated, e.g., a C$_3$ cycloalkyl such a cyclopropyl, a C$_4$ cycloalkyl such as cyclobutyl, etc. In one embodiment, the cycloalkyl is bicyclic, i.e., it has two rings. In another embodiment, the cycloalkyl is monocyclic, i.e., it has one ring. In another embodiment, the cycloalkyl is a C$_{3-5}$ cycloalkyl. In another embodiment, the cycloalkyl is a C$_{3-6}$ cycloalkyl, i.e., cyclopropyl, cyclobutyl, cyclopentyl, or cyclohexyl. In another embodiment, the cycloalkyl is a C$_5$ cycloalkyl, i.e., cyclopentyl. In another embodiment, the cycloalkyl is a C$_6$ cycloalkyl, i.e., cyclohexyl. Non-limiting exemplary C$_{3-12}$ cycloalkyl groups include cyclopropyl, cyclobutyl, cyclopentyl, cyclohexyl, cycloheptyl, cyclooctyl, norbornyl, decalin, adamantyl, cyclohexenyl, and spiro[3.3]heptane.

The term "optionally substituted cycloalkyl" as used herein by itself or as part of another group refers to a cycloalkyl group that is either unsubstituted or substituted with one, two, or three substituents, wherein each substituent is independently halo, nitro, cyano, hydroxy, amino (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, and R$^{58}$ are as defined in connection with the term "optionally substituted alkyl" and R$^{59}$ is (hydroxy)alkyl or (amino)alkyl. The term optionally substituted cycloalkyl also includes cycloalkyl groups having fused optionally substituted aryl or optionally substituted heteroaryl groups such as

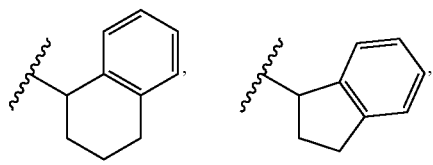

-continued

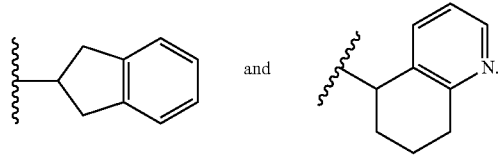

Non-limiting exemplary optionally substituted cycloalkyl groups include:

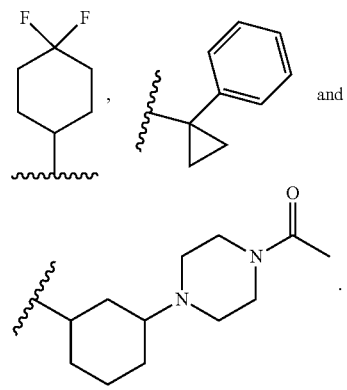

The term "heterocyclo" as used herein by itself or as part of another group refers to saturated and partially unsaturated, e.g., containing one or two double bonds, monocyclic, bicyclic, or tricyclic groups containing three to fourteen ring members, i.e., a 3- to 14-membered heterocyclo, comprising one, two, three, or four heteroatoms. Each heteroatom is independently oxygen, sulfur, or nitrogen. Each sulfur atom is independently oxidized to give a sulfoxide, i.e., S(=O), or sulfone, i.e., S(=O)$_2$.

The term heterocyclo includes groups wherein one or more —CH$_2$— groups is replaced with one or more —C(=O)— groups, including cyclic ureido groups such as imidazolidinyl-2-one, cyclic amide groups such as pyrrolidin-2-one or piperidin-2-one, and cyclic carbamate groups such as oxazolidinyl-2-one.

The term heterocyclo also includes groups having fused optionally substituted aryl or optionally substituted heteroaryl groups such as indoline, indolin-2-one, 2,3-dihydro-1H-pyrrolo[2,3-c]pyridine, 2,3,4,5-tetrahydro-1H-benzo[d]azepine, or 1,3,4,5-tetrahydro-2H-benzo[d]azepin-2-one.

In one embodiment, the heterocyclo group is a 4- to 8-membered cyclic group containing one ring and one or two oxygen atoms, e.g., tetrahydrofuran or tetrahydropyran, or one or two nitrogen atoms, e.g., pyrrolidine, piperidine, or piperazine, or one oxygen and one nitrogen atom, e.g., morpholine, and, optionally, one —CH$_2$— group is replaced with one —C(=O)— group, e.g., pyrrolidin-2-one or piperazin-2-one. In another embodiment, the heterocyclo group is a 5- to 8-membered cyclic group containing one ring and one or two nitrogen atoms and, optionally, one —CH$_2$— group is replaced with one —C(=O)— group. In another embodiment, the heterocyclo group is a 5- or 6-membered cyclic group containing one ring and one or two nitrogen atoms and, optionally, one —CH$_2$— group is replaced with one —C(=O)— group. In another embodiment, the heterocyclo group is a 8- to 12-membered cyclic group containing two rings and one or two nitrogen atoms. The heterocyclo can be linked to the rest of the molecule through any available carbon or nitrogen atom. Non-limiting exemplary heterocyclo groups include:

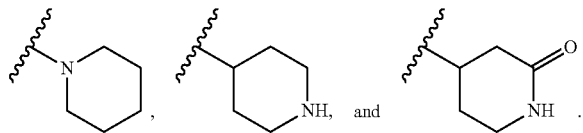

The term "optionally substituted heterocyclo" as used herein by itself or part of another group refers to a heterocyclo group that is either unsubstituted or substituted with one to four substituents, wherein each substituent is independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano) alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl." Substitution may occur on any available carbon or nitrogen atom of the heterocyclo group. Non-limiting exemplary optionally substituted heterocyclo groups include:

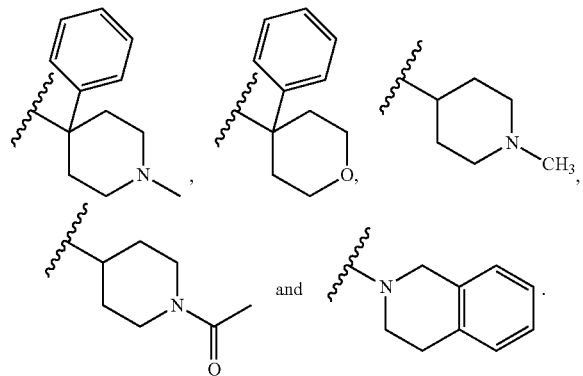

The term "aryl" as used herein by itself or as part of another group refers to an aromatic ring system having six to fourteen carbon atoms, i.e., $C_6$-$C_{14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

The term "optionally substituted aryl" as used herein by itself or as part of another group refers to aryl that is either unsubstituted or substituted with one to five substituents, wherein the substituents are each independently halo, nitro, cyano, hydroxy, amino, (e.g., —NH$_2$, alkylamino, dialkylamino, aralkylamino, hydroxylamino, or (heterocyclo) alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl."

In one embodiment, the optionally substituted aryl is an optionally substituted phenyl. In another embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl includes aryl groups having fused optionally substituted cycloalkyl groups and fused optionally substituted heterocyclo groups. Non-limiting examples include: 2,3-dihydro-1H-inden-1-yl, 1,2,3,4-tetrahydronaphthalen-1-yl, 1,3,4,5-tetrahydro-2H-benzo[c]azepin-2-yl, 1,2,3,4-tetrahydroisoquinolin-1-yl, and 2-oxo-2,3,4,5-tetrahydro-1H-benzo[d]azepin-1-yl.

The term "heteroaryl" as used herein by itself or as part of another group refers to monocyclic and bicyclic aromatic ring systems having five to 14 fourteen ring members, i.e., a 5- to 14-membered heteroaryl, comprising one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term heteroaryl also includes N-oxides. A non-limiting exemplary N-oxide is pyridyl N-oxide.

The term "optionally substituted heteroaryl" as used herein by itself or as part of another group refers to a heteroaryl that is either unsubstituted or substituted with one to four substituents, wherein the substituents are independently halo, nitro, cyano, hydroxy, amino, (e.g., —NH$_2$, alkylamino, dialkylamino, aralkylamino, hydroxyalkylamino, or (heterocyclo)alkylamino), heteroalkyl, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, optionally substituted alkyl, optionally substituted cycloalkyl, alkenyl, alkynyl, optionally substituted aryl, optionally substituted heteroaryl, optionally substituted heterocyclo, alkoxyalkyl, (amino)alkyl, (cyano)alkyl, (carboxamido)alkyl, mercaptoalkyl, (heterocyclo)alkyl, (heteroaryl)alkyl, —N(R$^{56a}$)C(=O)R$^{56b}$, —N(R$^{56c}$)S(=O)$_2$R$^{56d}$, —C(=O)R$^{57}$, —S(=O)R$^{56e}$, —S(=O)$_2$R$^{58}$, or —OR$^{59}$, wherein R$^{56a}$, R$^{56b}$, R$^{56c}$, R$^{56d}$, R$^{56e}$, R$^{57}$, R$^{58}$, and R$^{59}$ are as defined in connection with the term "optionally substituted cycloalkyl."

In one embodiment, the optionally substituted heteroaryl has two substituents. In another embodiment, the optionally substituted heteroaryl has one substituent. Any available carbon or nitrogen atom can be substituted.

The term "aryloxy" as used herein by itself or as part of another group refers to an optionally substituted aryl attached to a terminal oxygen atom. A non-limiting exemplary aryloxy group is PhO—.

The term "aralkyloxy" as used herein by itself or as part of another group refers to an aralkyl attached to a terminal oxygen atom. A non-limiting exemplary aralkyloxy group is PhCH$_2$O—.

The term "(cyano)alkyl" as used herein by itself or as part of another group refers to an alkyl substituted with one, two, or three cyano groups. In one embodiment, the alkyl is substituted with one cyano group. In another embodiment, the alkyl is a C$_1$-C$_6$ alkyl. In another embodiment, the alkyl is a C$_1$-C$_4$ alkyl and thus the (cyano)alkyl is referred to as a (cyano)C$_1$-C$_4$ alkyl. Non-limiting exemplary (cyano)alkyl groups include —CH$_2$CN, —CH$_2$CH$_2$CN and —CH$_2$CH$_2$CH$_2$CN.

The term "(cycloalkyl)alkyl" as used herein by itself or as part of another group refers to an alkyl substituted with one or two optionally substituted cycloalkyl groups. In one embodiment, the cycloalkyl group(s) is an optionally substituted C$_3$-C$_6$ cycloalkyl. In another embodiment, the alkyl is a C$_1$-C$_6$ alkyl. In another embodiment, the alkyl is a C$_1$-C$_4$ alkyl. In another embodiment, the alkyl is a C$_1$ or C$_2$ alkyl. In another embodiment, the alkyl is substituted with one optionally substituted cycloalkyl group. In another embodiment, the alkyl is substituted with two optionally substituted cycloalkyl groups. Non-limiting exemplary (cycloalkyl)alkyl groups include:

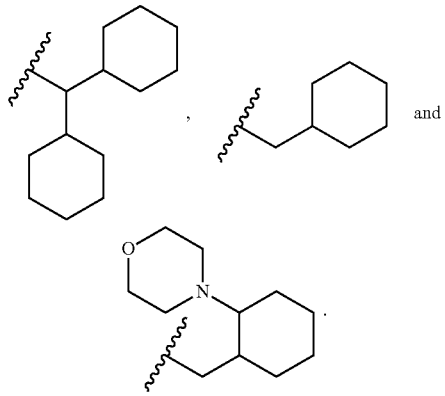

The term "sulfonamido" as used herein by itself or as part of another group refers to a radical of the formula —SO$_2$NR$^{50a}$R$^{50b}$, wherein R$^{50a}$ and R$^{50b}$ are each independently hydrogen, alkyl, optionally substituted cycloalkyl, optionally substituted heterocyclo, optionally substituted aryl, or optionally substituted heteroaryl; or R$^{50a}$ and R$^{50b}$ taken together with the nitrogen to which they are attached form a 3- to 8-membered optionally substituted heterocyclo group. Non-limiting exemplary sulfonamido groups include —SO$_2$NH$_2$, —SO$_2$N(H)CH$_3$, and —SO$_2$N(H)Ph.

The term "carboxamido" as used herein by itself or as part of another group refers to a radical of the formula —C(=O)NR$^{50c}$R$^{50d}$, wherein R$^{50c}$ and R$^{50d}$ are each independently hydrogen, alkyl, optionally substituted cycloalkyl, optionally substituted heterocyclo, optionally substituted aryl, or optionally substituted heteroaryl; or R$^{50c}$ and R$^{50d}$ taken together with the nitrogen to which they are attached form a 3- to 8-membered optionally substituted heterocyclo group. Non-limiting exemplary carboxamido groups include —C(=O)NH$_2$, —C(=O)(H)CH$_3$, and —C(=O)N(CH$_3$)$_2$.

The term "(carboxamido)alkyl" as used herein by itself or as part of another group refers to an alkyl substituted with one carboxamido group. In one embodiment, the alkyl is a C$_1$-C$_6$ alkyl. In another embodiment, the alkyl is a C$_1$-C$_4$ alkyl. In another embodiment, the alkyl is a C$_1$ or C$_2$ alkyl. Non-limiting exemplary (carboxamido)alkyl groups include —CH$_2$C(=O)NH$_2$, —CH$_2$C(=O)(H)CH$_3$, and —CH$_2$C(=O)N(CH$_3$)$_2$.

The term "alkylcarbonyl" as used herein by itself or as part of another group refers to a carbonyl group, i.e., —C(=O)—, substituted by an alkyl group. In one embodiment, the alkyl is a C$_1$-C$_4$ alkyl. A non-limiting exemplary alkylcarbonyl group is —COCH$_3$.

The term "arylcarbonyl" as used herein by itself or as part of another group refers to a carbonyl group, i.e., —C(=O)—, substituted by an optionally substituted aryl group. A non-limiting exemplary arylcarbonyl group is —COPh.

The term "alkylsulfonyl" as used herein by itself or as part of another group refers to a sulfonyl group, i.e., —SO$_2$—, substituted by an alkyl group. A non-limiting exemplary alkylsulfonyl group is —SO$_2$CH$_3$.

The term "arylsulfonyl" as used herein by itself or as part of another group refers to a sulfonyl group, i.e., —SO$_2$—, substituted by an optionally substituted aryl group. A non-limiting exemplary arylsulfonyl group is —SO$_2$Ph.

The term "mercaptoalkyl" as used herein by itself or as part of another group refers to an alkyl substituted by a —SH group.

The term "carboxy" as used by itself or as part of another group refers to a radical of the formula —C(=O)OH.

The term "ureido" as used herein by itself or as part of another group refers to a radical of the formula —NR$^{51a}$—C(=O)—NR$^{51b}$R$^{51c}$, wherein R$^{51a}$ is hydrogen or alkyl; and R$^{51b}$ and R$^{51C}$ are each independently hydrogen, alkyl, optionally substituted cycloalkyl, optionally substituted heterocyclo, optionally substituted aryl, or optionally substituted heteroaryl, or R$^{51b}$ and R$^{51c}$ taken together with the nitrogen to which they are attached form a 4- to 8-membered optionally substituted heterocyclo group. Non-limiting exemplary ureido groups include —NH—C(C=O)—NH$_2$ and —NH—C(C=O)—NHCH$_3$.

The term "guanidino" as used herein by itself or as part of another group refers to a radical of the formula —NR$^{52a}$—C(=NR$^{53}$)—NR$^{52b}$R$^{52c}$, wherein R$^{52a}$ is hydrogen or alkyl; R$^{52b}$ and R$^{53C}$ are each independently hydrogen, alkyl, optionally substituted cycloalkyl, optionally substituted heterocyclo, optionally substituted aryl, or optionally substituted heteroaryl; or R$^{52b}$ and R$^{52c}$ taken together with the nitrogen to which they are attached form a 4- to 8-membered optionally substituted heterocyclo group; and R$^{53}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, and —NH—C(C=NH)—NHCH$_3$.

The term "(heterocyclo)alkyl" as used herein by itself or as part of another group refers to an alkyl substituted with one, two, or three optionally substituted heterocyclo groups. In one embodiment, the alkyl is substituted with one optionally substituted 5- to 8-membered heterocyclo group. In another embodiment, alkyl is a C$_1$-C$_6$ alkyl. In another embodiment, alkyl is a C$_1$-C$_4$ alkyl. The heterocyclo group can be linked to the alkyl group through a carbon or nitrogen atom. Non-limiting exemplary (heterocyclo)alkyl groups include:

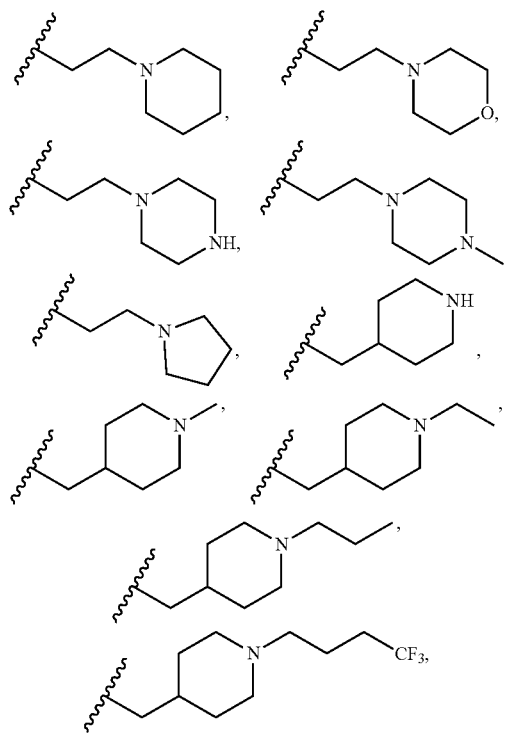

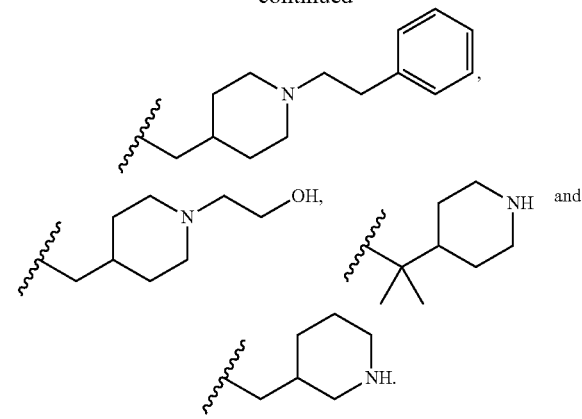

The term "carbamate" as used herein by itself or as part of another group refers to a radical of the formula —NR$^{54a}$—C(=O)—OR$^{54b}$, wherein R$^{54a}$ is hydrogen or alkyl, and R$^{54b}$ is hydrogen, alkyl, optionally substituted cycloalkyl, optionally substituted heterocyclo, optionally substituted aryl, or optionally substituted heteroaryl. A non-limiting exemplary carbamate group is —NH—(C=O)—OtBu.

The term "(heteroaryl)alkyl" as used herein by itself or as part of another group refers to an alkyl substituted with one or two optionally substituted heteroaryl groups. In one embodiment, the alkyl group is substituted with one optionally substituted 5- to 14-membered heteroaryl group. In another embodiment, the alkyl group is substituted with two optionally substituted 5- to 14-membered heteroaryl groups. In another embodiment, the alkyl group is substituted with one optionally substituted 5- to 9-membered heteroaryl group. In another embodiment, the alkyl group is substituted with two optionally substituted 5- to 9-membered heteroaryl groups. In another embodiment, the alkyl group is substituted with one optionally substituted 5- or 6-membered heteroaryl group. In another embodiment, the alkyl group is substituted with two optionally substituted 5- or 6-membered heteroaryl groups. In one embodiment, the alkyl group is a C$_1$-C$_6$ alkyl. In another embodiment, the alkyl group is a C$_1$-C$_4$ alkyl. In another embodiment, the alkyl group is a C$_1$ or C$_2$ alkyl. Non-limiting exemplary (heteroaryl)alkyl groups include:

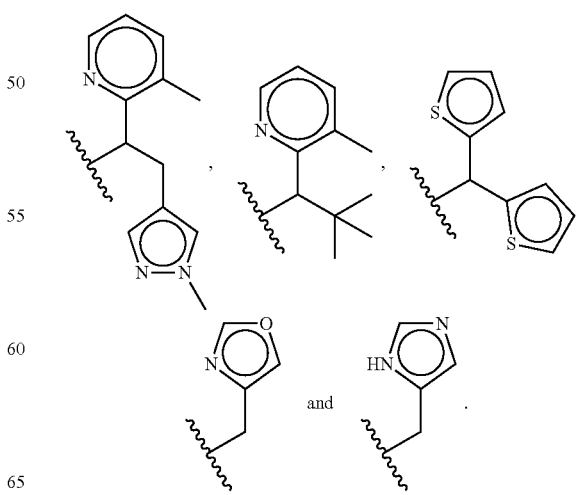

The terms "aralkyl" or "(aryl)alkyl" as used herein by themselves or as part of another group refers to an alkyl substituted with one, two, or three optionally substituted aryl groups. In one embodiment, the alkyl is substituted with one optionally substituted aryl group. In another embodiment, the alkyl is substituted with two optionally substituted aryl groups. In one embodiment, the aryl is an optionally substituted phenyl or optionally substituted naphthyl. In another embodiment, the aryl is an optionally substituted phenyl. In one embodiment, the alkyl is a $C_1$-$C_6$ alkyl. In another embodiment, the alkyl is a $C_1$-$C_4$ alkyl. In another embodiment, the alkyl is a $C_1$ or $C_2$ alkyl. Non-limiting exemplary (aryl)alkyl groups include benzyl, phenethyl, —CHPh$_2$, and —CH(4-F-Ph)$_2$.

The term "amido" as used herein by itself or as part of another group refers to a radical of formula —C(=O)NR$^{60a}$R$^{60b}$, wherein R$^{60a}$ and R$^{60b}$ are each independently hydrogen, optionally substituted alkyl, optionally substituted alkenyl, optionally substituted alkynyl, haloalkyl, (alkoxy)alkyl, (hydroxy)alkyl, (cyano)alkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl; or R$^{60a}$ and R$^{60b}$ taken together with the nitrogen to which they are attached from a 4- to 8-membered optionally substituted heterocyclo group. In one embodiment, R$^{60a}$ and R$^{60b}$ are each independently hydrogen or $C_1$-$C_6$ alkyl.

The term "amino" as used by itself or as part of another group refers to a radical of the formula —NR$^{55a}$R$^{55b}$, wherein R$^{55a}$ and R$^{55b}$ are independently hydrogen, optionally substituted alkyl, haloalkyl, (hydroxy)alkyl, (alkoxy)alkyl, (amino)alkyl, heteroalkyl, optionally substituted cycloalkyl, optionally substituted heterocyclo, optionally substituted aryl, optionally substituted heteroaryl, (aryl)alkyl, (cycloalkyl)alkyl, (heterocyclo)alkyl, or (heteroaryl)alkyl.

In one embodiment, the amino is —NH$_2$.

In another embodiment, the amino is an "alkylamino," i.e., an amino group wherein R$^{55a}$ is $C_{1-6}$ alkyl and R$^{55b}$ is hydrogen. In one embodiment, R$^{55a}$ is $C_1$-$C_4$ alkyl. Non-limiting exemplary alkylamino groups include —N(H)CH$_3$ and —N(H)CH$_2$CH$_3$.

In another embodiment, the amino is a "dialkylamino," i.e., an amino group wherein R$^{55a}$ and R$^{55b}$ are each independently $C_{1-6}$ alkyl. In one embodiment, R$^{55a}$ and R$^{55b}$ are each independently $C_1$-$C_4$ alkyl. Non-limiting exemplary dialkylamino groups include —N(CH$_3$)$_2$ and —N(CH$_3$)CH$_2$CH(CH$_3$)$_2$.

In another embodiment, the amino is a "hydroxyalkylamino," i.e., an amino group wherein R$^{55a}$ is (hydroxy)alkyl and R$^{55b}$ is hydrogen or $C_1$-$C_4$ alkyl.

In another embodiment, the amino is a "cycloalkylamino," i.e., an amino group wherein R$^{55a}$ is optionally substituted cycloalkyl and R$^{55b}$ is hydrogen or $C_1$-$C_4$ alkyl.

In another embodiment, the amino is a "aralkylamino," i.e., an amino group wherein R$^{55a}$ is aralkyl and R$^{55b}$ is hydrogen or $C_1$-$C_4$ alkyl. Non-limiting exemplary aralkylamino groups include —N(H)CH$_2$Ph, —N(H)CHPh$_2$, and —N(CH$_3$)CH$_2$Ph.

In another embodiment, the amino is a "(cycloalkyl)alkylamino," i.e., an amino group wherein R$^{55a}$ is (cycloalkyl)alkyl and R$^{55b}$ is hydrogen or $C_1$-$C_4$ alkyl. Non-limiting exemplary (cycloalkyl)alkylamino groups include:

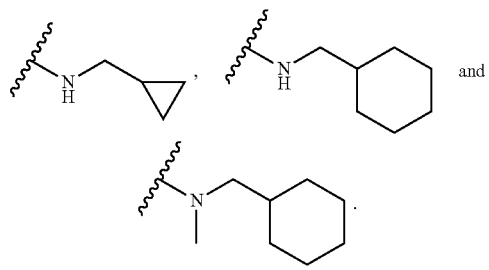

In another embodiment, the amino is a "(heterocyclo)alkylamino," i.e., an amino group wherein R$^{55a}$ is (heterocyclo)alkyl and R$^{55b}$ is hydrogen or $C_1$-$C_4$ alkyl. Non-limiting exemplary (heterocyclo)alkylamino groups include:

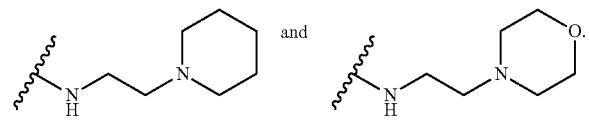 [SMILES: *NCCN1CCCCC1 ; *NCCN1CCOCC1]

The term "(amino)alkyl" as used herein by itself or as part of another group refers to an alkyl substituted with one amino group. In one embodiment, the amino group is —NH$_2$. In one embodiment, the amino group is an alkylamino. In another embodiment, the amino group is a dialkylamino. In another embodiment, the alkyl is a $C_1$-$C_6$ alkyl. In another embodiment, the alkyl is a $C_1$-$C_4$ alkyl. Non-limiting exemplary (amino)alkyl groups include —CH$_2$NH$_2$, CH$_2$CH$_2$N(H)CH$_3$, —CH$_2$CH$_2$N(CH$_3$)$_2$, CH$_2$N(H)cyclopropyl, —CH$_2$N(H)cyclobutyl, and —CH$_2$N(H)cyclohexyl, and —CH$_2$CH$_2$CH$_2$N(H)CH$_2$Ph and —CH$_2$CH$_2$CH$_2$N(H)CH$_2$(4-CF$_3$-Ph).

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. In one embodiment, provided is a compound wherein substantially all of the atoms at a position within the Compound of the Disclosure are replaced by an atom having a different atomic mass or mass number. In another embodiment, provided is a compound wherein substantially all of the atoms at a position within the Compound of the Disclosure are replaced by deuterium atoms, e.g., all of the hydrogen atoms of a —CH$_3$ group are replaced by deuterium atoms to give a —CD3 group. In another embodiment, provided is a compound wherein a portion of the atoms at a position within the Compound of the disclosure are replaced, i.e., the Compound of the Disclosure is enriched at a position with an atom having a different atomic mass or mass number. In another embodiment, provided is a compound wherein none of the atoms of the Compound of the Disclosure are replaced by an atom having a different atomic mass or mass number. Isotopically-labelled Compounds of the Disclosure can be prepared by methods known in the art.

Compounds of the Disclosure contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive. In one embodiment, Compounds of the Disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The term "about," as used herein, includes the recited number±10%. Thus, "about 10" means 9 to 11.

EXAMPLES

General Synthesis of Compounds of the Disclosure

General Scheme 1

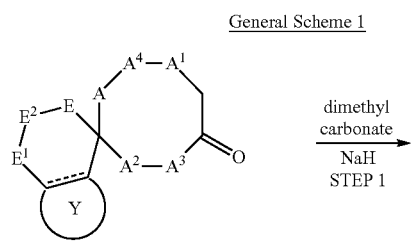

Formula XLVI
(wherein $R^{15}$ is hydrogen)

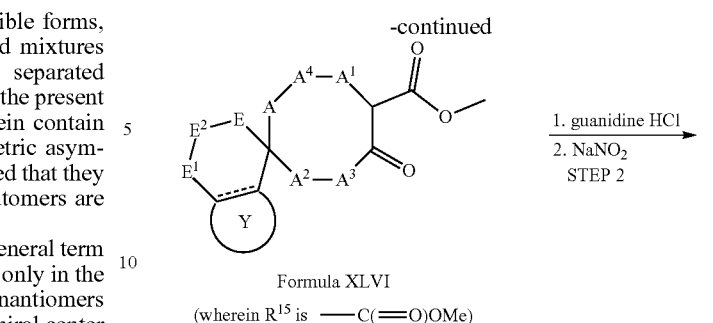

Formula XLVI
(wherein $R^{15}$ is —C(=O)OMe)

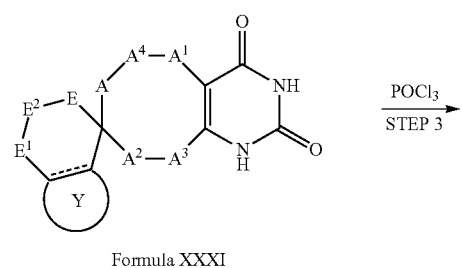

Formula XXXI

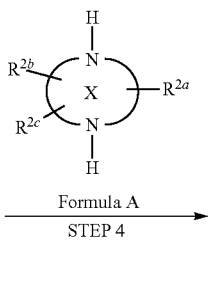

Formula XVI
(wherein $Z^1$ is Cl; $R^{12}$ is Cl, and Q is =N—)

Formula XVI
(wherein $R^{13}$ is H, $R^{12}$ is Cl, and Q is =N—)

105

-continued

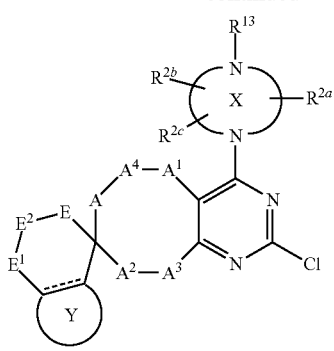

Formula XVI (wherein $R^{13}$ is —C(=O)$R^{14a}$
or —C(=O)O$R^{14b}$,
$R^{12}$ is Cl, and Q is =N—)

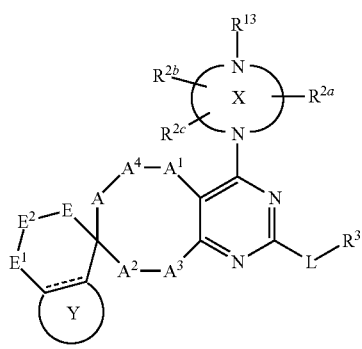

Formula XVI (wherein $R^{13}$ is —C(=O)$R^{14a}$
or —C(=O)O$R^{14b}$,
$R^{12}$ is —L$R^3$, and Q is =N—)

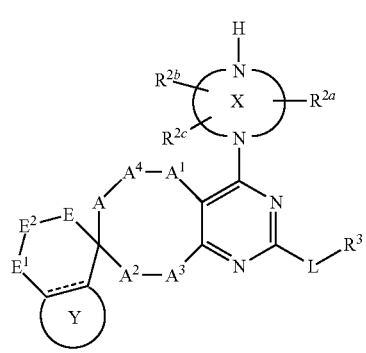

Formula XVI (wherein $R^{13}$ is H,
$R^{12}$ is —L$R^3$, and Q is =N—)

H—L$R^3$ / STEP 6 deprotect / STEP 7

$R^1$—Cl / STEP 8

106

-continued

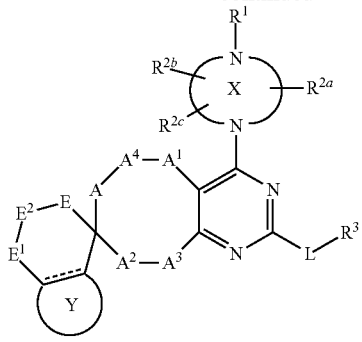

Formula I (wherein Q is =N—)

chiral resolution / STEP 9

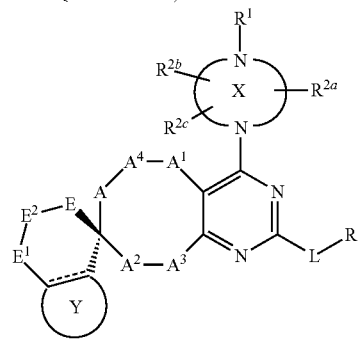

and

Formula II (wherein Q is =N—)

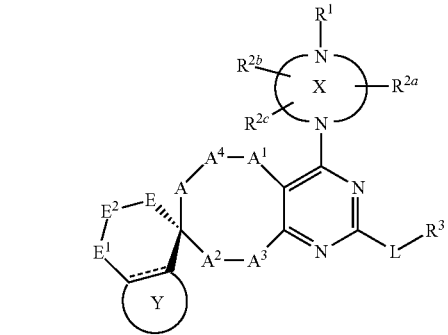

Formula III (wherein Q is =N—)

Compounds of the Disclosure can be prepared from Intermediates of the Disclosure according to General Scheme 1. Briefly, in STEP 1, a compound of Formula XLVI, wherein $R^{15}$ is hydrogen, is made to react with, for example, dimethyl carbonate in the presence of sodium hydride to give a compound of Formula XLVI, wherein $R^{15}$ is —C(=O)OMe.

In STEP 2, a compound of Formula XLVI, wherein $R^{15}$ is —C(=O)OMe, is converted to a compound of Formula XXXI by, for example, treatment first with guanidine HCl and then by sodium nitrite.

In STEP 3, to a compound of Formula XXXI is made to react with, for example, phosphoryl chloride, to give a compound of Formula XVI, wherein $Z^1$ is —Cl, $R^{12}$ is —Cl, and Q is =N—.

In STEP 4, a compound of Formula XVI, wherein $Z^1$ is —Cl, $R^{12}$ is —Cl, and Q is =N—, is made to react with a compound of Formula A, wherein $R^{2a}$, $R^{2b}$, $R^{2c}$, and X are as defined in connection with Formula I, to give a compound of Formula XVI, wherein $R^{12}$ is —Cl, $R^{13}$ is hydrogen, and Q is =N—.

In STEP 5, a compound of Formula XVI, wherein $R^{12}$ is —Cl, $R^{13}$ is hydrogen, and Q is =N—, is made to react with $R^{13}$—Cl, $R^{13}$—OH, or similar reagent to give a compound of Formula XVI, wherein $R^{12}$ is —Cl, $R^{13}$ is —C(=O)$R^{14a}$, or —C(=O)O$R^{14b}$; and Q is =N—.

In STEP 6, a compound of Formula XVI, wherein $R^{12}$ is —Cl, $R^{13}$ is —C(=O)$R^{14a}$, or —C(=O)O$R^{14b}$; and Q is =N—, is made to react with, for example, H-L$R^3$, to give a compound of Formula XVI, wherein $R^{12}$ is -L$R^3$, $R^{13}$ is —C(=O)$R^{14a}$, or —C(=O)O$R^{14b}$; and Q is =N—.

In STEP 7, a compound of Formula XVI, wherein $R^{12}$ is -L$R^3$, $R^{13}$ is —C(=O)$R^{14a}$, or —C(=O)O$R^{14b}$; and Q is =N— is deprotected to give a compound of Formula XVI, wherein $R^{12}$ is -L$R^3$, $R^{13}$ is hydrogen; and Q is =N—. For example, when $R^{13}$ is —C(=O)OtBu, a compound of Formula XVI can be treated, for example, with TFA to remove the —C(=O)OtBu group.

In STEP 8, a compound of Formula XVI, wherein $R^{12}$ is -L$R^3$, $R^{13}$ is hydrogen; and Q is =N— is made to react with $R^1$—Cl, $R^1$—OH or similar reagent to give a compound of Formula I, wherein Q is =N—.

In STEP 9, the isomers, e.g., diastereomers and/or enantiomers, of a compound of Formula I, wherein Q is =N— are resolved using chiral chromatography techniques, e.g., by supercritical fluid chromatography (SFC) using a chiral, e.g., CHIRALPAK® ID, column.

Example 1

Synthesis of Intermediates 1A and 1B: (S)-2-(piperazin-2-yl)acetonitrile (TFA Salt) and (R)-2-(piperazin-2-yl)acetonitrile (TFA Salt)

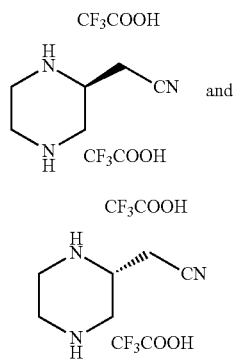

Step 1: 4-bromobut-2-enenitrile

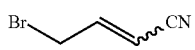

To a solution of but-3-enenitrile (52.9 g, 788 mmol) in a mixed solvent of t-BuOH (75 mL) and Hexane (300 mL) was added a solution of bromine (126.0 g, 788 mmol) in t-BuOH (75 mL) at 15° C. over 30 min, and the reaction mixture was stirred at room temperature for 2 h. After removal of the volatiles under reduced pressure, the residue was purified by silica gel column chromatoghraphy (hexane:ethyl actetate=4:1) to afford the title compound (115 g, quantitatively) as a slight yellow oil.

Step 2: 2-(1,4-dibenzylpiperazin-2-yl)acetonitrile

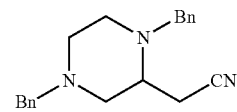

Under Ar at 0° C., to a solution of $N^1,N^2$-di benzyl ethane-1,2-diamine (107 g, 445 mmol) and Et$_3$N (90 g, 890 mmol) in dry toluene (400 mL) was dropwise added a solution of 4-bromobut-2-enenitrile (Step 1, 65.0 g, 445 mmol) in dry toluene (150 mL). The reaction mixture was stirred at room temperature overnight. After removal of the volatiles under reduced pressure, the residue was purified by silica gel column chromatoghraphy (hexane:ethyl acetate=4:1) to afford the title compound (68 g, 50%) as a yellow solid. $^1$H NMR (400 MHz, CDCl$_3$) δ 7.40-7.22 (m, 10H), 3.81 (d, J=13.3 Hz, 1H), 3.59-3.45 (m, 3H), 3.07-2.98 (m, 1H), 2.91 (dd, J=16.6, 8.0 Hz, 1H), 2.71-2.54 (m, 4H), 2.54-2.37 (m, 3H).

Step 3: 2-(piperazin-2-yl)acetonitrile dihydrochloride

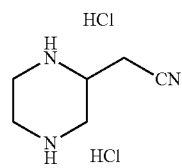

Under Ar at 0° C., to a solution of 2-(1,4-dibenzylpiperazin-2-yl)acetonitrile (Step 2, 52 g, 170 mmol) in DCE (300 mL) was added AcCl (97 g, 681 mmol) dropwise over 30 minutes. The reaction mixture was stirred at 85° C. for 24 h. After cooling down to room temperature and removal of the volatiles under reduced pressure, the residue was recrystallized with EtOH and water to afford the title compound as an off-white solid (23.0 g, 68%). $^1$H NMR (400 MHz, D$_2$O) δ 4.08-3.97 (m, 1H), 3.89-3.68 (m, 3H), 3.53-3.29 (m, 3H), 3.15 (d, J=6.1 Hz, 2H).

Step 4: tert-butyl 3-(cyanomethyl)piperazine-1-carboxylate

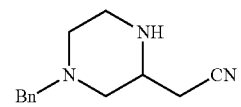 [SMILES: N#CCC1CN(Cc2ccccc2)CCN1]

Under Ar, to a solution of 2-(piperazin-2-yl)acetonitrile dihydrochloride (Step 3, 46 g, 0.23 mol) in MeOH (400 mL) was added Et$_3$N (78 g, 1.16 mol) and Boc$_2$O (51 g, 0.23 mol) at −15° C.; and the reaction mixture was stirred at 0° C. for 2 h. After removal of the volatiles under reduced pressure, the residue was purified by silica gel column chromatoghraphy (hexane:ethyl acetate=1:1) to afford the title compound (31.4 g, 63%) as a light yellow oil. $^1$H NMR (400 MHz, Chloroform-d) δ 4.00-3.95 (m, 1H), 3.91-3.82 (m, 1H), 3.09-2.91 (m, 3H), 2.89-2.58 (m, 2H), 2.57-2.40 (m, 2H), 1.81 (s, 1H), 1.49 (s, 9H).

Step 5: tert-butyl (S)-3-(cyanomethyl)piperazine-1-carboxylate and tert-butyl (R)-3-(cyanomethyl)piperazine-1-carboxylate

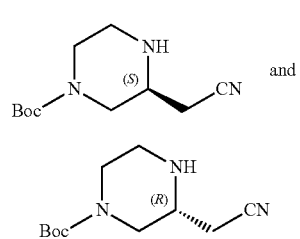

Isomer A and

Isomer B tert-Butyl 3-(cyanomethyl)piperazine-1-carboxylate (Step 4, 31.4 g) was subjected to chiral SFC resolution with CHIRALCEL® AY-H column to provide the title compounds (Isomer A: 14.9 g, 100% ee; Isomer B: 14.8 g, 99.7% ee) as white solid.

Step 6: (S)-2-(piperazin-2-yl)acetonitrile (TFA Salt) (Intermediate 1A)

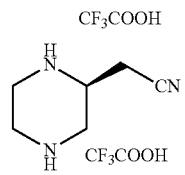

Tert-butyl (S)-3-(cyanomethyl)piperazine-1-carboxylate (Isomer A of Step 5, 2.2 g, 9.77 mmol) was dissolved in a mixed solvent of DCM (30 ml) and TFA (6 mL), and the reaction mixture was stirred at room temperature for 1 h. After removal of volatiles under reduced pressure, the title compound (3.5 g, quantitatively) as a white solid was directly used for the next step without purification. MS: 126.3 (M+H$^+$).

Step 7: (R)-2-(piperazin-2-yl)acetonitrile (TFA Salt) (Intermediate 1B)

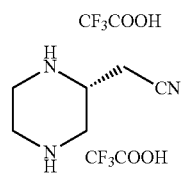

Tert-butyl (R)-3-(cyanomethyl)piperazine-1-carboxylate (Isomer B of Step 5, 1.1 g, 9.77 mmol) was dissolved in a mixed solvent of DCM (30 ml) and TFA (6 mL), and the reaction mixture was stirred at room temperature for 1 h. After removal of volatiles under reduced pressure, the title compound (1.7 g, quantitatively) as a white solid was directly used for the next step without purification. MS: 126.3 (M+H$^+$).

Example 2

Synthesis of Intermediate 2: 3',4'-dihydro-2'H-spiro[cyclohexane-1,1'-naphthalen]-3-one

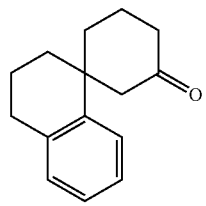

intermediate 2

Step 1: 1-allyl-2-bromobenzene

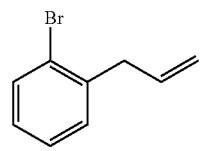

Under Ar at −78° C., to a solution of 1-bromo-2-(bromomethyl)benzene (100 g, 400 mmol) and 2,2'-bipyridine (6.25 g, 40 mmol) in dry toluene (350 mL) was added copper(I) iodide (7.62 g, 40 mmol) and vinylmagnesium bromide (1.1 L, 1.1 mol, 1 N solution in THF) subsequently and slowly. After the addition, the reaction mixture was stirred at room temperature overnight. Sat. NH$_4$Cl (100 mL) was added to quench the reaction, and the resulting mixture was extracted with EA twice. The combined organic layers were dried over Na$_2$SO$_4$, concentrated under reduce pressure to afford a brown oil, and purified by silica gel column chromatoghraphy (eluted with ethyl acetate and hexane from 0 to 5%) to afford the title compound (38 g, 48%) as a colourless oil. $^1$H NMR (400 MHz, CDCl$_3$) δ 7.61-7.54 (m, 1H), 7.32-7.18 (m, 2H), 7.17-7.04 (m, 1H), 6.08-5.93 (m, 1H), 5.22-5.01 (m, 2H), 3.58-3.50 (m, 2H).

Step 2: 2'-allyl-5,6-dihydro-[1,1'-biphenyl]-3(4H)-one

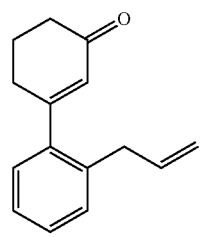 [SMILES: C=CCc1ccccc1C1=CC(=O)CCC1]

Under Ar, a mixture of 1-allyl-2-bromobenzene (Step 1, 15 g, 76 mmol), 3-(4,4,5,5-tetramethyl-1,3,2-dioxaborolan-2-yl)cyclohex-2-en-1-one (16.9 g, 76 mmol), PdCl₃(dppf)-CH₂Cl₂ adduct (3.11 g, 3.81 mmol), and Na₂CO₃ (24.20 g, 228 mmol) in a mixed solvent of DME (160 mL) and H₂O (40 mL) was stirred at 90° C. for 1 h. After cooling down to room temperature, H₂O (200 mL) was added and the resulting mixture was extracted with EA twice. The combined the organic layers were dried over Na₂SO₄, concentrated under reduced pressure to give a brown oil, and purified by silica gel column chromatoghraphy (eluted with ethyl acetate/hexane from 0% to 20%) to afford the title compound (11.3 g, 44%) as a colourless oil. ¹H NMR (400 MHz, CDCl₃) δ 7.37-7.20 (m, 3H), 7.17-7.08 (m, 1H), 6.05-5.98 (m, 1H), 6.01-5.84 (m, 1H), 5.13-5.04 (m, 1H), 5.06-4.94 (m, 1H), 3.43-3.34 (m, 2H), 2.69-2.55 (m, 2H), 2.56-2.46 (m, 2H), 2.23-2.08 (m, 2H).

Step 3: 3-(2-allylphenyl)-3-vinylcyclohexan-1-one and 3-(2-(prop-1-en-1-yl)phenyl)-3-vinylcyclo-hexan-1-one

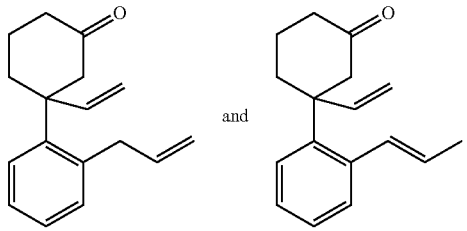 [SMILES: C=CCc1ccccc1C1(C=C)CCCC(=O)C1 ; C=CC1(c2ccccc2/C=C/C)CCCC(=O)C1]

Under Ar at −78° C., to a mixture of copper(I) iodide (22.88 g, 120 mmol) and LiCl (5.09 g, 120 mmol) in dry THF (300 mL) was added vinylmagnesium bromide (40 g, 304 mmol) dropwise over 30 min. The mixture was stirred at −78° C. for another 30 min. A solution of 2'-allyl-5,6-dihydro-[1,1'-biphenyl]-3(4H)-one (Step 2, 17 g, 80 mmol) in dry THF (70 mL) was added dropwise. The reaction mixture was stirred at −78° C. for 1 h and allowed to warm up to room temperature for 2 h. Sat. NH₄Cl (100 mL) was added to quench the reaction and the resulting mixture was extracted with ethyl acetate twice. The combined organic layers were dried over Na₂SO₄, concentrated under reduced pressure to give a brown oil, and purified by silica gel column chromatoghraphy (eluted with ethyl acetate/hexane from 0% to 15%) to afford the title compounds (9 g, 47%) as an inseparable mixture.
MS: 241.4 (M+H⁺).

Step 4: 4'H-spiro[cyclohexane-1,1'-naphthalen]-3-one and spiro[cyclohexane-1,1'-inden]-3-one

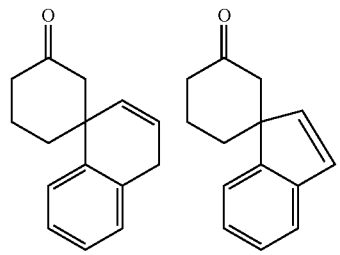

Under Ar, to a solution of 3-(2-allylphenyl)-3-vinylcyclohexan-1-one and 3-(2-(prop-1-en-1-yl)phenyl)-3-vinylcyclohexan-1-one (Step 3, 9 g, 37.4 mmol) in dry DCM (200 mL) was added Grubbs-II reagent (795 mg, 0.94 mmol) in small portions. The reaction mixture was stirred at room temperature for overnight. After removal of the volatiles under reduced pressure, the residue was purified by silica gel column and eluted with ethyl acetate/hexane from 0% to 10% to afford the two title compounds:
(4'H-Spiro[cyclohexane-1,1'-naphthalen]-3-one (5 g, 63%) as light yellow oil; ¹H NMR (400 MHz, Chloroform-d) δ 7.39 (d, J=7.9 Hz, 1H), 7.32-7.16 (m, 3H), 6.06-5.96 (m, 1H), 5.82 (dt, J=10.1, 2.1 Hz, 1H), 3.45-3.39 (m, 2H), 2.95 (d, J=13.7 Hz, 1H), 2.55-2.48 (m, 2H), 2.47-2.39 (m, 1H), 2.14-1.92 (m, 3H), 1.90-1.80 (m, 1H).
MS: 213.4 (M+H⁺); and
Spiro[cyclohexane-1,1'-inden]-3-one (1.2 g, 16%) as light yellow oil. ¹H NMR (400 MHz, CDCl₃) δ 7.39-7.19 (m, 4H), 6.76 (d, J=5.6 Hz, 1H), 6.49 (d, J=5.6 Hz, 1H), 2.76 (d, J=13.7 Hz, 1H), 2.65-2.52 (m, 2H), 2.37-2.24 (m, 1H), 2.20-2.10 (m, 2H), 2.09-1.98 (m, 1H), 1.70-1.66 (m, 1H).
MS: 199.3 (M+H⁺).

Step 5: 3',4'-dihydro-2'H-spiro[cyclohexane-1,1'-naphthalen]-3-one (Intermediate 2)

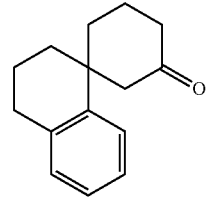 [SMILES: O=C1CCCC2(CCCc3ccccc32)C1]

Under Ar, to a solution of 4'H-spiro[cyclohexane-1,1'-naphthalen]-3-one (Step 4, 5 g, 23.6 mmol) in MeOH (70 mL) was added Pd/C (500 mg) at room temperature, then H₂ was introduced and the reaction mixture was stirred for 4 h. After filtration through celite and removal of the volatiles under reduced pressure, the crude title compound (5.0 g) as a colorless oil was directly used for the next step without purification. ¹H NMR (400 MHz, CDCl₃) δ 7.41 (d, J=7.9, 1.3 Hz, 1H), 7.27-7.05 (m, 3H), 2.82-2.70 (m, 3H), 2.50-2.37 (m, 3H), 2.25-2.15 (m, 1H), 2.07-1.88 (m, 2H), 1.87-1.61 (m, 5H).

Example 3

Synthesis of Intermediate 3: 2',3'-dihydrospiro[cyclohexane-1,1'-inden]-3-one

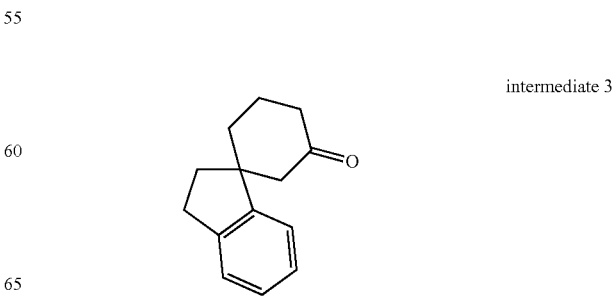

intermediate 3

Under Ar, to a solution of spiro[cyclohexane-1,1'-inden]-3-one (from intermediate 2, step 4; 1.2 g, 6 mmol) in MeOH (10 mL) was added Pd/C (150 mg) at room temperature, then H₂ was introduced and the reaction mixture was stirred for 4 h. After filtration through celite and removal of the volatiles under reduced pressure, the crude title compound (1.2 g) as a colorless oil was directly used for the next step without purification as a crude product.

MS: 201.3 [M+H⁺].

Example 4

Synthesis of Intermediate No. 21: Spiro[cyclohexane-1,1'-isochroman]-3-one

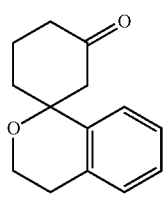 [SMILES: O=C1CCCC2(C1)OCCc1ccccc12]

Step 1: (2-Bromophenethoxy)(tert-butyl)dimethylsilane

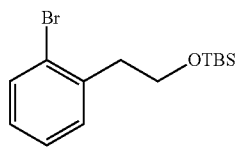 [SMILES: CC(C)(C)[Si](C)(C)OCCc1ccccc1Br]

Under Ar, to a solution of 2-(2-bromophenyl)ethan-1-ol (15 g, 74.6 mmol) in dry DCM (80 mL) was added imidazole (6.09 g, 90 mmol) and TBSCl (13.49 g, 90 mmol) at 0° C., and the reaction mixture was stirred at 0° C. for 2 h. After removal of the volatiles under reduced pressure, the residue was purified by silica gel column chromatoghraphy (hexane) to afford the title compound (16 g, 68%) as a colorless oil.

Step 2: 1,4-Dioxaspiro[4.5]decan-7-one

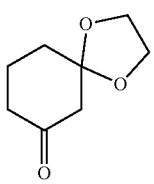 [SMILES: O=C1CCCC2(C1)OCCO2]

Under Ar, to a solution of cyclohexane-1,3-dione (20 g, 178 mmol) in THF (200 mL) was added ethane-1,2-diol (9.41 g, 152 mmol) and cat. TsOH.H₂O, and the reaction mixture was refluxed with Dean-Stark apparatus for 1.5 h. After cooling to room temperature and removal of the volatiles under reduced pressure, the residue was partitioned with aq. NaHCO₃ and DCM, the DCM layer was separated, washed with brine, dried over Na₂SO₄, and concentrated under reduced pressure to afford a yellow oil, which was purified by silica gel column (hexane:ethyl acetate=3:1) to afford the title compound (7 g, 25%) as a colorless liquid. ¹H NMR (400 MHz, CDCl₃): δ 3.98-3.90 (m, 4H), 2.57 (s, 2H), 2.33-2.30 (m, 2H), 1.88-1.82 (m, 4H); MS: 157.1 (M+H⁺).

Step 3: 7-(2-(2-((tert-butyldimethylsilyl)oxy)ethyl)phenyl)-1,4-dioxaspiro[4.5]decan-7-ol

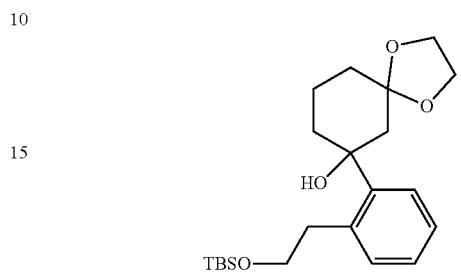

Under Ar, to a solution of (2-bromophenethoxy)(tert-butyl)dimethylsilane (Step 1, 15 g, 47.6 mmol) in dry THF (80 mL) was added BuLi (20.92 mL, 52.3 mmol, 2.5 M in hexane) at −78° C., then the mixture was stirred at −78° C. for 30 min. A solution of 1,4-dioxaspiro[4.5]decan-7-one (Step 2, 7.43 g, 47.6 mmol) in dry THF (10 mL) was added slowly, and the reaction mixture was stirred at −78° C. for 2 h. Aq. NH₄Cl was added to quench the reaction and the resulting mixture was extracted with EA twice. The combined EA layers were washed with brine, dried over Na₂SO₄, and concentrated under reduced pressure to afford a yellow oil, that was purified by silica gel column chromatoghraphy (hexane:ethyl acetate=5:1) to afford the title compound (11 g, 59%) as a colorless oil. ¹H NMR (400 MHz, CDCl₃): δ 7.35 (d, J=7.2 Hz, 1H), 7.23 (d, J=7.2 Hz, 1H), 7.19-7.12 (m, 2H), 4.56 (s, 1H), 4.06-3.96 (m, 4H), 3.87 (t, J=7.6 Hz, 2H), 3.22 (t, J=7.6 Hz, 2H), 2.17-1.97 (m, 4H), 1.86-1.70 (m, 3H), 1.63-1.56 (m, 1H), 0.89 (s, 9H), 0.03 (s, 6H). MS: 415.8 (M+Na⁺).

Step 4: 7-(2-(2-hydroxyethyl)phenyl)-1,4-dioxaspiro[4.5]decan-7-ol

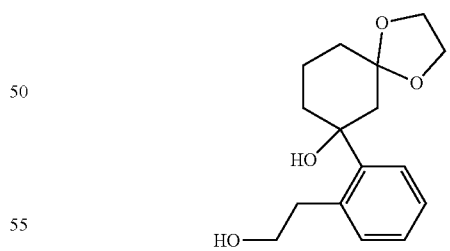

Under Ar, to a solution of 7-(2-(2-((tert-butyldimethylsilyl)oxy)ethyl)phenyl)-1,4-dioxaspiro[4.5]decan-7-ol (Step 3, 11 g, 28 mmol) in dry THF (40 mL) was added TBAF-3H₂O (7.33 g, 28.0 mmol) in small portions, and then the reaction mixture was stirred at room temperature for 1 h. After removal of the volatiles under reduced pressure, the residue was partitioned with water and ethyl acetate. The organic layer was separated, washed with brine, dried over Na₂SO₄, and concentrated under reduced pressure to afford a yellow oil, which was purified by silica gel column chromatoghraphy (hexane:ethyl acetate=1:1) to afford the title compound (7.8 g, quantitatively) as a colorless oil. MS: 301.4 (M+Na⁺).

Step 5: Dispiro[isochromane-1,1'-cyclohexane-3',2''-[1,3]dioxolane]

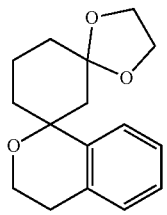 [SMILES: c1ccc2c(c1)CCOC21CCCC2(C1)OCCO2]

Under Ar, to a solution of 7-(2-(2-hydroxyethyl)phenyl)-1,4-dioxaspiro[4.5]decan-7-ol (Step 4, 4 g, 14.37 mmol) in dry THF (50 mL) was added BuLi (6 mL, 15 mmol, 2.5 M in hexane) at −50° C., then the mixture was stirred at −50° C. for 1 h. A solution of TsCl (3 g, 15.81 mmol) in dry THF (3 mL) was added slowly, and the reaction mixture was stirred at 0° C. for 30 min. The reaction mixture was cooled back down to −50° C., and 2$^{nd}$ batch of BuLi (6 mL, 15 mmol, 2.5 M in hexane) was added. The reaction mixture was stirred at 25° C. for 16 h. Aq. NH₄Cl was added to quench the reaction and the resulting mixture was extracted with ethyl acetate three times. The combined organic layers were washed with brine (100 mL), dried over Na₂SO₄, and concentrated under reduced pressure to afford a yellow oil that was purified by silica gel column (hexane:ethyl acetate=3:1) to afford the title compound (3.14 g, 84%) as a colorless oil. ¹H NMR (400 MHz, CDCl₃): δ 7.19-7.06 (m, 4H), 4.11-3.81 (m, 6H), 2.91-2.73 (m, 2H), 2.20-1.90 (m, 5H), 1.67-1.54 (m, 3H); MS: 261.3 (M+H⁺).

Step 6: Spiro[cyclohexane-1,1'-isochroman]-3-one (Intermediate No. 21)

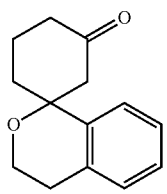 [SMILES: O=C1CCCC2(C1)OCCc1ccccc12]

To a solution of dispiro[isochromane-1,1'-cyclohexane-3',2''-[1,3]dioxolane] (Step 5, 3.25 g, 12.48 mmol) in acetone (20 mL) was added HCl (2M, 5 mL), and then the reaction mixture was stirred at room temperature for 2 h. After removal of the volatiles under reduced pressure, the residue was partitioned with aq. NaHCO₃ and ethyl acetate. The organic layer was separated, washed with brine, dried over Na₂SO₄, and concentrated under reduced pressure to afford a yellow oil, which was purified by silica gel column chromatoghraphy (hexane:ethyl acetate=3:1) to afford the title compound (2.19 g, 81%) as a white solid.
¹H NMR (400 MHz, CDCl₃): δ 7.24-7.10 (m, 4H), 3.93-3.83 (m, 2H), 2.88-2.75 (m, 2H), 2.72 (s, 2H), 2.50-2.34 (m, 2H), 2.22-2.07 (m, 3H), 1.99-1.94 (m, 1H); MS: 217.5 (M+H⁺).

Example 5

Synthesis of Intermediate No. 22: 7'-fluoro-3',4'-dihydro-2'H-spiro[cyclohexane-1,1'-naphthalen]-3-one

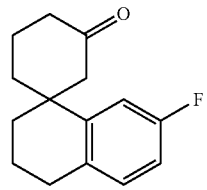 [SMILES: O=C1CCCC2(CCCc3ccc(F)cc32)C1]

Step 1: 2-bromo-1-(bromomethyl)-4-fluorobenzene

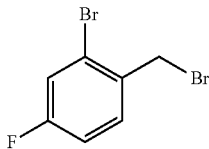

Under Ar, a mixture of 2-bromo-4-fluoro-1-methylbenzene (40 g, 212 mmol), NBS (37.7 g, 212 mmol), and benzoyl peroxide (1.025 g, 4.23 mmol) in CCl₄ (400 mL) was stirred for 14 h at 85° C. After the reaction, the resulting mixture was concentrated under reduced pressure to give the crude product that was purified by silica gel column chromatoghraphy (eluted with heptane) to give the title compound (36 g, 63.5%) as a white solid. ¹H NMR (400 MHz, Chloroform-d) δ 7.47 (dd, J=8.6, 5.8 Hz, 1H), 7.35 (dd, J=8.2, 2.6 Hz, 1H), 7.05 (ddd, J=8.6, 7.9, 2.6 Hz, 1H), 4.60 (s, 2H).

Step 2: 7'-fluoro-3',4'-dihydro-2'H-spiro[cyclohexane-1,1'-naphthalen]-3-one (Intermediate No. 22)

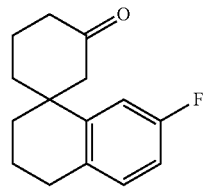 [SMILES: O=C1CCCC2(CCCc3ccc(F)cc32)C1]

Intermediate No. 22 was prepared essentially the same protocol of preparation of Intermediate 2 with 2-bromo-1-(bromomethyl)-4-fluorobenzene (Step 1) in place of 1-bromo-2-(bromomethyl)benzene (Intermediate 2; step 1) to afford the title compound (500 mg) as a colorless oil. ¹H NMR (400 MHz, Chloroform-if) δ 7.13-7.01 (m, 2H), 6.85 (td, J=8.3, 2.7 Hz, 1H), 2.74 (q, J=5.9 Hz, 2H), 2.67 (d, J=13.8 Hz, 1H), 2.52-2.34 (m, 3H), 2.14 (td, J=13.1, 4.2 Hz, 1H), 2.08-2.02 (m, 1H), 2.00-1.87 (m, 1H), 1.85-1.67 (m, 3H), 1.63-1.55 (m, 1H), 1.37-1.23 (m, 1H); MS: 233.3 (M+H⁺).

Example 6

Synthesis of Intermediate No. 23: 6'-methyl-2',3'-dihydrospiro[cyclohexane-1,1'-inden]-3-one

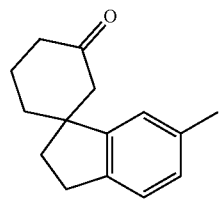 [SMILES: Cc1ccc2c(c1)C1(CCCC(=O)C1)CC2]

Step 1: 2-bromo-4-methyl-1-vinylbenzene

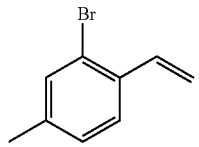

Under Ar, to a solution of methyltriphenylphosphinium bromide (21.54 g, 60.3 mmol) in THF (125 mL) was added n-butyllithium (56.3 mmol, in hexane) dropwise over 15 mins, and the resulting solution was stirred at 0° C. for 1 h. 2-bromo-4-methylbenzaldehyde (10 g, 50.2 mmol) in THF (75 mL) was added to the mixture dropwise over 15 mins, and the mixture was stirred at RT overnight. Saturated NH$_4$Cl (100 mL) was added and the mixture was extracted with ethyl acetate (100 mL×3). The combined organic layers were dried over Na$_2$SO$_4$, concentrated under reduced pressure, and purified by silica gel column chromatoghraphy (eluted with heptane) to give the title compound (8.3 g, 84%) as a light yellow oil. $^1$H NMR (400 MHz, Chloroform-d) δ 7.47 (d, J=7.9 Hz, 1H), 7.42-7.38 (m, 1H), 7.13-7.09 (m, 1H), 7.04 (dd, J=17.4, 11.0 Hz, 1H), 5.68 (dd, J=17.4, 1.1 Hz, 1H), 5.33 (dd, J=10.9, 1.1 Hz, 1H), 2.34 (s, 3H).

Step 2: 5'-methyl-2'-vinyl-5,6-dihydro-[1,1'-biphenyl]-3(4H)-one

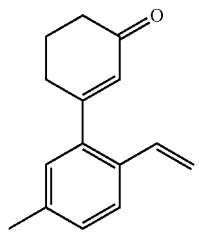 [SMILES: C=Cc1ccc(C)cc1C1=CC(=O)CCC1]

Under Ar, a mixture of 1-allyl-2-bromo-4-methylbenzene (8.3 g, 39.3 mmol, step 1), 3-(4,4,5,5-tetramethyl-1,3,2-dioxaborolan-2-yl)cyclohex-2-en-1-one (8.73 g, 39.3 mmol), 1-allyl-2-bromo-4-methylbenzene (8.3 g, 39.3 mmol), PdCl$_2$(dppf)-CH$_2$Cl$_2$ adduct (1.605 g, 1.966 mmol) and Na$_2$CO$_3$ (12.50 g, 118 mmol) in DME (100 mL) and water (25.00 mL) was stirred at 90° C. for 2 h. After the reaction, the volatiles were removed under reduced pressure to give a black crude product that was purified by silica gel column chromatoghraphy (eluted with EA/Heptane from 0-30%) to give the title compound (6 g, 67.4%) as a yellow oil. $^1$H NMR (400 MHz, Chloroform-d) δ 7.48 (d, J=7.9 Hz, 1H), 7.17 (d, J=8.2, 1.8 Hz, 1H), 6.99 (d, J=1.7 Hz, 1H), 6.72 (dd, J=17.4, 11.0 Hz, 1H), 6.07-6.01 (m, 1H), 5.68 (d, J=17.5, 1.1 Hz, 1H), 5.26 (d, J=10.9, 1.1 Hz, 1H), 2.62 (t, J=6.0, 1.6 Hz, 2H), 2.56-2.48 (m, 2H), 2.38 (s, 3H), 2.26-2.11 (m, 2H).

Step 3: 3-(5-methyl-2-vinylphenyl)-3-vinylcyclohexan-1-one

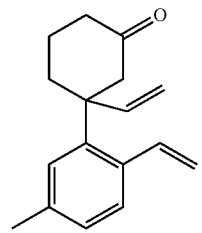 [SMILES: C=Cc1ccc(C)cc1C1(C=C)CCCC(=O)C1]

Under Ar, to a suspension of copper(I) iodide (4.84 g, 25.4 mmol) and LiCl (1.08 g, 25.4 mmol) in THF (50 mL) was added vinylmagnesium bromide (51.0 mmol) dropwise over 30 mins at −78° C. The reaction mixture was stirred for 1 h at −78° C., and 5'-methyl-2'-vinyl-5,6-dihydro-[1,1'-biphenyl]-3(4H)-one (3.6 g, 16.96 mmol, step 2) in THF (30 mL) was added to the mixture dropwise over 40 min. The reaction was stirred 1 h at −78° C., and saturated NH$_4$Cl was added to the reaction mixture. The mixture was extracted twice with ethyl acetate, and the combined organic layers were concentrated to give the crude product that was purified by silica gel column chromatoghraphy (eluted with ethyl acetate/hexane from 5% to 30%) to give the title compound (3.0 g, 73.6%) as a light yellow oil. $^1$H NMR (400 MHz, Chloroform-J) δ 7.36 (d, J=7.8 Hz, 1H), 7.26 (dd, J=17.3, 10.9 Hz, 1H), 7.16 (s, 1H), 7.10-7.05 (m, 1H), 6.02 (dd, J=17.5, 10.7 Hz, 1H), 5.45 (d, J=17.3, 1.7 Hz, 1H), 5.21-5.13 (m, 2H), 4.99 (d, J=17.6, 0.8 Hz, 1H), 2.83-2.68 (m, 2H), 2.62-2.51 (m, 1H), 2.36 (s, 3H), 2.45-2.24 (m, 2H), 2.12-2.01 (m, 1H), 1.94-1.80 (m, 1H), 1.63-1.51 (m, 1H).

Step 4: 6'-methylspiro[cyclohexane-1,1'-inden]-3-one

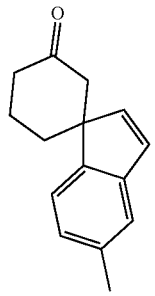 [SMILES: Cc1ccc2c(c1)C=CC21CCCC(=O)C1]

Under Ar, a mixture of 3-(5-methyl-2-vinylphenyl)-3-vinylcyclohexan-1-one (3 g, 12.48 mmol, step 3) and Grubbs-II reagent (0.530 g, 0.624 mmol) in DCM (5 mL) was stirred at RT for 5 h. After the reaction, the solvent was removed under reduced pressure to give the residual that was purified by silica gel column chromatoghraphy (eluted with ethyl acetate/hexane from 5% to 30%) to give 6'-methylspiro[cyclohexane-1,1'-inden]-3-one (2.53 g, 95%) as a colorless oil. $^1$H NMR (400 MHz, Chloroform-if) δ 7.23 (d, J=7.6 Hz, 1H), 7.19-7.14 (m, 1H), 7.14-7.07 (m, 1H), 6.72 (d, 0.7=5.6 Hz, 1H), 6.42 (d, 0.7=5.6 Hz, 1H), 2.75 (d, J=13.6 Hz, 1H), 2.64-2.53 (m, 2H), 2.42 (s, 3H), 2.36-2.23 (m, 1H), 2.19-1.97 (m, 3H), 1.69-1.61 (m, 1H). MS: 213.4 (M+H$^+$)

Step 5: 6'-methyl-2',3'-dihydrospiro[cyclohexane-1, 1'-inden]-3-one (Intermediate No. 23)

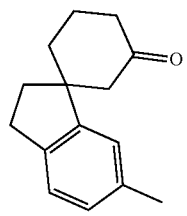 [SMILES: Cc1ccc2c(c1)C1(CCCC(=O)C1)CC2]

Under Ar, to a solution of 4'H-spiro[cyclohexane-1,1'-naphthalen]-3-one (Step 4, 1.86 g, 8.76 mmol) in MeOH (40 mL) was added Pd/C (180 mg) at room temperature. H$_2$ was introduced and the reaction mixture was stirred for 4 h. After filtration through celite and removal of the volatiles under reduced pressure, the crude title compound (1.88 g) as a colorless oil was directly used for the next step without purification. MS: 215.4 (M+H$^+$).

Example 7

Synthesis of 2-((S)-1-acryloyl-4-((R)-2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 1)

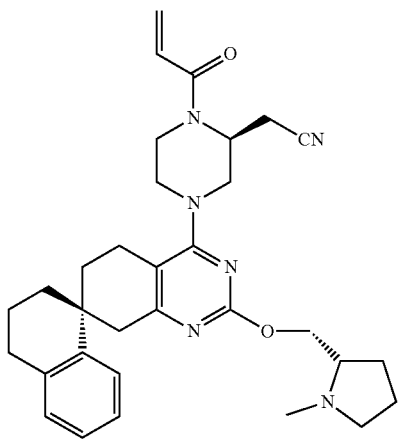

and 2-((S)-1-acryloyl-4-((S)-2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 2)

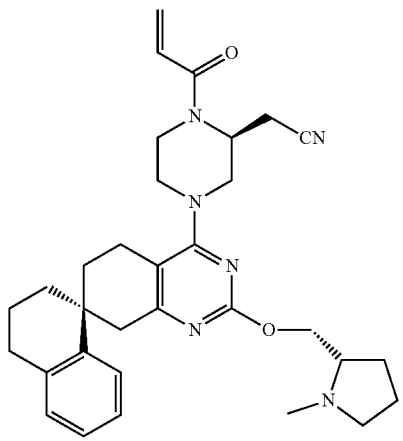

Step 1: Methyl 3-oxo-3',4'-dihydro-2'H-spiro[cyclohexane-1,1'-naphthalene]-4-carboxylate (Intermediate No. 24)

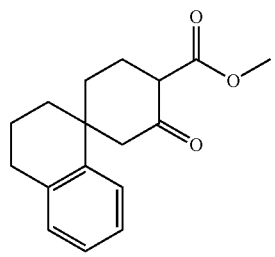 [SMILES: COC(=O)C1CCC2(CCCc3ccccc32)CC1=O]

Under Ar, to a solution of dimethyl carbonate (0.51 g, 117 mmol) in dry THF (40 mL) was added NaH (1.87 g, 46.7 mmol) with small portions, and then the mixture was heated to 70° C. and 4'H-spiro[cyclohexane-1,1'-naphthalen]-3-one (Intermediate 2, 5 g, 23.3 mmol) was added slowly. The reaction mixture was refluxed for 2 h. After cooling down to room temperature, sat. NH$_4$Cl was added to quench the reaction and the resulting mixture was extracted with ethyl acetate twice. The combined organic layers were dried over Na$_2$SO$_4$, and concentrated under reduce pressure to give a yellow oil, which was purified by silica gel column chromatoghraphy (eluted with ethyl acetate/hexane from 5% to 20%) to afford the title compound (5.4 g, 85% over 2 steps) as a light yellow oil. MS: 273.3 (M+H$^+$).

Step 2: 3,4,5',8'-tetrahydro-1'H,2H-spiro[naphthalene-1,7'-quinazoline]-2',4'(3'H,6'H)-dione (Intermediate No. 16)

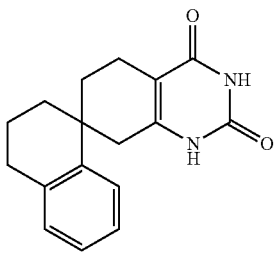

Under Ar, in a dried 100 mL round-bottomed flask, methyl 3-oxo-3',4'-dihydro-2'H-spiro[cyclohexane-1,1'-naphthalene]-4-carboxylate (Step 1, 590 mg, 2.17 mmol) was dissolved into dry DMF (7 mL), and guanidine hydrochloride (621 mg, 6.50 mmol) and K$_2$CO$_3$ (988 mg, 7.15 mmol) were added. The reaction mixture was stirred at 85° C. for 2 h. After cooling down to room temperature, the mixture was filtered and the filtrate was treated with H$_2$O (20 mL). AcOH was added to adjust to pH=6, and the formed 2'-amino-3,4,5',8'-tetrahydro-2H,3'H-spiro[naphthalene-1,7'-quinazolin]-4'(6'H)-one (600 mg) was collected as a white solid that was directly used for the next step without purification.

The 2'-amino-3,4,5',8'-tetrahydro-2H,3'H-spiro[naphthalene-1,7'-quinazolin]-4'(6'H)-one (720 mg, 2.56 mmol) was re-dissolved into AcOH (30 ml) under N2. At 70° C., a solution of sodium nitrite (3.5 g, 51.2 mmol) in H$_2$O (10 mL) was added dropwise over 40 minutes, and the reaction mixture was heated at 70° C. for 5 h. After cooling down to room temperature and removal of volatiles under reduced pressure, the residue was treated with H$_2$O (60 mL), and the formed precipitate was collected to afford the crude title product (510 mg) as a light yellow solid, which was directly used for the next step without purification.
MS: 283.1 (M+H$^+$).

Step 3: 2',4'-dichloro-3,4,5',8'-tetrahydro-2H,6'H-spiro[naphthalene-1,7'-quinazoline] (Intermediate No. 1)

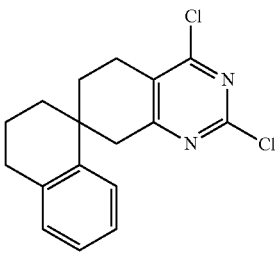 [SMILES: Clc1nc(Cl)c2c(n1)CC1(CCCc3ccccc31)CC2]

The crude 3,4,5',8'-tetrahydro-1'H,2H-spiro[naphthalene-1,7'-quinazoline]-2',4'(3'H,6'H)-dione (Step 2, 510 mg) was dissolved into POCl$_3$ (15 mL) under nitrogen, DIEPA (467 mg, 3.61 mmol) was added slowly, and the reaction mixture was stirred for 1 h at 110° C. After cooling to room temperature and removal of the volatiles under reduced pressure, the residue was re-taken into DCM (20 mL) and the resulting mixture was washed with aq.Na$_2$CO$_3$. The aqueous layer was extracted with DCM twice, the combined DCM layers were dried over Na$_2$SO$_4$, and concentrated under reduced pressure to give a yellow oil, which was purified by silica gel column chromatoghraphy (EA:Heptane=1:7) to afford the title compound (380 mg, 66% over 2 steps) as a white solid. $^1$H NMR (400 MHz, Chloroform-d) δ 7.29-7.11 (m, 4H), 3.20 (d, J=18.8 Hz, 1H), 3.06 (dd, J=18.7, 2.3 Hz, 1H), 3.01-2.89 (m, 1H), 2.88-2.73 (m, 3H), 2.30-2.17 (m, 1H), 2.00-1.91 (m, 1H), 1.90-1.73 (m, 2H), 1.71-1.62 (m, 2H).

Step 4: 2-((2S)-4-(2'-chloro-3,4,5',8'-tetrahydro-2H,6'H-spiro[naphthalene-1,7'-quinazolin]-4'-yl)piperazin-2-yl)acetonitrile (Intermediate No. 6)

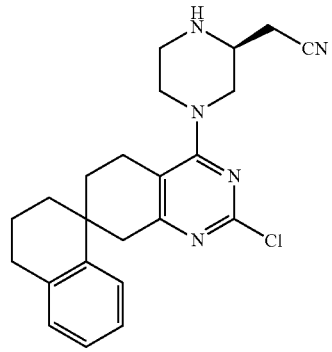 [SMILES: N#CC[C@H]1CN(c2nc(Cl)nc3c2CCC2(CCCc4ccccc42)C3)CCN1]

Under Ar, to a solution of 2',4'-dichloro-3,4,5',8'-tetrahydro-2H,6'H-spiro[naphthalene-1,7'-quinazoline] (Step 3, 820 mg, 2.58 mmol) in dry DMSO (20 mL) was added DIEPA (1.66 g, 12.84 mmol) and (S)-2-(piperazin-2-yl)acetonitrile bis(2,2,2-trifluoroacetate) (Intermediate 1, 902 mg, 2.83 mmol), and then the reaction mixture was stirred at 55° C. for overnight. After cooling to room temperature, H$_2$O (30 mL) was added to the reaction mixture followed by extraction with ethyl acetate three times. The combined organic layers were dried over Na$_2$SO$_4$, and concentrated under reduced pressure to give a yellow oil that was loaded onto a Biotage column and eluted with ethyl acetate/hexane from 0% to 100% to afford the title compound (786 mg, 75%) as a light yellow solid. MS: 408.2 (M+H$^+$).

Step 5: tert-butyl (2S)-4-(2'-chloro-3,4,5',8'-tetrahydro-2H,6'H-spiro[naphthalene-1,7'-quinazolin]-4'-yl)-2-(cyanomethyl)piperazine-1-carboxylate (Intermediate No. 29)

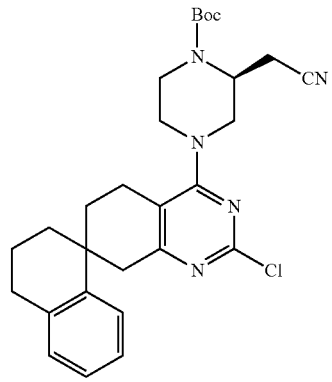 [SMILES: CC(C)(C)OC(=O)N1CCN(c2nc(Cl)nc3c2CCC2(CCCc4ccccc42)C3)C[C@@H]1CC#N]

Under Ar, to a solution of 2-((2S)-4-(2'-chloro-3,4,5',8'-tetrahydro-2H,6'H-spiro[naphthalene-1,7'-quinazolin]-4'-yl)piperazin-2-yl)acetonitrile (Step 4, 370 mg, 0.91 mmol) in dry THF (30 mL) was added Et₃N (184 mg, 1.81 mmol) and Boc₂O (400 mg, 1.81 mmol); and then the reaction mixture was stirred at room temperature for overnight. After removal of volatiles under reduced pressure, the residue was loaded onto a Biotage column and eluted with ethyl acetate/hexane from 0% to 100% to afford the title compound (420 mg, 91%) as a white solid. MS: 508.4 (M+H⁺).

Step 6: tert-butyl (2S)-2-(cyanomethyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazine-1-carboxylate (Intermediate No. 30)

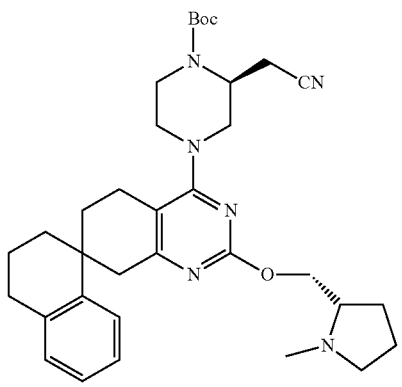

Under Ar, in a dried 100 mL round-bottomed flask, tert-butyl (2S)-4-(2'-chloro-3,4,5',8'-tetrahydro-2H,6'H-spiro[naphthalene-1,7'-quinazolin]-4'-yl)-2-(cyanomethyl)piperazine-1-carboxylate (Step 5, 250 mg, 0.49 mmol) was dissolved into dry toluene (10 mL), and (S)-(1-methylpyrrolidin-2-yl)methanol (110 mg, 0.98 mmol), BINAP (613 mg, 0.098 mmol), sodium tert-butoxide (118 mg, 1.23 mmol, 2.5) and Pd₂(dba)₃ (45.1 mg, 0.05 mmol) were added. The reaction mixture was stirred for 2 h at 110° C. After cooling down to room temperature and removal of the volatiles under reduced pressure, the residue was loaded onto a Biotage column and eluted with ethyl acetate/heptane from 10% to 100% and MeOH/DCM from 0% to 15% to afford the title compound (240 mg, 83%) as a white solid. MS: 587.8 (M+H⁺).

Step 7: 2-((2S)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Intermediate No. 31)

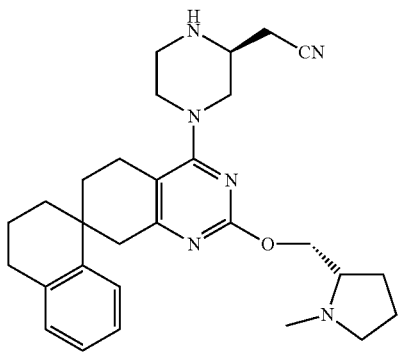

Tert-butyl (2S)-2-(cyanomethyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazine-1-carboxylate (Step 6, 240 mg, 0.41 mmol) was dissolved into a mixed solvent of DCM (6 mL) and TFA (2 mL), and the reaction was stirred at room temperature for 2 h. After removal of the volatiles under reduced pressure, the crude title compound was directly used for the next step without purification. MS: 488.3 (M+H⁺).

Step 8: 2-((2S)-1-acryloyl-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile

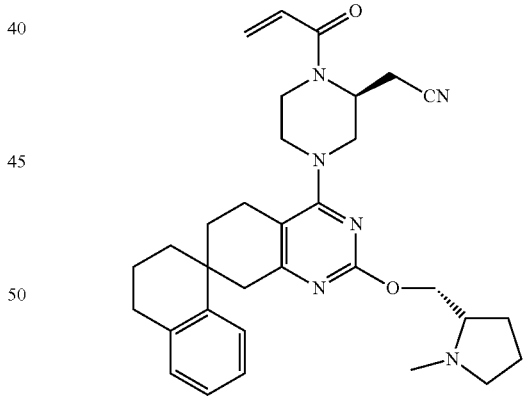

Under Ar, at 0° C. to a solution of the crude 2-((2S)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Step 7, 150 mg, 0.31 mmol) in dry DCM (10 mL) was added Et₃N (62.4 mg, 0.62 mmol) and acryloyl chloride (41.8 mg, 0.46 mmol). The reaction mixture was stirred for 1 h. H₂O was added to quench the reaction and the resulting mixture was extracted with DCM three times. The combined organic layers was washed with aq.NaCl, dried over Na₂SO₄, and concentrated under reduced pressure to give a yellow oil that was loaded onto a Biotage column and eluted with ethyl acetate/heptane from 10% to 100% and MeOH/DCM from 0% to 15% to afford the title compound (100 mg, 60%) as a white solid. MS: 541.4 (M+H$^+$).

Step 9: 2-((S)-1-acryloyl-4-((R)-2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile or 2-((S)-1-acryloyl-4-((S)-2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile 2-((2S)-1-acryloyl-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Step 8, 100 mg) was subjected to chiral SFC resolution using a CHIRALPAK® ID column to provide the title compounds as white solids. The stereochemistry of the asymmetric spirocarbon atom of these compounds has not been determined.

The first eluting stereoisomer (20.2 mg; 99% ee) was arbitrarily designated as Cpd. No. 1 having R stereochemistry at the spirocarbon atom pending further analysis.

$^1$H NMR (400 MHz, DMSO-de, 50° C.) δ 7.42-7.34 (m, 1H), 7.20-7.06 (m, 3H), 6.86 (br s, 1H), 6.20 (dd, J=16.7, 2.3 Hz, 1H), 5.79 (dd, J=10.5, 2.3 Hz, 1H), 4.28 (dd, J=10.8, 4.9 Hz, 1H), 4.06 (dd, J=10.7, 6.4 Hz, 1H), 3.95 (d, J=12.7 Hz, 1H), 3.87 (d, J=13.8 Hz, 1H), 3.30-3.20 (m, 2H), 3.05-2.86 (m, 4H), 2.86-2.61 (m, 5H), 2.58-2.50 (m, 4H), 2.36 (s, 3H), 2.20 (q, J=8.6 Hz, 1H), 2.09 (td, J=12.2, 5.4 Hz, 1H), 2.00-1.89 (m, 1H), 1.87-1.55 (m, 8H). MS: 541.4 (M+H$^+$).

The second eluting stereoisomer (17.4 mg; 99% ee) was arbitrarily designated as Cpd. No. 2 having S stereochemistry at the spirocarbon atom pending further analysis.

$^1$H NMR (400 MHz, DMSO-de, 50° C.) δ 7.36-7.28 (m, 1H), 7.20-7.08 (m, 3H), 6.86 (dd, J=16.7, 10.5 Hz, 1H), 6.20 (dd, J=16.7, 2.3 Hz, 1H), 5.79 (dd, J=10.5, 2.3 Hz, 1H), 4.27 (dd, J=10.7, 4.9 Hz, 1H), 4.08 (dd, J=10.8, 6.3 Hz, 1H), 3.94 (d, J=13.4 Hz, 1H), 3.81 (d, J=12.7 Hz, 1H), 3.30-3.20 (m, 1H), 3.12-2.90 (m, 5H), 2.86-2.67 (m, 4H), 2.63-2.52 (m, 5H), 2.37 (s, 3H), 2.21 (q, J=8.6 Hz, 1H), 2.14-2.03 (m, 1H), 2.03-1.90 (m, 1H), 1.88-1.56 (m, 8H). MS: 541.4 (M+H$^+$).

Example 8

Synthesis of 2-((2R)-1-acryloyl-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 3)

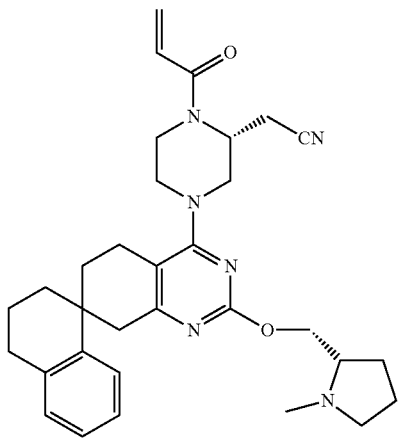

Cpd. No. 3 was prepared essentially the same protocol described in EXAMPLE 7 with (R)-2-(piperazin-2-yl)acetonitrile (TFA Salt) (Intermediate 1B) in place of (S)-2-(piperazin-2-yl)acetonitrile bis(2,2,2-trifluoroacetate) to afford the title compound (3 mg) as a white solid. MS: 541.4 (M+H$^+$).

Example 9

Synthesis of 2-((S)-1-acryloyl-4-((R)-2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 4)

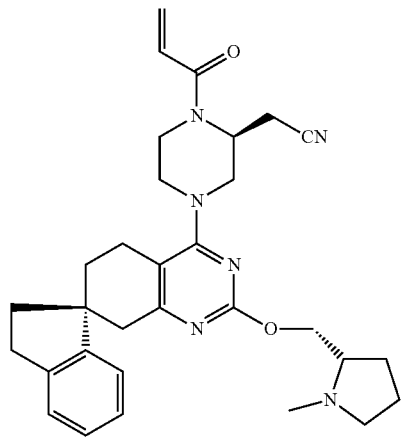

and 2-((S)-1-acryloyl-4-((S)-2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 5)

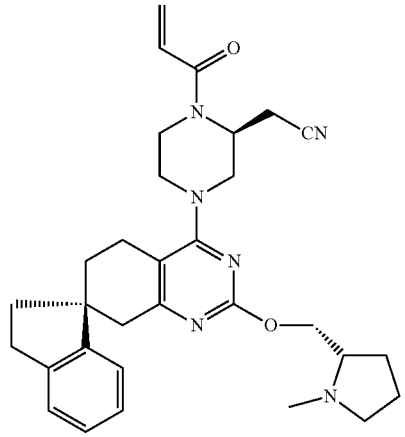

Cpd. Nos. 4 and 5 were prepared using essentially the same protocol as in EXAMPLE 7 with 2',3'-dihydrospiro[cyclohexane-1,1'-inden]-3-one (Intermediate 3) in place of 3',4'-dihydro-2'H-spiro[cyclohexane-1,1'-naphthalen]-3-one to afford the the title compounds as white solids. The stereochemistry of the asymmetric spirocarbon atom of these compounds has not been determined.

The first eluting stereoisomer (41.6 mg; 100% ee) was arbitrarily designated as Cpd. No. 4 having R stereochemistry at the spirocarbon atom pending further analysis. $^1$H NMR (400 MHz, DMSO-d$_6$, 50° C.) δ 7.30-7.23 (m, 1H), 7.22-7.15 (m, 3H), 6.93-6.78 (m, 1H), 6.20 (dd, J=16.7, 2.3 Hz, 1H), 5.78 (dd, J=10.5, 2.3 Hz, 1H), 4.28 (dd, J=10.7, 4.9 Hz, 1H), 4.06 (dd, J=10.7, 6.4 Hz, 1H), 3.98-3.84 (m, 2H), 3.24-3.16 (m, 1H), 3.06-2.85 (m, 5H), 2.83-2.64 (m, 4H), 2.59-2.52 (m, 5H), 2.36 (s, 3H), 2.20 (q, J=8.6 Hz, 1H), 2.10-1.88 (m, 4H), 1.79-1.54 (m, 4H). MS: 527.5 (M+H$^+$).

The second eluting stereoisomer (38.7 mg; 99.12% ee) was arbitrarily designated as Cpd. No. 5 having S stereochemistry at the spirocarbon atom pending further analysis. $^1$H NMR (400 MHz, DMSO-d$_6$, 50° C.) δ 7.29-7.25 (m, 1H), 7.24-7.09 (m, 3H), 6.93-6.79 (m, 1H), 6.20 (dd, J=16.7, 2.3 Hz, 1H), 5.79 (dd, J=10.5, 2.3 Hz, 1H), 4.27 (dd, J=10.8, 4.9 Hz, 1H), 4.09 (dd, J=10.7, 6.3 Hz, 1H), 3.92 (d, J=13.5 Hz, 1H), 3.83 (d, J=13.0 Hz, 1H), 3.25-3.07 (m, 2H), 3.06-2.87 (m, 5H), 2.83-2.69 (m, 3H), 2.63-2.53 (m, 5H), 2.37 (s, 3H), 2.21 (q, J=8.6 Hz, 1H), 2.08-1.88 (m, 4H), 1.76-1.56 (m, 4H).
MS: 527.5 (M+H$^+$)

Example 10

Synthesis of 2-((2S)-1-acryloyl-4-(2'-(((S)-1-methylpyrrolidin-2-yl)methoxy)-5',8'-dihydro-6'H-spiro[isochromane-1,7'-quinazolin]-4'-yl)piperazin-2-yl)acetonitrile (Cpd. No. 6)

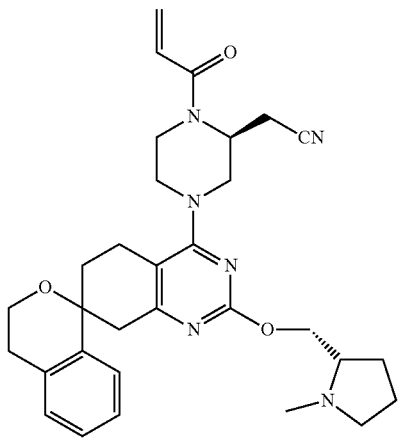

Step 1: ethyl 3-oxospiro[cyclohexane-1,1'-isochromane]-4-carboxylate (Intermediate No. 26)

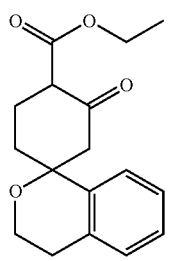 [SMILES: CCOC(=O)C1CCC2(CC1=O)OCCc1ccccc12]

Under Ar, to a solution of spiro[cyclohexane-1,1'-isochroman]-3-one (1.5 g, 6.94 mmol Intermediate No. 21) in dry THF (2 mL) was added LiHMDS (2.32 g, 13.87 mmol) at –70° C., after the mixture was stirred at –70° C. for 1 h, ethyl carbonocyanidate (3.44 g, 34.7 mmol) was added, and then the mixture was stirred at –70° C. for another 2 h. After the reaction, diluted with water, extracted twice with EA, the combined EA layers were washed with brine, dried over Na$_2$SO$_4$, concentrated to give the crude, which was purified by silica gel column (hexane:ethyl actetate=4:1) to give the title compound (890 mg, 44.5%) as a colorless oil. MS: 289.3 (M+H$^+$); $^1$H NMR (CDCl$_3$, 400 MHz): 512.28 (s, 1H), 7.23-7.05 (m, 4H), 4.24 (q, d=7.2 Hz, 2H), 3.97-3.86 (m, 2H), 2.92-2.58 (m, 4H), 2.50-2.31 (m, 2H), 2.10-2.02 (m, 1H), 1.88-1.80 (m, 1H). 1.32 (t, d=7.2 Hz, 3H).

Step 2: 2-((2S)-1-acryloyl-4-(2'-(((S)-1-methylpyrrolidin-2-yl)methoxy)-5',8'-dihydro-6'H-spiro[isochromane-1,7'-quinazolin]-4'-yl)piperazin-2-yl)acetonitrile (Cpd. No. 6)

Cpd. No. 6 was prepared using essentially the same protocol described in EXAMPLE 7 with ethyl 3-oxospiro[cyclohexane-1,1'-isochromane]-4-carboxylate (step 1) in place of methyl 3-oxo-3',4'-dihydro-2'H-spiro[cyclohexane-1,1'-naphthalene]-4-carboxylate to afford 13 mg as white solid. MS: 543.5 (M+H$^+$).

Example 11

Synthesis of 1-(4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-1-yl)prop-2-en-1-one (Cpd. No. 7)

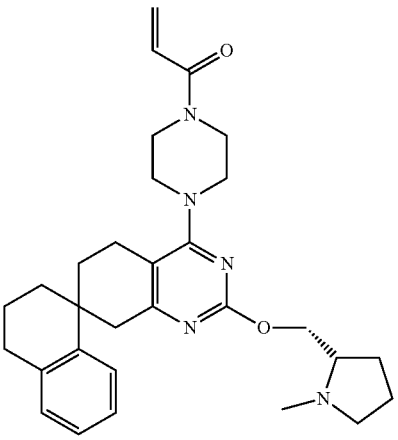

Cpd. No 7 was prepared using essentially the same protocol described in EXAMPLE 7 with tert-butyl piperazine-1-carboxylate in place of (S)-2-(piperazin-2-yl)acetonitrile bis(2,2,2-trifluoroacetate) to afford 21 mg) as white solid. MS: 502.5 (M+H$^+$).

Example 12

Synthesis of 1-((3S)-3-methyl-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-1-yl)prop-2-en-1-one (Cpd. No. 8)

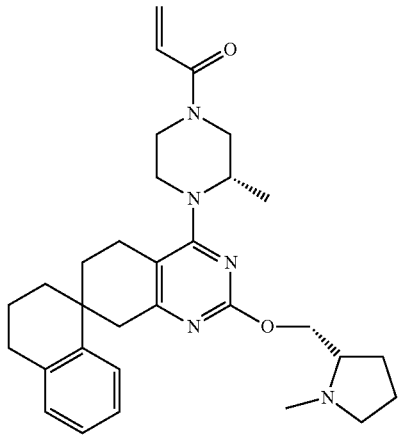

Cpd. No. 8 was prepared essentially the same protocol described in EXAMPLE 7 with ert-butyl (S)-3-methylpiperazine-1-carboxylatein place of (S)-2-(piperazin-2-yl)acetonitrile bis(2,2,2-trifluoroacetate) to afford 30 mg as white solid. MS: 516.5 (M+H$^+$).

Example 13

Synthesis of 1-(4-(2'-(((S)-1-methylpyrrolidin-2-yl)methoxy)-2,3,5',8'-tetrahydro-6'H-spiro[indene-1,7'-quinazolin]-4'-yl)piperazin-1-yl)prop-2-en-1-one (Cpd. No. 9)

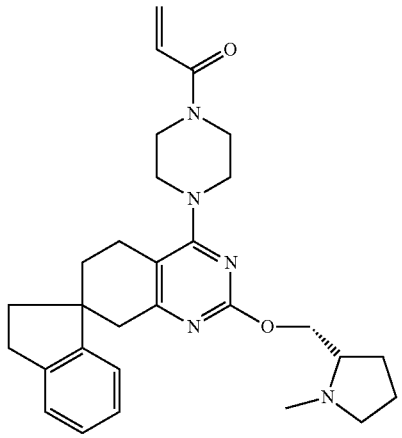

Cpd. No. 9 was prepared using essentially the same protocol described in EXAMPLE 7 with tert-butyl piperazine-1-carboxylate and 2',3'-dihydrospiro[cyclohexane-1,1'-inden]-3-one in place of (S)-2-(piperazin-2-yl)acetonitrile bis(2,2,2-trifluoroacetate) and 3',4'-dihydro-2'H-spiro[cy- clohexane-1,1'-naphthalen]-3-one to afford 30 mg as white solid.
MS: 488.6 (M+H$^+$).

Example 14

Synthesis of 1-((3S)-3-methyl-4-(2'-(((S)-1-methylpyrrolidin-2-yl)methoxy)-2,3,5',8'-tetrahydro-6'H-spiro[indene-1,7'-quinazolin]-4'-yl)piperazin-1-yl)prop-2-en-1-one (Cpd. No. 10)

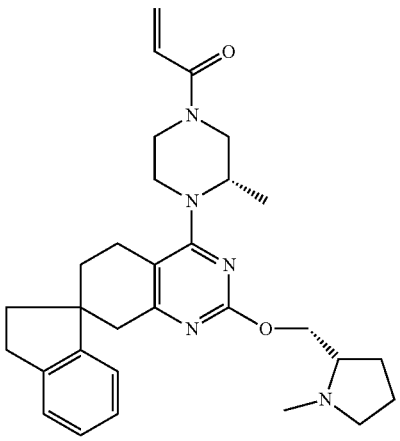

Cpd. No. 10 was prepared using essentially the same protocol described in EXAMPLE 7 with tert-butyl (S)-3-methylpiperazine-1-carboxylate and 2',3'-dihydrospiro[cyclohexane-1,1'-inden]-3-one in place of (S)-2-(piperazin-2-yl)acetonitrile bis(2,2,2-trifluoroacetate) and 3',4'-dihydro-2'H-spiro[cyclohexane-1,1'-naphthalen]-3-one (to afford 30 mg) as white solid. MS: 502.5 (M+H$^+$).

Example 15

Synthesis of 2-((2S)-1-acryloyl-4-(7-fluoro-2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 11)

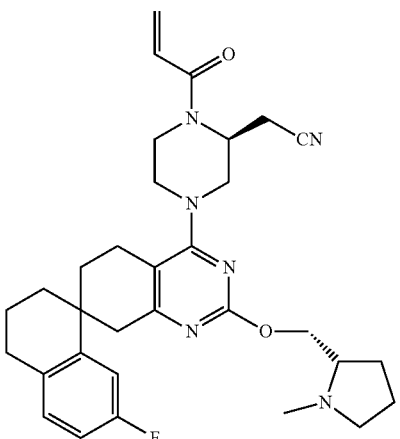

Cpd. No. 11 was prepared using essentially the same protocol described in EXAMPLE 7 with 7'-fluoro-3',4'-dihydro-2'H-spiro[cyclohexane-1,1'-naphthalen]-3-one in place of 3',4'-dihydro-2'H-spiro[cyclohexane-1,1'-naphthalen]-3-one to afford 2.4 mg as a white solid. MS: 589.6 (M+H⁺).

Example 16

Synthesis of 2-((2S)-1-acryloyl-4-(6-methyl-2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 12)

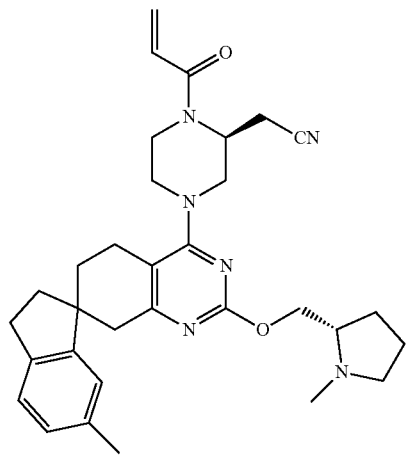 [SMILES: C=CC(=O)N1CCN(c2nc(OC[C@@H]3CCCN3C)nc3c2CCC2(CCc4ccc(C)cc42)C3)C[C@@H]1CC#N]

Cpd. No. 12 was prepared using essentially the same protocol described in EXAMPLE 7 with 6'-methyl-2',3'-dihydrospiro[cyclohexane-1,1'-inden]-3-one in place of 3',4'-dihydro-2'H-spiro[cyclohexane-1,1'-naphthalen]-3-one to afford 13 mg as white solid.
MS: 541.5 (M+H⁺).

Example 17

Synthesis of 2-((2S)-1-(2-fluoroacryloyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 13)

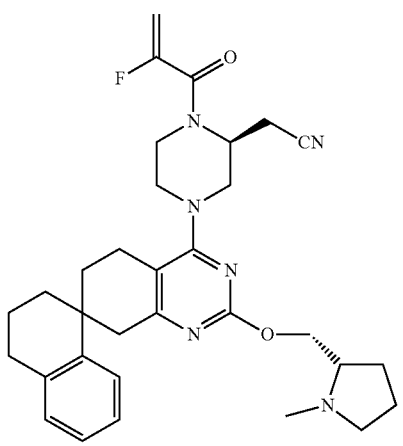

Under Ar, to a solution of 2-((2S)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (460 mg, 0.945 mmol), TEA (143 mg, 1.418 mmol), and 2-fluoroacrylic acid (102 mg, 1.134 mmol) in DMF (10 mL) was added HATU (539 mg, 1.418 mmol) at 0° C. The mixture was stirred at RT over night. After the reaction was complete, water was added and the mixture was extracted twice with EA. The combined organic layers were concentrated under reduced pressure and the residue was purified by silica gel column chromatography eluting with ethyl acetate/hexane from 0 to 100%, then methanol/dichloromethane from 0 to 10% to give the crude product as colourless oil that was further purified by Prep-HPLC to give the title compound (180 mg, 34.1%) as white solid.
MS: 559.5 [M+H⁺].

Example 18

Synthesis of 2-((2S)-1-((E)-but-2-enoyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 14)

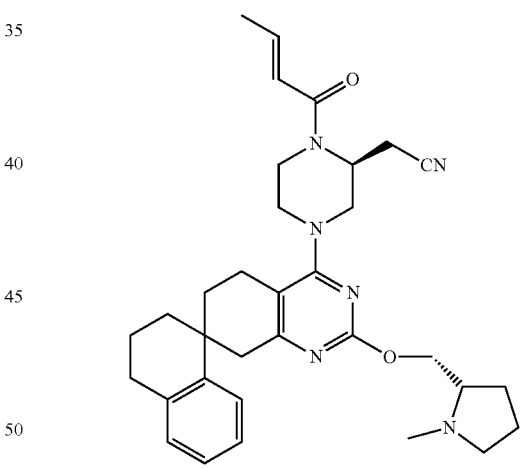

Essentially the same protocol described in EXAMPLE 17 was used to afford 2-((2S)-1-((E)-but-2-enoyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (3.4 mg) as a white solid. MS: 555.6 [M+H⁺].

Example 19

Synthesis of 2-((2S)-1-((E)-4-(dimethylamino)but-2-enoyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 15)

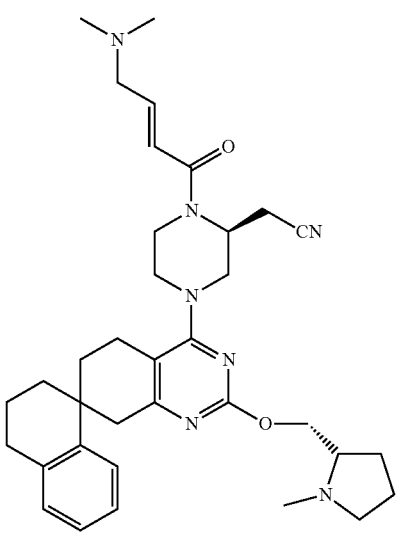

Essentially the same protocol described in EXAMPLE 17 was used to afford 2-((2S)-1-((E)-4-(dimethylamino)but-2-enoyl)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (3.6 mg) as a white solid. MS: 555.6 [M+H$^+$].

Example 20

Synthesis of 2-((2S)-4-(2'-(((S)-1-methylpyrrolidin-2-yl)methoxy)-3,4,5',8'-tetrahydro-2H,6'H-spiro[naphthalene-1,7'-quinazolin]-4'-yl)-1-(vinylsulfonyl)piperazin-2-yl)acetonitrile (Cpd. No. 16)

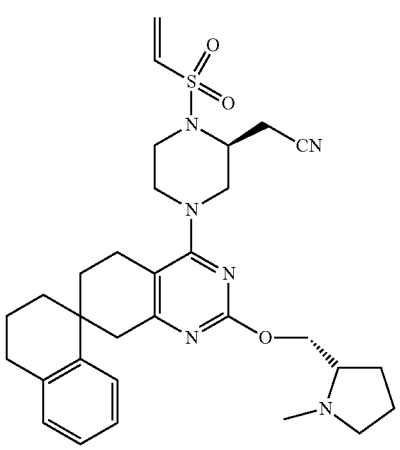

Under Ar, to a solution of 2-((2S)-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (40 mg, 0.082 mmol) and TEA (16.6 mg, 0.616 mmol) in DCM (10 mL) was added ethenesulfonyl chloride (15.6 mg, 0.12 mmol) at −50° C. After warming to 0° C. for 5 mins, water was added. The reaction mixture was extracted with DCM twice, and the combined organic layers were concentrated to give the crude product. The crude product was purified by silica gel column chromatography eluting with EA:Hep=10%-100%, then MeOH:DCM=0-15% to give 2-(1-acryloyl-4-(2'-(((S)-1-methylpyrrolidin-2-yl)methoxy)-3,4,5',8'-tetrahydro-2H,6'H-spiro[naphthalene-1,7'-quinazolin]-4'-yl)piperazin-2-yl)acetonitrile (35 mg, 73.8%) as a white solid. MS: 577.6 [M+H$^+$].

Example 21

Synthesis of 2-((2S)-1-acryloyl-4-(2'-(3-(dimethylamino)propoxy)-3,4,5',8'-tetrahydro-2H,6'H-spiro[naphthalene-1,7'-quinazolin]-4'-yl)piperazin-2-yl)acetonitrile (Cpd. No. 17)

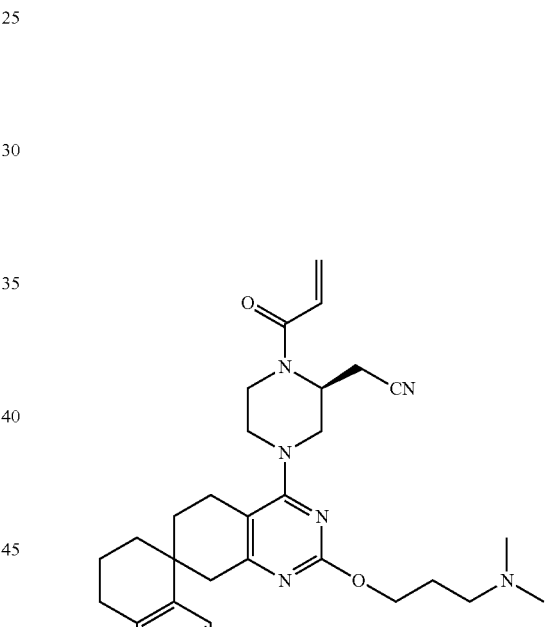

Cpd. No. 17 was prepared essentially the same protocol of preparation described in EXAMPLE 7 with 3-(dimethylamino)propan-1-ol in place of (S)-(1-methylpyrrolidin-2-yl)methanol to afford 3.1 mg as white solid. MS: 529.5 (M+H$^+$).

Example 22

Synthesis of 2-((2S)-1-acryloyl-4-(2'-(((S)-1-methylpiperidin-2-yl)methoxy)-3,4,5',8'-tetrahydro-2H,6'H-spiro[naphthalene-1,7'-quinazolin]-4'-yl)piperazin-2-yl)acetonitrile (Cpd. No. 18)

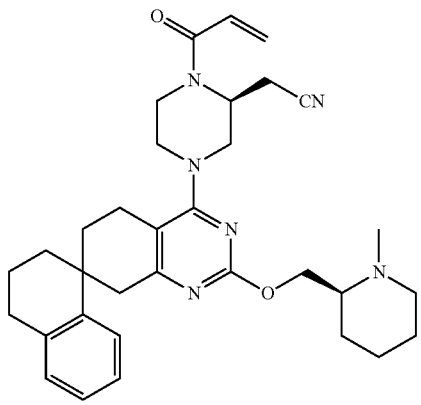 [SMILES: C=CC(=O)N1CCN(c2nc(OC[C@@H]3CCCCN3C)nc3c2CCC2(CCCc4ccccc42)C3)C[C@@H]1CC#N]

Cpd. No. 18 was prepared essentially the same protocol of preparation described in EXAMPLE 7 with (S)-(1-methylpiperidin-2-yl)methanol in place of (S)-(1-methylpyrrolidin-2-yl)methanol to afford 6 mg as white solid. MS: 555.6 (M+H$^+$).

Example 23

Synthesis of 2-((2S)-1-acryloyl-4-(2'-(3-morpholinopropoxy)-3,4,5',8'-tetrahydro-2H,6'H-spiro[naphthalene-1,7'-quinazolin]-4'-yl)piperazin-2-yl)acetonitrile (Cpd. No. 19)

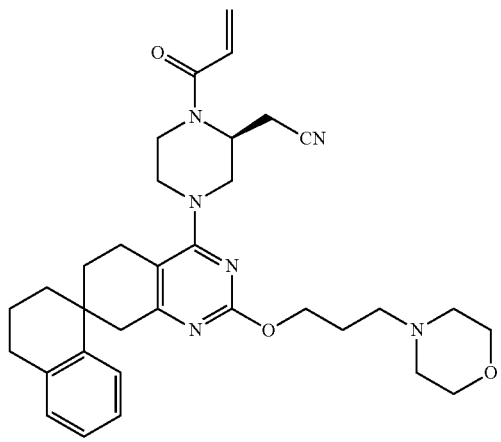 [SMILES: C=CC(=O)N1CCN(c2nc(OCCCN3CCOCC3)nc3c2CCC2(CCCc4ccccc42)C3)C[C@@H]1CC#N]

Cpd. No. 19 was prepared using essentially the same protocol described in EXAMPLE 7 with 3-morpholinopropan-1-ol in place of (S)-(1-methylpyrrolidin-2-yl)methanol to afford: 3.5 mg as white solid. MS: 571.7 (M+H$^+$).

Example 24

Synthesis of 2-((2S)-1-acryloyl-4-(2'-(((S)-4-methylmorpholin-2-yl)methoxy)-3,4,5',8'-tetrahydro-2H,6'H-spiro[naphthalene-1,7'-quinazolin]-4'-yl)piperazin-2-yl)acetonitrile (Cpd. No. 20)

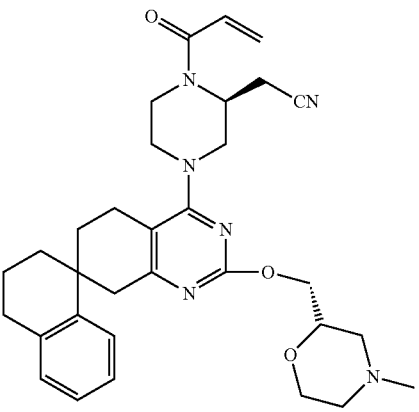

Cpd. No. 20 was prepared using essentially the same protocol described in EXAMPLE 7 with (S)-(4-methylmorpholin-2-yl)methanol in place of (S)-(1-methylpyrrolidin-2-yl)methanol to afford 3.4 mg as white solid. MS: 557.7 (M+H$^+$).

Example 25

2-((2S)-1-acryloyl-4-(2'-(((S)-1-methylpyrrolidin-2-yl)methoxy)-5',8'-dihydro-6'H-spiro[chromane-4,7'-quinazolin]-4'-yl)piperazin-2-yl)acetonitrile (Cpd. No. 21)

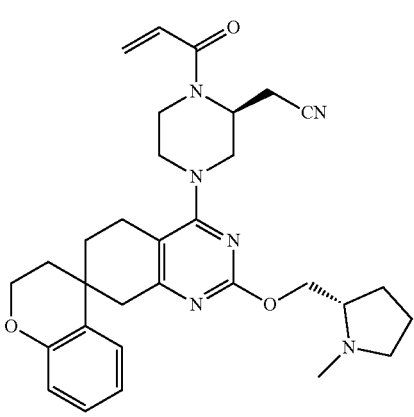 [SMILES: C=CC(=O)N1CCN(c2nc(OC[C@@H]3CCCN3C)nc3c2CCC2(CCOc4ccccc42)C3)C[C@@H]1CC#N]

Intermediate: spiro[chromane-4,1'-cyclohexan]-3'-one

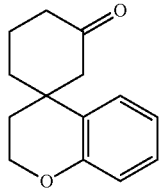

Step 1: 1-(2-bromoethoxy)-2-iodobenzene

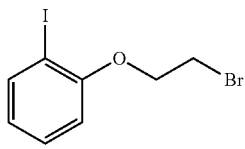 [SMILES: BrCCOc1ccccc1I]

Under Ar, the suspension of 2-iodophenol (10 g, 45.5 mmol), 1,2-dibromoethane (42.7 g, 227 mmol), potassium carbonate (12.56 g, 91 mmol) and KI (1.509 g, 9.09 mmol) in THF (50 mL) was stirred at 80° C. overnight. After cooling down to RT, the filtrate was concentrated in vacuo to give a residual, which was purified by silica gel column and eluted with PE/EA=9:1 to afford the title compound (12.19 g, 82%) as a colorless oil.

Step 2: 1-iodo-2-(vinyloxy)benzene

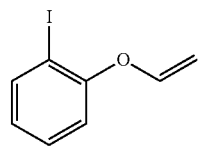

Under Ar, to the mixture of 1-(2-bromoethoxy)-2-iodobenzene (12.19 g, 37.3 mmol) in dry DMSO (50 mL) was added potassium 2-methylpropan-2-olate (6.28 g, 55.9 mmol) at RT, then the reaction mixture was stirred at RT for 2 hours. The filtrate was concentrated in vacuo to give a residual, which was purified by silica gel column and eluted with PE/EA=10:1 to give the title compound (8.35 g, 91%) as a colorless liquid. $^1$H NMR (400 MHz, Chloroform-d) δ 7.82-7.80 (m, 1H), 7.34-7.29 (m, 1H), 6.99-6.97 (m, 1H), 6.86-6.82 (m, 1H), 6.61-6.56 (m, 1H), 6.79-6.76 (m, 1H), 6.52-6.50 (m, 1H).

Step 3: 2'-(vinyloxy)-5,6-dihydro-[1,1'-biphenyl]-3(4H)-one

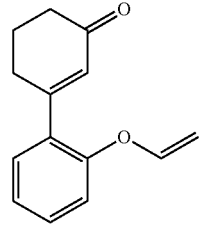 [SMILES: C=COc1ccccc1C1=CC(=O)CCC1]

Under Ar, the mixture of 1-iodo-2-(vinyloxy)benzene (4.6 g, 18.70 mmol), 3-(4,4,5,5-tetramethyl-1,3,2-dioxaborolan-2-yl)cyclohex-2-en-1-one (4.15 g, 18.70 mmol), sodium carbonate (4.95 g, 46.7 mmol) and Pd(dppf)Cl$_2$.DCM (0.763 g, 0.935 mmol) in DME (12 mL)/Water (3 mL) was stirred at 90° C. for 1 hour. After cooling down to RT, the resulting mixture was extracted with EA twice. The combined organic layers were concentrated in vacuo to give the residual, which was purified by silica gel column and eluted with ethyl acetate/hexane from 0 to 30% to afford the title compound (3.7 g, 92%) as a brown oil. MS: 215.6 (M+H$^+$).

Step 4: 3-vinyl-3-(2-(vinyloxy)phenyl)cyclohexan-1-one

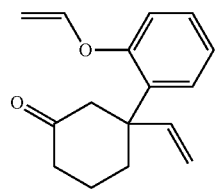 [SMILES: C=COc1ccccc1C1(C=C)CCCC(=O)C1]

Under Ar, to a suspension of copper(I) iodide (4.00 g, 21.00 mmol) and lithium chloride (0.890 g, 21.00 mmol) in dry THF was added vinyl magnesium bromide (7.35 g, 56.0 mmol) at −78° C., then the mixture was stirred at −78° C. for 0.5 hour. 2'-(vinyloxy)-5,6-dihydro-[1,1'-biphenyl]-3(4H)-one (3 g, 14.00 mmol) in dry THF was added (over 30 mins). Then the reaction mixture was stirred at −78° C. for 2 h.

Quenched with saturated NH$_4$Cl solution, the resulting mixture was extracted with EA twice. The combined organic layers were concentrated in vacuo to give the residual, which was purified by silica gel column and eluted with ethyl acetate/hexane from 0 to 10% to afford the title compound (2.53 g, 74.6%) as a colorless oil. MS: 243.5 (M+H$^+$).

Step 5: spiro[chromene-4,1'-cyclohexan]-3'-one

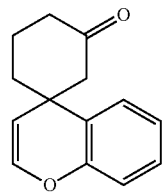 [SMILES: O=C1CCCC2(C=COc3ccccc32)C1]

Under Ar, The mixture of 3-vinyl-3-(2-(vinyloxy)phenyl) cyclohexan-1-one (2.53 g, 10.44 mmol) and Grubbs ii (0.886 g, 1.044 mmol) in DCM (250 mL) was stirred at RT overnight. The removal of volatiles to give a residual, which was purified by silica gel column and eluted with PE/EA=6:1 to give the title compound (2.18 g, 97%) as a brown oil.

MS: 215.2 (M+H⁺).

Step 6: spiro[chromane-4,1'-cyclohexan]-3'-one

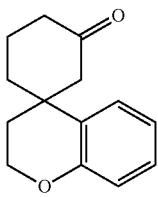 [SMILES: O=C1CCCC2(CCOc3ccccc32)C1]

The mixture of spiro[chromene-4,1'-cyclohexan]-3'-one (2.18 g, 10.17 mmol) and Pd/C (0.541 g, 5.09 mmol) in EA (30 mL) was stirred at RT under H$_2$ condition for 4 hour. The filtrate was concentrated to give the crude title compound (2.08 g, 95%) as a colorless oil. MS: 217.2 (M+H⁺).

Step 7: methyl 3'-oxospiro[chromane-4,1'-cyclohexane]-4'-carboxylate

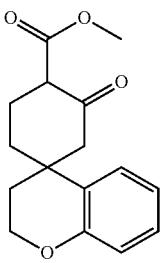 [SMILES: COC(=O)C1CCC2(CCOc3ccccc32)CC1=O]

Under Ar, to a suspension of NaH (1.154 g, 28.9 mmol) and dimethyl carbonate (4.33 g, 48.1 mmol) in THF (30 mL) was dropwise added spiro[chromane-4,1'-cyclohexan]-3'-one (2.08 g, 9.62 mmol) in THF at 70° C., then the resulting mixture was stirred at 70° C. for 2 h. After cooling down to RT, saturated NH$_4$Cl was added, followed by extraction with ethyl acetate three times. The combined organic layers were washed with brine, dried over Na$_2$SO$_4$, filtered and concentrated in vacuo to give a residual, which was purified by silica gel column and eluted with ethyl acetate/hexane=1:9 to afford the title compound (2.49 g, 94%) as a colorless oil. MS: 275.3 (M+H⁺).

Step 8: 2'-amino-5',8'-dihydro-6'H-spiro[chromane-4,7'-quinazolin]-4'-ol

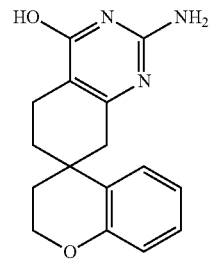 [SMILES: Nc1nc(O)c2c(n1)CC1(CCOc3ccccc31)CC2]

Under Ar, the mixture of guanidine hydrochloride (2.60 g, 27.2 mmol), potassium carbonate (4.14 g, 30.0 mmol) and methyl 3'-oxospiro[chromane-4,1'-cyclohexane]-4'-carboxylate (2.49 g, 9.08 mmol) in dry DMF (20 mL) was stirred at 85° C. for 3 h. After cooling down to RT, water was added, and the acidified by AcOH to pH=6. The precipitate was collected to give the title compound (2.6 g, crude). MS: 284.3 (M+H⁺).

Step 9: 5',8'-dihydro-6'H-spiro[chromane-4,7'-quinazoline]-2',4'-diol

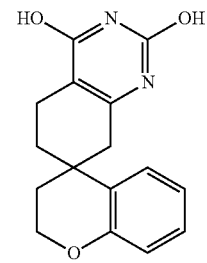

Under Ar, the mixture of 2'-amino-5',8'-dihydro-6'H-spiro[chromane-4,7'-quinazolin]-4'-ol (2.6 g, crude) in AcOH (20 mL) was added sodium nitrite (12.53 g, 182 mmol) in 10 ml of water, then the mixture was stirred at 70° C. for 2 h. After the reaction, AcOH was reduced in vacuo to give a residual, which was treated with cold water, and the precipitated solid was collected and dried in vacuo to afford the title compound (1.7 g, 65.9%) as a white solid. MS: 285.3 (M+H⁺).

Step 10: 2',4'-dichloro-5',8'-dihydro-6'H-spiro[chromane-4,7'-quinazoline]

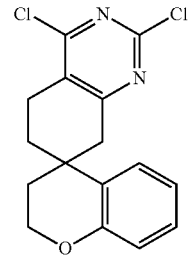 [SMILES: Clc1nc(Cl)c2c(n1)CC1(CCOc3ccccc31)CC2]

Under Ar, the mixture of 5',8'-dihydro-6'H-spiro[chromane-4,7'-quinazoline]-2',4'-diol (700 mg, 2.462 mmol) and DIEA (955 mg, 7.39 mmol) in POCl₃ (20 mL) was stirred at 110° C. for 2 h. After the removal off the volatiles under reduced pressure to give a residual, which was dissolved in EA, washed with NaHCO₃(aq), brine, dried over Na₂SO₄, filtered, concentrated in vacuo to give a residual, which was purified by silica gel column and eluted with PE/EA=5:1 to afford the title compound (550 mg, 69.5%) as a white solid. MS: 321.2 (M+H⁺).

Step 11: tert-butyl (2S)-4-(2'-chloro-5',8'-dihydro-6'H-spiro[chromane-4,7'-quinazolin]-4'-yl)-2-(cyanomethyl)piperazine-1-carboxylate

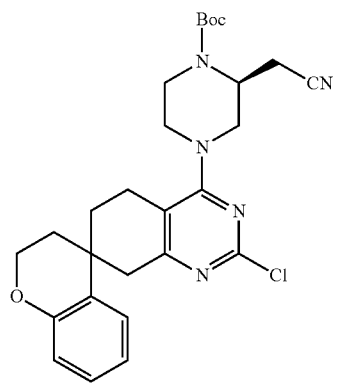 [SMILES: CC(C)(C)OC(=O)N1CCN(c2nc(Cl)nc3c2CCC2(CCOc4ccccc42)C3)C[C@@H]1CC#N]

Under Ar, the mixture of 2',4'-dichloro-5',8'-dihydro-6'H-spiro[chromane-4,7'-quinazoline] (550 mg, 1.712 mmol), (S)-2-(piperazin-2-yl)acetonitrile dihydrochloride (339 mg, 1.712 mmol) and N-ethyl-N-isopropylpropan-2-amine (885 mg, 6.85 mmol) in DMSO (10 mL) was stirred at 50° C. for 2 h. After the disappearance of the start material, di-tert-butyl dicarbonate (3737 mg, 17.12 mmol) was added, and the resulting mixture was stirred at 50° C. for another 1 h. After cooling down to RT, water was added, the resulting mixture was extracted with DCM three times. The combined organic layers were washed with brine, dried over Na₂SO₄, filtered, concentrated in vacuo to give a residual, which was purified by silica gel column and eluted with EA/PE from 0% to 30% to afford the title compound (798 mg, 91%) as a white solid. MS: 510.3 (M+H⁺).

Step 12: tert-butyl (2S)-2-(cyanomethyl)-4-(2'-(((S)-1-methylpyrrolidin-2-yl)methoxy)-5',8'-dihydro-6'H-spiro[chromane-4,7'-quinazolin]-4'-yl)piperazine-1-carboxylate

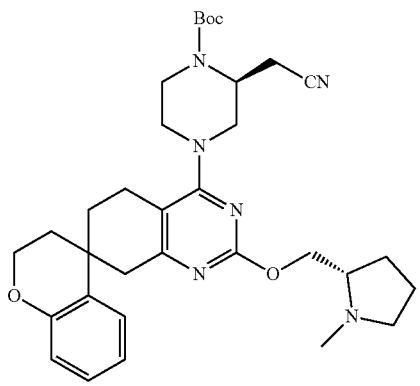 [SMILES: CN1CCC[C@H]1COc1nc2c(c(N3CCN(C(=O)OC(C)(C)C)[C@@H](CC#N)C3)n1)CCC1(CCOc3ccccc31)C2]

Under Ar, the mixture of tert-butyl (2S)-4-(2'-chloro-5',8'-dihydro-6'H-spiro[chromane-4,7'-quinazolin]-4'-yl)-2-(cyanomethyl)piperazine-1-carboxylate (790 mg, 1.549 mmol), (S)-(1-methylpyrrolidin-2-yl)methanol (268 mg, 2.323 mmol), Pd₂(dba)₃ (142 mg, 0.155 mmol), 2,2'-bis(diphenylphosphanyl)-1,1'-binaphthalene (96 mg, 0.155 mmol) and sodium 2-methylpropan-2-olate (298 mg, 3.10 mmol) in dry Toluene (12 mL) was stirred at 110° C. for 2 h. After the removal off the volatiles under reduced pressure to give a residual, which was purified by silica gel column and eluted with DCM/MeOH from 0% to 10% to afford the title compound (500 mg, 54.8%) as a brown solid. MS: 589.8 (M+H⁺).

Step 13: 2-((2S)-4-(2'-(((S)-1-methylpyrrolidin-2-yl)methoxy)-5',8'-dihydro-6'H-spiro[chromane-4,7'-quinazolin]-4'-yl)piperazin-2-yl)acetonitrile

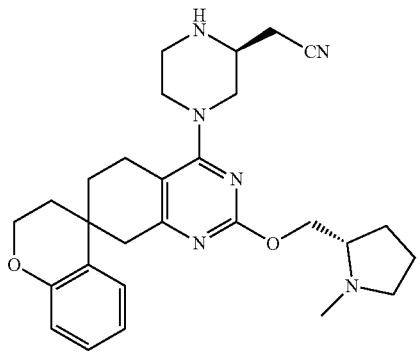 [SMILES: CN1CCC[C@H]1COc1nc2c(c(N3CCN[C@@H](CC#N)C3)n1)CCC1(CCOc3ccccc31)C2]

Under Ar, the mixture of tert-butyl (2S)-2-(cyanomethyl)-4-(2'-(((S)-1-methylpyrrolidin-2-yl)methoxy)-5',8'-dihydro-6'H-spiro[chromane-4,7'-quinazolin]-4'-yl)piperazine-1-carboxylate (500 mg, 0.849 mmol) in TFA (3 mL)/DCM (5 ml) was stirred at rt for 2 h. The volatiles were removed under reduced pressure to give a residual, which was portioned between DCM and NaHCO₃ solution, the separated organic layer was washed with brine, dried over Na₂SO₄, concentrated in vacuo to give the title compound (260 mg, 62%) as a light-yellow oil. MS: 489.4 (M+H⁺).

Step 14: 2-((2S)-1-acryloyl-4-(2'-(((S)-1-methylpyrrolidin-2-yl)methoxy)-5',8'-dihydro-6'H-spiro[chromane-4,7'-quinazolin]-4'-yl)piperazin-2-yl)acetonitrile

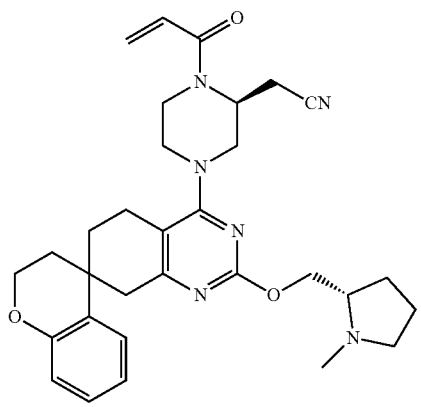 [SMILES: C=CC(=O)N1CCN(c2nc(OC[C@@H]3CCCN3C)nc3c2CCC2(CCOc4ccccc42)C3)C[C@@H]1CC#N]

Under Ar, to a solution of 2-((2S)-4-(2'-(((S)-1-methylpyrrolidin-2-yl)methoxy)-5',8'-dihydro-6'H-spiro[chromane-4,7'-quinazolin]-4'-yl)piperazin-2-yl)acetonitrile (260 mg, 0.53 mmol) and DIPEA (220 mg, 1.7 mmol) in DCM (5 mL) was added acryloyl chloride (154 mg, 1.699 mmol) at 0° C. After 30 mins later, water was added, the resulting mixture was extracted with DCM three times, and the combined organic layers were washed with brine, dried over $Na_2SO_4$, concentrated in vacuo to give a residual, which was purified by Pre-HPLC to afford the title compound (143 mg) concentrated to give the crude product which was purified by Pre-HPLC to give the pure product as a white solid. MS: 543.8 (M+H$^+$). $^1$H NMR (400 MHz, DMSO-d6) 7.31-7.21 (m, 1H), 7.09 (t, J=7.6 Hz, 1H), 6.91-6.81 (m, 2H), 6.76 (d, J=8.0 Hz, 1H), 6.20-6.16 (m, 1H), 5.77 (d, J=10.8 Hz, 1H), 4.96-4.76 (m, 1H), 4.39-3.61 (m, 8H), 3.23-2.49 (m, 11H), 2.33 (s, 3H), 2.18-2.06 (m, 2H), 1.96-1.84 (m, 2H), 1.72-1.54 (m, 4H).

Example 26

2-((2S)-1-acryloyl-4-(8-chloro-2'-(((S)-1-methylpyrrolidin-2-yl)methoxy)-5',8'-dihydro-6'H-spiro[chromane-4,7'-quinazolin]-4'-yl)piperazin-2-yl)acetonitrile (Cpd. No. 22)

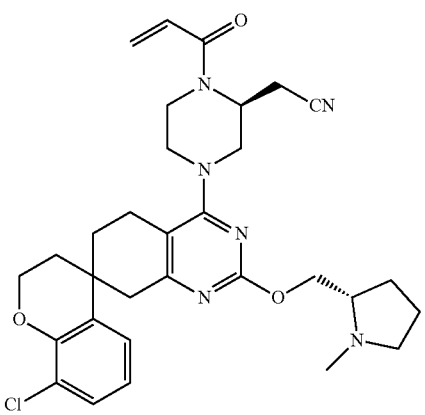 [SMILES: C=CC(=O)N1CCN(c2nc(OC[C@@H]3CCCN3C)nc3c2CCC2(CCOc4c(Cl)cccc42)C3)C[C@@H]1CC#N]

Example 26 was prepared essentially the same protocol described in EXAMPLE 25 With 8-chlorospiro[chromane-4,1'-cyclohexan]-3'-one to afford 3.1 mg as a white solid. MS: 578.4 (M+H$^+$). $^1$H NMR (400 MHz,) δ 7.44-7.35 (m, 1H), 7.15-7.12 (m, 1H), 6.94-6.79 (m, 2H), 6.20-6.16 (m, 1H), 6.78-6.76 (m, 1H), 4.95-4.75 (m, 1H), 4.26-3.63 (m, 7H), 3.27-2.61 (m, 10H), 2.34 (s, 3H), 2.18-1.83 (m, 6H), 1.75-1.45 (m, 4H).

Example 27

2-((2S)-1-acryloyl-4-(6,8-dichloro-2'-(((S)-1-methylpyrrolidin-2-yl)methoxy)-5',8'-dihydro-6'H-spiro[chromane-4,7'-quinazolin]-4'-yl)piperazin-2-yl)acetonitrile (Cpd. No. 23)

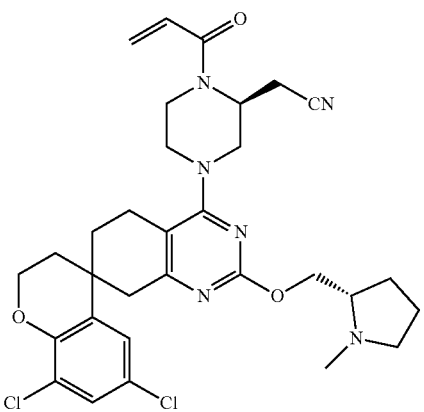 [SMILES: C=CC(=O)N1CCN(c2nc(OC[C@@H]3CCCN3C)nc3c2CCC2(CCOc4c(Cl)cc(Cl)cc42)C3)C[C@@H]1CC#N]

Example 27 was prepared essentially the same protocol described in EXAMPLE 25
With 6,8-dichlorospiro[chromane-4,1'-cyclohexan]-3'-one to afford 2.7 mg as a white solid. MS: 612.9 (M+H$^+$). $^1$H NMR (400 MHz, DMSO-d6) δ 7.22-7.14 (m, 1H), 6.91-6.81 (m, 2H), 6.18 (dd, J=16.8, 1.6 Hz, 1H), 5.77 (d, J=10.8 Hz, 1H), 4.94-4.74 (m, 1H), 4.34-3.93 (m, 7H), 3.27-2.49 (m, 10H), 2.34 (s, 3H), 2.21-1.89 (m, 6H), 1.68-1.42 (m, 4H).

Example 28

2-((2S)-1-acryloyl-4-(2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 24)

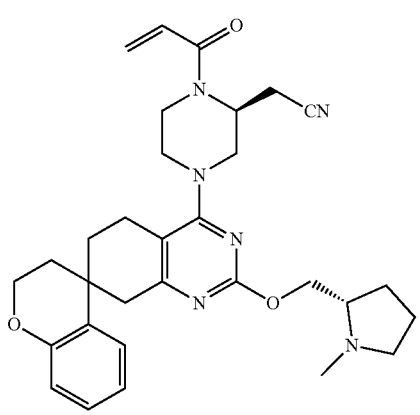 [SMILES: C=CC(=O)N1CCN(c2nc(OC[C@@H]3CCCN3C)nc3c2CCC2(CCOc4ccccc42)C3)C[C@@H]1CC#N]

Intermediate: spiro[cyclohexane-1,4'-isochroman]-3-one

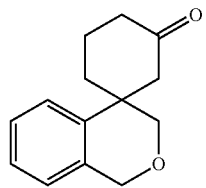 [SMILES: O=C1CCCC2(COCc3ccccc32)C1]

Step 1: 3-(benzyloxy)spiro[cyclohexane-1,4'-isochroman]-3'-one

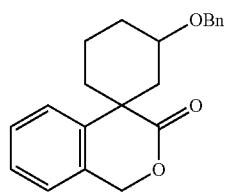 [SMILES: O=C1OCc2ccccc2C12CCCC(OCc1ccccc1)C2]

Under Ar, to a mixture of Isochroman-3-one (12.0 g, 80.1 mmol) and (((1,5-diiodopentan-2-yl)oxy)methyl)benzene (36.56 g, 85.02 mmol) in 125 mL DMF were added sodium hydride (6.48 g, 160.2 mmol) at 0° C. slowly (1 hour), and then the mixture was stirred at RT overnight. Quenched with saturated NH$_4$Cl (30 mL) solution, the resulting mixture was extracted with EA three times, the combined organic layers were washed by saturated brine, dried, and concentrated in vacuo to give a residual, which was purified by silica gel column and eluted with ethyl acetate/hexane from 5% to 40% to afford the title compound (10.4 g, 39.8%) as a light yellow oil. MS: 323.2 (M+H$^+$).

Step 2: (3-(benzyloxy)-1-(2-(hydroxymethyl)phenyl)cyclohexyl)methanol

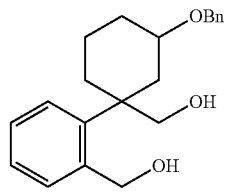 [SMILES: OCc1ccccc1C1(CO)CCCC(OCc2ccccc2)C1]

Under Ar, the THF solution of LiAlH4 (2.5 M, 2.4 g, 63.2 mmol) was dropwise added to 3-(benzyloxy) spiro[cyclohexane-1,4'-isochroman]-3'-one (8.0 g, 24.81 mmol) in THF (125 mL) at 0° C., and then the reaction mixture was stirred at RT for 1 hour. Water (3 mL) and 3 ml 15% NaOH aq (3 mL) were added to the reaction mixture at ice-water condition, followed by adding another batch of water (6 mL) and stirred RT for 30 mins. Na$_2$SO$_4$ was added and the mixture was stirred for another 30 mins. The filtrate was concentrated in vacuo to give a residual, which was purified by silica gel column and eluted with ethyl acetate/hexane from 0 to 50% to afford the title compound (5.3 g, 65.4%). MS: 327.2 (M+H$^+$).

Step 3: 3-(benzyloxy)spiro[cyclohexane-1,4'-isochromane]

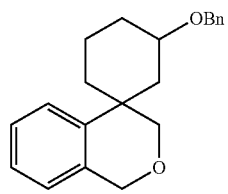 [SMILES: c1ccc(COC2CCCC3(COCc4ccccc43)C2)cc1]

Under Ar, diisopropyl-diazene-1,2-dicarboxylate (2.60 g, 12.88 mmol, 1.05) in 15 ml toluene was added to the solution of triphenylphosphane (3.54 g, 12.88 mmol) in THF (30 mL) at 0° C., after stirring at this temperature for 20 mins. (3-(benzyloxy)-1-(2-(hydroxymethyl)phenyl) cyclohexyl) methanol (step 2, 4.0 g, 12.24 mmol) in toluene (10 mL) was added to the reaction mixture, and stirred at room temperature overnight. Water was added, the resulting mixture was extracted with EA three times, the combined organic layers were concentrated in vacuo to give a residual, which was purified by silica gel column and eluted with ethyl acetate/hexane from 0-30% to afford the title compound (1.5 g, 39.7%) as a colorless oil. MS: 309.2 (M+H$^+$). $^1$H NMR (400 MHz, CDCl3) δ 7.49-7.04 (m, 8H), 6.96 (d, J=7.5 Hz, 1H), 4.78 (s, 2H), 4.55 (s, 2H), 3.87 (d, J=11.6 Hz, 1H), 3.74 (d, J=11.5 Hz, 1H), 3.61-3.48 (m, 1H), 2.25-2.15 (m, 2H), 1.94-1.44 (m, 5H), 1.45-1.16 (m, 1H).

Step 4: spiro[cyclohexane-1,4'-isochroman]-3-ol

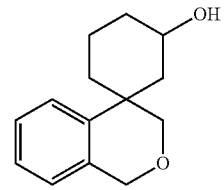 [SMILES: OC1CCCC2(COCc3ccccc32)C1]

The mixture of PdOH$_2$ (769.6 mg, 4.84 mmol) and 3-(benzyloxy)spiro[cyclohexane-1,4'-isochromane] (1.5 g, 4.84 mmol) in MeOH (30 mL) was stirred at 50° C. under H$_2$ condition overnight. After the reaction, the filtrate was concentrated in vacuo to afford the title compound (1.0 g, 94.3%). MS: 219.2 (M+H$^+$). $^1$H NMR (400 MHz, CDCl3) δ 7.39 (d, J=8.0, 1.2 Hz, 1H), 7.28-7.11 (m, 2H), 6.96 (d, J=7.6, 1.4 Hz, 1H), 4.78 (s, 2H), 3.89 (d, J=11.6 Hz, 1H), 3.86-3.78 (m, 1H), 3.75 (d, J=11.6 Hz, 1H), 2.14-2.07 (m, 1H), 2.07-1.99 (m, 1H), 1.87-1.79 (m, 1H), 1.80-1.72 (m, 1H), 1.71-1.65 (m, 1H), 1.64-1.50 (m, 1H), 1.50-1.44 (m, 1H), 1.38-1.23 (m, 1H).

Step 5: spiro[cyclohexane-1,4'-isochroman]-3-one

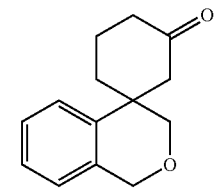 [SMILES: O=C1CCCC2(COCc3ccccc32)C1]

Under Ar, DMP (3.35 g, 7.90 mmol) was added to the solution of spiro[cyclohexane-1,4'-isochroman]-3-ol (1.15 g, 5.27 mmol) in DCM (10 mL) at RT, and then the mixture was stirred at RT for 2 hours. Quenched with the solution of Na$_2$S$_2$SO$_3$, followed by adding water. The resulting mixture was extracted with EA three times, the combined organic layers were washed with brine, dried over Na$_2$SO$_4$, concentrated in vacuo to give a residual, which was purified by silica gel column and eluted with ethyl acetate/hexane from 0 to 50% to afford the title compound (1.0 g, 88%). MS: 217.2 (M+H$^+$).

Example 28 was prepared essentially the same protocol described in EXAMPLE 25 With spiro[cyclohexane-1,4'-isochroman]-3-one to afford 108 mg as a white solid. MS: 543.3 (M+H$^+$).

Example 29

2-((2S)-1-acryloyl-4-(2-methyl-2'-(((S)-1-methylpyrrolidin-2-yl)methoxy)-5',8'-dihydro-6'H-spiro[chromane-4,7'-quinazolin]-4'-yl)piperazin-2-yl)acetonitrile (Cpd. No. 25)

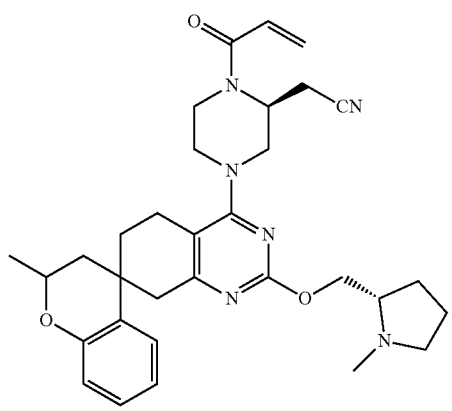 [SMILES: C=CC(=O)N1CCN(c2nc(OC[C@@H]3CCCN3C)nc3c2CCC2(C3)CC(C)Oc3ccccc32)C[C@@H]1CC#N]

Intermediate: 2-methylspiro[chromane-4,1'-cyclohexan]-3'-one

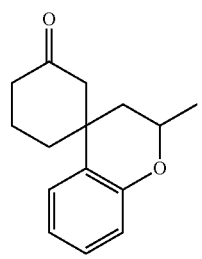 [SMILES: CC1CC2(CCCC(=O)C2)c2ccccc2O1]

Step 1: methyl 2-(2-bromophenoxy)propanoate

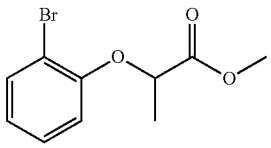

In a nitrogen flushed 250 mL two-necked round-bottomed flask, 2-bromophenol (17.2 g, 99 mmol), triphenylphosphine (26.1 g, 99 mmol) and methyl 2-hydroxypropanoate (9.83 g, 94 mmol) were dissolved in THF (100 mL) under nitrogen. DIAD (21.11 g, 104 mmol) was added to the reaction mixture dropwise at 0° C. The result solution was stirred for 16 hours. The result solution was concentrated to give a residual, which was purified by silica gel column and eluted with EA/Hep form 0-20% to give the title compound (17 g, 66.0%) as a yellow oil.

$^1$H NMR (400 MHz, CDCl$_3$) δ 7.57 (dd, J=7.9, 1.6 Hz, 1H), 7.27-7.19 (m, 1H), 6.90 (td, 0.7=7.7, 1.4 Hz, 1H), 6.84 (dd, J=8.2, 1.3 Hz, 1H), 4.79 (q, 0.7=6.8 Hz, 1H), 3.78 (s, 3H), 1.71 (d, 0.7=6.8 Hz, 3H).

Step 2: 2-(2-bromophenoxy)propan-1-ol

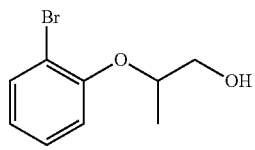

In a nitrogen flushed 250 mL two-necked round-bottomed flask, methyl 2-(2-bromophenoxy)propanoate (7.5 g, 28.9 mmol) was dissolved in MeOH (50 mL) under nitrogen. NaBH$_4$ (3.83 g, 101 mmol) was added to the reaction mixture at 0° C. The resulting solution was stirred at RT for 2 hours, then quenched with saturated NH$_4$Cl (10 mL) and concentrated. H$_2$O (50 mL) was added, the resulting mixture was extraction with ethyl acetate (20 mL×3), the combined organic layers were washed with brine, dried over Na$_2$SO$_4$, concentrated in vacuo to give the crude title compound (6.3 g, 94%) as a yellow oil. $^1$H NMR (400 MHz, CDCl$_3$) δ 7.57 (dd, J=7.9, 1.6 Hz, 1H), 7.32-7.23 (m, 1H), 7.01 (dd, J=8.3, 1.4 Hz, 1H), 6.89 (td, J=7.7, 1.4 Hz, 1H), 4.57-4.54 (m, 1H), 3.85-3.72 (m, 2H), 2.24 (t, J=6.6 Hz, 1H), 1.37 (d, J=6.2 Hz, 3H).

Step 3: 1-bromo-2-((1-iodopropan-2-yl)oxy)benzene

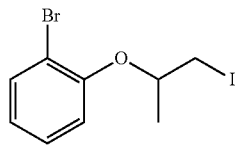

In a nitrogen flushed 250 mL two-necked round-bottomed flask, imidazole (2.56 g, 37.6 mmol) and triphenylphosphine (9.15 g, 34.9 mmol) were dissolved in DCM (80 mL) under nitrogen. 2-(2-bromophenoxy)propan-1-ol (6.2 g, 26.8 mmol) in DCM (40 mL) was added to the reaction mixture dropwise at 0° C. The resulting solution was stirred at RT for 0.5 hour. Iodine (10.21 g, 40.2 mmol, 1.5) was added to the reaction mixture in one portion. The resulting solution was stirred at RT for another 3 hours. The reaction was quenched with saturated Na$_2$S$_2$O$_3$ solution, the resulting mixture was extracted with DCM three times, concentrated in vacuo to give a residual, which was purified by silica gel column and eluted with EA/Hep from 0% to 10% to give 1-bromo-2-((1-iodopropan-2-yl)oxy)benzene (6 g, 65.6%) as a yellow oil. $^1$H NMR (400 MHz, CDCl$_3$) δ 7.58 (dd, J=7.9, 1.6 Hz, 1H), 7.33-7.23 (m, 1H), 6.96 (dd, J=8.3, 1.4 Hz, 1H), 6.90 (td, J=7.6, 1.4 Hz, 1H), 4.50-4.38 (m, 1H), 3.46 (dd, J=10.2, 4.5 Hz, 1H), 3.35 (dd, J=10.2, 6.8 Hz, 1H), 1.55 (d, 0.7=6.1 Hz, 3H).

Step 4: 1-bromo-2-(prop-1-en-2-yloxy)benzene

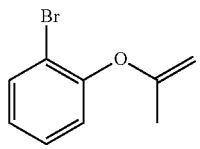

Under Ar, the mixture of 1-bromo-2-((1-iodopropan-2-yl)oxy)benzene (6 g, 17.60 mmol) and potassium 2-methylpropan-2-olate (3.95 g, 35.2 mmol) in 1,4-Dioxane (60 mL) was stirred at 80° C. for 2 hours. The filtrate was concentrated in vacuo to give a residual, which was purified by silica gel column and eluted with Heptane/EA from 0 to 10% to afford the title compound (3 g, 80%) as a yellow oil.

$^1$H NMR (400 MHz, CDCl$_3$) δ 7.61 (dd, J=8.0, 1.6 Hz, 1H), 7.32 (td, J=7.8, 1.6 Hz, 1H), 7.13 (dd, J=8.1, 1.6 Hz, 1H), 7.05 (td, J=7.7, 1.6 Hz, 1H), 4.19-4.12 (m, 1H), 3.81 (d, 0.7=2.0 Hz, 1H), 2.06 (d, J=0.9 Hz, 3H).

Step 5: 2'-(prop-1-en-2-yloxy)-5,6-dihydro-[1,1'-biphenyl]-3(4H)-one

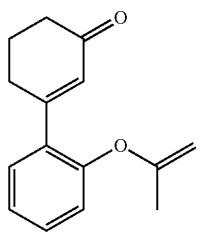 [SMILES: C=C(C)Oc1ccccc1C1=CC(=O)CCC1]

In a nitrogen flushed 250 mL round-bottomed flask, 1-bromo-2-(prop-1-en-2-yloxy)benzene (3 g, 14.08 mmol, 1.000) was dissolved in DME (80 mL) and water (26 mL). 3-(4,4,5,5-tetramethyl-1,3,2-dioxaborolan-2-yl)cyclohex-2-en-1-one (3.75 g, 16.90 mmol), PdCl$_2$(dppf)-CH$_2$Cl$_2$ adduct (0.575 g, 0.704 mmol), Na$_2$CO$_3$ (4.48 g, 42.2 mmol) were added to the reaction mixture in one portion. The resulting mixture was stirred at 90° C. for 2 hours. After cooling down to RT, the resulting mixture was extracted with EA three times, concentrated in vacuo to give the crude, which was purified by silica gel column and eluted with EA/Heptane from 0-30% to give the title compound (2.3 g, 71.6%) as a yellow oil.

MS: 229.3 (M+H$^+$).

Step 6: 3-(2-(prop-1-en-2-yloxy)phenyl)-3-vinylcyclohexan-1-one

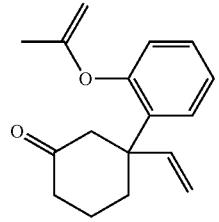 [SMILES: C=CC1(c2ccccc2OC(=C)C)CCCC(=O)C1]

Under Ar, to a solution of copper(I) iodide (626 mg, 3.29 mmol) and lithium chloride (139 mg, 3.29 mmol) in THF (10 mL) was dropwise added vinylmagnesium bromide (862 mg, 6.57 mmol) in THF (6.5 mL) at −78° C., after 30 mins, 2'-(prop-1-en-2-yloxy)-5,6-dihydro-[1,1'-biphenyl]-3(4H)-one (500 mg, 2.190 mmol) in THF (5 mL) was added to the mixture, stirred for 1 hour. And then stirred at room temperature overnight. Quenched with saturated NH$_4$Cl solution, the resulting mixture was extracted with EA three times, the combined organic layers were washed with brine, concentrated in vacuo to give the crude, which was purified by silica gel column and eluted with EA/Heptane from 0-15% to afford the title compound (200 mg, 35.6%) as a yellow oil.

$^1$H NMR (400 MHz, CDCl$_3$) δ 7.34 (dd, J=7.9, 1.8 Hz, 1H), 7.23 (tt, J=7.5, 1.8 Hz, 1H), 7.10-7.01 (m, 2H), 6.05-5.93 (m, 1H), 5.17 (dd, J=10.9, 1.6 Hz, 1H), 5.04 (dd, J=17.6, 1.7 Hz, 1H), 4.23 (d, J=1.8 Hz, 1H), 4.03 (d, J=1.8 Hz, 1H), 2.97-2.86 (m, 1H), 2.86-2.77 (m, 1H), 2.64-2.52 (m, 1H), 2.42-2.25 (m, 2H), 2.06-2.01 (m, 1H), 1.98 (d, J=1.4 Hz, 3H), 1.97-1.80 (m, 1H), 1.79-1.67 (m, 1H).

Step 7: 2-methylspiro[chromene-4,1'-cyclohexan]-3'-one

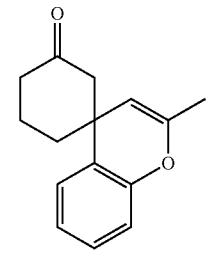 [SMILES: CC1=CC2(CCCC(=O)C2)c2ccccc2O1]

In a nitrogen flushed 50 mL round-bottomed flask, the mixture of 3-(2-(prop-1-en-2-yloxy)phenyl)-3-vinylcyclohexan-1-one (1.2 g, 4.68 mmol) and Grubbs ii (0.199 g, 0.234 mmol) in DCM (10 mL) was stirred at RT for 14 hours. After removal of the volatiles under reduced pressure to give the crude residual, which was purified by silica gel column and eluted with EA/Heptane from 0 to 10% to afford the title compound (1.1 g, 103%) as a yellow oil. MS: 229.3 (M+H$^+$).

Step 8: 2-methylspiro[chromane-4,1'-cyclohexan]-3'-one

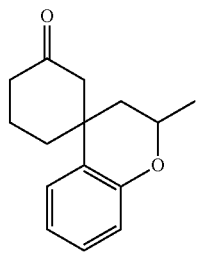 [SMILES: CC1CC2(CCCC(=O)C2)c2ccccc2O1]

The mixture of 2-methylspiro[chromene-4,1'-cyclohexan]-3'-one (1.5 g, 6.57 mmol) and Pd/C (0.070 g, 0.657 mmol) in EA (20 mL) was stirred at 35° C. under H2 condition overnight. The filtrate was concentrated in vacuo to give the title compound (1.2 g, 79%) as a yellow oil. MS: 231.1 (M+H$^+$).

Example 29 was prepared essentially the same protocol described in EXAMPLE 25 With 2-methylspiro[chromane-4,1'-cyclohexan]-3'-one to afford 200 mg as a white solid.

MS: 557.3 (M+H$^+$). $^1$H NMR (400 MHz, DMSO) δ 7.39 (d, J=7.9 Hz, 1H), 7.10 (t, J=7.7 Hz, 1H), 6.90 (t, J=7.5 Hz, 1H), 6.83 (dd, J=15.8, 8.0 Hz, 1H), 6.77 (d, J=8.0 Hz, 1H), 6.19 (d, J=16.5 Hz, 1H), 5.78 (d, J=10.7 Hz, 1H), 4.99-4.69 (m, 1H), 4.40-4.29 (m, 1H), 4.28-3.98 (m, 3H), 3.97-3.70 (m, 2H), 3.29-3.05 (m, 3H), 3.03-2.78 (m, 4H), 2.77-2.54 (m, 1H), 2.48-2.42 (m, 2H), 2.35 (s, 3H), 2.24-2.06 (m, 2H), 2.04-1.81 (m, 3H), 1.78-1.42 (m, 5H), 1.41-1.23 (m, 3H).

Example 30

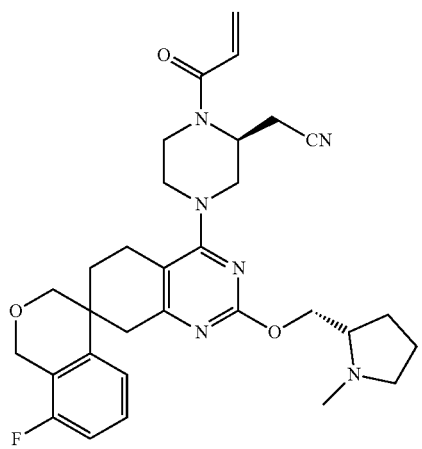

Intermediate: 8'-fluorospiro[cyclohexane-1,4'-isochroman]-3-one

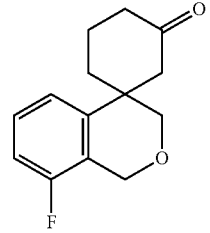 [SMILES: O=C1CCCC2(COCc3c(F)cccc32)C1]

Step 1: 2-(2-ethoxy-2-oxoethyl)-6-fluorobenzoic acid

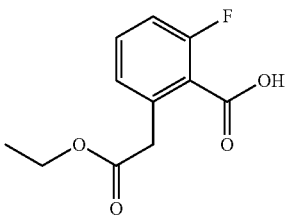 [SMILES: CCOC(=O)Cc1cccc(F)c1C(=O)O]

Under Ar, to the mixture of ethyl 3-oxobutanoate (2.377 g, 18.26 mmol) and sodium ethanolate (1.864 g, 27.4 mmol) in Ethanol (30 mL) was added 2-bromo-6-fluorobenzoic acid (2 g, 9.13 mmol) and copper(I) bromide (1.310 g, 9.13 mmol) at RT, then the mixture was stirred at reflux for 2 hour. After cooling down to RT, the filtrate was concentrated in vacuo to give a residual, which was acidified with 2M HCl solution, and the resulting mixture was extracted CH$_2$Cl$_2$ three times. The combined organic layers were washed with NaHCO$_3$ solution, the separated aqueous layer was acidified with 2M HCl to pH 1 and extracted with CH$_2$Cl$_2$ twice again. The organic layers were washed with brine, dried over Na$_2$SO$_4$ and concentrated in vacuo to give the title product (1.84 g, 89%) as an oil. MS: 209.3 (M–H$_2$O+H$^+$). $^1$H NMR (400 MHz, DMSO-d6) δ 13.52 (br, 1H), 7.50-7.44 (m, 1H), 7.25-1.18 (m, 2H), 4.05 (q, J=6.8 Hz, 2H), 3.84 (s, 2H), 1.16 (t, J=6.8 Hz, 3H).

Step 2: 2-(2-ethoxy-2-oxoethyl)-6-fluorobenzoic acid

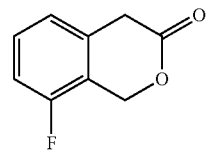 [SMILES: O=C1Cc2cccc(F)c2CO1]

Under Ar, ethyl carbonochloridate (9.50 g, 88 mmol) was added to a solution of 2-(2-ethoxy-2-oxoethyl)-6-fluorobenzoic acid (18 g, 80 mmol) and TEA (8.86 g, 88 mmol) in DCM (160 mL) at 0° C. After stirring for 2 h at RT, the mixture was quenched by addition of 1M HCl and the mixture was extracted with CH$_2$Cl$_2$. The organic layers were washed with brine, dried (Na$_2$SO$_4$) and concentrated to give a residual, which was dissolved in THF (200 mL). and then a cold (0° C.) water (60 mL) solution of NaBH$_4$ (6.02 g, 159 mmol) was added to the above mixture at −15° C. After stirring at −15° C. for 1 hour, the mixture was quenched by addition of 1M HCl and extracted with Et$_2$O twice. The organic layers were washed with sat. aq. NaHCO$_3$, water and brine, dried (Na$_2$SO$_4$) and concentrated. The crude product was heated together with Ts-OH (0.757 g, 3.98 mmol) in Toluene (180 mL) at 80° C. for 1 hour. After cooling to RT, the mixture was concentrated, diluted with EA and washed with sat. aq. NaHCO$_3$, water and brine, dried (Na$_2$SO4) and concentrated to dryness. The residue was purified by silical gel column and eluted with PE/EA=3:1 to give the title compound (9.45 g, 71.5%) as a brown solid. MS: 167.1 (M+H$^+$). $^1$H NMR (400 MHz, DMSO-d6) δ 7.43-7.37 (m, 1H), 7.19-7.15 (m, 2H), 5.42 (s, 2H), 3.87 (s, 2H).

Step 3: 3-(benzyloxy)-8'-fluorospiro[cyclohexane-1, 4'-isochroman]-3'-one

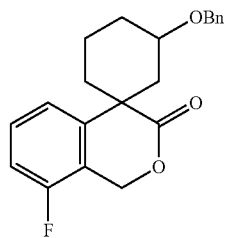 [SMILES: O=C1OCc2c(F)cccc2C12CCCC(OCc1ccccc1)C2]

Under Ar, a solution of 8-fluoroisochroman-3-one (3.5 g, 21.07 mmol) and (((1,5-diiodopentan-2-yl)oxy)methyl)benzene (9.51 g, 22.12 mmol) in DMF (20 mL) was dropwise to a solution of sodium hydride (1.769 g, 44.2 mmol) in 20 ml DMF at RT, then the reaction was stirred at RT overnight. Quenched with saturated NH$_4$Cl solution, the resulting mixture was extracted with EA three times. The combined organic layers were washed with brine, concentrated to give a residual, which was purified by silica gel column and eluted with ethyl acetate/hexane from 5% to 40% to give the title compound (4.28 g, 59.7%) as a yellow oil. MS: 341.5 (M+H$^+$).

Step 4: (3-(benzyloxy)-1-(2-(hydroxymethyl)phenyl)cyclohexyl)methanol

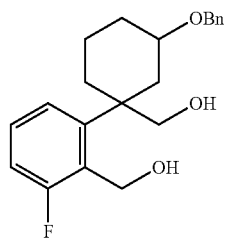 [SMILES: OCc1c(F)cccc1C1(CO)CCCC(OCc2ccccc2)C1]

Under Ar, to a solution of 3-(benzyloxy)-8'-fluorospiro [cyclohexane-1,4'-isochroman]-3'-one (4.28 g, 12.57 mmol) in THF (50 mL) was added LiAlH4 (1.432 g, 37.7 mmol) at ice-water condition. After stirred at RT for 3 hours, 1.4 ml of water was added dropwise carefully at ice-water condition, followed 1.4 ml of 2 M NaOH, 1.4 ml of water, then the mixture was diluted with EA, and the mixture was stirred at RT for 1 Hour. The filtrate was concentrated in vacuo to give a residue, which was purified by silica gel column and eluted with PE/EA=1:1 to afford the title compound (2.33 g, 56.8%) as a colorless oil.

MS: 345.3 (M+H$^+$). $^1$H NMR (400 MHz, Chloroform-d) δ 7.32-7.21 (m, 5H), 7.06-6.99 (m, 3H), 4.88 (d, J=2.4 Hz, 2H), 4.53-4.39 (m, 2H), 3.85-3.77 (m, 3H), 2.37-2.29 (m, 3H), 2.16-2.02 (m, 2H), 1.95-1.79 (m, 3H), 1.60-1.54 (m, 2H).

Step 5: 3-(benzyloxy)-8'-fluorospiro[cyclohexane-1, 4'-isochromane]

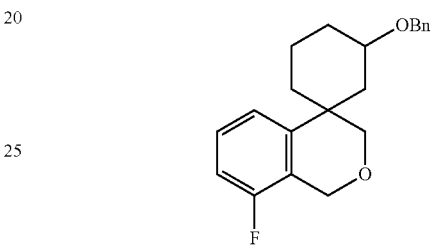

Under Ar, In a three 100 mL three neck bottles, triphenylphosphane (2.102 g, 8.01 mmol) was dissolved in THF (40 mL) The reaction mixture was cooled to 0° C., diisopropyl (E)-diazene-1,2-dicarboxylate (1.620 g, 8.01 mmol) in 10 mL THF was added to the mixture reaction, after 10 mins, (3-(benzyloxy)-1-(3-fluoro-2-(hydroxymethyl)phenyl)cyclohexyl)methanol (step 4, 2.3 g, 6.68 mmol) in 20 mL dry THF was added to the reaction mixture. And then, the mixture was stirred at room temperature overnight. After the reaction, the volatiles were removed in vacuo to give the crude residual, which was purified by silica gel column and eluted with PE/EA=5:1 to give the title compound (1.22 g, 56.0%) as a colorless oil. 327.3 (M+H$^+$).

Step 6: 8'-fluorospiro[cyclohexane-1,4'-isochroman]-3-ol

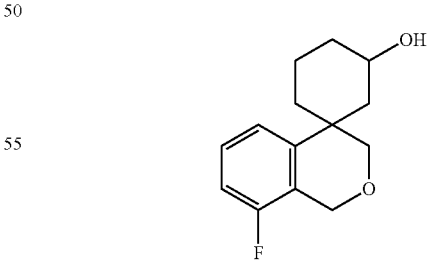

The mixture of 3-(benzyloxy)-8'-fluorospiro[cyclohexane-1,4'-isochromane] (1.22 g, 3.74 mmol) and Pd(OH)$_2$ (0.157 g, 1.121 mmol) in MeOH (10 mL) was stirred at RT under H$_2$ overnight. The filtrate was concentrated in vacuo to give a title compound (800 mg, 91%) as a colorless oil. 219.2 (M−H$_2$O+H$^+$).

155

Step 7: 8'-fluorospiro[cyclohexane-1,4'-isochroman]-3-one

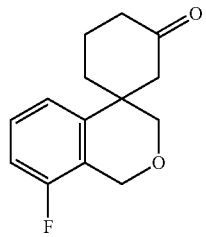 [SMILES: O=C1CCCC2(COCc3c(F)cccc32)C1]

Under Ar, to a solution of 8'-fluorospiro[cyclohexane-1,4'-isochroman]-3-ol (167 mg, 0.707 mmol) in DCM (10 mL) was added DMP (450 mg, 1.060 mmol) at RT, then the mixture was stirred at rt for 2 hours. Saturated NaHCO$_3$, saturated Na$_2$S$_2$O$_3$ solution was added, the resulting mixture was extracted with DCM twice, the combined organic layers were dried over Na$_2$SO$_4$, concentrated in vacuo to give the residual, which was purified by silica gel column and eluted with PE/EA=3:1 to give the title compound (110 mg, 66.4%) as colorless oil. 235.3 (M–H$_2$O+H$^+$).

Example 30 was prepared essentially the same protocol described in EXAMPLE 25 With 8'-fluorospiro[cyclohexane-1,4'-isochroman]-3-one to afford 66 mg as a white solid.

MS: 561.7 (M+H$^+$). $^1$H NMR (400 MHz, DMSO-d6) δ 7.32-7.24 (m, 2H), 7.07-7.03 (m, 1H), 6.93-6.79 (m, 1H), 6.18 (dd, J=16.8, 1.6 Hz, 1H), 5.76 (d, J=11.2 Hz, 1H), 4.95-4.74 (m, 3H), 4.38-3.99 (m, 3H), 3.91-3.55 (m, 4H), 3.27-2.53 (m, 11H), 2.32 (s, 3H), 2.18-2.05 (m, 2H), 1.96-1.54 (m, 5H).

Example 31

2-((2S)-1-acryloyl-4-(5-fluoro-2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 27)

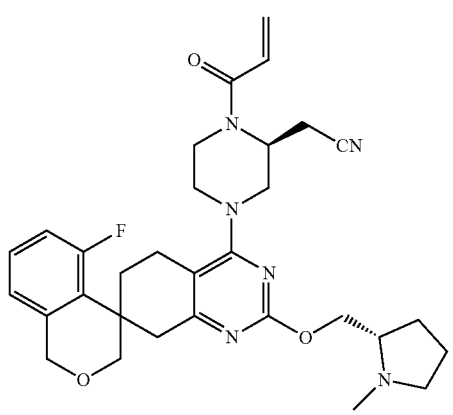 [SMILES: C=CC(=O)N1CCN(c2nc(OC[C@@H]3CCCN3C)nc3c2CCC2(COCc4cccc(F)c42)C3)C[C@@H]1CC#N]

156

Intermediate: 5'-fluorospiro[cyclohexane-1,4'-isochroman]-3-one

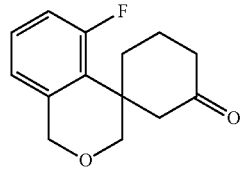 [SMILES: O=C1CCCC2(COCc3cccc(F)c32)C1]

Step 1: methyl 3-fluoro-2-methylbenzoate

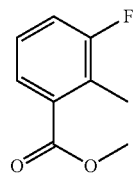

Under Ar, the mixture of 3-fluoro-2-methylbenzoic acid (5 g, 32.4 mmol) and H$_2$SO$_4$ (1 mL) in MeOH (80 mL) was stirred at 80° C. overnight. After removal of the volatile under reduced pressure, the solution of NaHCO$_3$ was added. The resulting mixture was extracted three times with EA, the combined organic layers was washed with brine, dried over Na$_2$SO$_4$, and concentrated to give the title compound (4.14 g, 76%) as a light-yellow oil.

Step 2: methyl 2-(bromomethyl)-3-fluorobenzoate

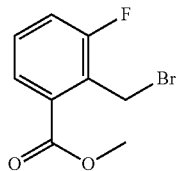

Under Ar, the mixture of methyl 3-fluoro-2-methylbenzoate (2.07 g, 12.31 mmol), AIBN (0.707 g, 4.31 mmol), NBS (2.213 g, 12.43 mmol) in CCl$_4$ (75 mL) was stirred at 80° C. overnight. After cooling sown to RT, the filtrate was concentrated in vacuo to give a residual, which was purified by silica gel column and eluted with EA/Hex from 0 to 30% to afford the title compound (3.0 g, 99%) as a colorless oil Step 3: methyl 2-(cyanomethyl)-3-fluorobenzoate Under Ar, to a solution of TMS-CN (1.205 g, 12.14 mmol) and TBAF (3.17 g, 12.14 mmol) in THF (80 ml) was added methyl 2-(bromomethyl)-3-fluorobenzoate (3 g, 12.14 mmol) at 0° C. then was added to the mixture, it was stirred for 4 h at rt. water was added to the mixture, extracted with EA 3 times, the combined EA was washed with brine, drive over Na$_2$S04, filtrated and concentrated to give a residue which was purified by silica gel column chromatography (EA/HEX from 0 to 30%) to give the title compound (2.1 g, 90%) solid.

MS: 194.2 (M+H$^+$).

Step 4: 2-(2-fluoro-6-(hydroxymethyl)phenyl)acetonitrile

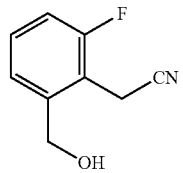 [SMILES: N#CCc1c(F)cccc1CO]

Under Ar, to a solution of methyl 2-(cyanomethyl)-3-fluorobenzoate (6.5 g, 33.6 mmol) in THF (100 mL) was added LiBH$_4$ (1.466 g, 67.3 mmol) patch-wise at RT, and then the mixture was stirred at RT overnight. Quenched with NH$_4$Cl aq, the resulting mixture was extracted with EA three times. The combined organic layers were washed with brine, dried over Na$_2$SO$_4$, and concentrated under reduced pressure to give a crude title compound (5.5 g) as a white solid, which was used in next step without further purification Step 5: 2-(2-fluoro-6-(hydroxymethyl)phenyl)acetic acid

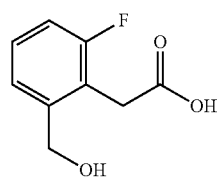 [SMILES: O=C(O)Cc1c(F)cccc1CO]

Under Ar, the mixture of sodium hydroxide (1.332 g, 33.3 mmol), 2-(2-fluoro-6-(hydroxymethyl)phenyl)acetonitrile (5.5 g, 33.3 mmol) in EtOH (50 mL)/Water (50 mL) was stirred at 105° C. overnight. After removal of volatile, the resulting mixture was acidified with HCl solution, and extracted with DCM three times, the combined organic layers were washed with brine, dried over Na$_2$SO$_4$, concentrated in vacuo to give the crude title compound (5 g) as a colorless oil, which was used in next step without further purification.

Step 6: 5-fluoroisochroman-3-one

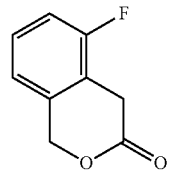 [SMILES: O=C1Cc2c(F)cccc2CO1]

Under Ar, the mixture of Ts-OH (6.51 g, 34.2 mmol) and 2-(2-fluoro-6-(hydroxymethyl)phenyl)acetic acid (6.3 g, 34.2 mmol) in Toluene (60 mL) was stirred at 60° C. for 2 hours. The solvent was removed in vacuo to give a residual, which was purified by silica gel column and eluted with EA/HEX from 0 to 30% to afford the title compound (1.72 g, 30.3%) as a white solid.

Step 7: 3-(benzyloxy)-5'-fluorospiro[cyclohexane-1,4'-isochroman]-3'-one

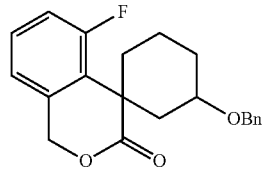 [SMILES: O=C1OCc2cccc(F)c2C12CCCC(OCc1ccccc1)C2]

Under Ar, to a solution of sodium hydride (60.7 mg, 2.53 mmol) in DMF (20 mL) was added the mixture of 5-fluoroisochroman-3-one (200 mg, 1.204 mmol) and (((1,5-diiodopentan-2-yl)oxy)methyl)benzene (518 mg, 1.204 mmol) in DMF (20 mL) at 35° C., and then the mixture was stirred at 60° C. for 30 mins. After cooling down to RT, water was added, the resulting mixture was extracted with EA three times, the combined organic layers were washed with brine, dried over Na$_2$SO$_4$, and concentrated to give a residue, which was purified by silica gel column and eluted with EA/HEX from 0% to 30% to afford the title compound (293 mg, 71.5%) as a white solid. MS: 341.6 (M+H$^+$).

Step 8: (3-(benzyloxy)-1-(2-fluoro-6-(hydroxymethyl)phenyl)cyclohexyl)methanol

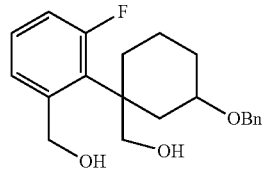 [SMILES: OCc1cccc(F)c1C1(CO)CCCC(OCc2ccccc2)C1]

Under Ar, To a solution of (benzyloxy)-5'-fluorospiro [cyclohexane-1,4'-isochroman]-3'-one (1.5 g, 4.41 mmol) in THF (50 mL) was added LAH$_4$ (0.334 g, 8.81 mmol) at 0° C., then the mixture was stirred at RT for 3 hours. Water was added, the resulting mixture was extracted with EA three times, the combined organic layers was washed with brine, dried over Na$_2$SO$_4$, filtrated and concentrated to give a residue, which was purified by silica gel column and eluted with EA/HEX from 0% to 50% to afford the title compound (550 mg, 38.2%) as a white solid.

Step 9: Synthesis of 3-(benzyloxy)-5'-fluorospiro [cyclohexane-1,4'-isochromane]

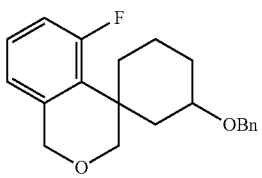 [SMILES: Fc1cccc2c1C1(CCCC(OCc3ccccc3)C1)COC2]

Under Ar, to a mixture of Ph$_3$P (1293 mg, 4.93 mmol) and DIAD (997 mg, 4.93 mmol, 1.2) in THF (10 mL) was added DIAD (997 mg, 4.93 mmol, 1.2) was dropwise added (3-(benzyloxy)-1-(2-fluoro-6-(hydroxymethyl)phenyl)cyclohexyl)methanol (1415 mg, 4.11 mmol) dissolved in THF (10 mL) at 0° C., and then the mixture was stirred at RT for 6 hours. Water was added, the resulting mixture was extracted with EA three times, the combined organic layers were washed with brine, dried over Na$_2$SO$_4$, filtrated and concentrated to give a residue, which was purified by silica gel column and eluted with EA/HEX from 0% to 10% to afford the title compound (880 mg, 65.6%) as a white solid. $^1$H NMR (400 MHz, DMSO) δ 7.37-7.17 (m, 6H), 7.01 (dd, J=13.1, 8.0 Hz, 1H), 6.89 (d, J=7.5 Hz, 1H), 4.67 (s, 2H), 4.49 (s, 2H), 3.85 (d, J=11.8 Hz, 1H), 3.71 (d, J=11.8 Hz, 1H), 3.60-3.49 (m, 1H), 2.18-1.84 (m, 4H), 1.71-1.57 (m, 2H), 1.57-1.42 (m, 1H), 1.23-1.11 (m, 1H).

Step 10: Synthesis of 5'-fluorospiro[cyclohexane-1, 4'-isochroman]-3-ol

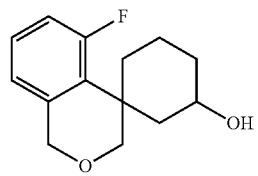 [SMILES: OC1CCCC2(COCc3cccc(F)c32)C1]

The mixture of Pd(OH)$_2$ (404 mg, 2.88 mmol) and 3-(benzyloxy)-5'-fluorospiro[cyclohexane-1,4'-isochromane] (940 mg, 2.88 mmol) in MeOH (20 mL) was stirred at 25° C. overnight. The filtrate was concentrated in vacuo to give the crude title compound (678 mg) as a white solid.

Step 11: 5'-fluorospiro[cyclohexane-1,4'-isochroman]-3-one

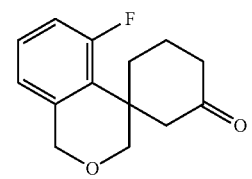 [SMILES: O=C1CCCC2(COCc3cccc(F)c32)C1]

Under Ar, to a solution of 5'-fluorospiro[cyclohexane-1, 4'-isochroman]-3-ol (678 mg, 2.87 mmol) in DCM (30 mL) was added PCC (3093 mg, 14.35 mmol) at 0° C., then it was stirred at RT for 3 hours. The filtrate was concentrated in vacuo to give the crude, which was purified by silica gel column and eluted with EA/HEX from 0% to 30% to give the title compound (551 mg, 82%). MS: 235.3 (M+H$^+$).

Example 31 was prepared essentially the same protocol described in EXAMPLE 25 With 5'-fluorospiro[cyclohexane-1,4'-isochroman]-3-one to afford 40 mg as a white solid.

MS: 561.7 (M+H$^+$). $^1$H NMR (400 MHz, DMSO) δ 7.27 (dd, J=12.9, 7.6 Hz, 1H), 7.11-7.02 (m, 1H), 6.95 (d, J=7.4 Hz, 1H), 6.90-6.74 (m, 1H), 6.18 (d, J=16.6 Hz, 1H), 5.77 (d, J=10.3 Hz, 1H), 5.03-4.62 (m, 3H), 4.46-3.96 (m, 3H), 3.96-3.53 (m, 5H), 3.28-3.12 (m, 2H), 3.10-2.58 (m, 8H), 2.33 (s, 3H), 2.26-2.04 (m, 2H), 1.98-1.79 (m, 2H), 1.76-1.51 (m, 3H)

Example 32

2-((2S)-1-acryloyl-4-(5-fluoro-2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 28)

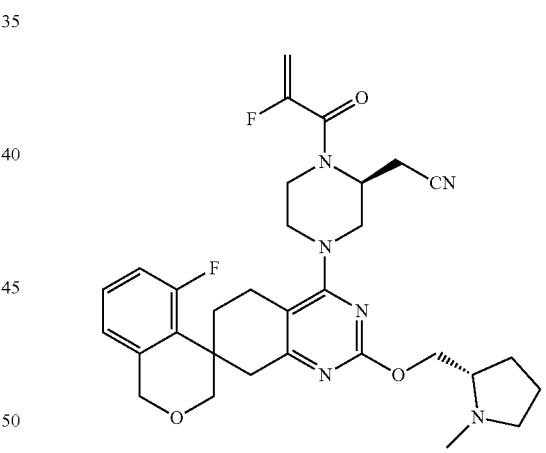

Example 32 was prepared using essentially the same protocol described and afford 36 mg as white solid. MS: 579.9 (M+H$^+$). $^1$H NMR (400 MHz, DMSO) δ 7.27 (td, J=7.9, 5.3 Hz, 1H), 7.05 (dd, J=12.4, 8.2 Hz, 1H), 6.95 (d, J=7.6 Hz, 1H), 5.47-5.14 (m, 2H), 5.03-4.00 (m, 4H), 3.98-3.68 (m, 4H), 3.30-3.27 (m, 3H), 3.21 (dd, J=13.8, 3.5 Hz, 1H), 3.05-2.75 (m, 4H), 2.64 (d, J=4.7 Hz, 2H), 2.56-2.50 (m, 3H), 2.33 (s, 3H), 2.27-2.10 (m, 2H), 1.98-1.79 (m, 2H), 1.74-1.51 (m, 3H).

Example 33

1-(3-(5-fluoro-2'-(((S)-1-methylpyrrolidin-2-yl)methoxy)-5',8'-dihydro-6'H-spiro[isochromane-4,7'-quinazolin]-4'-yl)-3,8-diazabicyclo[3.2.1]octan-8-yl)prop-2-en-1-one (Cpd. No. 29)

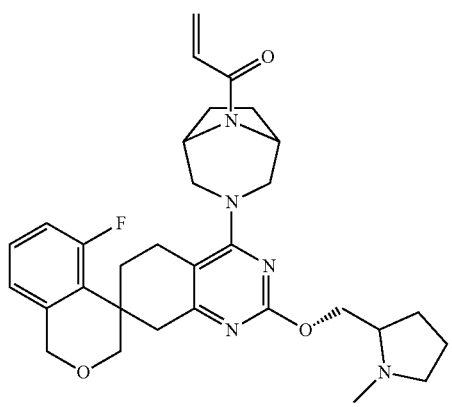

Example 33 was prepared essentially the same protocol described in EXAMPLE 25 with 3,8-diazabicyclo[3.2.1]octane in place of (S)-2-(piperazin-2-yl)acetonitrile hydrochloride to afford 28 mg as a white solid. MS: 548.7 (M+H$^+$). $^1$H NMR (400 MHz, DMSO) δ 7.34-7.20 (m, 1H), 7.04 (dd, J=12.6, 8.1 Hz, 1H), 6.94 (d, J=7.6 Hz, 1H), 6.84-6.67 (m, 1H), 6.20 (d, J=16.8 Hz, 1H), 5.72 (d, J=10.5 Hz, 1H), 5.02-4.54 (m, 4H), 4.22 (dd, J=10.7, 4.8 Hz, 1H), 4.16-3.94 (m, 2H), 3.83-3.69 (m, 2H), 3.64 (d, J=12.8 Hz, 1H), 3.28-3.12 (m, 1H), 3.02-2.59 (m, 5H), 2.55-2.51 (m, 2H), 2.33 (s, 3H), 2.22-2.21 (m, 2H), 2.08-1.48 (m, 9H).

Example 34

2-((2S)-1-acryloyl-4-(2-methyl-2'-(((S)-1-methylpyrrolidin-2-yl)methoxy)-2,3,5',8'-tetrahydro-1H,6'H-spiro[isoquinoline-4,7'-quinazolin]-4'-yl)piperazin-2-yl)acetonitrile (Cpd. No. 30)

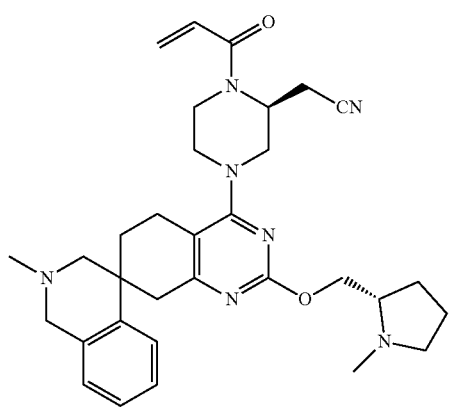 [SMILES: C=CC(=O)N1CCN(c2nc(OC[C@@H]3CCCN3C)nc3c2CCC2(C3)CN(C)Cc3ccccc32)C[C@@H]1CC#N]

Intermediate: 2'-methyl-2',3'-dihydro-1'H-spiro[cyclohexane-1,4'-isoquinolin]-3-one

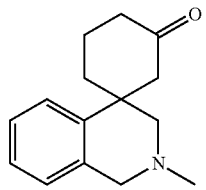 [SMILES: CN1Cc2ccccc2C2(CCCC(=O)C2)C1]

Step 1: 1,5-diiodopentan-2-yl acetate

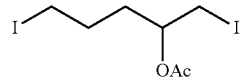 [SMILES: CC(=O)OC(CI)CCCI]

Under Ar, the mixture of Chlorotrimethylsilane (66.24 g, 609.6 mmol), sodium iodide (208 g, 1392 mmol) and (tetrahydrofuran-2-yl)methyl acetate (80.0 g, 555.2 mmol) in Acetonitrile (1000 mL) was stirred at RT overnight. The filtrate was concentrated in vacuo to give a residual, which was purified by silica gel column and eluted with ethyl acetate/Heptane from 0 to 40% to afford the title compound (128.0 g, 60.4%) as an oil. MS: 382.9 (M+H$^+$). $^1$H NMR (400 MHz, CDCl3) δ 4.80-4.68 (m, 1H), 3.33 (dd, J=10.6, 5.3 Hz, 1H), 3.26 (dd, J=10.6, 5.3 Hz, 1H), 3.19 (t, J=6.4 Hz, 2H), 2.09 (s, 3H), 1.94-1.75 (m, 4H).

Step 2: 3'-oxospiro[cyclohexane-1,4'-isochroman]-3-yl acetate

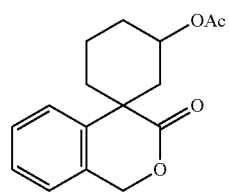 [SMILES: CC(=O)OC1CCCC2(C1)C(=O)OCc1ccccc12]

Under Ar, the solution of Isochroman-3-one (20.0 g, 135.0 mmol) and 1,5-diiodopentan-2-yl acetate (54.25 mg, 141.75 mmol) in DMF (100 mL) was dropwise added to a solution of sodium hydride (10.8 g, 270 mmol) in 80 mL DMF at ice-water condition, and then the mixture was stirred at RT overnight. Quenched with saturated NH$_4$Cl (100 mL) solution, the resulting mixture was extracted with EA three times, the combined organic layers were washed with brine, dried over Na$_2$SO$_4$, filtrated and concentrated to give a residue, which was purified by silica gel column and eluted with EA/HEX from 0% to 10% to afford the title compound (23.0 g, 62.1%) as a light yellow oil. MS: 275.2 (M+H$^+$). $^1$H NMR (400 MHz, CDCl3) δ 7.45-7.36 (m, 2H), 7.30 (td, J=7.3, 1.3 Hz, 1H), 7.18 (d, J=7.4 Hz, 1H), 5.63-5.48 (m, 2H), 5.34 (d, J=14.7 Hz, 1H), 2.51-2.33 (m, 1H), 2.30-2.15 (m, 2H), 2.03 (s, 4H), 1.94-1.87 (m, 1H), 1.87-1.77 (m, 1H), 1.62 (s, 1H), 1.50-1.38 (m, 1H), 1.38-1.13 (m, 1H).

Step 3: 3-hydroxyspiro[cyclohexane-1,4'-isochroman]-3'-one

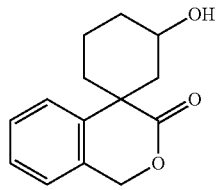 [SMILES: O=C1OCc2ccccc2C12CCCC(O)C2]

Under Ar, the mixture of 3'-oxospiro[cyclohexane-1,4'-isochroman]-3-yl acetate (3.0 g, 83.8 mmol) and $K_2CO_3$ (11.53 g, 83.7 mmol, 1.0) in 100 mL MeOH was stirred at RT for 2 hour. The filtrate was concentrated in vacuo to afford the crude title compound (16.3 g, 83.70%) as an oil. MS: 233.2 (M+H$^+$).

Step 4: 3-((tert-butyldimethylsilyl)oxy)spiro[cyclohexane-1,4'-isochroman]-3'-one

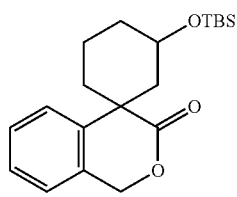 [SMILES: CC(C)(C)[Si](C)(C)OC1CCCC2(C1)C(=O)OCc1ccccc12]

Under Ar, the mixture of 3-hydroxyspiro[cyclohexane-1,4'-isochroman]-3'-one (16.3 g, 70.17 mmol), imidazole (7.17 g, 105.30 mmol) and TBS-C$_1$ (15.49 g, 105.30 mmol) in DMF (85 mL) was stirred at RT for 3 hours. Water was added, the resulting mixture was extracted with EA three times, the combined organic layers were washed with brine, dried over $Na_2SO_4$, filtrated and concentrated to give a residue, which was purified by silica gel column and eluted with EA/HEX form 0% to 10% to afford the title compound (16.0 g, 65.82%) as a colorless oil. $^1$H NMR (400 MHz, CDCl3) δ 7.46 (d, J=7.9 Hz, 1H), 7.38 (t, J=7.5 Hz, 1H), 7.33-7.27 (m, 1H), 7.17 (d, J=7.4 Hz, 1H), 5.53 (d, J=14.6 Hz, 1H), 5.32 (d, J=14.6 Hz, 1H), 4.49 (tt, J=10.2, 4.6 Hz, 1H), 2.32-2.23 (m, 1H), 2.21-2.14 (m, 1H), 2.06-1.95 (m, 1H), 1.85-1.64 (m, 2H), 1.46-1.35 (m, 1H), 1.34-1.19 (m, 2H), 0.91 (s, 9H), 0.11 (d, J=2.3 Hz, 6H).

Step 5: (3-((tert-butyldimethylsilyl)oxy)-1-(2 (hydroxymethyl) phenyl)cyclohexyl) methanol

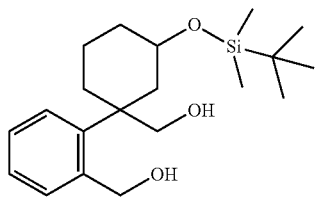 [SMILES: CC(C)(C)[Si](C)(C)OC1CCCC(CO)(c2ccccc2CO)C1]

Under Ar, LiAlH$_4$ (5.24 g, 138.24 mmol) was added to the solution of 3-((tert-butyldimethylsilyl) oxy)spiro[cyclohexane-1,4'-isochroman]-3'-one (16.0 g, 46.24 mmol) in THF (75 mL) at 0° C., then the mixture was stirred at RT for 1 hour. $H_2O$ (4 mL) was added to the reaction mixture, followed added 4 mL 15% NaOH solution, stirred 5 mins, added 8 mL $H_2O$ again, stirred for 15 mins. At last, $Na_2SO_4$ was added the mixture and the filtrate was concentrated in vacuo to give a residual, which was purified by silica gel column and eluted with ethyl acetate/hexane from 0% to 50% to afford the title compound (8.0 g, 49.4%) as a colorless oil. MS: 351.3 (M+H$^+$).
$^1$H NMR (400 MHz, CDCl3) δ 7.50 (dd, J=8.0, 1.4 Hz, 1H), 7.40 (dd, J=7.4, 1.8 Hz, 1H), 7.33 (td, J=7.6, 1.8 Hz, 1H), 7.27 (td, J=7.3, 1.4 Hz, 1H), 4.95-4.81 (m, 2H), 3.94 (dd, J=8.3, 4.7 Hz, 3H), 2.44-2.32 (m, 1H), 2.17 (d, J=12.5 Hz, 1H), 1.94-1.70 (m, 3H), 1.42-1.21 (m, 3H), 0.87 (s, 9H), 0.08 (d, J=6.3 Hz, 6H).

Step 6: 2-(3-((tert-butyldimethylsilyl)oxy)-1-(((methylsulfonyl)oxy)methyl)cyclo hexyl)benzyl methanesulfonate

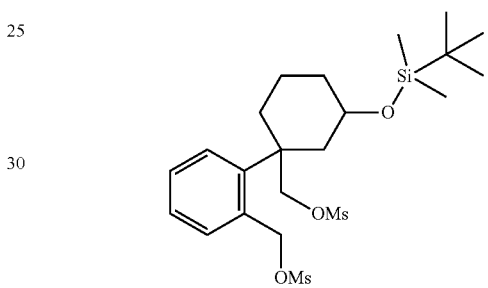

Under Ar, to a solution of (3-((tert-butyldimethylsilyl)oxy)-1-(2-(hydroxymethyl)phenyl)cyclohexyl)methanol (3.9 g, 11.12 mmol) and TEA (4.50 g, 44.5 mmol) in DCM (35 mL) was added Ms-C$_1$ (6.37 g, 55.6 mmol) at 0° C. After 15 mins, quenched with water, the resulting mixture was extracted with DCM three times, the combined organic layers were washed with brine, dried over $Na_2SO_4$, filtrated and concentrated to give the crude title compound (5.5 g) as an oil. MS: 507.2 (M+H$^+$).

Step 7: 3-((tert-butyldimethylsilyl)oxy)-2'-methyl-2',3'-dihydro-1'H-spiro[cyclohexane-1,4'-isoquinoline]

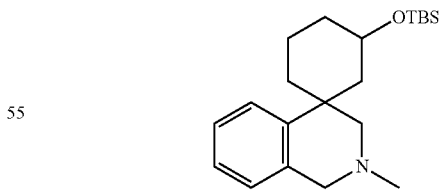

Under Ar, the mixture of 2-(3-((tert-butyldimethylsilyl)oxy)-1-(((methylsulfonyl)oxy)methyl) cyclohexyl) benzyl methanesulfonate (2.5 g, 4.93 mmol) and methanamine (24.67 mmol) in Ethanol (5 mL) was stirred at 100° C. under microwave condition for 1 hour. After the reaction, the volatile was removed in vacuo to give a residual, which was purified by silica gel column and eluted with ethyl acetate/hexane from 0 to 50% to afford the title compound (1.0 g, 58.7%). MS: 346.3 (M+H⁺). $^1$H NMR (400 MHz, CDCl3) δ 7.38 (d, J=7.9 Hz, 1H), 7.19 (t, J=7.5 Hz, 1H), 7.10 (t, J=7.4 Hz, 1H), 6.99 (d, J=7.6 Hz, 1H), 3.87-3.68 (m, 1H), 3.58 (d, J=14.6 Hz, 1H), 3.46 (d, J=14.6 Hz, 1H), 2.65 (d, J=11.6 Hz, 1H), 2.42 (s, 4H), 2.02-1.90 (m, 2H), 1.85-1.66 (m, 3H), 1.63-1.44 (m, 2H), 1.42-1.23 (m, 1H), 0.88 (s, 9H), 0.06 (d, J=8.2 Hz, 6H).

Step 8: 2'-methyl-2',3'-dihydro-1'H-spiro[cyclohexane-1,4'-isoquinolin]-3-ol

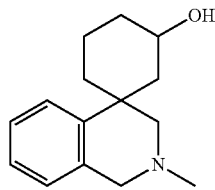 [SMILES: CN1Cc2ccccc2C2(CCCC(O)C2)C1]

Under Ar, TBAF (1.97 g, 7.52 mmol) was added to the solution of 3-((tert-butyldimethylsilyl)oxy)-2'-methyl-2',3'-dihydro-1'H-spiro[cyclohexane-1,4'-isoquinoline](1.3 g, 3.76 mmol) in 15 mL THF, and the reaction was stirred at RT overnight. Water was added to the mixture, the resulting mixture was extracted with DCM three times, the combined organic layers were washed with brine, dried over Na₂SO₄, filtrated and concentrated to give a residual, which was purified by silica gel column and eluted with ethyl acetate/hexane from 0 to 100% to afford the title compound (783 mg, 90%) as an oil.

MS: 232.2 (M+H⁺).

Step 9: 2'-methyl-2',3'-dihydro-1'H-spiro[cyclohexane-1,4'-isoquinolin]-3-one

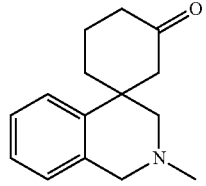 [SMILES: CN1Cc2ccccc2C2(CCCC(=O)C2)C1]

Under Ar, to a solution of 2'-methyl-2',3'-dihydro-1'H-spiro[cyclohexane-1,4'-isoquinolin]-3-ol (783 mg, 3.38 mmol) in DCM (15 mL) was added DMP (4.31 g, 10.15 mmol) at RT. After the mixture was stirred at RT for 2 hours, quenched with Na₂S₂SO₃ solution, the resulting mixture was extracted with DCM three times, the combined organic layers were washed with brine, dried over Na₂SO₄, filtrated and concentrated to give a residual, which was purified by silica gel column and eluted with ethyl acetate/hexane from 0 to 100% to afford the title compound (682 mg, 88%) as a colorless oil. MS: 230.5 (M+H⁺).

Example 34 was prepared essentially the same protocol described in EXAMPLE 25 with 2'-methyl-2',3'-dihydro-1'H-spiro[cyclohexane-1,4'-isoquinolin]-3-one to afford 20 mg as a white solid. MS: 556.4 (M+H⁺).

Example 35

2-((2S)-1-acryloyl-4-(2'-(((S)-1-methylpyrrolidin-2-yl)methoxy)-2,2-dioxido-5',8'-dihydro-6'H-spiro[isothiochromane-4,7'-quinazolin]-4'-yl)piperazin-2-yl)acetonitrile (Cpd. No. 31)

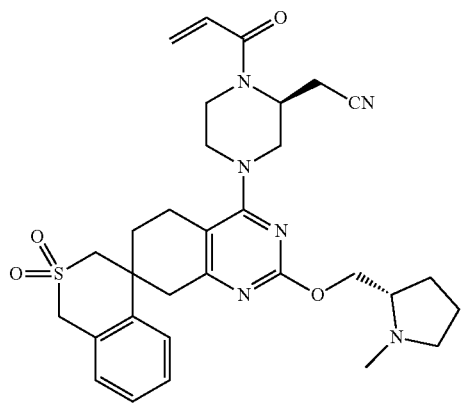 [SMILES: C=CC(=O)N1CCN(c2nc(OC[C@@H]3CCCN3C)nc3c2CCC2(C3)CS(=O)(=O)Cc3ccccc32)C[C@@H]1CC#N]

Step 1: methyl 3-oxospiro[cyclohexane-1,4'-isothiochromane]-4-carboxylate

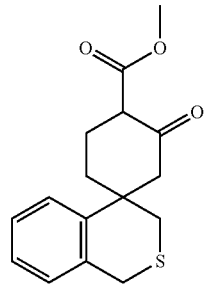 [SMILES: COC(=O)C1CCC2(CSCc3ccccc32)CC1=O]

Under Ar, to a mixture Dimethyl carbonate (1.55 g, 17.22 mmol) and NaH (275 mg, 6.89 mmol) in THF (8 mL) was dropwise added spiro[cyclohexane-1,4'-isothiochroman]-3-one (800 mg, 3.44 mmol) in THF (5 mL) at 70° C., then the mixture was stirred at this temperature for 3 hours. After cooling down to RT, quenched with NH₄Cl solution, the resulting mixture was extracted with EA three times, the combined organic layers were washed with brine, dried over Na₂SO₄, filtrated and concentrated to give a residual, which was purified by silica gel column and eluted with ethyl acetate/hexane from 0 to 40% to afford the title compound (480 mg, 48.0%) as a colorless oil. MS: 291.2 (M+H⁺). $^1$H NMR (400 MHz, CDCl3) δ 12.18 (s, 1H), 7.30 (dd, J=8.0, 1.4 Hz, 1H), 7.27-7.21 (m, 1H), 7.16-7.06 (m, 2H), 3.85 (d, J=15.9 Hz, 1H), 3.79 (s, 3H), 3.73 (d, J=15.9 Hz, 1H), 2.84 (dd, J=13.7, 1.4 Hz, 1H), 2.77 (d, J=13.7 Hz, 1H), 2.72-2.67 (m, 2H), 2.45-2.34 (m, 1H), 2.34-2.23 (m, 1H), 2.17-2.03 (m, 1H), 1.88-1.77 (m, 1H).

Step 2: 5',8'-dihydro-1'H-spiro[isothiochromane-4,7'-quinazoline]-2',4'(3'H,6'H)-dione

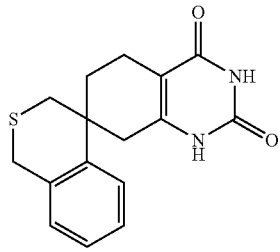 [SMILES: O=c1[nH]c2c(c(=O)[nH]1)CCC1(CSCc3ccccc31)C2]

Under Ar, the mixture of Methyl 3-oxospiro[cyclohexane-1,4'-isothiochromane]-4-carboxylate (480 mg, 1.65 mmol), guanidine hydrochloride (361 mg, 3.31 mmol) and $K_2CO_3$ (685 mg, 4.96 mmol) in DMF (10 ml), was stirred at 85° C. for 2 hours. After cooling down to room temperature, water (15 mL) was added. AcOH was added to adjust pH=6, and the precipitate was got as 2'-amino-5',8'-dihydro-3'H-spiro[isothiochromane-4,7'-quinazolin]-4'(6'H)-one, which was re-dissolved in AcOH (12 mL), sodium nitrite (2.28 g, 33.1 mmol) in water (6 mL) was dropwise added to the above solution at 70° C., and then the mixture was stirred at this temperature for another 30 mins. After removal off the volatile under reduced pressure to give a residual, which was treat with water (6 mL), and formed precipitate was collected to afford the title compound (411 mg, 82.9%) as a light-yellow solid. MS: 301.2 (M+H$^+$).

Step 3: 2',4'-dichloro-5',8'-dihydro-6'H-spiro[isothiochromane-4,7'-quinazoline]

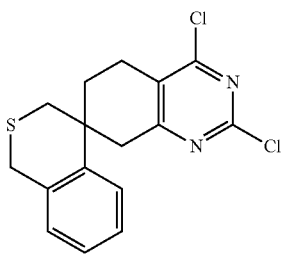 [SMILES: Clc1nc(Cl)c2c(n1)CC1(CC2)CSCc2ccccc21]

Under Ar, 5',8'-dihydro-1'H-spiro[isothiochromane-4,7'-quinazoline]-2',4'(3'H,6'H)-dione (500 mg, 1.66 mmol) and DIPEA (357 mg, 5.31 mmol) was in POCl$_3$ (15 mL) was refluxed for 5 hours. After removal off POCl$_3$ under reduced to give a residual, which was dissolved in DCM, the resulting mixture was washed with saturated NaHCO$_3$ solution, brine, dried over Na$_2$SO$_4$, concentrated in vacuo to give a residual, which was purified by silica gel column and eluted with ethyl acetate/hexane from 0 to 30% to afford the title compound (350 mg, 62.3%) as a white solid. MS: 338.1 (M+H$^+$).

Step 4: tert-butyl (2S)-4-(2'-chloro-5',8'-dihydro-6'H-spiro[isothiochromane-4,7'-quinazolin]-4'-yl)-2-(cyanomethyl)piperazine-1-carboxylate

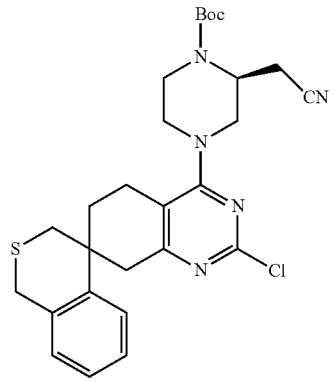 [SMILES: CC(C)(C)OC(=O)N1CCN(c2nc(Cl)nc3c2CCC2(CSCc4ccccc42)C3)C[C@@H]1CC#N]

Under Ar, the mixture of 2',4'-dichloro-5',8'-dihydro-6'H-spiro[isothiochromane-4,7'-quinazoline] (350 mg, 1.038 mmol), DIPEA (671 mg, 5.19 mmol) and (S)-2-(piperazin-2-yl)acetonitrile dihydrochloride (411 mg, 2.076 mmol) in DMSO (8 mL) was stirred at 50° C. for 3 hour. Boc-anhydride (222.4 mg, 1.02 mmol) was added to the above mixture, and stirred at 55° C. for another 1 hour. After cooling down to RT, water was added, the resulting mixture was washed with brine, dried over Na$_2$SO$_4$, concentrated in vacuo to give a residual, which was purified by silica gel column and eluted with ethyl acetate/hexane from 0 to 50% to afford the title compound (450 mg, 82.42%). MS: 526.3 (M+H$^+$).

Step 5: tert-butyl (2S)-2-(cyanomethyl)-4-(2'-(((S)-1-methylpyrrolidin-2-yl)methoxy)-5',8'-dihydro-6'H-spiro[isothiochromane-4,7'-quinazolin]-4'-yl)piperazine-1-carboxylate

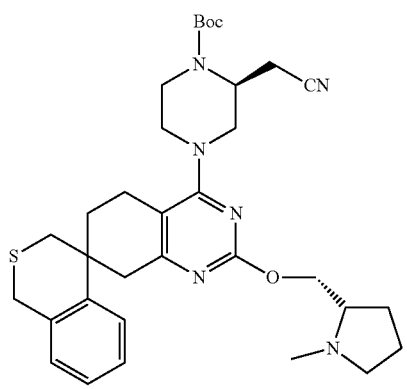

Under Ar, the mixture of Tert-butyl 4-(2'-chloro-5',8'-dihydro-6'H-spiro[isothiochromane-4,7'-quinazolin]-4'-yl)-2-(cyanomethyl)piperazine-1-carboxylate (400 mg, 0.760 mmol), (S)-(1-methylpyrrolidin-2-yl)methanol (175 mg, 1.521 mmol), BINAP (95 mg, 0.152 mmol), sodium tert-butoxide (183 mg, 1.901 mmol) and Pd$_2$(dba)$_3$ (69.6 mg, 0.076 mmol) Toluene (12 mL) was stirred at 110° C. for 3 hours. After removal off the volatile in vacuo to give a black residual, which was purified by silica gel column and eluted with MeOH/DCM from 0% to 10% to give the title compound (320 mg, 69.6%) as a solid.

MS: 605.4 (M+H⁺).

Step 6: tert-butyl (2S)-2-(cyanomethyl)-4-(2'-(((S)-1-methylpyrrolidin-2-yl)methoxy)-2,2-dioxido-5',8'-dihydro-6'H-spiro[isothiochromane-4,7'-quinazolin]-4'-yl)piperazine-1-carboxylate

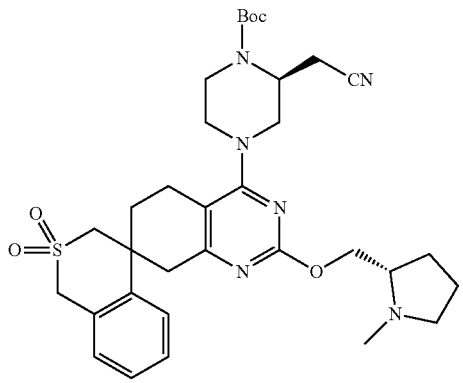 [SMILES: CN1CCC[C@H]1COc1nc2c(c(N3CCN(C(=O)OC(C)(C)C)[C@@H](CC#N)C3)n1)CCC1(C2)CS(=O)(=O)Cc2ccccc21]

Under Ar, to a solution of tert-butyl (2S)-2-(cyanomethyl)-4-(2'-(((S)-1-methylpyrrolidin-2-yl)methoxy)-5',8'-dihydro-6'H-spiro[isothiochromane-4,7'-quinazolin]-4'-yl)piperazine-1-carboxylate (320 mg, 0.529 mmol) in MeOH (8 mL)/acetone (4 mL)/H₂O (4 mL) was added Potassium monopersulfate triple salt (161 mg, 1.058 mmol) was added at RT, and then the mixture was stirred at RT for 2 hours. After the reaction, quenched with Na₂S₂SO₃ solution, all the solvent was removed under reduced pressure to give a residual, which was purified by silica gel column and eluted with methanol/dichloromethane from 0 to 30% to give the crude title compound (240 mg, 71.2%). MS: 637.4 (M+H⁺).

Step 7: 2-((2S)-1-acryloyl-4-(2'-(((S)-1-methylpyrrolidin-2-yl)methoxy)-2,2-dioxido-5',8'-dihydro-6'H-spiro[isothiochromane-4,7'-quinazolin]-4'-yl)piperazin-2-yl)acetonitrile

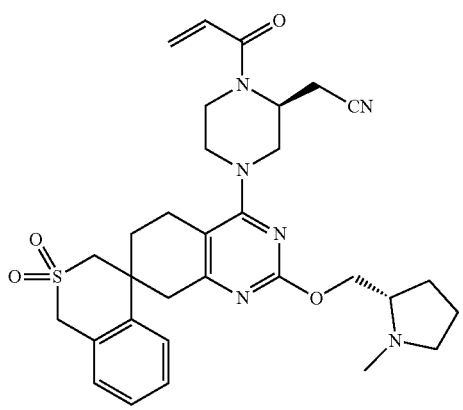 [SMILES: C=CC(=O)N1CCN(c2nc(OC[C@@H]3CCCN3C)nc3c2CCC2(C3)CS(=O)(=O)Cc3ccccc32)C[C@@H]1CC#N]

Under Ar, the mixture of tert-butyl (2S)-2-(cyanomethyl)-4-(2'-(((S)-1-methylpyrrolidin-2-yl)methoxy)-2,2-dioxido-5',8'-dihydro-6'H-spiro[isothiochromane-4,7'-quinazolin]-4'-yl)piperazine-1-carboxylate (240 mg, crude) in TFA (1 mL)/DCM (4 mL) was stirred at RT for 2 hours. After removal off all the solvent under reduced pressure to give a residual, which was dissolved in DCM (5 mL), TEA (152 mg, 1.5 mmol) and acryloyl chloride (53 mg. 0.6 mmol) was added to the above mixture at ice-water condition. After 1 hour, water was added, the resulting mixture was extracted three times with DCM, the combined organic layers were washed with brine, dried over Na₂S04, concentrated in vacuo to give a residual, which was purified by Pre-HPLC to afford the title compound (16 mg, 7.2%) as a white solid. MS: 591.3 (M+H⁺).

Example 36

2-((2S)-1-acryloyl-4-(1-methyl-2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 32)

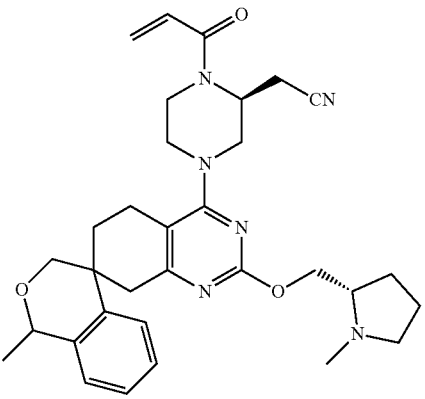 [SMILES: C=CC(=O)N1CCN(c2nc(OC[C@@H]3CCCN3C)nc3c2CCC2(COC(C)c4ccccc42)C3)C[C@@H]1CC#N]

Intermediate: 1'-methylspiro[cyclohexane-1,4'-isochroman]-3-one

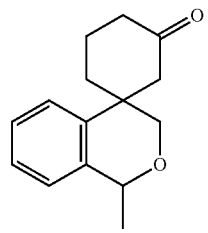 [SMILES: CC1OCC2(CCCC(=O)C2)c2ccccc21]

Step 1: 3-(benzyloxy)spiro[cyclohexane-1,4'-isochroman]-1'-one

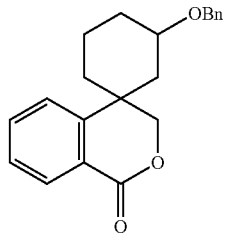 [SMILES: O=C1OCC2(CCCC(OCc3ccccc3)C2)c2ccccc21]

MnO$_2$ (6.39 g, 73.5 mmol) was added to the solution of (3-(benzyloxy)-1-(2-(hydroxymethyl)phenyl)cyclohexyl) methanol (2.4 g, 7.35 mmol) in THF (30 mL), and then, the reaction mixture was stirred at 60° C. for 3 hour.

The filtrate was concentrated in vacuo to give a residual, which was purified by silica gel column and eluted with ethyl acetate/hexane from 0% to 20% to afford the title compound (2.0 g, 84%) as a light yellow solid. MS: 323.2 (M+H$^+$).

$^1$H NMR (400 MHz, CDCl3) δ 8.12 (dd, J=7.8, 1.4 Hz, 1H), 7.61 (td, J=7.7, 1.5 Hz, 1H), 7.46-7.38 (m, 2H), 7.37-7.21 (m, 5H), 4.61-4.53 (m, 2H), 4.39 (d, J=11.4 Hz, 1H), 4.31 (d, J=11.4 Hz, 1H), 3.69-3.56 (m, 1H), 2.30-2.21 (m, 1H), 2.21-2.11 (m, 1H), 1.92-1.74 (m, 2H), 1.68-1.50 (m, 2H), 1.43-1.22 (m, 2H).

Step 2: 3-(benzyloxy)-1'-methylspiro[cyclohexane-1,4'-isochroman]-1'-ol

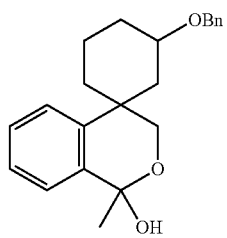 [SMILES: CC1(O)OCC2(CCCC(OCc3ccccc3)C2)c2ccccc21]

Under Ar, to a solution of 3-(benzyloxy)spiro[cyclohexane-1,4'-isochroman]-1'-one (4.3 g, 13.34 mmol, 1.00) in THF (40 mL) was added 3M Methylmagnesium bromide (4.77 g, 40.0 mmol) at 0° C., after the mixture was stirred overnight at room temperature. Quenched with saturated NH$_4$Cl (30 mL), the resulting mixture was extracted with ethyl acetate (50 mL×3). The combined organic layers were concentrated to give a residual, which was purified by silica gel column and eluted with ethyl acetate/hexane from 5% to 30% to afford the title compound (3.6 g, 80%) as a solid. MS: 339.2 (M+H$^+$).

Step 3: 3-(benzyloxy)-1'-methylspiro[cyclohexane-1,4'-isochromane]

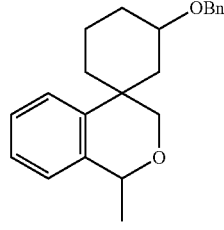 [SMILES: CC1OCC2(CCCC(OCc3ccccc3)C2)c2ccccc21]

Under Ar, to a solution of 3-(benzyloxy)-1'-methylspiro[cyclohexane-1,4'-isochroman]-1'-ol (3.2 g, 9.45 mmol) in TFA (20 mL) was added triethylsilane (4.40 g, 37.8 mmol), then the mixture was stirred at 60° C. for 1 hour. The volatiles were removed in vacuo to give a residual, ethyl acetate was added, the resulting mixture was washed with saturated NaHCO$_3$ (100 mL), brine dried over Na$_2$SO$_4$, filtered and concentrated in vacuo to give the crude residual, which was purified by silica gel column and eluted with ethyl acetate/hexane from 5% to 30% to afford the title compound (2.8 g, 92%) as a white solid.

$^1$H NMR (400 MHz, CDCl$_3$) δ 7.45-7.36 (m, 1H), 7.36-7.29 (m, 4H), 7.28-7.11 (m, 3H), 7.06 (d, J=7.7 Hz, 1H), 4.91-4.82 (m, 1H), 4.57-4.50 (m, 2H), 4.16-4.01 (m, 1H), 3.57-3.41 (m, 2H), 2.29-2.15 (m, 1H), 2.09-1.69 (m, 4H), 1.64-1.49 (m, 5H), 1.46-1.24 (m, 1H).

Step 4: 1'-methylspiro[cyclohexane-1,4'-isochroman]-3-ol

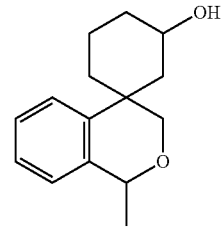 [SMILES: CC1OCC2(CCCC(O)C2)c2ccccc21]

The mixture of Pd (OH)$_2$ (1.341 g, 9.55 mmol) and 3-(benzyloxy)-1'-methylspiro[cyclohexane-1,4'-isochromane] (2.8 g, 8.68 mmol) 30 mL MeOH was stirred at 50° C. for 4 hours under H$_2$ condition. After the reaction, the filtrate was concentrated in vacuo to give the title compound (1.9 g, 94%). MS: 233.2 (M+H$^+$).

Step 5: 1'-methylspiro[cyclohexane-1,4'-isochroman]-3-one

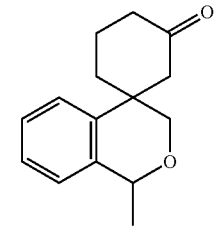 [SMILES: CC1OCC2(CCCC(=O)C2)c2ccccc21]

DMP (5.20 g, 12.27 mmol) was added to the solution of 1'-methylspiro[cyclohexane-1,4'-isochroman]-3-ol (1.9 g, 8.18 mmol) DCM (30 mL) at 0° C., and then the mixture was stirred at RT for 1 hour, Na₂S₂SO₃ solution was added. The resulting mixture was extracted with dichloromethane three times. The combined organic layers were washed with saturated NaHCO₃ aq, brine, dried over Na₂SO₄, filtered and concentrated in vacuo to give a residual, which was purified by silica gel column and eluted with ethyl acetate/hexane from 10% to 70% to afford the title compound (1.53 g, 81%) as a colorless oil. MS: 231.2 (M+H⁺).

Example 36 was prepared essentially the same protocol described in EXAMPLE 25 With 1'-methylspiro[cyclohexane-1,4'-isochroman]-3-one to afford 630 mg as a white solid.

MS: 557.4 (M+H⁺).

Example 37

2-((2S)-1-acryloyl-4-(2'-(((S)-1-methylpyrrolidin-2-yl)methoxy)-1-(trifluoromethyl)-5',8'-dihydro-6'H-spiro[isochromane-4,7'-quinazolin]-4'-yl)piperazin-2-yl)acetonitrile (Cpd. No. 33)

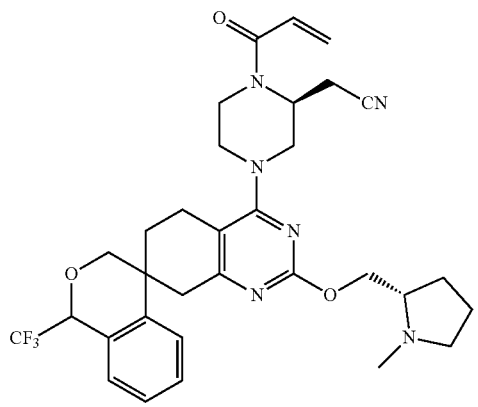 [SMILES: C=CC(=O)N1CCN(c2nc(OC[C@@H]3CCCN3C)nc3c2CCC2(COC(C(F)(F)F)c4ccccc42)C3)C[C@@H]1CC#N]

Intermediate: 1'-(trifluoromethyl)spiro[cyclohexane-1,4'-isochroman]-3-one

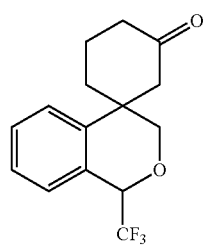 [SMILES: O=C1CCCC2(COC(C(F)(F)F)c3ccccc32)C1]

Step 1: ((3-(benzyloxy)-1'-(trifluoromethyl)spiro[cyclohexane-1,4'-isochroman]-1'-yl)oxy)trimethyl-silane

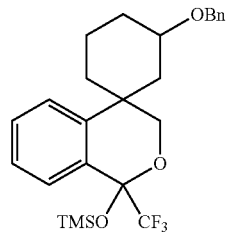

Under Ar, to a solution of 3-(benzyloxy)spiro[cyclohexane-1,4'-isochroman]-1'-one (1.8 g, 5.58 mmol) and trimethyl(trifluoromethyl)silane (1.191 g, 8.37 mmol) in THF (20 mL) was added TBAF (0.219 g, 0.837 mmol) in THF (0.8 mL) at ice-water condition. After stirred at RT for 1 hour, the volatiles was removed in vacuo to give a residual, which was purified by silica gel column and eluted with EA/Heptane from 0~10% to give the title compound (2.1 g, 81%) as a yellow oil.

Step 2: 3-(benzyloxy)-1'-(trifluoromethyl)spiro[cyclohexane-1,4'-isochroman]-1'-ol

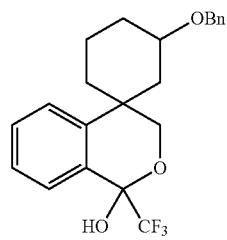 [SMILES: OC1(C(F)(F)F)OCC2(CCCC(OCc3ccccc3)C2)c2ccccc21]

Under Ar, the mixture of ((3-(benzyloxy)-1'-(trifluoromethyl)spiro[cyclohexane-1,4'-isochroman]-1'-yl)oxy)trimethylsilane (2.3 g, 4.95 mmol) and tetrabutylammonium fluoride (1.29 g, 4.95 mmol) w in THF (20 mL) was stirred at RT for 1 hour. After removal of the volatiles under reduced pressure to give the crude product, which was purified by silica gel column and eluted with EA/Heptane from 0-15% to afford the title compound (1.7 g, 87%) as a yellow oil. MS: 375.1 (M–H₂O+H⁺).

Step 3: 3-(benzyloxy)-1'-(trifluoromethyl)spiro[cyclohexane-1,4'-isochromane]

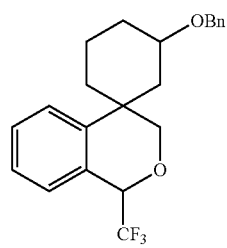 [SMILES: FC(F)(F)C1OCC2(CCCC(OCc3ccccc3)C2)c2ccccc21]

Under Ar, to a solution of 3-(benzyloxy)-1'-(trifluoromethyl)spiro[cyclohexane-1,4'-isochroman]-1'-ol (800 mg, 2.039 mmol) in TFA (6 mL) was added triethylsilane (948 mg, 8.15 mmol) at ice-water condition. After stirred at RT for 1 hour, the volatiles were removed in vacuo to give a residual, EA was added, the resulting mixture was washed with brine, dried over $Na_2SO_4$, concentrated in vacuo to give a residual, which was purified by silica gel column and eluted with EA/Heptane from 0~10% to give the title compound (600 mg, 78%) as a yellow oil. MS: 377.2 (M+H$^+$). $^1$H NMR (400 MHz, CDCl$_3$) δ 7.51 (dd, J=8.0, 1.2 Hz, 1H), 7.40 (d, J=7.4 Hz, 1H), 7.37-7.32 (m, 5H), 7.32-7.29 (m, 1H), 7.28-7.23 (m, 1H), 5.22-5.08 (m, 1H), 4.57 (d, J=4.0 Hz, 2H), 4.12-3.99 (m, 1H), 3.90-3.73 (m, 1H), 3.64-3.50 (m, 1H), 2.29-2.10 (m, 2H), 1.93-1.60 (m, 4H), 1.55-1.25 (m, 2H).

Step 4: 1'-(trifluoromethyl)spiro[cyclohexane-1,4'-isochroman]-3-ol

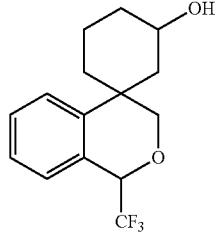 [SMILES: OC1CCCC2(COC(C(F)(F)F)c3ccccc32)C1]

The mixture of 3-(benzyloxy)-1'-(trifluoromethyl)spiro[cyclohexane-1,4'-isochromane] (800 mg, 2.125 mmol) and Pd(OH)$_2$ (328 mg, 2.338 mmol) in 10 mL MeOH was stirred at 50° C. for 4 hours under H$_2$ condition. The filtrate was concentrated in vacuo to give the crude title compound (600 mg, 99%) as a yellow oil. MS: 269.1 (M–H$_2$O+H$^+$).

Step 5: 1'-(trifluoromethyl)spiro[cyclohexane-1,4'-isochroman]-3-one

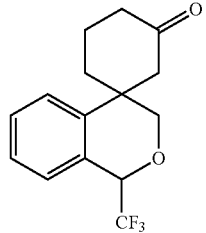 [SMILES: O=C1CCCC2(COC(C(F)(F)F)c3ccccc32)C1]

Under Ar, to a solution of 1'-(trifluoromethyl)spiro[cyclohexane-1,4'-isochroman]-3-ol (1.0 g, 3.49 mmol) in DCM (10 mL) was added DMP (1.481 g, 3.49 mmol) at RT. After 1 hour later, $Na_2S_2O_3$ solution was added. The resulting mixture was extracted with dichloromethane three times. The combined organic layers were washed with saturated NaHCO$_3$ aq, brine, dried over Na$_2$SO$_4$, filtered and concentrated in vacuo to give a residual, which was purified by silica gel column and eluted with ethyl acetate/hexane from 0-15% to afford the title compound (900 mg, 91%) as a yellow oil. MS: 285.1 (M+H$^+$).

Example 37 was prepared essentially the same protocol described in EXAMPLE 25 with 1'-(trifluoromethyl)spiro[cyclohexane-1,4'-isochroman]-3-one to afford 630 mg as a white solid. MS: 611.4 (M+H$^+$). $^1$H NMR (400 MHz, CDCl$_3$) δ 7.42-7.33 (m, 4H), 6.59 (s, 1H), 6.41 (d, J=16.5 Hz, 1H), 5.84 (d, J=10.6 Hz, 1H), 5.34-4.98 (m, 1H), 4.44-4.34 (m, 1H), 4.21-3.99 (m, 4H), 3.97-3.90 (m, 2H), 3.78 (t, J=10.4 Hz, 1H), 3.43-3.28 (m, 1H), 3.16-2.94 (m, 4H), 2.91-2.78 (m, 2H), 2.74-2.65 (m, 3H), 2.64-2.56 (m, 1H), 2.50 (s, 3H), 2.34-1.97 (m, 3H), 1.96-1.67 (m, 4H).

Example 38

2-((2S)-1-acryloyl-4-(1,1-dimethyl-2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 34)

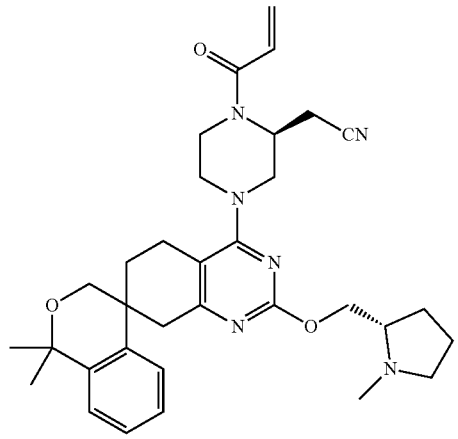 [SMILES: C=CC(=O)N1CCN(c2nc(OC[C@@H]3CCCN3C)nc3c2CCC2(COC(C)(C)c4ccccc42)C3)C[C@@H]1CC#N]

Intermediate: 1',1'-dimethylspiro[cyclohexane-1,4'-isochroman]-3-one

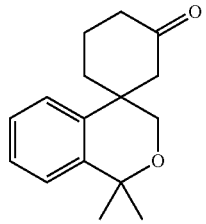 [SMILES: CC1(C)OCC2(CCCC(=O)C2)c2ccccc21]

Step 1: 3-(benzyloxy)-1-(2-bromophenyl)cyclohexane-1-carbonitrile

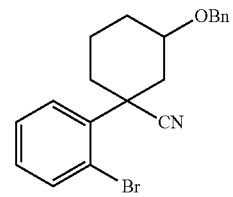 [SMILES: N#CC1(c2ccccc2Br)CCCC(OCc2ccccc2)C1]

Under Ar, in a 3-necked, round-bottomed flask, equipped with a magnetic stirrer and a thermometer, was charged with DMF (10 mL). Then NaH (0.898 g, 22.44 mmol) was added and the mixture of 2-(2-bromophenyl)acetonitrile (2 g, 10.20 mmol) and (((1,5-diiodopentan-2-yl)oxy)methyl)benzene (4.61 g, 10.71 mmol) in DMF (10 mL) was added dropwise under ice-water bath. The reaction was quenched with sat. NH$_4$Cl solution, the mixture was partitioned between EtOAc/H$_2$O, the separated organics were rinsed with brine, dried over anhydrous Na$_2$SO$_4$, filtered and concentrated to give the crude product, which was further purified by silica gel chromatography eluting with PE:EtOAc=10:1 to afford the desired compound (2.6 g, 68.8%) as a colorless oil. MS: 370.1 (M+H$^+$).

Step 2: 3-(benzyloxy)-1-(2-bromophenyl)cyclohexane-1-carbaldehyde

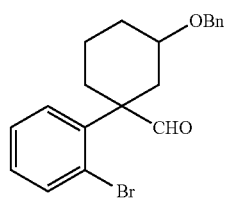 [SMILES: O=CC1(c2ccccc2Br)CCCC(OCc2ccccc2)C1]

Under Ar, in a 3-necked, round-bottomed flask, equipped with a magnetic stirrer and a thermometer, was charged with 3-(benzyloxy)-1-(2-bromophenyl)cyclohexane-1-carbonitrile (5.1 g, 13.77 mmol) in anhydrous DCM (30 mL) at −78° C. Then 1N DIBAL-H (3.92 g, 27.5 mmol) was added dropwise and the reaction was stirred for 1 h. The reaction was quenched by 1N HCl solution, the solution was partitioned between DCM/H$_2$O, the organics were rinsed with brine, dried over anhydrous Na$_2$SO$_4$, filtered and concentrated to give the crude product, which was purified by silica gel column and eluted with ethyl acetate/hexane from 0 to 10% to the title compound (3.2 g, 62.2%) as a colorless oil. MS: 264.9 (M-BnO$^-$).

Step 3: (3-(benzyloxy)-1-(2-bromophenyl)cyclohexyl)methanol

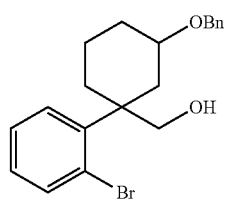 [SMILES: OCC1(c2ccccc2Br)CCCC(OCc2ccccc2)C1]

Under Ar, to a solution of 3-(benzyloxy)-1-(2-bromophenyl)cyclohexane-1-carbaldehyde (500 mg, 1.339 mmol) in THF (10 mL) and MeOH (5 mL) was added NaBH$_4$ (76 mg, 2.009 mmol) at 0° C., then the mixture was stirred at RT for 30 mins. Saturated NH$_4$Cl was added to the reaction mixture, followed by extraction with ethyl acetate. The combined organic layers were dried Na$_2$SO$_4$, filtered and concentrated in vacuo to afford the title compound (500 mg, 99%) as a colorless oil.

Step 4: 2-((3-(benzyloxy)-1-(2-bromophenyl)cyclohexyl)methoxy)tetrahydro-2H-pyran

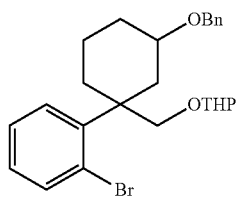

Under Ar, the mixture of (3-(benzyloxy)-1-(2-bromophenyl)cyclohexyl)methanol (500 mg, 1.332 mmol), DHP (224 mg, 2.66 mmol) and PPTS (33.5 mg, 0.133 mmol) in THF (10 mL) was stirred for 12 h at 55° C. After cooling down to RT, Saturated NaCl solution was added to the reaction mixture followed by extraction with ethyl acetate. The combined organic layers were dried Na$_2$SO$_4$, filtered and concentrated in vacuo to give a residual, which was purified by silica gel column and eluted with ethyl acetate/hexane from 0% to 10% to afford the title compound (630 mg, 103%) as a colorless oil.

Step 5: 2-((3-(benzyloxy)-1-(2-(prop-1-en-2-yl)phenyl)cyclohexyl)methoxy)tetrahydro-2H-pyran

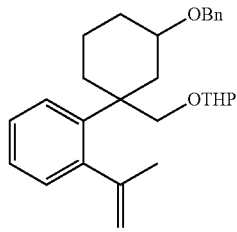

Under Ar, the mixture of 2-((3-(benzyloxy)-1-(2-bromophenyl)cyclohexyl)methoxy)tetrahydro-2H-pyran (950 mg, 2.068 mmol), 4,4,5,5-tetramethyl-2-(prop-1-en-2-yl)-1,3,2-dioxaborolane (1042 mg, 6.20 mmol), K$_2$CO$_3$ (857 mg, 6.20 mmol) and PdCl$_2$(dppf) (303 mg, 0.414 mmol) in Dioxane (12 mL)/Water (4 mL) was stirred for 5 h at 100° C. After cooling down to RT, H$_2$O was added to the reaction mixture followed by extraction with ethyl acetate. The combined organic layers were dried Na$_2$SO$_4$, filtered and concentrated in vacuo to give a residual, which was purified by silica gel column and eluted with ethyl acetate/hexane from 0% to 10% to afford the title compound (680 mg, 78%) as a colorless oil. MS: 421.4 (M+H$^+$).

Step 6: (3-(benzyloxy)-1-(2-(prop-1-en-2-yl)phenyl)cyclohexyl)methanol

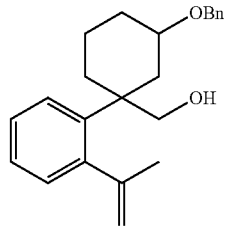 [SMILES: C=C(C)c1ccccc1C1(CO)CCCC(OCc2ccccc2)C1]

Under Ar, the mixture of 2-((3-(benzyloxy)-1-(2-(prop-1-en-2-yl)phenyl)cyclohexyl)methoxy)tetrahydro-2H-pyran (680 mg, 1.617 mmol) and PPTS (40.6 mg, 0.162 mmol) in MeOH (20 mL) was stirred for 8 h at 60° C. After removal off the volatiles under reduced pressure to give a residual, which was purified by silica gel column and eluted with ethyl acetate/hexane from 0% to 20% to afford the title compound (560 mg, 103%) as a colorless oil. MS: 319.2 (M–H$_2$O+H$^+$).

Step 7: 3-(benzyloxy)-1',1'-dimethylspiro[cyclohexane-1,4'-isochromane]

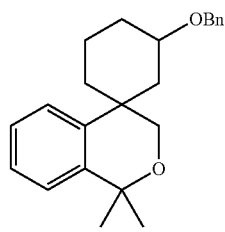 [SMILES: CC1(C)OCC2(CCCC(OCc3ccccc3)C2)c2ccccc21]

Under Ar, the mixture of (3-(benzyloxy)-1-(2-(prop-1-en-2-yl)phenyl)cyclohexyl)methanol (560 mg, 1.664 mmol) and 57% HI (74.7 mg, 0.333 mmol) in MeCN (15 mL) was stirred for 1.5 h at rt. Saturated NaHCO$_3$ was added to the reaction mixture followed by extraction with ethyl acetate. The combined organic layers were dried Na$_2$SO$_4$, filtered and concentrated to give a residual, which was purified by silica gel column and eluted with ethyl acetate/hexane from 0% to 10% to afford the title compound (380 mg, 67.9%) as a colorless oil. $^1$H NMR (400 MHz, DMSO) δ 7.40-7.31 (m, 6H), 7.23-7.14 (m, 2H), 7.10-7.05 (m, 1H), 4.55 (s, 2H), 3.85-3.71 (m, 2H), 3.63-3.51 (m, 1H), 2.26-2.09 (m, 2H), 1.86-1.60 (m, 4H), 1.54 (s, 3H), 1.52 (s, 3H), 1.44-1.35 (m, 2H).

Step 8: 1',1'-dimethylspiro[cyclohexane-1,4'-isochroman]-3-ol

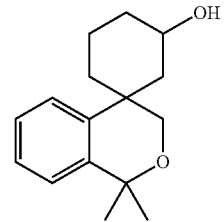 [SMILES: CC1(C)OCC2(CCCC(O)C2)c2ccccc21]

The mixture of 3-(benzyloxy)-1',1'-dimethylspiro[cyclohexane-1,4'-isochromane](380 mg, 1.129 mmol) and Pd(OH)$_2$ (238 mg, 0.339 mmol) in MeOH (10 mL) was stirred at RT for 26 hours under H$_2$. The filtrate was concentrated in vacuo to give the title compound (270 mg, 97%). MS: 229.3 (M–H$_2$O+H$^+$).

Step 9: 1',1'-dimethylspiro[cyclohexane-1,4'-isochroman]-3-one

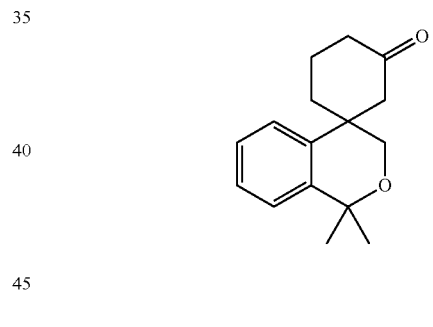

The mixture of 1',1'-dimethylspiro[cyclohexane-1,4'-isochroman]-3-ol (270 mg, 1.096 mmol) and PCC (0.709 g, 3.29 mmol) in DCM (30 ml) was stirred for 6 h at RT. The reaction mixture was filtered through a silica gel and the filter cake was rinsed with dichloromethane. The combined organic layers were concentrated in vacuo to give a residual, which was purified by silica gel column and eluted with ethyl acetate/hexane from 0% to 10% to afford the title compound (250 mg, 93%) as a white solid. $^1$H NMR (400 MHz, DMSO) δ 7.25-7.18 (m, 3H), 7.13-7.08 (m, 1H), 3.73-3.62 (m, 2H), 2.71 (d, J=14.3 Hz, 1H), 2.50-2.43 (m, 2H), 2.34 (d, J=14.4 Hz, 1H), 2.11-1.86 (m, 4H), 1.54 (s, 3H), 1.52 (s, 3H). MS: 245.1 (M+H$^+$).

Example 38 was prepared essentially the same protocol described in EXAMPLE 25 with 1',1'-dimethylspiro[cyclohexane-1,4'-isochroman]-3-one to afford 17 mg as a white solid. MS: 571.2 (M+H$^+$).

Example 39

2-((2S)-1-acryloyl-4-(8-fluoro-1-methyl-2'-(((S)-1-methylpyrrolidin-2-yl)methoxy)-5',8'-dihydro-6'H-spiro[isochromane-4,7'-quinazolin]-4'-yl)piperazin-2-yl)acetonitrile (Cpd. No. 35)

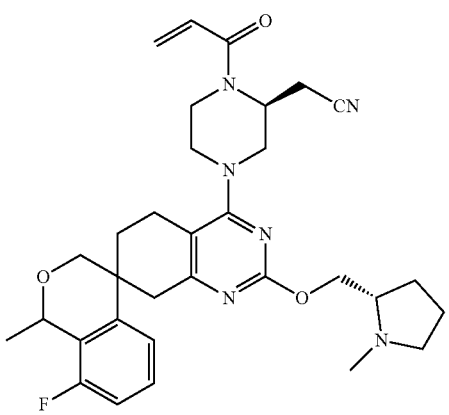 [SMILES: C=CC(=O)N1CCN(c2nc(OC[C@@H]3CCCN3C)nc3c2CCC2(COC(C)c4c(F)cccc42)C3)C[C@@H]1CC#N]

Intermediate: 8'-fluoro-1'-methylspiro[cyclohexane-1,4'-isochroman]-3-one

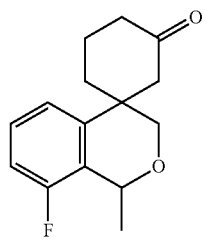 [SMILES: CC1OCC2(CCCC(=O)C2)c2cccc(F)c21]

Step 1: 2-bromo-1-(bromomethyl)-3-fluorobenzene

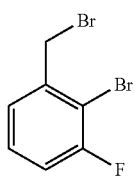

In a nitrogen flushed 250 mL round-bottomed flask, 2-bromo-1-fluoro-3-methylbenzene (5 g, 26.5 mmol) was dissolved in CCl$_4$ (60 mL), NBS (4.71 g, 26.5 mmol) and benzoyl peroxide (0.320 g, 1.323 mmol) were added to the reaction mixture in one portion. After stirred at 90° C. for 2 hours, all the volatiles were removed in vacuo to give a residual, which was purified by silica gel column and eluted with PE to give the title compound (5 g, 70.6%) as a white solid.

Step 2: 2-(2-bromo-3-fluorophenyl)acetonitrile

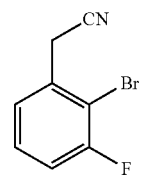 [SMILES: N#CCc1cccc(F)c1Br]

Under Ar, to the mixture of 2-bromo-1-(bromomethyl)-3-fluorobenzene (5 g, 18.66 mmol) and TMS-CN (1.851 g, 18.66 mmol) in dry THF (60 mL) was added TBAF (4.88 g, 18.66 mmol) at RT, and then mixture was stirred at RT overnight. EA was added, the resulting mixture was washed with water, brine, dried over Na$_2$SO$_4$, filtered, concentrated in vacuo to give a residual, which was purified by silica gel column and eluted with PE/EA=5:1 to afford the title compound (3.18 g, 80%) as a colorless solid. $^1$H NMR (400 MHz, Chloroform-d) δ 7.36-7.34 (m, 2H), 7.16-7.12 (m, 1H), 3.87 (s, 2H).

Step 3: 3-(benzyloxy)-1-(2-bromo-3-fluorophenyl)cyclohexane-1-carbonitrile

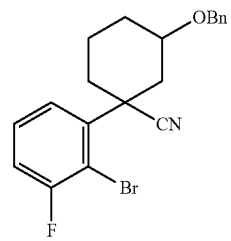 [SMILES: N#CC1(c2cccc(F)c2Br)CCCC(OCc2ccccc2)C1]

In a 100 mL round-bottomed flask, the mixture of 2-(2-bromo-3-fluorophenyl)acetonitrile (3.1 g, 14.48 mmol) and (((1,5-diiodopentan-2-yl)oxy)methyl)benzene (6.23 g, 14.48 mmol) in DMF (30 mL) in were dropwise added to a solution of sodium hydride (1.216 g, 30.4 mmol) in DMF (20 mL) at ice-water condition. After the mixture was stirred at RT overnight, saturated NH$_4$Cl solution was added, the resulting mixture was extracted with ethyl acetate three time, the combined organic layers were washed with brine, dried over Na$_2$SO$_4$, filtrated and concentrated to give a residue, which was purified by silica gel column and eluted with EA/HEX form 0% to 40% to afford the title compound (2.57 g, 45.7%) as a light yellow oil.
MS: 388.1. 390.1 (M+H$^+$).

Step 4: 3-(benzyloxy)-1-(2-bromo-3-fluorophenyl)cyclohexane-1-carbaldehyde

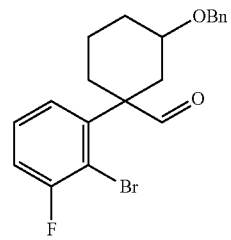 [SMILES: O=CC1(c2cccc(F)c2Br)CCCC(OCc2ccccc2)C1]

Under Ar, to a solution of 3-(benzyloxy)-1-(2-bromo-3-fluorophenyl)cyclohexane-1-carbonitrile (2.57 g, 6.62 mmol) in DCM (5 mL) was added DIBAL-H (147 mg, 1.034 mmol) at −78° C. After stirred at −78° C. for 1 hour, quenched with 1N HCl solution and the resulting mixture was extracted with DCM three times, the combined organic layers were washed with brine, dried over $Na_2SO_4$, filtered and concentrated to give the title compound (2.13 g, 82%) as a colorless oil.

Step 5: (3-(benzyloxy)-1-(2-bromo-3-fluorophenyl)cyclohexyl)methanol

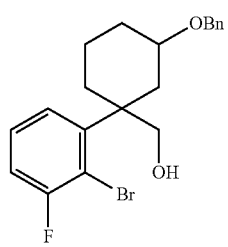 [SMILES: OCC1(c2cccc(F)c2Br)CCCC(OCc2ccccc2)C1]

Under Ar, to a solution of 3-(benzyloxy)-1-(2-bromo-3-fluorophenyl)cyclohexane-1-carbaldehyde (2.13 g, 5.44 mmol) in THF (20 mL)/MeOH (10 mL) was added sodium tetrahydroborate (0.412 g, 10.89 mmol) at 0° C., and then the mixture was stirred at 25° C. for 3 hour. Quenched with saturated $NH_4Cl$ solution, the resulting mixture was extracted with ethyl acetate three times. The combined organic layers were washed with brine, dried over $Na_2SO_4$, filtered and concentrated in vacuo to give a residual, which was purified by silica gel column and eluted with ethyl acetate/hexane from 0 to 25% to give the title compound (1.9 g, 89%) as a colorless oil. MS: 393.6 (M+H$^+$).

Step 6: 2-((3-(benzyloxy)-1-(2-bromo-3-fluorophenyl)cyclohexyl)methoxy)tetrahydro-2H-pyran

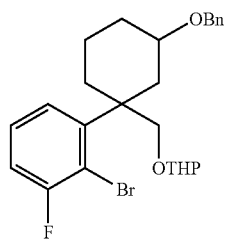

Under Ar, the mixture of (3-(benzyloxy)-1-(2-bromo-3-fluorophenyl)cyclohexyl)methanol (1.9 g, 4.83 mmol0), TsOH (0.121 g, 0.483 mmol), and DHP (0.813 g, 9.66 mmol) in THF (15 mL) was stirred at 50° C. for 10 hours. Quenched with saturated NaCl solution, the resulting mixture was extracted with ethyl acetate three times. The combined organic layers were washed with brine, dried over $Na_2SO_4$, filtered and concentrated in vacuo to give a residual, which was purified by silica gel column and eluted with ethyl acetate/hexane from 0 to 10% to afford the title compound (1.92 g, 83%) as a color oil. MS: 499.2 (M+Na$^+$).

Step 7: 2-((3-(benzyloxy)-1-(3-fluoro-2-vinylphenyl)cyclohexyl)methoxy)tetrahydro-2H-pyran

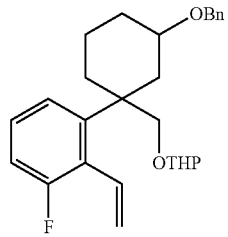

Under Ar, the mixture of 4,4,5,5-tetramethyl-2-vinyl-1,3,2-dioxaborolane (1.742 g, 11.31 mmol, 3), 2-((3-(benzyloxy)-1-(2-bromo-3-fluorophenyl)cyclohexyl)methoxy)tetrahydro-2H-pyran (1.8 g, 3.77 mmol), $K_2CO_3$ (1.563 g, 11.31 mmol) and $PdCl_2$(dppf) (0.552 g, 0.754 mmol) in Dioxane (40 mL)/water (10 mL) was stirred at 100° C. for 2 days. After cooling down to RT, the resulting mixture was extracted with EA three times, the combined organic layers were washed with brine, dried over $Na_2SO_4$, filtered and concentrated in vacuo to give a residual, which was purified by silica gel column and eluted with ethyl acetate/hexane from 0 to 10% to afford the title compound (1.44 g, 90%) as a colorless oil. MS: 425.4 (M+H$^+$).

Step 8: (3-(benzyloxy)-1-(3-fluoro-2-vinylphenyl)cyclohexyl)methanol

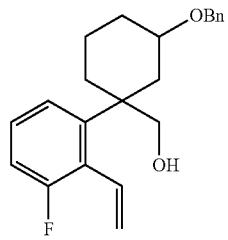 [SMILES: C=Cc1c(F)cccc1C1(CO)CCCC(OCc2ccccc2)C1]

Under Ar, the mixture of 2-((3-(benzyloxy)-1-(3-fluoro-2-vinylphenyl)cyclohexyl)methoxy)tetrahydro-2H-pyran (1.44 g, 3.39 mmol) and TsOH (0.085 g, 0.339 mmol) in MeOH (20 mL) was stirred at 60° C. for 6 hours. After removal of the volatiles under reduced pressure to give a residual, which was purified by silica gel column and eluted with ethyl acetate/hexane from 0 to 30% to give the title compound (1.06 g, 92%) as a color oil. MS: 341.8 (M+H$^+$).

Step 9: 3-(benzyloxy)-8'-fluoro-1'-methylspiro[cyclohexane-1,4'-isochromane]

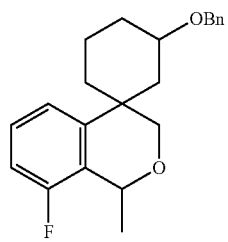 [SMILES: CC1OCC2(CCCC(OCc3ccccc3)C2)c2cccc(F)c21]

Under Ar, to a solution of (3-(benzyloxy)-1-(3-fluoro-2-vinylphenyl)cyclohexyl)methanol (808 mg, 2.373 mmol), 1-fluoro-2,4,6-trimethylpyridin-1-ium trifluoromethanesulfonate (1373 mg, 4.75 mmol) and Co$^{+2}$ chelate of 6,6'-(((1E,1'E)-((2,3-dimethylbutane-2,3-diyl)bis(azaneylylidene))bis(methaneylylidene))bis(2,4-di-tert-butylphenol) (71.9 mg, 0.119 mmol) in toluene (20 mL) was dropwise added the solution of 1,1,3,3-tetramethyldisiloxane (638 mg, 4.75 mmol) in 20 mL of toluene at RT, then the mixture was stirred at RT for 20 hours. Ethyl acetate was added to the mixture and washed with brine, dried over anhydrous sodium sulfate, and concentrated in vacuo to give a residual, which was purified by silica gel column and eluted with PE/EA=8:1 to give the title compound (708 mg, 88%) as a brown oil. 341.6 (M+H$^+$).

Step 10: 8'-fluoro-1'-methylspiro[cyclohexane-1,4'-isochroman]-3-ol

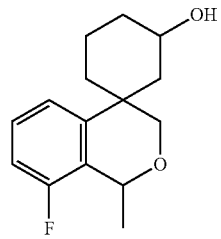 [SMILES: CC1OCC2(CCCC(O)C2)c2cccc(F)c21]

The mixture of 3-(benzyloxy)-8'-fluoro-1'-methylspiro[cyclohexane-1,4'-isochromane] (708 mg, 2.080 mmol) and Pd(OH)$_2$ (292 mg, 2.080 mmol) in MeOH (10 mL) was stirred at RT under H$_2$ overnight. The filtrate was concentrated in vacuo to give a crude title compound (508 mg, 98%) as a light brown oil. MS: 251.3 (M+H$^+$).

Step 11: 8'-fluoro-1'-methylspiro[cyclohexane-1,4'-isochroman]-3-one

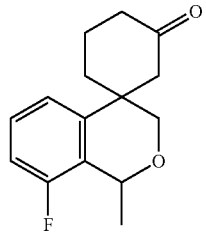 [SMILES: CC1OCC2(CCCC(=O)C2)c2cccc(F)c21]

To the mixture of 8'-fluoro-1'-methylspiro[cyclohexane-1,4'-isochroman]-3-ol (508 mg, 2.029 mmol) in DCM (20 mL) was added DMP (1722 mg, 4.06 mmol) at 0° C., then the mixture was stirred at RT for 3 hours. Quenched with Saturated NaHCO$_3$ and Na$_2$SO$_3$, the resulting mixture was extracted with DCM three times, dried over Na$_2$SO$_4$, filtered, concentrated in vacuo to give a residual, which was purified by silica gel column and eluted with PE/EA=4:1 to afford the title compound (468 mg, 93%) as a colorless oil. MS: 249.3 (M+H$^+$).

Example 39 was prepared essentially the same protocol described in EXAMPLE 25 with 8'-fluoro-1'-methylspiro[cyclohexane-1,4'-isochroman]-3-one to afford 15 mg as a white solid. MS: 575.6 (M+H$^+$). $^1$H NMR (400 MHz, DMSO-d6) δ 7.31-7.19 (m, 2H), 7.07-7.02 (m, 1H), 6.87-6.78 (m, 1H), 6.17 (dd, J=12.4, 1.6 Hz, 1H), 5.76 (dd, J=10.4, 2.0 Hz, 1H), 5.09-4.99 (m, 1H), 4.94-4.35 (m, 1H), 4.27-4.22 (m, 1H), 4.05-3.78 (m, 4H), 3.61-3.55 (m, 1H), 3.26-2.51 (m, 12H), 2.37 (s, 3H), 2.21-1.55 (m, 7H), 1.50 (d, J=6.0 Hz, 3H).

Example 40

2-((2S)-4-(8-fluoro-1-methyl-2'-(((S)-1-methylpyrrolidin-2-yl)methoxy)-5',8'-dihydro-6'H-spiro[isochromane-4,7'-quinazolin]-4'-yl)-1-(2-fluoroacryloyl)piperazin-2-yl)acetonitrile (Cpd. No. 36)

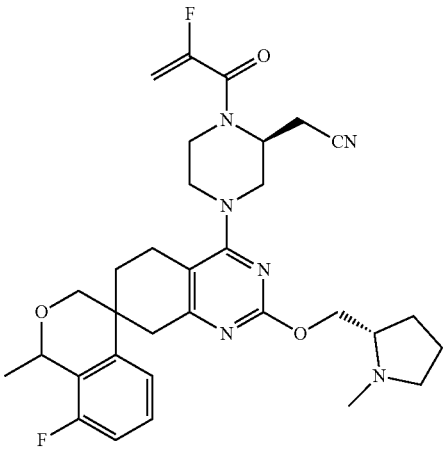 [SMILES: C=C(F)C(=O)N1CCN(c2nc(OC[C@@H]3CCCN3C)nc3c2CCC2(COC(C)c4c(F)cccc42)C3)C[C@@H]1CC#N]

Example 40 was prepared using essentially the same protocol described and afford 57 mg as white solid. MS: 593.7 (M+H$^+$). $^1$HNMR (400 MHz, DMSO-d6) δ 7.31-7.18 (m, 2H), 7.07-7.03 (m, 1H), 5.41-5.20 (m, 2H), 5.09-4.99 (m, 1H), 4.27-4.22 (m, 1H), 4.04-4.00 (m, 1H), 3.93-3.83 (m, 3H), 3.60-3.56 (m, 1H), 3.22-2.49 (m, 13H), 2.32 (s, 3H), 2.17-1.54 (m, 7H), 1.50 (d, J=2.4 Hz, 3H).

Example 41

2-((2S)-1-acryloyl-4-(2-methyl-2'-(((S)-1-methylpyrrolidin-2-yl)methoxy)-1-oxo-2,3,5',8'-tetrahydro-1H, 6'H-spiro[isoquinoline-4,7'-quinazolin]-4'-yl)piperazin-2-yl)acetonitrile (Cpd. No. 37)

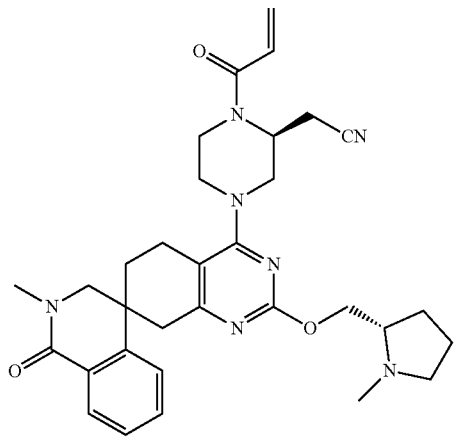 [SMILES: C=CC(=O)N1CCN(c2nc(OC[C@@H]3CCCN3C)nc3c2CCC2(C3)CN(C)C(=O)c3ccccc32)C[C@@H]1CC#N]

Intermediate: 2'-methyl-2',3'-dihydro-1'H-spiro[cyclohexane-1,4'-isoquinoline]-1',3-dione

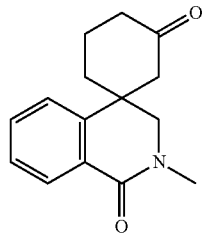 [SMILES: CN1CC2(CCCC(=O)C2)c2ccccc2C1=O]

Step 1: methyl 2-(3-acetoxy-1-cyanocyclohexyl)benzoate

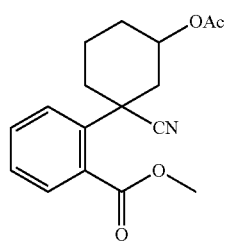 [SMILES: COC(=O)c1ccccc1C1(C#N)CCCC(OC(C)=O)C1]

Under Ar, the mixture of methyl 2-(cyanomethyl)benzoate (3.8 g, 21.69 mmol) and 1,5-diiodopentan-2-yl acetate (8.70 g, 22.78 mmol) DMF (20 mL) was dropwise added to a solution of sodium hydride (1.822 g, 45.6 mmol) in DMF (20 mL) at ice-water condition, and then the mixture was stirred at RT overnight. Quenched with saturated NH₄Cl solution, the resulting mixture was extracted with ethyl acetate three times. The combined organic layers were washed with brine, dried over Na₂SO₄, filtered and concentrated in vacuo to give a residual, which was purified by silica gel column and eluted with ethyl acetate/hexane from 5% to 40% to afford the title compound (2.1 g, 32.1%) as a light yellow oil. MS: 302.2 (M+H⁺). ¹HNMR (400 MHz, Chloroform-d) δ 7.67-7.64 (m, 1H), 7.52-7.47 (m, 2H), 7.42-7.35 (m, 1H), 5.21-5.12 (m, 1H), 3.98 (s, 3H), 2.85-2.80 (m, 1H), 2.46-2.42 (m, 1H), 2.24-2.19 (m, 1H), 2.03-1.97 (m, 5H), 1.90-1.82 (m, 2H), 1.41-1.31 (m, 1H).

Step 2: methyl 2-(3-acetoxy-1-cyanocyclohexyl)benzoate

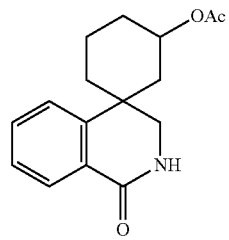 [SMILES: CC(=O)OC1CCCC2(CNC(=O)c3ccccc32)C1]

Under Ar, to a solution of methyl 2-(3-acetoxy-1-cyanocyclohexyl)benzoate (2.1 g, 6.97 mmol) and cobalt(II) chloride hexahydrate (4.97 g, 20.91 mmol) in MeOH (100 mL) was added NaBH₄ (853 mg, 21.4 mmol) portion wise at ice-water condition, after stirred at this temperature for 0.5 hour. Quenched with NH₄Cl solution, the resulting mixture was extracted with ethyl acetate three times. The combined organic layers were washed with brine, dried over Na₂SO₄, filtered and concentrated in vacuo to give a residual, which was purified by silica gel column and eluted with ethyl acetate/hexane from 5% to 100% to afford the title compound (1.4 g, 73.5%) as a white solid. MS: 274.5 (M+H⁺).

Step 3: 3-hydroxy-2'-methyl-2',3'-dihydro-1'H-spiro[cyclohexane-1,4'-isoquinolin]-1'-one

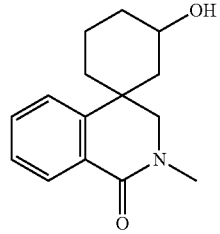 [SMILES: CN1CC2(CCCC(O)C2)c2ccccc2C1=O]

Under Ar, to a solution of 1'-oxo-2',3'-dihydro-1'H-spiro[cyclohexane-1,4'-isoquinolin]-3-yl acetate (1.8 g, 6.59 mmol) in dry DMF (30 mL) was added NaH (0.790 g, 19.76 mmol) at 0° C., then the mixture was stirred at 0° C. for 30 mins. Iodomethane (1.869 g, 13.17 mmol) was added to the mixture, then the mixture was stirred at RT for 2 hours. Quenched with saturated NH₄Cl solution, the resulting mixture was extracted with EA twice, and the organic layers were washed with brine, dried over Na₂SO₄, filtered, concentrated in vacuo to give a residual, which was dissolved in the solution of K₂CO₃ (4.55 g, 32.9 mmol) in MeOH (30 mL), and stirred at RT overnight. The filtrate was concentrated in vacuo to give a residual, which was purified by silica gel column and eluted with EA to give the title compound (1.43 g, 89%) as a colorless oil. MS: 246.5 (M+H⁺).

Step 4: 2'-methyl-2',3'-dihydro-1'H-spiro[cyclohexane-1,4'-isoquinoline]-1',3-dione

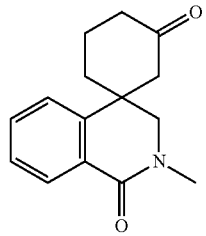 [SMILES: CN1CC2(CCCC(=O)C2)c2ccccc2C1=O]

Under Ar, the mixture of 3-hydroxy-2'-methyl-2',3'-dihydro-1'H-spiro[cyclohexane-1,4'-isoquinolin]-1'-one (1.38 g, 5.63 mmol) and PCC (3.64 g, 16.88 mmol) in DCM (10 mL) was stirred at 0° C. overnight. After removal off the volatile under reduced pressure to give a residual, which was purified by silica gel column and eluted with PE/EA=1:0-0:1 to afford the title compound (900 mg, 65.8%) as a brown solid. MS: 244.5 (M+H⁺).

Example 41 was prepared essentially the same protocol described in EXAMPLE 25 With 2'-methyl-2',3'-dihydro-1'H-spiro[cyclohexane-1,4'-isoquinoline]-1',3-dione to afford 24 mg as a white solid. MS: 570.5 (M+H⁺). ¹H NMR (400 MHz, DMSO-d6) δ 7.93 (d, J=7.6 Hz, 1H), 7.52-7.37 (m, 2H), 7.27-7.10 (m, 1H), 6.89-6.73 (m, 1H), 6.19-6.15 (m, 1H), 5.77-5.74 (m, 1H), 4.93-4.72 (m, 1H), 4.31-4.24 (m, 1H), 4.08-3.51 (m, 7H), 3.13-2.54 (m, 12H), 2.35 (d, J=3.6 Hz, 3H), 2.19-1.56 (m, 8H).

Example 42

2-((2S)-1-acryloyl-4-(4'-fluoro-2''-(((S)-1-methylpyrrolidin-2-yl)methoxy)-5'',8''-dihydro-2'H,6''H-dispiro[cyclopropane-1,3'-indene-1',7''-quinazolin]-4''-yl)piperazin-2-yl)acetonitrile (Cpd. No. 38)

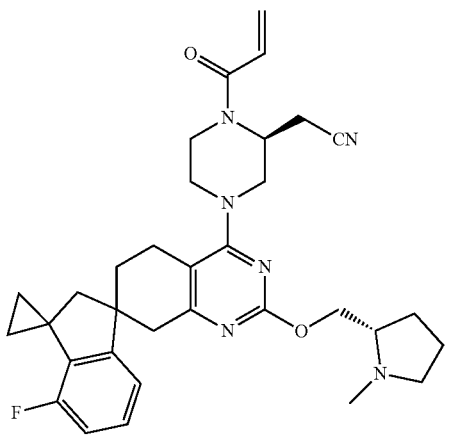 [SMILES: C=CC(=O)N1CCN(c2nc(OC[C@@H]3CCCN3C)nc3c2CCC2(C3)CC3(CC3)c3c(F)cccc32)C[C@@H]1CC#N]

Intermediate: 4'-fluoro-2'H-dispiro[cyclohexane-1,1'-indene-3',1''-cyclopropan]-3-one

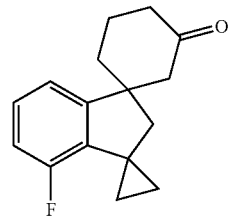 [SMILES: O=C1CCCC2(C1)CC1(CC1)c1c(F)cccc12]

Step 1: 4-fluorodispiro[indene-1,1'-cyclohexane-3',2''-[1,3]dioxolane]

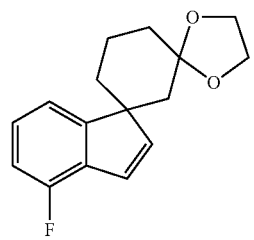 [SMILES: Fc1cccc2c1C=CC21CCCC2(C1)OCCO2]

Under Ar, the mixture of 4'-fluorospiro[cyclohexane-1,1'-inden]-3-one (30 g, 139 mmol), ethane-1,2-diol (12.92 g, 208 mmol) and p-TsOH (26.4 g, 139 mmol) in Toluene (120 mL) was stirred at 110° C. overnight. After all the volatiles were removed under reduced pressure to give a residual, which was purified by silica gel column and eluted with EA/HEX from 0% to 20% to afford the title compound (29 g, 80%) as a yellow oil. MS: 261.2 (M+H⁺).

step 2: 4-fluorodispiro[indene-1,1'-cyclohexane-3',2''-[1,3]dioxolan]-3(2H)-one

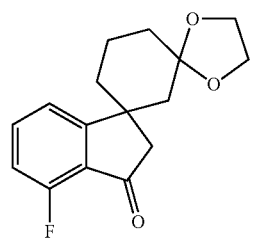 [SMILES: O=C1CC2(CCCC3(C2)OCCO3)c2cccc(F)c21]

Under Ar, to a solution of 9-BBN (14.5 g, 119 mmol) in THF (120 mL) was dropwise added 4-fluorodispiro[indene-1,1'-cyclohexane-3',2''-[1,3]dioxolane] (27 g, 104 mmol) at room temperature, then the mixture was stirred at 70° C. for 5 hours. After the removal off the volatiles under reduced pressure to give a residual, which was re-dissolved in DCM (200 mL). PCC (112 g, 519 mmol) was added very slowly to the above mixture at 25° C., and then the mixture was stirred at RT overnight. The filtrate was concentrated under reduced pressure to give a black residual, which was purified by silica gel column and eluted with EA/HEX from 0% to 30% to afford the title compound (20 g, 70%) as white solid. MS: 277.8 (M+H⁺).

Step 3: 4-fluoro-3-methylene-2,3-dihydrodispiro[indene-1,1'-cyclohexane-3',2''-[1,3]dioxolane]

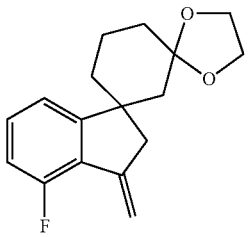 [SMILES: C=C1CC2(CCCC3(C2)OCCO3)c2cccc(F)c21]

Under Ar, to a solution of methyltriphenylphosphonium bromide (4.27 g, 11.94 mmol) in dry THF was added potassium butan-1-olate (1.523 g, 13.57 mmol) at 0° C. and then the mixture was stirred at RT for 1 h. 4-fluorodispiro[indene-1,1'-cyclohexane-3',2''-[1.3]dioxolan]-3(2H)-one (1.5 g, 5.43 mmol) was added, then the mixture was stirred at RT for 16 h. Diluted with water, extracted with EA for three times. The combined organic layers were washed with brine, dried over anhydrous Na$_2$SO$_4$ and concentrated in vacuo to give a residue, which was purified by silica gel column and eluted with Hex/EA=20:1 to afford the title compound (980 mg, 65.8%) as colorless oil. MS: 275.1 (M+H$^+$).

Step 4: 4'-fluoro-2'H-trispiro[cyclopropane-1,3'-indene-1',1''-cyclohexane-3'',2'''-[1.3] dioxolane]

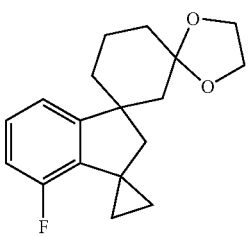 [SMILES: Fc1cccc2c1C1(CC1)CC21CCCC2(C1)OCCO2]

Under Ar, to a mixture of Et$_2$O (40 mL) and 1N KOH aq (76 mL) was added 1-methyl-1-nitrosourea (3.9 g, 37.8 mmol) in portions at 0° C., then the mixture was stirred at 0° C. for 20 mins. The separated organic layer was added to a solution of 4-fluoro-3-methylene-2,3-dihydrodispiro[indene-1,1'-cyclohexane-3',2''-[1,3] dioxolane] (980 mg, 3.57 mmol) in Et$_2$O (30 mL) at –70° C. Diacetoxypalladium (40 mg, 0.179 mmol) was added and the mixture and the resulting mixture was stirred at from –70° C. to –20° C. for 2 hours. After the removal off the volatiles under reduced pressure to give a residual, which was purified by silica gel column and eluted with Hex/EA=10:1 to afford the title compound (930 mg, 90%) as colorless oil. MS: 289.2 (M+H$^+$).

Step 5: 4'-fluoro-2'H-dispiro[cyclohexane-1,1'-indene-3',1''-cyclopropan]-3-one

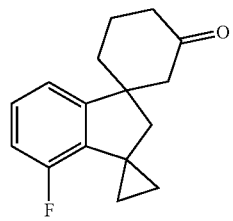 [SMILES: O=C1CCCC2(C1)CC1(CC1)c1c(F)cccc12]

Under Ar, the mixture of 4'-fluoro-2'H-trispiro[cyclopropane-1,3'-indene-1',1''-cyclohexane-3'',2'''-[1,3] dioxolane] (930 mg, 3.23 mmol) in 3N HCl (10 mL) and THF (15 mL) was stirred at RT for 12 h. Diluted with water, extracted with EA for three times. The combined organic layers were washed with brine, dried over anhydrous Na$_2$SO$_4$ and concentrated in vacuo to give a residual, which was purified by silica gel column and eluted with Hex/EA=10:1 to afford the title compound (780 mg, 99%) as yellow oil. MS: 245.3 (M+H$^+$).

Example 42 was prepared essentially the same protocol described in EXAMPLE 25 with 4'-fluoro-2'H-dispiro[cyclohexane-1,1'-indene-3',1''-cyclopropan]-3-one to afford 47 mg as a white solid. MS: 571.5 (M+H$^+$). $^1$H NMR (400 MHz, DMSO) δ 7.23-7.16 (m, 1H), 7.11-6.81 (m, 3H), 6.21 (dd, J=16.6, 2.0 Hz, 1H), 5.80 (d, J=10.6 Hz, 1H), 4.99-4.78 (m, 1H), 4.28-4.00 (m, 3H), 3.98-3.75 (m, 2H), 3.70-3.45 (m, 1H), 3.30-2.60 (m, 10H), 2.37 (s, 3H), 2.25-1.55 (m, 9H), 1.33-1.23 (m, 2H), 0.94-0.89 (m, 2H).

Example 43

2-((2S)-1-acryloyl-4-(2-fluoro-2'-(((S)-1-methylpyrrolidin-2-yl)methoxy)-1a,5',6a,8'-tetrahydro-1H,6'H-spiro[cyclopropa[a]indene-6,7'-quinazolin]-4'-yl)piperazin-2-yl)acetonitrile (Cpd. No. 39)

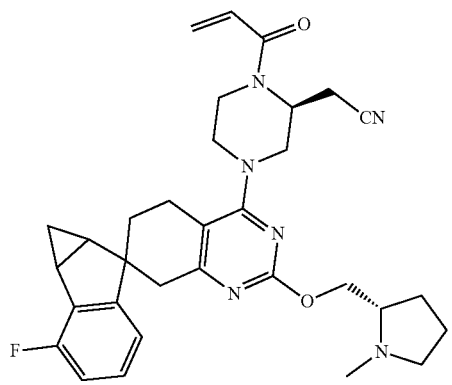 [SMILES: C=CC(=O)N1CCN(c2nc(OC[C@@H]3CCCN3C)nc3c2CCC2(C3)c3cccc(F)c3C3CC32)C[C@@H]1CC#N]

Intermediate: 2'-fluoro-1a',6a'-dihydro-1'H-spiro[cyclohexane-1,6'-cyclopropa[a]inden]-3-one

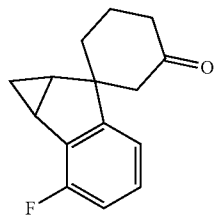 [SMILES: O=C1CCCC2(C1)c1cccc(F)c1C1CC12]

Step 1: 2-fluoro-1a,6a-dihydro-1H-dispiro[cyclopropa[a]indene-6,1'-cyclohexane-3',2''-[1,3]dioxolane]

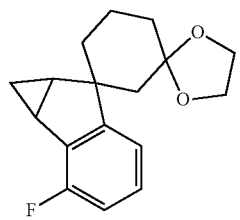 [SMILES: Fc1cccc2c1C1CC1C21CCCC2(C1)OCCO2]

Under Ar, to a solution of diethylzinc (294 mg, 2.382 mmol) in dry DCM was added slowly a solution of TFA (272 mg, 2.382 mmol) in DCM at 0° C. After 30 mins later, a solution of diiodomethane (638 mg, 2.382 mmol) in DCM was added the above mixture, and the mixture was stirred at 0° C. for another 30 mins. At last, a solution of 4-fluoro-dispiro[indene-1,1'-cyclohexane-3',2''-[1,3]dioxolane] (310 mg, 1.191 mmol) in DCM was dropwise added at 0° C., then the mixture was stirred at RT for 30 mins. Quenched with saturated NH$_4$Cl solution, extracted with DCM three times. The combined organic layers were washed with brine, dried over sodium sulfate, filtered, concentrated in vacuo to give a residual, which was purified by silica gel column and eluted with ethyl acetate/hexane from 0% to 30% to afford the title compound (300 mg, 92%) as a colorless oil. MS: 275.5 (M+H$^+$).

Step 2: 2'-fluoro-1a', 6a'-dihydro-1'H-spiro[cyclohexane-1,6'-cyclopropa[a]inden]-3-one

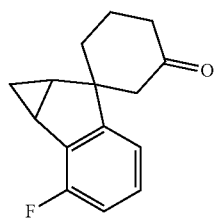 [SMILES: O=C1CCCC2(C1)c1cccc(F)c1C1CC12]

Under Ar, the mixture of 2'H-trispiro[cyclopropane-1,1''-indene-3',1'''-cyclohexane-3'',2''''-[1,3]dioxolane] (300 mg, 1.19 mmol) in Acetone (5 mL) and 4N HCl (5 mL) was stirred at RT for 1 hour. After removal off the volatiles under reduced pressure, the resulting mixture was extracted with ethyl acetate three times. The combined organic layers were washed with brine, concentrated under reduced pressure to give a residual, which was purified by silica gel column and eluted with ethyl acetate/hexane from 0% to 30% to afford the title compound (250 mg, 94%) as a white solid. MS: 231.1 (M+H$^+$).

Example 43 was prepared essentially the same protocol described in EXAMPLE 25 With 2'-fluoro-1a', 6a'-dihydro-1'H-spiro[cyclohexane-1,6'-cyclopropa[a]inden]-3-one to afford 47 mg as a white solid. MS: 557.3 (M+H$^+$). $^1$HNMR (400 MHz, DMSO-d$_4$) δ 7.20-7.13 (m, 1H), 7.04-6.83 (m, 3H), 6.23-6.19 (m, 1H), 5.81-5.78 (m, 1H), 4.99-4.78 (m, 1H) 4.45-4.25 (m, 1H), 4.09-3.83 (m, 4H), 3.66-3.45 (m, 1H), 3.32-2.91 (m, 7H), 2.84-2.52 (m, 4H), 2.36 (s, 3H), 2.21-2.09 (m, 2H), 2.03-1.85 (m, 2H), 1.78-1.55 (m, 4H), 1.08-1.03 (m, 1H), 0.19-0.19 (m, 1H).

Example 44

2-((2S)-1-((E)-4-methoxybut-2-enoyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 40)

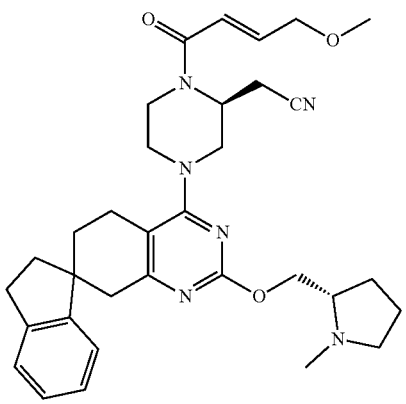 [SMILES: COC/C=C/C(=O)N1CCN(c2nc(OC[C@@H]3CCCN3C)nc3c2CCC2(CCc4ccccc42)C3)C[C@@H]1CC#N]

Under Ar, the mixture of 2-((2S)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (200 mg, 0.423 mmol), DIPEA (164 mg, 1.269 mmol), (E)-4-methoxybut-2-enoic acid (49.1 mg, 0.423 mmol) and HATU (193 mg, 0.508 mmol) in DMF (5 mL) was stirred at RT for 1 h. Water was added, the resulting mixture was extracted with ethyl acetate three times. The combined organic layers were dried washed with brine, dried over Na$_2$SO$_4$, filtered and concentrated in vacuo to give a residual, which was purified by Pre-HPLC to afford the title compound (21 mg, 8.70%) as a white solid. MS: 571.4 (M+H$^+$).

Example 45

2-((2S)-1-((E)-4-(3-fluoroazetidin-1-yl)but-2-enoyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 41)

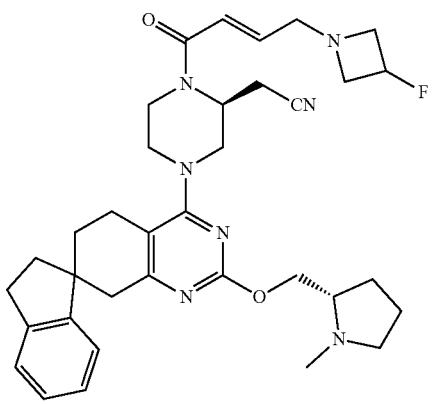 [SMILES: CN1CCC[C@H]1COc1nc2c(c(N3CCN(C(=O)/C=C/CN4CC(F)C4)[C@@H](CC#N)C3)n1)CCC1(CCc3ccccc31)C2]

Intermediate: Step 1 tert-butyl (E)-4-bromobut-2-enoate

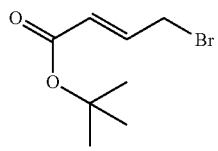

Under Ar, the mixture of tert-butyl (E)-but-2-enoate (3.20 g, 22.47 mmol), NBS (4 g, 22.47 mmol), and benzoyl peroxide (0.163 g, 0.674 mmol) in CCl$_4$ (15 mL) was stirred at 85° C. overnight. After cooling down to RT, the filtrate was concentrated in vacuo to give a residual, which was purified by silica gel column and eluted with EA/Hex from 0% to 5% to afford the title compound (3.5 g, 70.4%) as a colorless oil.

Step 2: tert-butyl (E)-4-(3-fluoroazetidin-1-yl)but-2-enoate

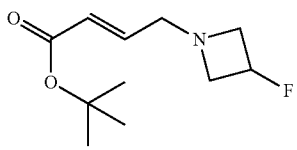

Under Ar, the mixture of tert-butyl (E)-4-bromobut-2-enoate (1 g, 4.52 mmol), 3-fluoroazetidine (0.340 g, 4.52 mmol) and DIPEA (1.754 g, 13.57 mmol) in THF (15 mL) was stirred at 60° C. overnight. After the removal off the volatiles under reduced pressure to give a residual, which was purified by silica gel column and eluted with EA/Hexane from 0% to 35% to afford the title compound (400 mg, 41.1%) as a light-yellow oil. MS: 216.1 (MEED).

Step 3: (E)-4-(3-fluoroazetidin-1-yl)but-2-enoic acid

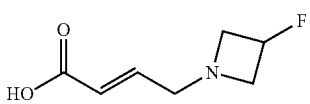 [SMILES: O=C(O)/C=C/CN1CC(F)C1]

Under Ar, the mixture of tert-butyl (E)-4-(3-fluoroazetidin-1-yl)but-2-enoate (400 mg, 1.858 mmol) in 6M HCl (4 mL) was stirred at RT for 6 hours. All the solvents were removed under reduced pressure to give the title compound (260 mg). MS: 160.1 (M+H$^+$).

Step 4: 2-((2S)-1-((E)-4-(3-fluoroazetidin-1-yl)but-2-enoyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile Example 45 was prepared essentially the same protocol described in EXAMPLE 44 with (E)-4-(3-fluoroazetidin-1-yl)but-2-enoic acid to afford 8 mg as a white solid. MS: 614.7 (M+H$^+$).

Example 46

2-((2S)-1-(2-(methoxymethyl)acryloyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 42)

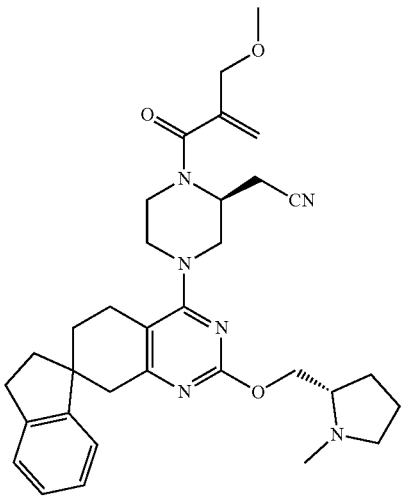 [SMILES: C=C(COC)C(=O)N1CCN(c2nc(OC[C@@H]3CCCN3C)nc3c2CCC2(CCc4ccccc42)C3)C[C@@H]1CC#N]

Intermediate: Step 1: 1-(2-(ethoxycarbonyl)allyl)-1,4-diazabicyclo[2.2.2]octan-1-ium bromide

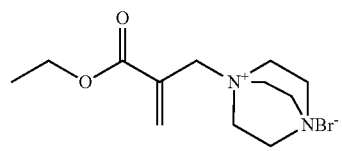

Under Ar, the mixture of Ethyl 2-(bromomethyl)acrylate (2 g, 10.36 mmol) and DABCO (1.395 g, 12.43 mmol) in THF (60 mL) was stirred at RT for 2 h. The precipitate was collected and rinsed with DCM to give the title compound (2 g, 63.2%) as a solid.

Step 2: ethyl 2-(methoxymethyl)acrylate

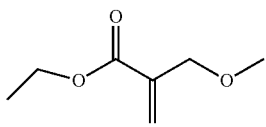

Under Ar, the mixture of 1-(2-(ethoxycarbonyl)allyl)-1,4-diazabicyclo[2.2.2]octan-1-ium bromide (2 g, 6.55 mmol) and TEA (0.663 g, 6.55 mmol) in MeOH (20 mL) was stirred at RT for 2 h. After the removal off the volatiles to give a residual, which was purified by silica gel column and eluted with EA/PE from 0% to 10% to give the desired title compound (0.45 g, 47%) as an oil. MS: 145.1 (M+H$^+$).

Step 3: 2-(methoxymethyl)acrylic acid

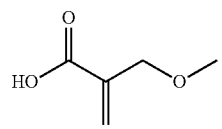

Under Ar, the mixture of ethyl 2-(methoxymethyl)acrylate (900 mg, 6.24 mmol) and NaOH (749 mg, 18.73 mmol) in H$_2$O (2 mL) and THF (10 mL) was stirred at RT overnight. Acidified with 1M HCl, the resulting mixture was extracted with dichloromethane twice. The combined organic layers were dried over Na$_2$SO$_4$, filtered and concentrated in vacuo to afford the crude (350 mg, 48.3%) as a brown oil. MS: 117.1 (M+H$^+$).

Step 4: 2-((2S)-1-(2-(methoxymethyl)acryloyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile Example 46 was prepared essentially the same protocol described in EXAMPLE 44 with 2-(methoxymethyl)acrylic acid to afford 17 mg as a white solid. MS: 571.4 (M+H$^+$).

Example 47

2-((2S)-1-((E)-4-fluorobut-2-enoyl)-4-(2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 43)

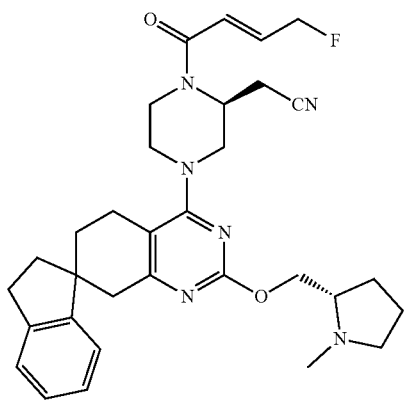

Example 47 was prepared essentially the same protocol described in EXAMPLE 44 with (E)-4-fluorobut-2-enoic acid to afford 17 mg as a white solid. MS: 559.4 (M+H$^+$).

Example 48

2-((S)-1-acryloyl-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)piperazin-2-yl)acetonitrile (Cpd. No. 44)

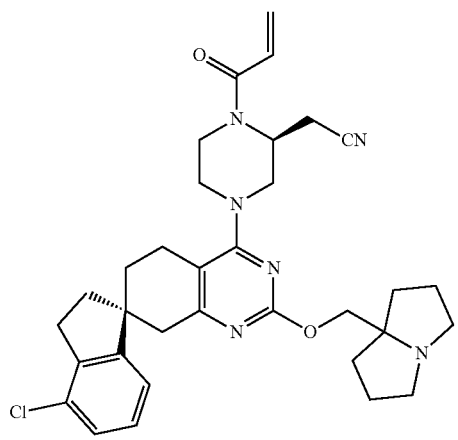 [SMILES: C=CC(=O)N1CCN(c2nc(OCC34CCCN3CCC4)nc3c2CC[C@@]2(CCc4c(Cl)cccc42)C3)C[C@@H]1CC#N]

Step 1: 1-bromo-3-chloro-2-vinylbenzene

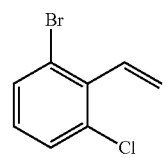

Under Ar, to a solution of methyltriphenylphosphonium bromide (58.6 g, 164 mmol) in THF (500 mL) was dropwise added n-butyllithium (10.51 g, 164 mmol) in Hexane at 0° C., the resulting mixture was stirred at ice-water condition for 1 hour. 2-bromo-6-chlorobenzaldehyde (30 g, 137 mmol) in THF (60 mL) was added to the above mixture, and then the mixture was stirred at RT for 2 hours. Quenched with saturated NH$_4$Cl solution, the resulting mixture was extracted with EA three times. The combined organic layers were washed with brine, dried over Na$_2$SO$_4$, filtered and concentrated in vacuo to give a residual, which was purified by silica gel column and eluted with PE to afford the title compound (25 g, 84%) as an oil.

Step 2: 3'-chloro-2'-vinyl-5,6-dihydro-[1,1'-biphenyl]-3(4H)-one

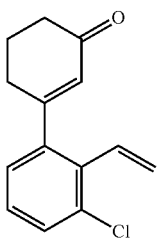 [SMILES: C=Cc1c(Cl)cccc1C1=CC(=O)CCC1]

Under Ar, the mixture of 1-bromo-3-chloro-2-vinylbenzene (50 g, 230 mmol), 3-(4,4,5,5-tetramethyl-1,3,2-dioxaborolan-2-yl)cyclohex-2-en-1-one (61.3 g, 276 mmol), 1-bromo-3-chloro-2-vinylbenzene (50 g, 230 mmol), PdCl$_2$(dppf)-CH$_2$Cl$_{1-2}$ adduct (9.39 g, 11.49 mmol) and Na$_2$CO$_3$ (73.1 g, 690 mmol) in DME (750 mL) and H$_2$O (150 mL) was stirred for 2 h at 90° C. After cooling down to RT, water was added, the resulting mixture was extracted with EA three times. The combined organic layers were washed with brine, dried over Na$_2$SO$_4$, filtered and concentrated in vacuo to give a residual, which was purified by silica gel column and eluted with EA/Heptane from 0% to 30% to afford the title compound (33 g, 61.7%) as a light-yellow oil. $^1$H NMR (400 MHz, CDCl$_3$) δ 7.38 (dd, J=8.0, 1.3 Hz, 1H), 7.20 (t, J=7.8 Hz, 1H), 7.05 (dd, J=7.7, 1.3 Hz, 1H), 6.87 (dd, J=17.7, 11.4 Hz, 1H), 6.11 (d, J=1.6 Hz, 1H), 5.56-5.43 (m, 2H), 2.57-2.50 (m, 2H), 2.50-2.41 (m, 2H), 2.12-2.00 (m, 2H).

Step 3: 3-(3-chloro-2-vinylphenyl)-3-vinylcyclohexan-1-one

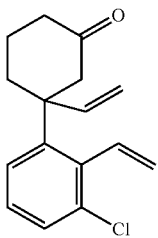 [SMILES: C=Cc1c(Cl)cccc1C1(C=C)CCCC(=O)C1]

Under Ar, to a solution of copper(I) iodide (36.8 g, 193 mmol) and lithium chloride (8.20 g, 193 mmol) in THF (180 mL) was dropwise added 1M Vinylmagnesium bromide (50.8 g, 387 mmol) in THF at −78° C., then the mixture was stirred at −78° C. for 1 hour. 3'-chloro-2'-vinyl-5,6-dihydro-[1,1'-biphenyl]-3(4H)-one (30.0 g, 129 mmol) in THF (120 mL) was dropwise added to the above solution at −78° C., then the mixture was stirred at at −78° C. for 1 h, and allowed to warm to room temperature slowly, stirred for another 30 mins. Quenched with saturated NH$_4$Cl solution, the resulting mixture was extracted with ethyl acetate three times. The combined organic layers were washed with brine, dried over Na$_2$SO$_4$, filtered and concentrated in vacuo to give the crude, which was purified by silica gel column and eluted with ethyl acetate/hexane from 0% to 20% to afford the title compound (8.6 g, 25.6%) as a colorless oil. MS: 261.2 (M+H$^+$).

Step 4: 4'-chlorospiro[cyclohexane-1,1'-inden]-3-one

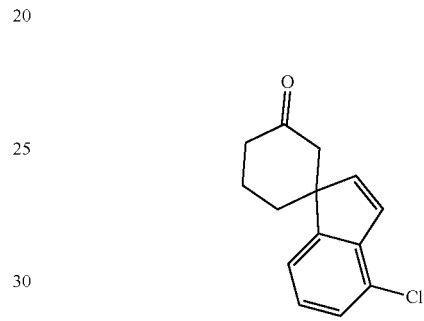

Under Ar, the mixture of 3-(3-chloro-2-vinylphenyl)-3-vinylcyclohexan-1-one (8.6 g, 33.0 mmol) and Grubbs ii (4.20 g, 4.95 mmol) in DCM (1200 mL) was stirred at 30° C. for 12 hours. After the removal off the volatiles under reduced pressure to give a residual, which was purified by silica gel column and eluted with ethyl acetate/hexane from 0% to 15% to afford the title compound (6.1 g, 79%) as a light-yellow solid. MS: 233.2 (M+H$^+$).

Step 5: 4'-chloro-2',3'-dihydrospiro[cyclohexane-1,1'-inden]-3-one

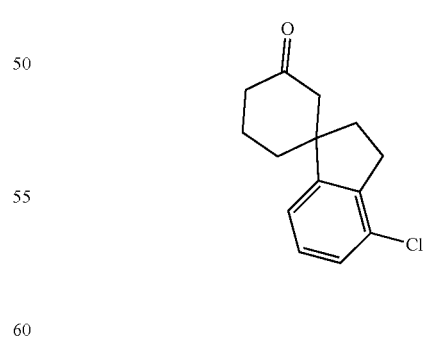

The mixture of Platinum (IV) oxide (0.878 g, 3.87 mmol) and 4'-chlorospiro[cyclohexane-1,1'-inden]-3-one (6 g, 25.8 mmol) in Ethyl acetate (150 mL) was stirred for 1 h under H$_2$ condition. The filtrate was concentrated in vacuo to give the title compound (5.8 g, 96%) as a colorless oil. MS: 235.3 (M+H$^+$).

Step 6: methyl 4'-chloro-3-oxo-2',3'-dihydrospiro[cyclohexane-1,1'-indene]-4-carboxylate

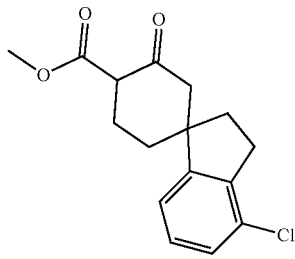 [SMILES: COC(=O)C1CCC2(CCc3c(Cl)cccc32)CC1=O]

Under Ar, to a mixture of Dimethyl carbonate (11.13 g, 124 mmol) and NaH (4.94 g, 123.5 mmol) in THF (35 mL) was dropwise added the solution of 4'-chloro-2',3'-dihydrospiro[cyclohexane-1,1'-inden]-3-one (5.8 g, 24.71 mmol) at 70° C., then the mixture was stirred at 70° C. for 1.5 hour. After cooling down to RT, quenched with saturated NH$_4$Cl solution, the resulting mixture was extracted with ethyl acetate three times. The combined organic layers were concentrated in vacuo to give a residual, which was purified by silica gel column and eluted with ethyl acetate/hexane from 5% to 80% to afford the title compound (5.6 g, 77%) as an oil. MS: 293.1 (M+H$^+$). $^1$H NMR (400 MHz, CDCl$_3$) δ 12.19 (d, J=1.1 Hz, 1H), 7.19-7.09 (m, 2H), 7.02-6.97 (m, 1H), 3.79 (d, J=1.1 Hz, 3H), 2.96 (t, J=7.2 Hz, 2H), 2.47-2.40 (m, 1H), 2.38-2.29 (m, 3H), 2.01-1.92 (m, 2H), 1.89-1.76 (m, 1H), 1.69-1.58 (m, 1H).

Step 7: 4-chloro-2,3,5',8'-tetrahydro-1'H-spiro[indene-1,7'-quinazoline]-2',4'(3'H,6'H)-dione

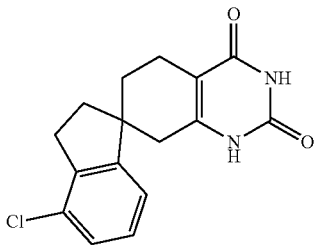 [SMILES: O=c1[nH]c2c(c(=O)[nH]1)CCC1(CCc3c(Cl)cccc31)C2]

Under Ar, the mixture of K$_2$CO$_3$ (8.62 g g, 58.8 mmol), guanidine hydrochloride (9.93 g, 98 mmol) and Methyl 4'-chloro-3-oxospiro[cyclohexane-1,1'-indene]-4-carboxylate (step 1, 5.7 g, 19.60 mmol) in DMF (40 mL) was stirred at 85° C. for 2 h. water was added, the precipitate was collected and dried under reduced pressure to give the intermediate: 2'-amino-4-chloro-2,3,5',8'-tetrahydro-3'H-spiro[indene-1,7'-quinazolin]-4'(6'H)-one (5.1 g) as a white solid. The intermediate (5.1 g) was re-dissolved in AcOH (40 mL), followed by addition the solution of NaNO$_2$ (23.2 g, 338 mmol) in H2O (20 mL) at 70° C. after stirred at 70° C. for 1.5 hours, and all the volatiles were removed in vacuo to give a residual, which was treated with water, and the precipitate was collected and dried under reduced pressure to give the title compound (4.55 g, 89%) as a white solid. MS: 303.1 (M+H$^+$).

Step 8: 2',4,4'-trichloro-2,3,5',8'-tetrahydro-6'H-spiro[indene-1,7'-quinazoline]

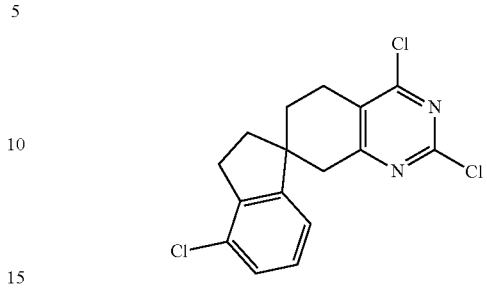

Under Ar, the mixture of 4-chloro-2,3,5',8'-tetrahydro-1'H-spiro[indene-1,7'-quinazoline]-2',4'(3'H,6'H)-dione (6.16 g, 19.45 mmol), DIPEA (2.51 g, 19.45 mmol) and DMF (0.2 mL), POCl$_3$ (80 mL) was stirred at 110° C. for 2 h. After the removal off the POCl$_3$ under reduced pressure to give a residual, which was re-dissolved in DCM (120 mL), the resulting mixture was added to the NaHCO$_3$ solution, the separated organic layer was washed with brine, dried over Na$_2$SO$_4$ and concentrated in vacuo to give a residual, which was purified by silica gel column and eluted with EA/Hep from 0% to 20% to afford the title compound (5.75 g, 87%) as a white solid.

Step 9: tert-butyl (2S)-2-(cyanomethyl)-4-(2',4-dichloro-2,3,5',8'-tetrahydro-6'H-spiro[indene-1,7'-quinazolin]-4'-yl)piperazine-1-carboxylate Boc

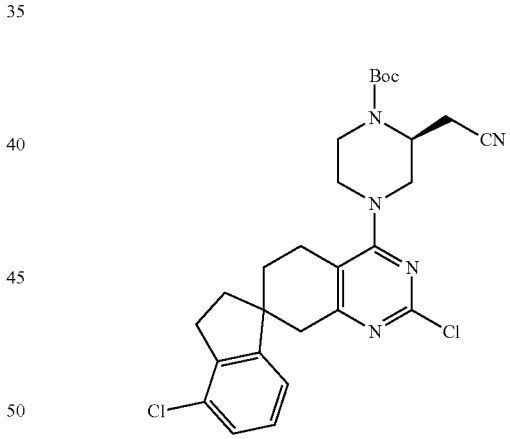

Under Ar, the mixture of 2',4,4'-trichloro-2,3,5',8'-tetrahydro-6'H-spiro[indene-1,7'-quinazoline] (7.35 g, 17.17 mmol), DIPEA (11.07 g, 85.85 mmol) and (S)-2-(piperazin-2-yl)acetonitrile dihydrochloride (3.74 g, 18.89 mmol) in DMSO (50 mL) was stirred at 55° C. for 4 h. Then Boc$_2$O (5.61 g, 25.75 mmol) was added to the above mixture, the resulting mixture was stirred at this temperature for 1 h. After cooling down to RT, water was added, the resulting mixture was extracted with ethyl acetate three times. The combined organic layers were washed with brine, concentrated under reduced pressure to give a residual, which was purified by silica gel column and eluted with ethyl acetate/hexane from 0% to 40% to afford the title compound (8.39 g, 92.5%) as a white solid. MS: 530.3 (M+H$^+$).

Step 10: tert-butyl (S)-2-(cyanomethyl)-4-((R)-2',4-dichloro-2,3,5',8'-tetrahydro-6'H-spiro[indene-1,7'-quinazolin]-4'-yl)piperazine-1-carboxylate and tert-butyl (S)-2-(cyanomethyl)-4-((S)-2',4-dichloro-2,3,5',8'-tetrahydro-6'H-spiro[indene-1,7'-quinazolin]-4'-yl)piperazine-1-carboxylate Isomer A

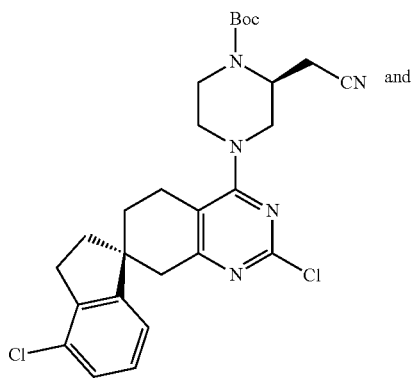

and

Isomer B

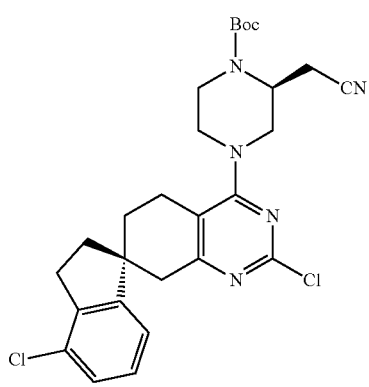 [SMILES: CC(C)(C)OC(=O)N1CCN(c2nc(Cl)nc3c2CCC2(CCc4c(Cl)cccc42)C3)C[C@@H]1CC#N]

tert-butyl (2S)-2-(cyanomethyl)-4-(2',4-dichloro-2,3,5',8'-tetrahydro-6'H-spiro[indene-1,7'-quinazolin]-4'-yl)piperazine-1-carboxylate (8.9 g) was subjected to chiral SFC resolution using a CHIRALPAK IG column to provide the title compounds as white solids. The stereochemistry of the asymmetric spirocarbon atom these compounds has not been determined.

Tert-butyl (S)-2-(cyanomethyl)-4-((R)-2',4-dichloro-2,3,5',8'-tetrahydro-6'H-spiro[indene-1,7'-quinazolin]-4'-yl)piperazine-1-carboxylate: The first eluting stereoisomer (3 g; 100% ee) was arbitrarily designated as Isomer A having R stereochemistry at the spirocarbon atom pending further analysis.

Tert-butyl (S)-2-(cyanomethyl)-4-((S)-2',4-dichloro-2,3,5',8'-tetrahydro-6'H-spiro[indene-1,7'-quinazolin]-4'-yl)piperazine-1-carboxylate: The second eluting stereoisomer (4.3 g; 99% ee) was arbitrarily designated as Isomer B having S stereochemistry at the spirocarbon atom pending further analysis.

Step 11: tert-butyl (S)-4-((R)-4-chloro-2'-(methylthio)-2,3,5',8'-tetrahydro-6'H-spiro[indene-1,7'-quinazolin]-4'-yl)-2-(cyanomethyl)piperazine-1-carboxylate

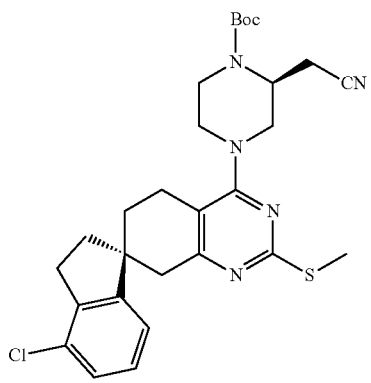 [SMILES: CSc1nc2c(c(N3CCN(C(=O)OC(C)(C)C)[C@@H](CC#N)C3)n1)CC[C@@]1(CCc3c(Cl)cccc31)C2]

Under Ar, to a solution of tert-butyl (S)-2-(cyanomethyl)-4-((R)-2',4-dichloro-2,3,5',8'-tetrahydro-6'H-spiro[indene-1,7'-quinazolin]-4'-yl)piperazine-1-carboxylate (1.0 g, 1.89 mmol) in DMSO (10 mL) was added 20% NaSCH$_3$ (662.9 mg, 9.45 mmol) in DMSO at RT, and then the mixture was stirred at RT for 1.5 h. Water was added, the resulting mixture was extracted with ethyl acetate three times. The combined organic layers were washed with brine, dried over Na$_2$SO$_4$, filtered and concentrated in vacuo to give the crude, which was purified by silica gel column and eluted with ethyl acetate/hexane from 0% to 30% to afford the title compound (869 mg, 85%) as a white solid. MS: 540.2 (M+H$^+$).

Step 12: tert-butyl(2S)-4-((1R)-4-chloro-2'-(methylsulfinyl)-2,3,5',8'-tetrahydro-6'H-spiro[indene-1,7'-quinazolin]-4'-yl)-2-(cyanomethyl)piperazine-1-carboxylate

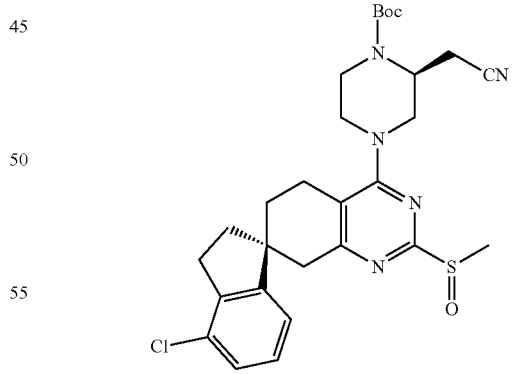

Under Ar, to a solution of Tert-butyl(S)-4-((R)-4-chloro-2'-(methylthio)-2,3,5',8'-tetrahydro-6'H-spiro[indene-1,7'-quinazolin]-4'-yl)-2-(cyanomethyl)piperazine-1-carboxylate (869 mg, 1.61 mmol) in CH$_2$Cl$_2$ (10 mL) was added 3-chlorobenzoperoxoic acid (305.62 mg, 1.77 mmol) at 0° C., and then mixture was stirred at RT for 2 h. Quenched with Na$_2$S$_2$SO$_3$ solution, water was added, the resulting mixture was extracted with DCM three times. The combined organic layers were washed with saturated NaHCO₃ twice, brine, dried over Na₂SO₄, filtered and concentrated in vacuo to afford the title compound (730 mg, 81.6%) as a light yellow solid. MS: 557.2 (M+H⁺).

Step 13: tert-butyl (S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)-2-(cyanomethyl)piperazine-1-carboxylate

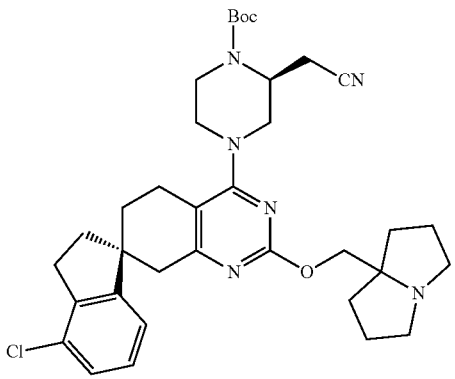 [SMILES: CC(C)(C)OC(=O)N1CCN(c2nc(OCC34CCCN3CCC4)nc3c2CC[C@@]2(CCc4c(Cl)cccc42)C3)C[C@@H]1CC#N]

Under Ar, to a solution of (tetrahydro-1H-pyrrolizin-7a (5H)-yl)methanol (457 mg, 3.24 mmol) in THF (10 mL) was added to sodium hydride (173 mg, 4.32 mmol) in THF (10 ml) at 0° C., then the mixture was stirred at 0° C. for 10 mins. Tert-butyl (2S)-4-((1R)-4-chloro-2'-(methylsulfinyl)-2,3,5',8'-tetrahydro-6'H-spiro[indene-1,7'-quinazolin]-4'-yl)-2-(cyanomethyl)piperazine-1-carboxylate (1.2 g, 2.16 mmol) in THF (8 mL) was added to the above mixture and at 0° C. After stirred at this temperature for 30 mins, quenched with saturated NH₄Cl solution, the resulting mixture was extracted with dichloromethane three times. The combined organic layers were washed with brine, dried over Na₂SO₄, filtered and concentrated in vacuo to give a residual, which was purified by silica gel column and eluted with MeOH/DCM from 0% to 10% to afford the title compound (1.1 g, 81%) as a foamed solid. MS: 633.4 (M+H⁺).

Step 14: 2-((S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)piperazin-2-yl)acetonitrile

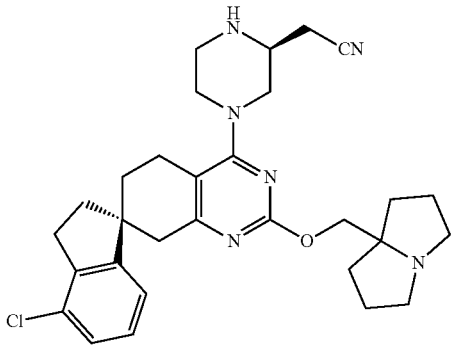 [SMILES: N#CC[C@H]1CN(c2nc(OCC34CCCN3CCC4)nc3c2CC[C@@]2(CCc4c(Cl)cccc42)C3)CCN1]

Under Ar, the mixture of Tert-butyl (S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)-2-(cyanomethyl)piperazine-1-carboxylate (1.2 g, 1.90 mmol) in CH₂Cl₂ (30 mL) and TFA (5 mL) was stirred at RT for 1 h. After the reaction, the volatiles was removed under reduced pressure to give the title compound (1.0 g, crude) as the TFA salt. MS: 533.3 (M+H⁺).

Step 15: 2-((S)-1-acryloyl-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl) piperazin-2-yl)acetonitrile Under Ar, to a solution of 2-((S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)piperazin-2-yl)acetonitrile (40 mg, 0.075 mmol) and triethylamine (30 mg, 0.3 mmol) in DCM (8 mL) was added acryloyl chloride (13.58 mg, 0.150 mmol) at 0° C. After 20 mins later, water was added, the resulting mixture was extracted with DCM three times. The combined organic layers were washed with brine, dried over Na₂SO₄, filtered and concentrated in vacuo to give a residual, which was purified by Pre-HPLC to afford the title compound (18 mg, 40.9%) as a white solid. MS: 588.3 (M+H⁺). ¹H NMR (400 MHz, DMSO) δ 7.30-7.22 (m, 2H), 7.22-7.12 (m, 1H), 6.93-6.74 (m, 1H), 6.18 (d, J=16.8 Hz, 1H), 5.77 (d, J=10.5 Hz, 1H), 5.10-4.25 (m, 1H), 4.22-3.41 (m, 5H), 3.41-2.36 (m, 15H), 2.12-2.00 (m, 1H), 1.99-1.89 (m, 2H), 1.87-1.61 (m, 7H), 1.62-1.46 (m, 2H).

Example 49

2-((S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 45)

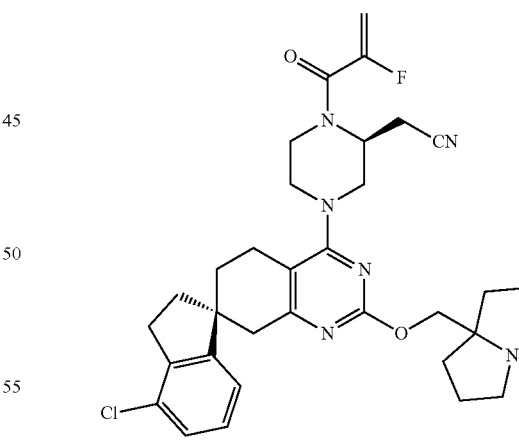

Under Ar, to a solution of 2-((S)-4-((R)-4-chloro-2'-((tetrahydro-1H-pyrrolizin-7a(5H)-yl)methoxy)-2,3,5',8'-tetrahydro-6'H-spiro[indene-1,7'-quinazolin]-4'-yl)piperazin-2-yl)acetonitrile (1.0 g, 1.88 mmol), DMAP (0.23 g, 1.88 mmol), TEA (0.57 g, 5.63 mmol) and 2-fluoroacrylic acid (0.51 g, 5.63 mmol) in DCM (20 mL) was added T₃P (2.39 g, 3.75 mmol) at 0° C., then the mixture was stirred at RT for 1 hour. Water was added, the resulting mixture was extracted with DCM three times. The combined organic layers were washed with brine, dried over $Na_2SO_4$, filtered and concentrated in vacuo to give a residual, which was purified by Pre-HPLC to afford the title compound (410 mg, 36.1%) as a white solid.

MS: 605.3 (M+H$^+$). $^1$H NMR (400 MHz, DMSO) δ 7.30-7.18 (m, 2H), 7.14 (dd, J=7.0, 1.2 Hz, 1H), 5.39 (dd, J=18.0, 4.1 Hz, 1H), 5.35-5.15 (m, 1H), 5.08-4.40 (m, 1H), 4.32-3.61 (m, 6H), 3.34-3.09 (m, 2H), 3.05-2.81 (m, 6H), 2.80-2.54 (m, 6H), 2.11-2.03 (m, 1H), 1.98-1.65 (m, 9H), 1.63-1.49 (m, 2H).

Example 50

2-((2S)-1-acryloyl-4-(((1R)-4-chloro-2'-((4-methyl-4-azaspiro[2.4]heptan-5-yl)methoxy)-2,3,5',8'-tetrahydro-6'H-spiro[indene-1,7'-quinazolin]-4'-yl)piperazin-2-yl)acetonitrile (Cpd. No. 46)

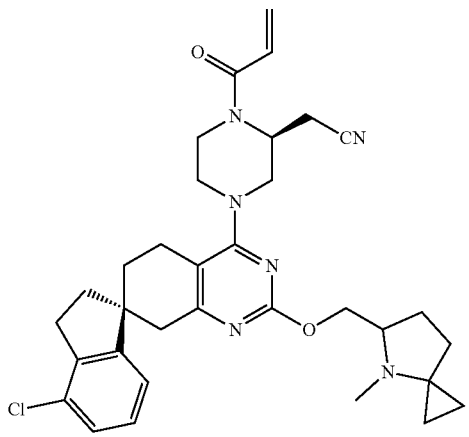 [SMILES: C=CC(=O)N1CCN(c2nc(OCC3CCC4(CC4)N3C)nc3c2CC[C@@]2(CCc4c(Cl)cccc42)C3)C[C@@H]1CC#N]

Intermediate Step 1: methyl (S)-1-methyl-5-oxopyrrolidine-2-carboxylate

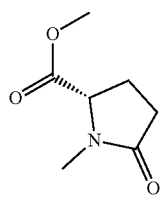

Under Ar, (S)-5-oxopyrrolidine-2-carboxylic acid (10 g, 77 mmol) in DMF (30 mL) was dropwise added to the solution of sodium hydride (5.58 g, 232 mmol) in DMF (150 mL) at ice-water condition, after the addition, the mixture was stirred at ice-water condition for 1 hour. iodomethane (24.19 g, 170 mmol) was added to the above mixture and then stirred at RT overnight. Quenched with saturated $NH_4Cl$ solution, water was added, the resulting mixture was extracted with EA three times, the combined organic layers were washed with brine, concentrated in vacuo to give a residual, which was purified by silica gel column and eluted with MeOH/DCM from 0% to 4% to afford the title compound (5.4 g, 44.4%) as a colorless oil. MS: 158.1 (M+H$^+$).

$^1$H NMR (400 MHz, CDCl$_3$) δ 4.18-4.07 (m, 1H), 3.78 (s, 3H), 2.85 (s, 3H), 2.57-2.42 (m, 1H), 2.41-2.29 (m, 2H), 2.17-2.01 (m, 1H).

Step 2: (S)-5-(hydroxymethyl)-1-methylpyrrolidin-2-one

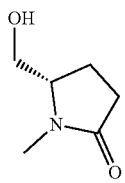

Under Ar, to a solution of methyl (S)-1-methyl-5-oxopyrrolidine-2-carboxylate (5.2 g, 33.1 mmol) in THF (50 mL) was added LiAlH$_4$ (0.628 g, 16.54 mmol) at −78° C. The resulting mixture was stirred at −78° C. for 1 hour, then the mixture was warmed up to 0° C. for 1 hour. 15% NaOH solution was added, stirred for 10 minutes, then 0.62 mL H2O and Na$_2$SO$_4$ were added and the mixture stirred at RT for 0.5 h. The filtrate was concentrated in vacuo to give the title compound (3.1 g, 72.5%) as a light-yellow oil. MS: 130.1 (M+H$^+$). $^1$H NMR (400 MHz, CDCl$_3$) δ 3.90-3.81 (m, 1H), 3.64-3.52 (m, 2H), 2.87 (s, 3H), 2.52-2.42 (m, 1H), 2.36-2.25 (m, 1H), 2.18-2.04 (m, 1H), 2.04-1.91 (m, 1H).

Step 3: (S)-5-(((tert-butyldimethylsilyl)oxy)methyl)-1-methylpyrrolidin-2-one

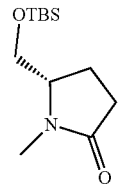 [SMILES: CN1C(=O)CC[C@H]1CO[Si](C)(C)C(C)(C)C]

Under Ar, the mixture of (S)-5-(hydroxymethyl)-1-methylpyrrolidin-2-one (3.1 g, 24.00 mmol), $^1$H-imidazole (3.27 g, 48.0 mmol) and tert-butylchlorodimethylsilane (5.43 g, 36.0 mmol) in THF (25 mL) was stirred at RT overnight. After the removal off the volatiles under reduced pressure to give a residual, which was purified by silica gel column and eluted with methanol/dichloromethane from 0% to 5% to afford the title compound (5.1 g, 87%) as an oil. MS: 244.2 (M+H$^+$). $^1$H NMR (400 MHz, CDCl$_3$) δ 3.74 (dd, J=10.4, 3.4 Hz, 1H), 3.65-3.52 (m, 2H), 2.86 (s, 3H), 2.50-2.38 (m, 1H), 2.36-2.23 (m, 1H), 2.16-2.02 (m, 1H), 1.89-1.80 (m, 1H), 0.89 (s, 9H), 0.06 (s, 6H).

Step 4: (S)-5-(((tert-butyldimethylsilyl)oxy)methyl)-4-methyl-4-azaspiro[2.4]heptane

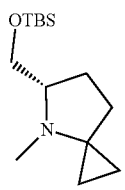 [SMILES: CN1[C@H](CO[Si](C)(C)C(C)(C)C)CCC12CC2]

Under Ar, to a solution of ethylmagnesium bromide (5.61 g, 42.1 mmol) in THF (72 mL) was dropwise added the titanium(IV) isopropoxide (5.27 g, 18.53 mmol) in THF (10 mL) at −78° C. After the addition, the mixture was stirred at −78° C. for 10 mins, (S)-5-(((tert-butyldimethylsilyl)oxy)methyl)-1-methylpyrrolidin-2-one (4.1 g, 16.84 mmol) in THF (10 mL) was dropwise added to the above mixture at −78° C. after warmed to RT gradually, the resulting mixture was stirred at refluxing for 4 hours. After cooling down to RT, Quenched with saturated NH$_4$Cl, water was added, the resulting mixture was extracted with EA three times, the combined organic layers were washed with brine, concentrated in vacuo to give a residual, which was purified by silica gel column and eluted with EA/Heptane from 0% to 30% to afford the title compound (680 mg, 15.80%) as a light yellow oil. MS: 256.2 (M+H$^+$).

Step 5: (S)-(4-methyl-4-azaspiro[2.4]heptan-5-yl)methanol

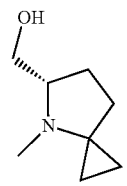

Under Ar, the mixture of (S)-5-(((tert-butyldimethylsilyl)oxy)methyl)-4-methyl-4-azaspiro[2.4]heptane (300 mg, 1.174 mmol) and TBAF (307 mg, 1.174 mmol) in THF (10 ml) was stirred at RT overnight. After the removal off the volatiles under reduced pressure to give a residual, which was purified by silica gel column and eluted with MeOH/DCM from 0% to 20% to afford the title compound (100 mg, 60.3%) as a colorless oil. MS: 142.1 (M+H$^+$).

Step 6: 2-((2S)-1-acryloyl-4-((1R)-4-chloro-2'-((4-methyl-4-azaspiro[2.4]heptan-5-yl)methoxy)-2,3,5',8'-tetrahydro-6'H-spiro[indene-1,7'-quinazolin]-4'-yl)piperazin-2-yl)acetonitrile Example 50 was prepared essentially the same protocol described in EXAMPLE 44 The title compound was prepared essentially the same protocol described with (S)-(4-methyl-4-azaspiro[2.4]heptan-5-yl)methanol in stand of (tetrahydro-1H-pyrrolizin-7a(5H)-yl)methanol to afford 20 mg as a white solid. MS: 587.4 (M+H+). 1H NMR (400 MHz, CDCl3) δ 7.26-7.08 (m, 2H), 7.01-6.89 (m, 1H), 6.66-6.55 (m, 1H), 6.41 (d, J=16.6 Hz, 1H), 5.84 (d, J=10.5 Hz, 1H), 5.07-2.55 (m, 17H), 2.22 (s, 3H), 2.17-1.60 (m, 9H), 0.96-0.85 (m, 1H), 0.70-0.59 (m, 1H), 0.55-0.47 (m, 1H), 0.34-0.24 (m, 1H).

Example 51

2-((S)-1-acryloyl-4-((R)-4-chloro-2'-(((1R,2S,5S)-3-methyl-3-azabicyclo[3.1.0]hexan-2-yl)methoxy)-2,3,5',8'-tetrahydro-6'H-spiro[indene-1,7'-quinazolin]-4'-yl)piperazin-2-yl)acetonitrile (Cpd. No. 47)

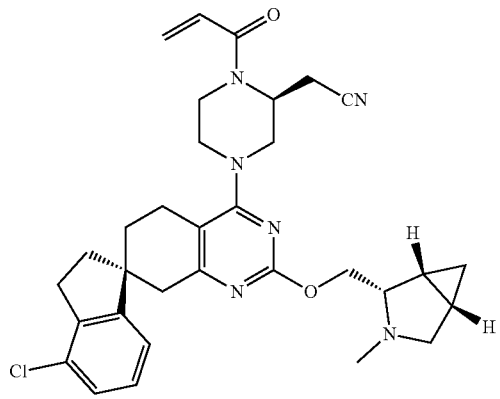 [SMILES: C=CC(=O)N1CCN(c2nc(OC[C@@H]3[C@@H]4C[C@@H]4CN3C)nc3c2CC[C@@]2(CCc4c(Cl)cccc42)C3)C[C@@H]1CC#N]

Intermediate Step 1: ((1R,2S,5S)-3-methyl-3-azabicyclo[3.1.0]hexan-2-yl)methanol

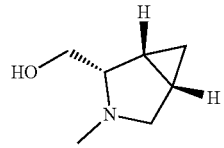

Under Ar, to a solution of (1R,2S,5S)-3-(tert-butoxycarbonyl)-3-azabicyclo[3.1.0]hexane-2-carboxylic acid (100 mg, 0.440 mol) in THF (2 mL) was added LiAlH$_4$ (41.8 mg, 1.100 mmol) in THF (1.1 mL) at ice-water condition, then the mixture was stirred at 60° C. for 3 h. After Cooling down to RT, 10% NaOH (5 mL) was added, the resulting mixture was extracted with dichloromethane three times. The combined organic layers were dried over Na$_2$SO$_4$, filtered and concentrated in vacuo to give a residual, which was purified by silica gel column and eluted with methanol/dichloromethane from 0% to 10% to afford the title compound (50 mg, 89%) as a yellow oil. MS: 128.1 (M+H$^+$).

Step 2: 2-((S)-1-acryloyl-4-((R)-4-chloro-2'-(((1R,2S,5S)-3-methyl-3-azabicyclo[3.1.0]hexan-2-yl)methoxy)-2,3,5',8'-tetrahydro-6'H-spiro[indene-1,7'-quinazolin]-4'-yl)piperazin-2-yl)acetonitrile Example 51 was prepared essentially the same protocol described in EXAMPLE 44 The title compound was prepared essentially the same protocol described with ((1R,2S,5S)-3-methyl-3-azabicyclo[3.1.0]hexan-2-yl)methanol in stand of (tetrahydro-1H-pyrrolizin-7a(5H)-yl)methanol to afford 15 mg as a white solid. MS: 573.4 (M+H$^+$).

Example 52

2-((S)-1-acryloyl-4-((R)-4-chloro-2'-(((1S,2S,5R)-3-methyl-3-azabicyclo[3.1.0]hexan-2-yl)methoxy)-2,3,5',8'-tetrahydro-6'H-spiro[indene-1,7'-quinazolin]-4'-yl)piperazin-2-yl)acetonitrile (Cpd. No. 48)

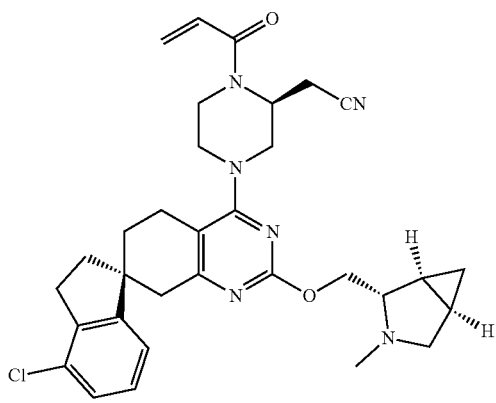 [SMILES: C=CC(=O)N1CCN(c2nc(OC[C@@H]3[C@H]4C[C@H]4CN3C)nc3c2CC[C@@]2(CCc4c(Cl)cccc42)C3)C[C@@H]1CC#N]

Intermediate Step 1: ((1S,2S,5R)-3-methyl-3-azabicyclo[3.1.0]hexan-2-yl)methanol

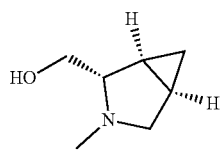

Under Ar, to a solution of (1R,2S,5R)-3-(tert-butoxycarbonyl)-3-azabicyclo[3.1.0]hexane-2-carboxylic acid (100 mg, 0.440 mol) in THF (2 mL) was added LiAlH$_4$ (41.8 mg, 1.100 mmol) in THF (1.1 mL) at ice-water condition, then the mixture was stirred at 60° C. for 3 h. After Cooling down to RT, 10% NaOH (5 mL) was added, the resulting mixture was extracted with dichloromethane three times. The combined organic layers were dried over Na$_2$SO$_4$, filtered and concentrated in vacuo to give a residual, which was purified by silica gel column and eluted with methanol/dichloromethane from 0% to 10% to afford the title compound (50 mg, 89%) as a yellow oil. MS: 128.1 (M+H$^+$).

Step 2: 2-((S)-1-acryloyl-4-((R)-4-chloro-2'-(((1S,2S,5R)-3-methyl-3-azabicyclo[3.1.0]hexan-2-yl)methoxy)-2,3,5',8'-tetrahydro-6'H-spiro[indene-1,7'-quinazolin]-4'-yl)piperazin-2-yl)acetonitrile Example 52 was prepared essentially the same protocol described in EXAMPLE 44 The title compound was prepared essentially the same protocol described in with ((1R,2S,5R)-3-methyl-3-azabicyclo[3.1.0]hexan-2-yl)methanol in stand of (tetrahydro-1H-pyrrolizin-7a(5H)-yl)methanol to afford 22 mg as a white solid. MS: 573.4 (M+H$^+$).

Example 53

2-((2S)-4-(4-(difluoromethyl)-2'-((tetrahydro-1H-pyrrolizin-7a(5H)-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 49)

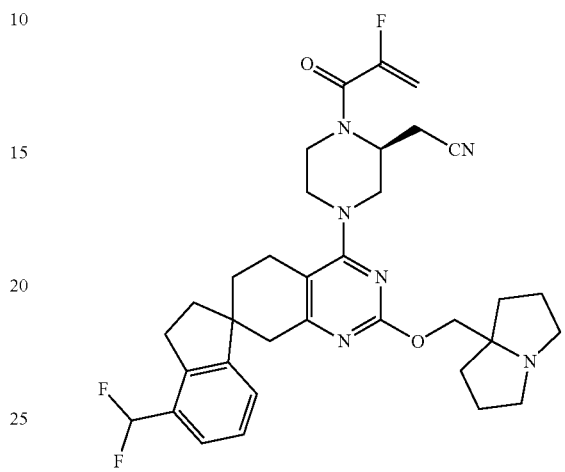

Intermediate 4'-(difluoromethyl)-2',3'-dihydrospiro[cyclohexane-1,1'-inden]-3-one

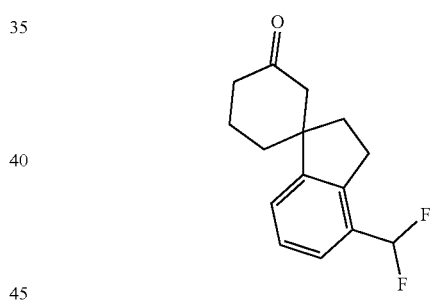

Step 1: 2-bromo-3-(difluoromethyl)phenol

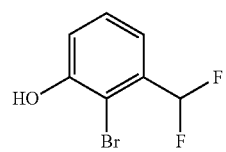 [SMILES: Oc1cccc(C(F)F)c1Br]

Under Ar, to a solution of 2-bromo-3-hydroxybenzaldehyde (30 g, 149 mmol) in DCM (300 m) was added DAST (36.1 g, 224 mmol) at 0° C., then one drop of EtOH was added, the resulting mixture was stirred at RT for 3 hours. Quenched with saturated NaHCO$_3$ solution, the resulting mixture was extracted with DCM three times. The combined organic layers were washed with brine, dried Na$_2$SO$_4$ and concentrated in vacuo to afford the title compound (30 g, 90%) as a yellow oil.

Step 2: 2-bromo-3-(difluoromethyl)phenyl trifluoromethanesulfonate

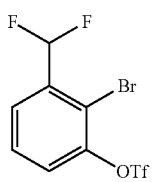

Under Ar, to a solution of 2-bromo-3-(difluoromethyl)phenol (30 g, 135 mmol) and 2,6-dimethylpyridine (21.62 g, 202 mmol) in DCM (200 mL) was dropwise added Tf$_2$O (43.6 g, 155 mmol) at 0° C. After 1 hour later, quenched with 1M HCl solution, the resulting mixture was extracted with dichloromethane twice. The combined organic layers were washed with brine, dried over Na$_2$SO$_4$, concentrated in vacuo to give a residual, which was purified by silica gel column and eluted with PE 100% to afford the title compound (24 g, 50.2%) as a yellow oil.

Step 3: 2'-bromo-3'-(difluoromethyl)-5,6-dihydro-[1,1'-biphenyl]-3(4H)-one

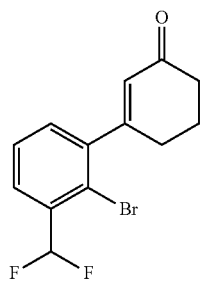 [SMILES: O=C1C=C(c2cccc(C(F)F)c2Br)CCC1]

Under Ar, the mixture of 2-bromo-3-(difluoromethyl)phenyl trifluoromethanesulfonate (2 g, 5.63 mmol), sodium bicarbonate (0.946 g, 11.27 mmol), 3-(4,4,5,5-tetramethyl-1,3,2-dioxaborolan-2-yl)cyclohex-2-en-1-one (0.876 g, 3.94 mmol), and Pd(Ph$_3$P)$_4$ (0.195 g, 0.169 mmol) in DME (20 mL)/Water (5 mL) was stirred at 90° C. for 14 hours. After cooling sown to RT, water was added, the resulting mixture was extracted with ethyl acetate twice. The combined organic layers were washed with brine, dried over Na$_2$SO$_4$, concentrated in vacuo to give a residual, which was purified by silica gel column and eluted with EA/PE from 0% to 20% to afford the title compound (0.6 g, 35.4%) as a yellow oil. MS: 302. 97 (M+H$^+$).

Step 4: 3-(2-bromo-3-(difluoromethyl)phenyl)-3-vinylcyclohexan-1-one

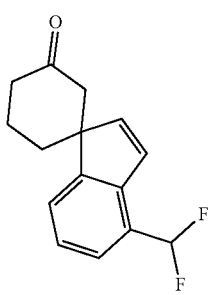 [SMILES: O=C1CCCC2(C=Cc3c(C(F)F)cccc32)C1]

Under Ar, to a solution of lithium chloride (0.697 g, 16.44 mmol) and copper(I) iodide (3.13 g, 16.4 mmol,) in THF (50 mL) was drop wise added solution of vinylmagnesium bromide (4.32 g, 32.9 mmol) in THF at −78° C., then the mixture was stirred at −78° C. for 1 h, 2'-bromo-3'-(difluoromethyl)-5,6-dihydro-[1,1'-biphenyl]-3(4H)-one (3.3 g, 10.96 mmol) in THF (20 mL) was dropwise added to the above mixture at −78° C., then the mixture was for another 1 h at −78° C. quenched with saturated NH$_4$Cl solution, the resulting mixture was extracted with EA three times. The combined organic layers were washed with brine, dried over Na$_2$SO$_4$, filtrated and concentrated to give a residue, which was purified by silica gel column and eluted with EA/HEX from 0% to 20% to afford the title compound (2.2 g, 61.0%) as a yellow oil. MS: 311.2 (M+H$^+$).

Step 5: 4'-(difluoromethyl)spiro[cyclohexane-1,1'-inden]-3-one

Under Ar, the mixture of 3-(2-bromo-3-(difluoromethyl)phenyl)-3-vinylcyclohexan-1-one (3.46 g, 10.51 mmol), PdCl$_2$(dppf) (0.769 g, 1.051 mmol,) Na$_2$CO$_3$ (1.114 g, 10.51 mmol) in DMF (80 mL) was stirred at 100° C. for 4 h. After cooling down to RT, water was added, the resulting mixture was extracted with EA three times. The combined organic layers were washed with brine, dried over Na$_2$SO$_4$, filtrated and concentrated to give a residue, which was purified by silica gel column and eluted with EA/HEX from 0% to 30% to afford the title compound (2.221 g, 85%) as a yellow oil. MS: 249.2 (M+H$^+$).

215

Step 6: 4'-(difluoromethyl)-2',3'-dihydrospiro[cyclohexane-1,1'-inden]-3-one

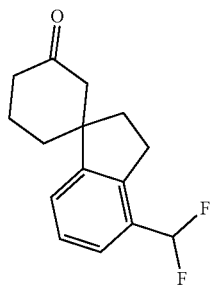 [SMILES: O=C1CCCC2(CCc3c(C(F)F)cccc32)C1]

The mixture of 4'-(difluoromethyl)spiro[cyclohexane-1,1'-inden]-3-one (1.0 g, 4.03 mmol) and Pd/C (0.429 g) in Ethyl acetate (80 mL) was stirred at RT for 3 hours under H$_2$ condition. The filtrate was concentrated in vacuo to give the title compound (900 mg, crude) as a colorless oil. MS: 251.2 (M+H$^+$).

Example 53 was prepared essentially the same protocol described in EXAMPLE 45 The title compound was prepared essentially the same protocol described with 4'-(difluoromethyl)-2',3'-dihydrospiro[cyclohexane-1,1'-inden]-3-one to afford 13 mg as a white solid. MS: 621.8 (M+H$^+$). $^1$H NMR (400 MHz, DMSO-d6) δ 7.43-7.23 (m, 3H), 7.25-6.90 (m, 1H), 5.43-5.12 (m, 2H), 4.03-3.75 (m, 4H), 3.55-2.5 (m, 17H), 2.12-1.50 (m, 12H).

Example 54

2-((S)-4-((R)-4-chloro-2'-(((2R,7aS)-2-fluorotetrahydro-1H-pyrrolizin-7a(5H)-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 50)

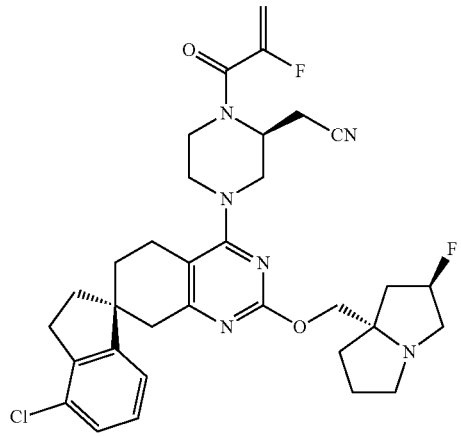 [SMILES: C=C(F)C(=O)N1CCN(c2nc(OC[C@@]34CCCN3C[C@H](F)C4)nc3c2CC[C@@]2(CCc4c(Cl)cccc42)C3)C[C@@H]1CC#N]

The title compound was prepared essentially the same protocol described with ((2R,7aS)-2-fluorotetrahydro-1H-pyrrolizin-7a(5H)-yl)methanol in stand of (tetrahydro-1H-pyrrolizin-7a(5H)-yl)methanol to afford 28 mg as a white solid. MS: 624.6 (M+H$^+$). $^1$H NMR (400 MHz, DMSO-d6) δ 7.27-7.21 (m, 2H), 7.16-7.14 (m, 1H), 5.42-5.19 (m, 3H), 3.98-3.83 (m, 4H), 3.31-2.68 (m, 16H), 2.08-1.71 (m, 11H).

Example 55

2-((2S)-4-((1R)-4-chloro-2'-((2,2-difluorotetrahydro-1H-pyrrolizin-7a(5H)-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 51)

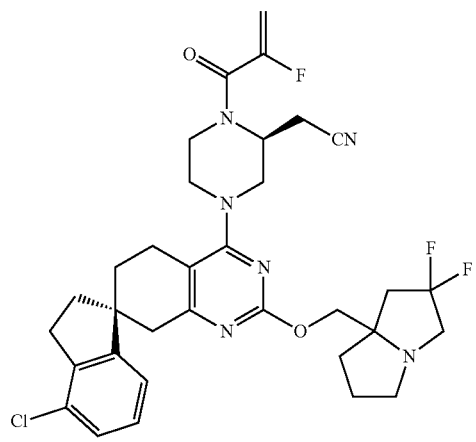 [SMILES: C=C(F)C(=O)N1CCN(c2nc(OCC34CCCN3CC(F)(F)C4)nc3c2CC[C@@]2(CCc4c(Cl)cccc42)C3)C[C@@H]1CC#N]

The title compound was prepared essentially the same protocol described with (2,2-difluorotetrahydro-1H-pyrrolizin-7a(5H)-yl)methanol to afford 20 mg as a white solid. MS: 641.2, 643.2 (M+H$^+$). $^1$H NMR (400 MHz, DMSO-d6) δ 7.27-7.21 (m, 2H), 7.16-7.14 (m, 1H), 5.66-5.16 (m, 2H), 5.08-3.61 (m, 6H), 3.54-2.50 (m, 14H), 2.47-2.23 (m, 2H), 2.16-1.61 (m, 8H).

Example 56

2-((2S)-4-((1R)-4-chloro-2'-((hexahydro-1H-pyrrolizin-3-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 52)

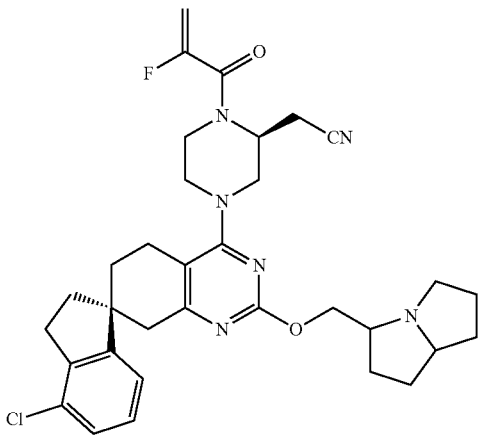 [SMILES: C=C(F)C(=O)N1CCN(c2nc(OCC3CCC4CCCN43)nc3c2CC[C@@]2(CCc4c(Cl)cccc42)C3)C[C@@H]1CC#N]

Intermediate Step 1: benzyl (4-(methoxy(methyl)amino)-4-oxobutyl) carbamate

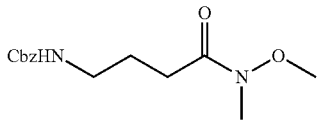 [SMILES: CON(C)C(=O)CCCNC(=O)OCc1ccccc1]

Under Ar, to a solution of 4-(((benzyloxy) carbonyl) amino) butanoic acid (5.0 g, 21.07 mmol) and TEA (6.4 g, 63.2 mmol) in dry DCM (100 mL) was added T$_3$P (8.05 g, 25.3 mmol) and N, O-dimethylhydroxylamine (1.93 g, 31.6 mmol) at 0° C. Then the mixture was stirred at RT for 16 h. Washed with water, brine, dried over anhydrous Na$_2$SO$_4$ and concentrated in vacuo to give a residue, which was purified by flash chromatography eluted with Hex/EA from 3:1 to 1:1 to afford the title compound (5.5 g, 93%) as colorless oil. MS: 281.3 (M+H$^+$).

Step 2: benzyl (4-oxooct-7-en-1-yl) carbamate

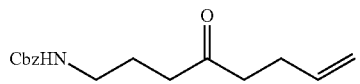 [SMILES: C=CCCC(=O)CCCNC(=O)OCc1ccccc1]

Under Ar, to a solution of benzyl (4-(methoxy(methyl) amino)-4-oxobutyl) carbamate (4.4 g, 15.7 mmol) in dry THF (50 mL) was added but-3-en-1-ylmagnesium bromide (7.5 g, 47.1 mmol) at 0° C. The reaction mixture was stirred at rt for 1 h. Adjust pH=3-4 using HCl aq and extracted with EA for 3 times. The combined EA layers were washed with brine, dried over anhydrous Na$_2$SO$_4$ and concentrated in vacuo to give a residue, which was purified by flash chromatography eluted with Hex/EA from 10:1 to 3:1 to afford the title compound (3.3 g, 76%) as colorless oil. $^1$H NMR (400 MHz, CDCl$_3$) δ 7.35 (m, 5H), 5.79 (m, 1H), 5.09 (s, 2H), 5.00 (m, 2H), 4.82 (s, 1H), 3.20 (m, 2H), 2.54-2.42 (m, 4H), 2.31 (m, 2H), 1.84-1.73 (m, 2H).

Step 3: benzyl 2-(but-3-en-1-yl) pyrrolidine-1-carboxylate

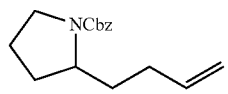 [SMILES: C=CCCC1CCCN1C(=O)OCc1ccccc1]

Under Ar, to a solution of triphenylsilane (5.62 g, 21.6 mmol) in dry DCM (50 ml) was added BF$_3$OEt$_2$ (6.23 g, 43.9 mmol) at rt. The reaction mixture was stirred at rt for 10 min prior to cooling to −70° C. A solution of benzyl (4-oxooct-7-en-1-yl) carbamate (3.3 g, 11.98 mmol) in DCM (50 mL) was added to the above mixture and stirred at −70° C. for 30 mins. The reaction mixture was stirred at rt for 2 h. Quenched with NaHCO$_3$ aq and extracted with DCM for 3 times. The combined DCM layers were washed with brine, dried over anhydrous Na$_2$SO$_4$ and concentrated in vacuo. The residue was purified by flash chromatography eluted with Hex/EA from 10:1 to 4:1 to give the title compound (2.6 g, 84%) as colorless oil. $^1$H NMR (400 MHz, DMSO) δ 7.45-7.38 (m, 5H), 5.83 (m, 1H), 5.17 (m, 2H), 5.05 (d, J=17.2 Hz, 1H), 4.98 (d, J=10.2 Hz, 1H), 3.90 (m, 1H), 3.54-3.37 (m, 2H), 2.15-2.01 (m, 2H), 2.01-1.81 (m, 4H), 1.77-1.68 (m, 1H), 1.50-1.39 (m, 1H).

Step 4: benzyl 2-(2-(oxiran-2-yl) ethyl) pyrrolidine-1-carboxylate

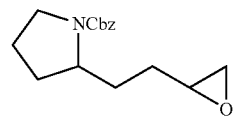 [SMILES: O=C(OCc1ccccc1)N1CCCC1CCC1CO1]

To a solution of oxone (30.8 g, 50.1 mmol) and NaHCO$_3$ (12.63 g, 150 mmol) in ACE/H$_2$O (75 mL/150 mL) was added benzyl 2-(but-3-en-1-yl) pyrrolidine-1-carboxylate (2.6 g, 10.0 mmol) at 0° C. The reaction mixture was stirred at rt for 2 h. Diluted with water, extracted with EA for 3 times. The combined EA layers were washed with brine, dried over anhydrous Na$_2$SO$_4$ and concentrated in vacuo. The residue was purified by flash chromatography eluted with Hex/EA from 10:1 to 4:1 to give the title compound (1.8 g, 65.2%) as colorless oil. MS: 276.3 (M+H$^+$).

Step 5: (hexahydro-1H-pyrrolizin-3-yl) methanol

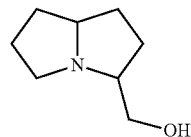

A mixture of benzyl 2-(2-(oxiran-2-yl) ethyl) pyrrolidine-1-carboxylate (1.8 g, 6.54 mmol, 1.0 eq) and Pd/C (600 mg) in MeOH (50 mL) was stirred at rt under H$_2$ for 16 h. Filtered and concentrated in vacuo. The residue was purified by flash chromatography eluted with DCM/MeOH (1% NH$_4$OH) from 50:1 to 20:1 to afford the title compound (450 mg, 49%) as yellow oil. MS: 142.1 (M+H$^+$).
$^1$H NMR (400 MHz, CDCl$_3$) δ 4.02 (s, 1H), 3.65-3.54 (m, 2H), 3.46 (dd, J=10.8, 5.2 Hz, 1H), 3.04 (m, 1H), 2.88 (m, 1H), 2.71 (m, 1H), 2.09-1.66 (m, 6H), 1.55-1.38 (m, 2H).

Step 6: 2-((2S)-4-((1R)-4-chloro-2'-((hexahydro-1H-pyrrolizin-3-yl)methoxy)-2,3,5',8'-tetrahydro-6'H-spiro[indene-1,7'-quinazolin]-4'-yl)-1-(2-fluoroacryloyl)piperazin-2-yl)acetonitrile Example 56 was prepared essentially the same protocol described in EXAMPLE 49 The title compound was prepared essentially the same protocol described with (hexahydro-1H-pyrrolizin-3-yl)methanol to afford 14 mg as a white solid. MS: 605.4 (M+H$^+$).

Example 57

2-((S)-1-acryloyl-4-((R)-4-chloro-2'-(((S)-1-methylpyrrolidin-2-yl)methoxy)-2,3,5',8'-tetrahydro-6'H-spiro[indene-1,7'-quinazolin]-4'-yl)piperazin-2-yl)acetonitrile (Cpd. No. 53)

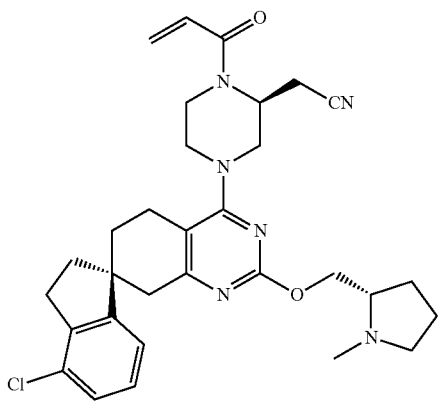 [SMILES: C=CC(=O)N1CCN(c2nc(OC[C@@H]3CCCN3C)nc3c2CC[C@@]2(CCc4c(Cl)cccc42)C3)C[C@@H]1CC#N]

Example 57 was prepared essentially the same protocol described in EXAMPLE 48 The title compound was prepared essentially the same protocol described with (S)-(1-methylpyrrolidin-2-yl)methanol to afford 21 mg as a white solid. MS: 561.3 (M+H$^+$). 1H NMR (400 MHz, DMSO) δ 7.30-7.22 (m, 2H), 7.22-7.12 (m, 1H), 6.93-6.74 (m, 1H), 6.18 (d, J=16.8 Hz, 1H), 5.77 (d, J=10.5 Hz, 1H), 5.10-4.25 (m, 1H), 4.22-3.41 (m, 5H), 3.41-2.36 (m, 13H), 2.32 (s, 3H), 2.21-2.02 (m, 2H), 2.01-1.85 (m, 3H), 1.80-1.46 (m, 4H).

Example 58

2-((S)-4-((R)-4-chloro-2'-(((S)-1-methylpyrrolidin-2-yl)methoxy)-2,3,5',8'-tetrahydro-6'H-spiro[indene-1,7'-quinazolin]-4'-yl)-1-(2-fluoroacryloyl)piperazin-2-yl)acetonitrile (Cpd. No. 54)

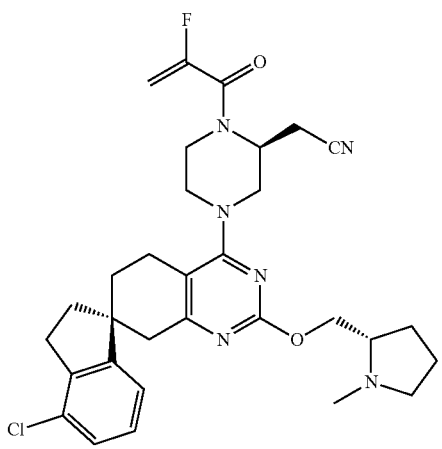 [SMILES: C=C(F)C(=O)N1CCN(c2nc(OC[C@@H]3CCCN3C)nc3c2CC[C@@]2(CCc4c(Cl)cccc42)C3)C[C@@H]1CC#N]

Example 58 was prepared essentially the same protocol described in EXAMPLE 49 The title compound was prepared essentially the same protocol described to afford 17 mg as a white solid. MS: 579.3 (M+H$^+$).

Example 59

Biology Assays

Cell Proliferation Assay:

NCI-H358 cell and MIA PaCa-2 cell was cultured in RPMI-1640 supplemented with 10% FBS in humidified incubator at 37° C., 5% $CO_2$. To asses the effect of Compounds of the Disclosure on cell proliferation, exponentially growing cells (5000 cells/well) were plated onto 96-well plates. After cell seeding, a representative Compounds of the Disclosure were added to the cell media (in concentrations ranging from 0 to 10 μM, 3/dilution series). After 3 days, 30 μL Celltiter-Glo reagent was added, and the luminescent signal was determined according to supplier's instruction. The dose response curves and $IC_{50}$ values were generated using Prism. The results are provided in Table 1.

Example 60

Biological Example: Mouse PK Studies

The pharmacokinetic (PK) profile of compounds following single i.v. and p.o. in CD1 mice obtained from Zhejiang Vital River Laboratory Animal Technology Co., Ltd. Was determined. Three male rats of weight 200-300 g were used. Compounds were prepared at 0.4 mg/mL and 2 mg/mL with the formulation of 10% DMSO, 5% Solutol HS15, 85% Saline and 20% DMSO, 10% Solutol HS15, 70% Distilled water respectively. Blood samples (0.3 mL) were collected at 0.083, 0.25, 0.5, 1, 2, 4, 6, 8, 24 h for i.v. and 0.25, 0.5, 1, 2, 4, 6, 8, 24 h for p.o. post dose at 2 mg/kg and 10 mg/kg, respectively.

The collected blood samples were centrifuged within 30 mins and the plasma was separated and transferred into tubes before storage at −75±15° C. prior to analysis. Aliquots of the plasma unknowns, blank and calibration standards were added to 200 μL of acetonitrile containing IS mixture for precipitating protein respectively. Then the samples were vortexed for 30 s. After centrifugation at 4 degree Celsius, 3900 rpm for 15 min, the supernatant was diluted 3 times with water. The supernatant was injected into the LC/MS/MS system for quantitative analysis.

The LC-MS/MS system consisted of two Shimadzu LC-30AD pumps, a DGU-20A5R degasser, a Rack changer II and an AB Sciex Triple Quad 5500 LC/MS/MS mass spectrometer. Chromatographic separation was performed on a YMC-Triart C18 5 μm (50*2.1 mm) column at room temperature. The mobile phase was composed of A: 95% water (0.1% formic acid); B: 95% acetonitrile (0.1% formic acid). The flow rate was 0.6 mL/min. The injection volume was 5 μL.

To improve the sensitivity of the test compound screening. A MRM method in positive electrospray ionization mode was employed. Mass spectrometry data was acquired and analysed using AB Sciex Analyst version 1.6.2 version. The pharmacokinetic parameters were derived using standard noncompartmental methods with Phoenix WinNonlin Professional Version 6.1. The following pharmacokinetics parameters were calculated. The following pharmacokinetic parameters were calculated, whenever possible from the plasma concentration versus time data:

IV administration: $T_{1/2}$(terminal half-life), C0, $AUC_{last}$, $AUC_{inf}$, $MRT_{inf}$, $C_1$, Vss, Number of Points for Regression.

PO administration: $T_{1/2}$(terminal half-life), $C_{max}$, $T_{max}$, $MRT_{inf}$, $AUC_{inf}$, $AUC_{last}$, F %, Number of Points for Regression. The pharmacokinetic data was described using descriptive statistics such as mean, standard deviation.

| Compound | Dose | $AUC_{last}$ (h * ng/mL) | $AUC_{inf}$ (h * ng/mL) | $C_{max}$ (ng/mL) | Vss (L/Kg) | $T_{1/2}$ (h) | $MRT_{inf}$ (h) | F % |
|---|---|---|---|---|---|---|---|---|
| Cpd. No 45 | IV 2 mpk | 3109 | 3121 | / | 1.22 | 2.52 | 1.91 | / |
|  | PO 10 mpk | 7387 | 7403 | 1215 | / | 2.58 | 4.77 | 47.4% |
| Cpd. No 53 | IV 2 mpk | 1199 | 1203 | / | 1.37 | 1.45 | 0.824 | / |
|  | PO 10 mpk | 2646 | 2902 | 856 | / | 2.39 | 3.26 | 48.2% |
| Cpd. No 54 | IV 2 mpk | 852 | 862 | / | 2.27 | 1.43 | 0.97 | / |
|  | PO 10 mpk | 2264 | 2750 | 570 | / | 3.04 | 4.73 | 58.9% |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound of Formula VII:

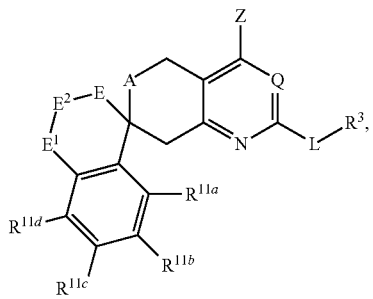

VII wherein:

Z is

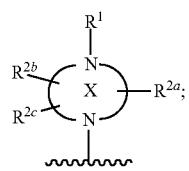

X represents a 6- to 12-membered monocyclic or bicyclic heterocyclo;

$R^1$ is selected from the group consisting of —C(=O)$R^{1a}$, —C(=O)—C$R^{4a}$=C$R^{4b}R^{4c}$, —C(=O)—C≡C$R^{5a}$, —S(=O)$_2$C$R^{4e}$=C$R^{4f}R^{4g}$, and —S(=O)$_2$—C≡C$R^{5b}$;

$R^{1a}$ is selected from the group consisting of $C_1$-$C_4$ alkyl, $C_1$-$C_4$ haloalkyl, and $C_3$-$C_6$ cycloalkyl;

$R^{4a}$, $R^{4b}$, and $R^{4c}$ are independently selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (optionally substituted heterocyclo)$C_1$-$C_4$ alkyl;

$R^{5a}$ is selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (optionally substituted heterocyclo)$C_1$-$C_4$ alkyl;

$R^{4e}$, $R^{4f}$, and $R^{4g}$ are independently selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (optionally substituted heterocyclo)$C_1$-$C_4$ alkyl;

$R^{5b}$ is selected from the group consisting of hydrogen, halogen, $C_1$-$C_6$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, and (optionally substituted heterocyclo)$C_1$-$C_4$ alkyl;

$R^{2a}$ is selected from the group consisting of hydrogen, $C_1$-$C_4$ alkyl, $C_1$-$C_4$ haloalkyl, (cyano)$C_1$-$C_4$ alkyl, (hydroxy)$C_1$-$C_4$ alkyl, (alkoxy)$C_1$-$C_4$ alkyl, (amino)$C_1$-$C_4$ alkyl, (optionally substituted heterocyclo)$C_1$-$C_4$ alkyl, (optionally substituted aryl)$C_1$-$C_4$ alkyl, (optionally substituted hetereoaryl)$C_1$-$C_4$ alkyl, $C_2$-$C_4$ alkynyl, heteroalkyl, cyano, —C(=O)O$R^{5c}$, —C(=O)N$R^{5d}R^{5e}$, and —N$R^{5f}R^{5g}$;

$R^{2b}$ and $R^{2c}$ are independently selected from the group consisting of hydrogen and $C_1$-$C_4$ alkyl; or $R^{2b}$ and $R^{2c}$ are attached to the same carbon atom and are taken together to form a —C(=O)— group;

$R^{5c}$ is selected from the group consisting hydrogen and $C_1$-$C_4$ alkyl;

$R^{5d}$ and $R^{5e}$ are independently selected from the group consisting hydrogen and $C_1$-$C_4$ alkyl; or $R^{5d}$ and $R^{5e}$ taken together with the nitrogen atom to which they are attached form an optionally substituted 4- to 8-membered heterocyclo;

$R^{5f}$ and $R^{5g}$ are independently selected from the group consisting hydrogen and $C_1$-$C_4$ alkyl; or $R^{5f}$ and $R^{5g}$ taken together with the nitrogen atom to which they are attached form an optionally substituted 4- to 8-membered heterocyclo;

L is selected from the group consisting of —O—, —S—, and —N($R^7$)—; or L is a bond;

$R^7$ is selected from the group consisting of hydrogen and $C_1$-$C_4$ alkyl;

$R^3$ is selected from the group consisting of hydrogen, $C_1$-$C_4$ alkyl, $C_3$-$C_6$ cycloalkyl, (amino)$C_1$-$C_4$ alkyl, (hydroxy)$C_1$-$C_4$ alkyl, (alkoxy)$C_1$-$C_4$ alkyl, (carboxamido)$C_1$-$C_4$ alkyl, (optionally substituted heterocyclo)$C_1$-$C_4$ alkyl, (optionally substituted aryl)$C_1$-$C_4$ alkyl, and (optionally substituted hetereoaryl)$C_1$-$C_4$ alkyl;

A is —CH$_2$—;

E is —CH$_2$—;

$E^1$ is —CH$_2$—;

$E^2$ is —O—;

Q is selected from the group consisting of =C($R^{10}$)— and =N—;

$R^{10}$ is selected from the group consisting of hydrogen, $C_1$-$C_4$ alkyl and $C_3$-$C_6$ cycloalkyl; and $R^{11a}$, $R^{11b}$, $R^{11c}$, and $R^{11d}$ are independently selected from the group consisting of hydrogen, halo, cyano, hydroxy, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, and (hydroxy)$C_1$-$C_4$ alkyl, or a pharmaceutically acceptable salt or solvate thereof.

2. The compound of claim 1 of Formula VIII:

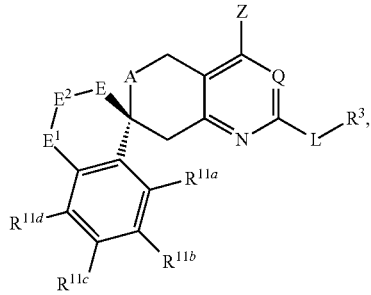

or a pharmaceutically acceptable salt or solvate thereof.

3. The compound of claim 1 of Formula IX:

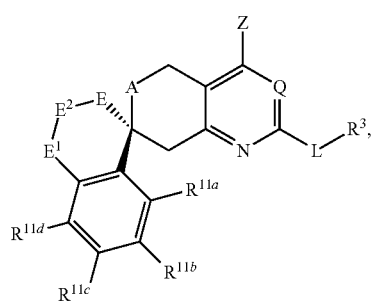

or a pharmaceutically acceptable salt or solvate thereof.

4. The compound of claim 1, wherein Q is =N—; and L is —O—, or a pharmaceutically acceptable salt or solvate thereof.

5. The compound of claim 1, wherein $R^3$ is selected from the group consisting of (amino)$C_1$-$C_4$ alkyl, (carboxamido)$C_1$-$C_4$ alkyl, and (optionally substituted heterocyclo)$C_1$-$C_4$ alkyl, or a pharmaceutically acceptable salt or solvate thereof.

6. The compound of claim 1, wherein $R^3$ is:

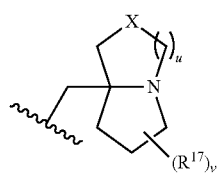

wherein:
X is selected from the group consisting of —O— and —CR$^{18a}$R$^{18b}$;
each $R^{17}$ is independently selected from the group consisting of halo, $C_1$-$C_3$ alkyl, $C_1$-$C_3$ haloalkyl, and (hydroxyl)$C_1$-$C_3$ alkyl;
$R^{18a}$ and $R^{18b}$ are each independently selected from the group consisting of hydrogen, halo, $C_1$-$C_3$ alkyl, $C_1$-$C_3$ haloalkyl, and (hydroxyl)$C_1$-$C_3$ alkyl; or $R^{18a}$ and $R^{18b}$ taken together with the carbon atom to which they are attached form an optionally substituted 3- to 6-membered cycloalkyl;
u is 1, 2, or 3; and
v is 0, 1, or 2,
with the proviso that u is 2 or 3 when X is —O—.

7. The compound of claim 1, wherein $R^3$ is selected from the group consisting of:

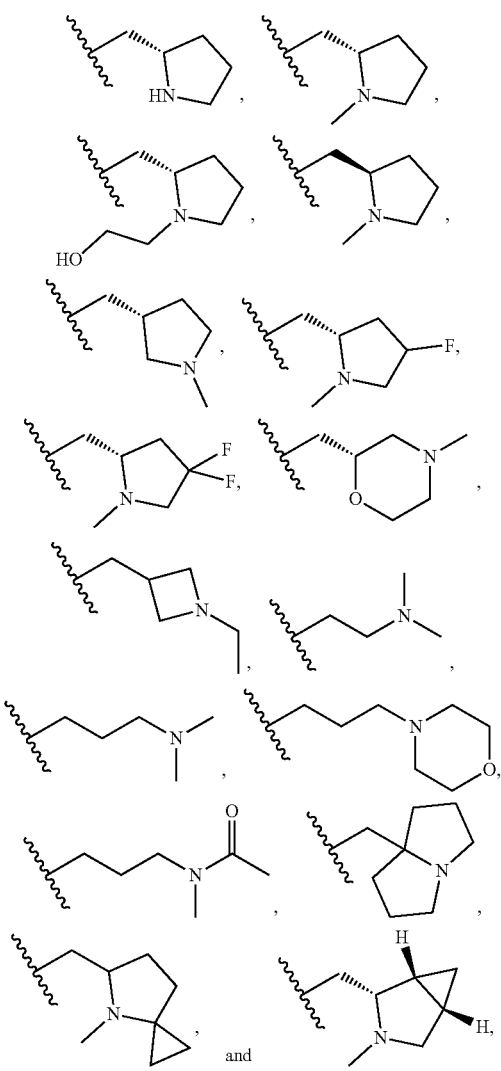

or a pharmaceutically acceptable salt or solvate thereof.

8. The compound of claim 1, wherein Z is selected from the group consisting of:

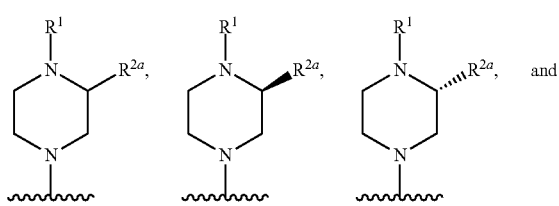

-continued

wherein $R^{2a}$ is —CH$_2$CN, or a pharmaceutically acceptable salt or solvate thereof.

9. The compound of claim 1, wherein $R^1$ is selected from the group consisting of —C(=O)—CR$^{4a}$=CHR$^{4b}$, —C(=O)—CCR$^{5a}$, and —S(=O)$_2$CH=CHR$^{4f}$, or a pharmaceutically acceptable salt or solvate thereof.

10. The compound of claim 1, wherein $R^1$ is selected from the group consisting of:

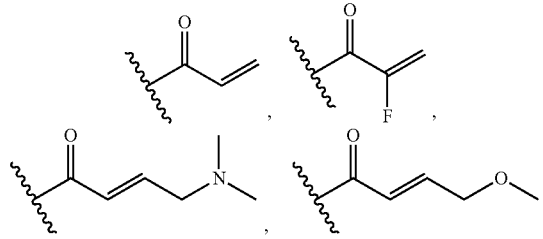

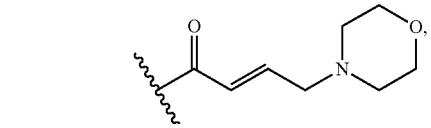

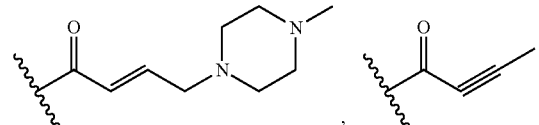

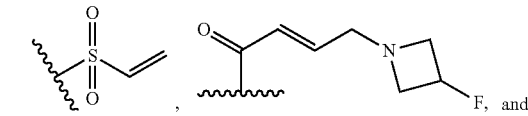

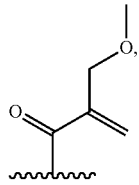

or a pharmaceutically acceptable salt or solvate thereof.

11. A pharmaceutical composition comprising the compound of claim 1, or a pharmaceutically acceptable salt or solvate thereof, and a pharmaceutically acceptable carrier.

12. The compound of claim 5, wherein $R^3$ is (optionally substituted heterocyclo)C$_1$-C$_4$ alkyl, or a pharmaceutically acceptable salt or solvate thereof.

13. The compound of claim 10, wherein $R^1$ is:

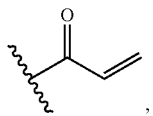

or a pharmaceutically acceptable salt or solvate thereof.

14. A compound selected from the group consisting of:

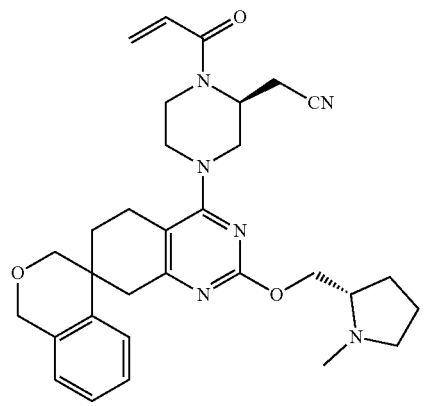

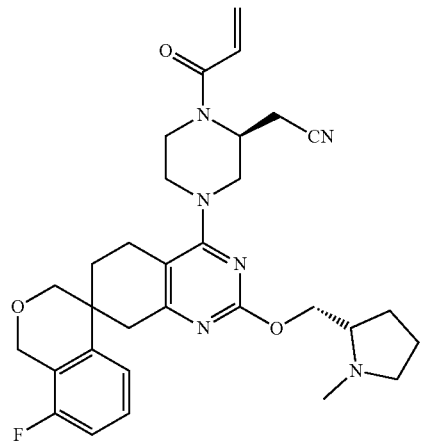

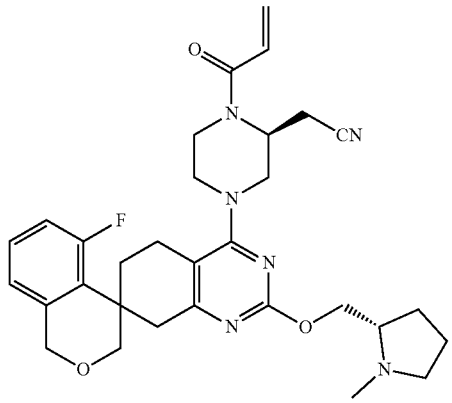

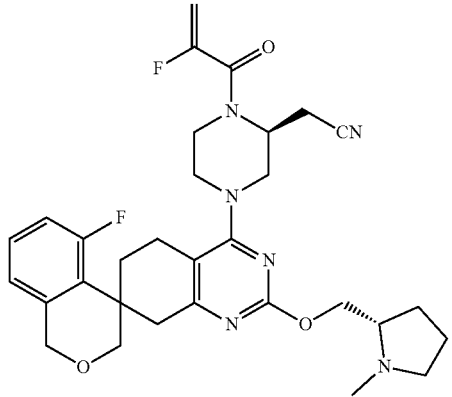

227
-continued
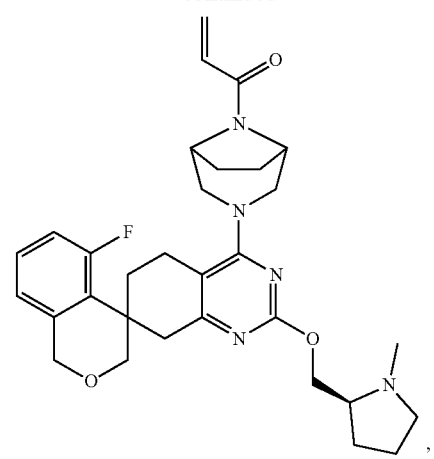
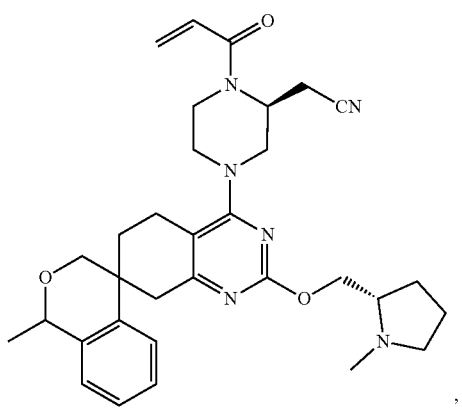
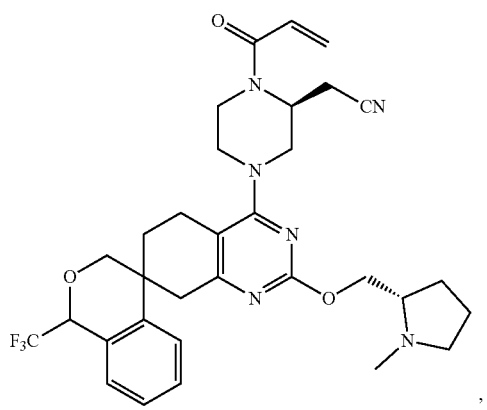
228
-continued
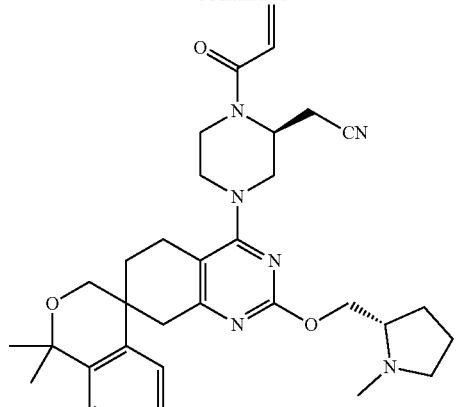
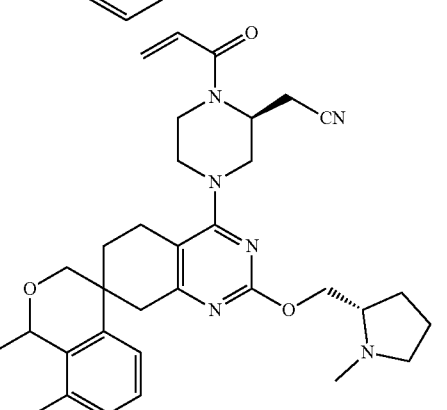
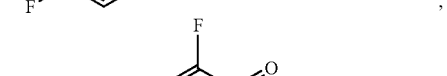, and
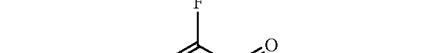
or a pharmaceutically acceptable salt or solvate thereof.
* * * * *